US009260525B2

(12) United States Patent
Chang et al.

(10) Patent No.: US 9,260,525 B2
(45) Date of Patent: Feb. 16, 2016

(54) ANTIBODY MOLECULES TO ONCOGENIC ISOFORMS OF FIBROBLAST GROWTH FACTOR RECEPTOR-2 AND USES THEREOF

(71) Applicants: Xiao-jia Chang, Lincoln, MA (US); Ullrich S. Schwertschlag, Indian Creek, IL (US); Katherine Jane Turner, Acton, MA (US)

(72) Inventors: Xiao-jia Chang, Lincoln, MA (US); Ullrich S. Schwertschlag, Indian Creek, IL (US); Katherine Jane Turner, Acton, MA (US)

( * ) Notice: Subject to any disclaimer, the term of this patent is extended or adjusted under 35 U.S.C. 154(b) by 152 days.

(21) Appl. No.: 13/765,236

(22) Filed: Feb. 12, 2013

(65) Prior Publication Data

US 2013/0142802 A1 Jun. 6, 2013

Related U.S. Application Data

(63) Continuation-in-part of application No. 12/866,013, filed as application No. PCT/US2009/033031 on Feb. 4, 2009, now abandoned, application No. 13/765,236, which is a continuation-in-part of application No. PCT/US2011/047650, filed on Aug. 12, 2011.

(60) Provisional application No. 61/373,072, filed on Aug. 12, 2010, provisional application No. 61/025,947, filed on Feb. 4, 2008.

(51) Int. Cl.
*C07K 16/28* (2006.01)
*A61K 39/00* (2006.01)
*A61K 39/395* (2006.01)

(52) U.S. Cl.
CPC ............ *C07K 16/2863* (2013.01); *A61K 39/00* (2013.01); *A61K 39/39541* (2013.01); *A61K 39/39558* (2013.01); *A61K 2039/505* (2013.01); *C07K 16/28* (2013.01); *C07K 2317/21* (2013.01); *C07K 2317/24* (2013.01); *C07K 2317/33* (2013.01); *C07K 2317/34* (2013.01); *C07K 2317/622* (2013.01); *C07K 2317/64* (2013.01); *C07K 2317/732* (2013.01); *C07K 2317/76* (2013.01); *C07K 2317/92* (2013.01)

(58) Field of Classification Search
CPC ............ A61K 39/00; A61K 39/39541; A61K 39/39558; A61K 2039/505; C07K 16/28; C07K 2317/24
USPC ........... 530/350, 387.1, 387.3, 397.9, 388.22, 530/388.8
See application file for complete search history.

(56) References Cited

U.S. PATENT DOCUMENTS

| | | | |
|---|---|---|---|
| 2004/0044181 | A1 | 3/2004 | Tang et al. |
| 2005/0019845 | A1 | 1/2005 | Harkins et al. |
| 2007/0248605 | A1 | 10/2007 | Hestir et al. |
| 2008/0260748 | A1 | 10/2008 | Iwamoto et al. |
| 2008/0300204 | A1 | 12/2008 | Federoff et al. |
| 2009/0137002 | A1 | 5/2009 | Petrul et al. |
| 2010/0196364 | A1 | 8/2010 | Kim et al. |

FOREIGN PATENT DOCUMENTS

| | | |
|---|---|---|
| WO | 20071014123 A2 | 2/2007 |
| WO | 2009100105 A2 | 8/2009 |
| WO | 2012021841 A2 | 2/2012 |

OTHER PUBLICATIONS

Extended European Search Report dated Aug. 28, 2014 from European Application No. 11817134.7.
International Search Report and Written Opinion, International Application No. PCT/US09/33031, date of mailing Aug. 21, 2009.
Hajihosseini, M.K., et al., "A Splicing Switch and Gain-of-Function Mutation in FgfR2-IIIc Hemizygotes Causes Apert/Pfeiffer-Syndrome-Like Phenotypes", PNAS. 98(7):3855-3860. Mar. 27, 2001.
International Search Report, International Application No. PCT/US2011/47650, dated Apr. 13, 2012.
Chang, J., et al., "Targeting Prostate Cancer Specific Isoform Proteins," The 15th Annual Prostate Cancer Foundation Scientific Retreat, Lake Tahoe, CA, Oct. 2008.
Carstens, R.P., et al., "Alternative Splicing of Fibroblast Growth Factor Receptor 2 (FGF-R2) in Human Prostate Cancer," Oncogene, 15:3059-3065 (1997).
Sahadevan, K., et al., "Selective Over-Expression of Fibroblast Growth Factor Receptors 1 and 4 in Clinical Prostate Cancer," Journal of Pathology (2007).
Matsuda, Y., et al., "Fibroblast Growth Factor Receptor 2 IIIc as a Therapeutic Target for Colorectal Cancer Cells," Mol. Cancer Ther., Published OnlineFirst Jul. 9, 2012.
Ishiwata, T., et al., "Enhanced Expression of Fibroblast Growth Factor Receptor 2 IIc Promotes Human Pancreatic Cancer Cell Proliferation," The American Journal of Pathology, 180(5):1928-1941, May 2012.
Stancovski, I., et al., "Mechanistic Aspects of the Opposing Effects of Monoclonal Antibodies to the ERBB2 Receptor on Tumor Growth," Proc. Natl. Acad. Sci., USA, 88:8691-8695 (1991).

*Primary Examiner* — Stephen Rawlings
(74) *Attorney, Agent, or Firm* — Hamre, Schumann, Mueller & Larson, P.C.

(57) ABSTRACT

Antibody molecules that specifically bind to one or more isoforms expressed and/or associated with oncogenic phenotypes in a hyperproliferative cell (e.g., a cancerous or tumor cell) are disclosed. The isoform-binding antibody molecules can be used to treat, prevent and/or diagnose cancerous conditions and/or disorders. Methods of using the isoform-binding molecules to selectively detect oncogenic isoforms, to reduce the activity and/or induce the killing of a hyperproliferative cell expressing an oncogenic isoform in vitro, ex vivo or in vivo are also disclosed. Diagnostic and/or screening methods and kits for evaluating the function or expression of an oncogenic isoform are also disclosed.

12 Claims, 62 Drawing Sheets

```
                         difference in IIIc
IIIc:  301  YGPDGLPYLKVLKAAGVNTTDKEIEVLYIRNVTFEDAGEYTCLAGNSIGISFHSAWLTVL  (SEQ ID NO: 2)   360
            YGPDGLPYLKVLK +G+N+++ E+  L+  NVT  DAGEY C  N IG +  SAWLTVL
IIIB:  301  YGPDGLPYLKVLKHSGINSSNAEVLALF--NVTEADAGEYICKVSNYIGQANQSAWLTVL (SEQ ID NO: 65)  358
```

FIG. 2

```
  1 mvswgrficl vvvtmatlsl arpsfslved ttlepeeppt kyqisqpevy vaapgeslev
 61 rcllkdaavi swtkdgvhlg pnnrtvlige ylqikgatpr dsglyactas rtvdsetwyf
121 mvnvtdaiss gddeddtdga edfvsensnn krapywtnte kmekrlhavp aantvkfrcp
181 aggnpmptmr wlkngkefkq ehriggykvr nqhwslimes vvpsdkgnyt cvveneygsi
241 nhtyhldvve rsphrpilqa glpanastvv ggdvefvckv ysdaqphiqw ikhvekngsk
301 ygpdglpylk vlkaagvntt dkeievlyir nvtfedagey tclagnsigi sfhsawltvl
361 papgrekeit aspdyleiai ycigvfliac mvvtvilcrm knttkkpdfs sqpavhkltk
421 riplrrqvtv saessssmns ntplvrittr lsstadtpml agvseyelpe dpkwefprdk
481 ltlgkplgeg cfgqvvmaea vgidkdkpke avtvavkmlk ddatekdlsd lvsememmkm
541 igkhkniinl lgactqdgpl yviveyaskg nlreylrarr ppgmeysydi nrvpeeqmtf
601 kdlvsctyql argmeylasq kcihrdlaar nvlvtennvm kiadfglard innidyykkt
661 tngrlpvkwm apealfdrvy thqsdvwsfg vlmweiftlg gspypgipve elfkllkegh
721 rmdkpanctn elymmmrdcw havpsqrptf kqlvedldri ltlttneeyl dlsqpleqys
781 psypdtrssc ssgddsvfsp dpmpyepclp qyphingsvk t (SEQ ID NO: 19)
```

FIG. 3A

```
   1 atggtcagct ggggtcgttt catctgcctg gtcgtggtca ccatggcaac cttgtccctg
  61 gcccggcect ccttcagttt agttgaggat accacattag agccagaaga gccaccaacc
 121 aaataccaaa tctctcaacc agaagtgtac gtggctgcac cagggagtc gctagaggtg
 181 cgctgcctgt tgaaagatgc cgccgtgatc agttggacta aggatggggt gcacttgggg
 241 cccaacaata ggacagtgct tattggggag tacttgcaga taaagggcgc cacgcctaga
 301 gactccggcc tctatgcttg tactgccagt aggactgtag acagtgaaac ttggtacttc
 361 atggtgaatg tcacagatgc catctcatcc ggagatgatg aggatgacac cgatggtgcg
 421 gaagattttg tcagtgagaa cagtaacaac aagagagcac catactggac caacacagaa
 481 aagatggaaa agcggctcca tgctgtgcct gcggccaaca ctgtcaagtt tcgctgccca
 541 gccgggggga acccaatgcc aaccatgcgg tggctgaaaa acgggaagga gtttaagcag
 601 gagcatcgca ttggaggcta caaggtacga aaccagcact ggagcctcat tatggaaagt
 661 gtggtcccat ctgacaaggg aaattatacc tgtgtggtgg agaatgaata cgggtccatc
 721 aatcacacgt accacctgga tgttgtggag cgatcgcctc accggcccat cctccaagcc
 781 ggactgccgg caaatgcctc cacagtggtc ggaggagacg tagagtttgt ctgcaaggtt
 841 tacagtgatg cccagcccca catccagtgg atcaagcacg tggaaaagaa cggcagtaaa
 901 tacgggcccg acgggctgcc ctacctcaag gttctcaagg ccgccggtgt taacaccacg
 961 gacaaagaga ttgaggttct ctatattcgg aatgtaactt tgaggacgc tggggaatat
1021 acgtgcttgg cgggtaattc tattgggata tcctttcact ctgcatggtt gacagttctg
1081 ccagcgcctg gaagagaaaa ggagattaca gcttccccag actacctgga gatagccatt
1141 tactgcatag gggtcttctt aatcgcctgt atggtggtaa cagtcatcct gtgccgaatg
1201 aagaacacga ccaagaagcc agacttcagc agccagccgg ctgtgcacaa gctgaccaaa
1261 cgtatccccc tgcggagaca ggtaacagtt tcggctgagt ccagctcctc catgaactcc
1321 aacaccccgc tggtgaggat aacaacacgc ctctcttcaa cggcagacac ccccatgctg
1381 gcagggagtct ccgagtatga acttccagag acccaaaat gggagtttcc aagagataag
1441 ctgacactgg gcaagcccct gggagaaggt tgctttgggc aagtggtcat ggcggaagca
1501 gtgggaattg acaaagacaa gcccaaggag gcggtcaccg tggccgtgaa gatgttgaaa
1561 gatgatgcca cagagaaaga cctttctgat ctggtgtcag agatggagat gatgaagatg
1621 attgggaaac acaagaatat cataaatctt cttggagcct gcacacagga tgggcctctc
1681 tatgtcatag ttgagtatgc ctctaaaggc aacctccgag aatacctccg agccggagg
1741 ccacccggga tggagtactc ctatgacatt aaccgtgttc ctgaggagca gatgaccttc
1801 aaggacttgg tgtcatgcac ctaccagctg gccagaggca tggagtactt ggcttcccaa
1861 aaatgtattc atcgagattt agcagccaga aatgtttttgg taacagaaaa caatgtgatg
1921 aaaatagcag actttggact cgccagagat atcaacaata tagactatta caaaaagacc
1981 accaatgggc ggcttccagt caagtggatg gctccagaag ccctgtttga tagagtatac
2041 actcatcaga gtgatgtctg gtccttcggg gtgttaatgt gggagatctt cactttaggg
2101 ggctcgccct acccagggat tcccgtggag aacttttta agctgctgaa ggaaggacac
2161 agaatggata gccagccaa ctgcaccaac gaactgtaca tgatgatgag ggactgttgg
2221 catgcagtgc cctcccagag accaacgttc aagcagttgg tagaagactt ggatcgaatt
2281 ctcactctca caaccaatga ggaatacttg gacctcagcc aacctctcga acagtattca
2341 cctagttacc ctgacacaag aagttcttgt tcttcaggag atgattctgt tttttctcca
2401 gaccccatgc cttacgaacc atgccttcct cagtatccac acataaacgg cagtgttaaa
2461 acatga (SEQ ID NO: 20)
```

FIG. 3B tacgggcccgacgggctgccctacctcaaggttctcaaggccgccggtgttaacaccacg
gacaaagagattgaggttctctatattcggaatgtaacttttgaggacgctggggaatat
Acgtgcttggcgggtaattctattgggatatcctttcactctgcatggttgacagttctg
(SEQ ID NO: 1)

FIG. 4A

TACGGGCCCGACGGGCTGCCCTACCTCAAGGTTCTCAAGCACTCGGGGATAAATAGTTCCA
ATGCAGAAGTGCTGGCTCTGTTCAATGTGACCGAGGCGGATGCTGGGGAATATATATGTAA
GGTCTCCAATTATATAGGGCAGGCCAACCAGTCTGCCTGGCTCACTGTCCTG
(SEQ ID NO: 64)

FIG. 4B

IIIc-314:
    A  A  G  V  N  T  T  D  K  E  I      (314 – 324) (SEQ ID NO: 4)
    gcc gcc ggt gtt aac acc acg gac aaa gag att      (SEQ ID NO: 3)

FIG. 5A

IIIc-328    Y  I  R  N  V  T  F  E  D  A    (328 – 337) (SEQ ID NO: 6)
            tat att cgg aat gta act ttt gag gac gct      (SEQ ID NO: 5)

FIG. 5B

IIIc-350    I  S  F  H    (350 – 353) (SEQ ID NO: 8)
            ata tcc ttt cac    (SEQ ID NO: 7)

FIG. 5C

FGFR2IIIb (Loop3-C') fragment: amino acids 314–351

HSGINSSNAEVLALFNVTEADAGEYICKVSNYIGQANQ (SEQ ID NO: 56)

CACTCGGGGATAAATAGTTCCAATGCAGAAGTGCTGGCTCTGTTCAAT
GTGACCGAGGCGGATGCTGGGGAATATATATGTAAGGTCTCCAATTA
TATAGGGCAGGCCAACCAG (SEQ ID NO: 60)

FIG. 6A

FGFR2IIIb Epitope: amino acids 314-328

HSGINSSNAEVLALF (SEQ ID NO: 57)

CACTCGGGGATAAATAGTTCCAATGCAGAAGTGCTGGCTCTGTTC
(SEQ ID NO: 61)

FIG. 6B

FGFR2IIIb Epitope: amino acids 340-351

CKVSNYIGQANQ (SEQ ID NO: 58)

TGTAAGGTCTCCAATTATATAGGGCAGGCCAACCAG (SEQ ID
NO: 62)

FIG. 6C

AAT GGC AAA GAA TTC AAA CCT GAC CAC AGA ATT GGA GGC TAC AAG
 N   G   K   E   F   K   P   D   H   R   I   G   G   Y   K

//ACT GCT GGA GTT AAT ACC ACC GAC AAA GAG ATG GAG GTG CTT CAC (SEQ ID NO: 9)
// T   A   G   V   N   T   T   D   K   E   M   E   V   L   H  (SEQ ID NO: 10)

```
Cct ggc tcc tgg caa cag gac cac tgc cca cct aag ctt act gag // Gag cca
 P   G   S   W   Q   Q   D   H   C   P   P   K   L   T   E  //  E   P gtg ctg ata gca gtg caa ccc ctc ttt ggc cca cgg gca (SEQ ID NO: 11)
 V   L   I   A   V   Q   P   L   F   G   P   R   A  (SEQ ID NO: 12)
```

FIG. 9

```
Atg atg tgc att att gtg Atg att ctg acc tac aaa tat tta cag // gtt gtt
 M   M   C   I   I   V   M   I   L   T   Y   K   Y   L   Q  //  V   V Gag gag ata aat gga aac aat tat gtt tac ata gac cca   (SEQ ID NO: 13)
 E   E   I   N   G   N   N   Y   V   Y   I   D   P   (SEQ ID NO: 14)
```

FIG. 10

```
tgc gcg acc aca agc ctg aat ccg gat tat cgg gaa gag gac acg //gat gtg agg (SEQ ID NO: 15)
 C   A   T   T   S   L   N   P   D   Y   R   E   E   D   T //  D   V   R  (SEQ ID NO: 16)
```

FIG. 11

```
Ctcactgagatcaccactgatgtggaaaagattcaggaaataagg//aataatgaaact
  L  T  E  I  T  T  D  V  E  K  I  Q  E  I  R    N  N  E  T Tcctggactattttggccaacaatgtctcaaac (SEQ ID NO: 17)
  S  W  T  I  L  A  N  N  V  S  N  (SEQ ID NO: 18)
```

FIG. 12

| FGFR2 beta-ECD (262 aa) | R S | hIgG 1-Fc (227 aa) |

FIG. 13A

ATGGTCAGCTGGGGTCGTTTCATCTGCCTGGTCGTGGTCACCATGGCAACCTTGTCCCTGGCCCGGCCCT
CCTTCAGTTTAGTTGAGGATACCACATTAGAGCCAGAAGGAGCACCATACTGGACCAACACAGAAAAGAT
GGAAAAGCGGCTCCATGCTGTGCCTGCGGCCAACACTGTCAAGTTTCGCTGCCCAGCCGGGGGGAACCCA
ATGCCAACCATGCGGTGGCTGAAAAACGGGAAGGAGTTTAAGCAGGAGCATCGCATTGGAGGCTACAAGG
TACGAAACCAGCACTGGAGCCTCATTATGGAAAGTGTGGTCCCATCTGACAAGGGAAATTATACCTGTGT
GGTGGAGAATGAATACGGGTCCATCAATCACACGTACCACCTGGATGTTGTGGAGCGATCGCCTCACCGG
CCCATCCTCCAAGCCGGACTGCCGGCAAATGCCTCCACAGTGGTCGGAGGAGACGTAGAGTTTGTCTGCA
AGGTTTACAGTGATGCCCAGCCCCACATCCAGTGGATCAAGCACGTGGAAAAGAACGGCAGTAAATACGG
GCCCGACGGGCTGCCCTACCTCAAGGTTCTCAAGGCCGCCGGTGTTAACACCACGGACAAAGAGATTGAG
GTTCTCTATATTCGGAATGTAACTTTTGAGGACGCTGGGGAATATACGTGCTTGGCGGGTAATTCTATTG
GGATATCCTTTCACTCTGCATGGTTGACAGTTCTGCCAGCGCCTGGAAGAGAAAAGGAGATTACAGCTTC
CCCAGACTACCTGGAG<ins>AGATCT</ins>GACAAAACTCACACATGCCCACCGTGCCCAGCACCTGAACTCCTGGGG
GGACCGTCAGTCTTCCTCTTCCCCCCAAAACCCAAGGACACCCTCTACATCACCCGGGAACCTGAGGTCA
CATGCGTGGTGGTGGACGTGAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCACAGGTGTACACCCTGCCCCC
ATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACT
CCGACGGCTCCTTCTTCCTCTACAGCAAGCTCACCGTGGACAAGAGCAGGTGGCAGCAGGGGAACGTCTT
CTCATGCTCCGTGATGCATGAGGCTCTGAAGTTCCACTACACGCAGAAGAGCCTCTCCCTGTCTCCGGGT
AAATGA (SEQ ID NO: 54)

FIG. 13B

MVSWGRFICLVVVTMATLSLARPSFSLVEDTTLEPEGAPYWTNTEKMEKRLHAVPAANTVKFRCPAGGNP
MPTMRWLKNGKEFKQEHRIGGYKVRNQHWSLIMESVVPSDKGNYTCVVENEYGSINHTYHLDVVERSPHR
PILQAGLPANASTVVGGDVEFVCKVYSDAQPHIQWIKHVEKNGSKYGPDGLPYLKVLKAAGVNTTDKEIE
VLYIRNVTFEDAGEYTCLAGNSIGISFHSAWLTVLPAPGREKEITASPDYLERSDKTHTCPPCPAPELLG
GPSVFLFPPKPKDTLYITREPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALKFHYTQKSLSLSPG
K (SEQ ID NO: 55)

FIG. 13C

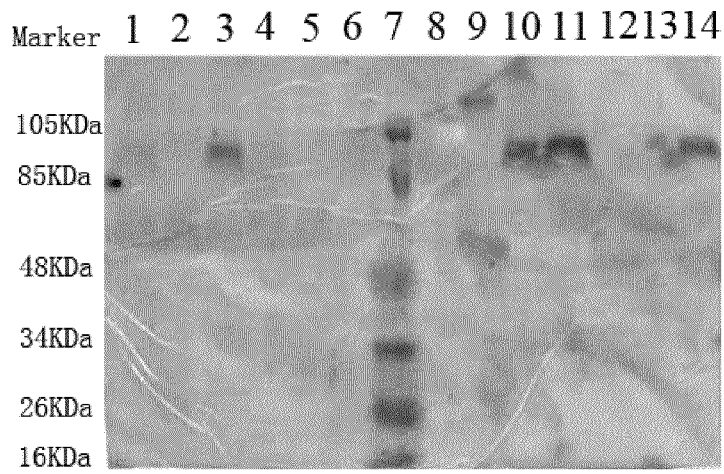

FIG. 13D

IIIc:
Human  LPYLKVLKAAGVNTTDKEIEVLYIRNVTFEDAGEYTCLAGNSIGISFH (amino acids 6-53 of SEQ ID NO: 2)
Rat    LPYLKVLKAAGVNTTDKEIEVLYIRNVTFEDAGEYTCLAGNSIGISFH (SEQ ID NO: 67)

IIIb:
Human  LPYLKVLKHSGINSSNAEVLALFNVTEADAGEYICKVSNYIGQANQ (amino acids 6-51 of SEQ ID NO: 65)
Rat    LPYLKVLKHSGINSSNAEVLALFNVTEMDAGEYICKVSNYIGQANQ (SEQ ID NO: 68)

FIG. 14

```
  1 mvswgrficl vvvtmatlsl arpsfslved ttlepeeppt kyqisqpevy vaapgeslev
 61 rcllkdaavi swtkdgvhlg pnnrtvlige ylqikgatpr dsglyactas rtvdsetwyf
121 mvnvtdaiss gddeddtdga edfvsensnn krapywtnte kmekrlhavp aantvkfrcp
181 aggnpmptmr wlkngkefkq ehriggykvr nqhwslimes vvpsdkgnyt cvveneygsi
241 nhtyhldvve rsphrpilqa glpanastvv ggdvefvckv ysdaqphiqw ikhvekngsk
301 ygpdglpylk vlkaagvntt dkeievlyir nvtfedagey tclagnsigi sfhsawltvl
361 papgrekeit aspdyleiai ycigvfliac mvvtvilcrm knttkkpdfs sqpavhkltk
421 riplrrqvtv saessssmns ntplvrittr lsstadtpml agvseyelpe dpkwefprdk
481 ltlgkplgeg cfgqvvmaea vgidkdkpke avtvavkmlk ddatekdlsd lvsememmkm
541 igkhkniinl lgactqdgpl yviveyaskg nlreylrarr ppgmeysydi nrvpeeqmtf
601 kdlvsctyql argmeylasq kcihrdlaar nvlvtennvm kiadfglard innidyykkt
661 tngrlpvkwm apealfdrvy thqsdvwsfg vlmweiftlg gspypgipve elfkllkegh
721 rmdkpanctn elymmmrdcw havpsqrptf kqlvedldri ltlttneeyl dlsqpleqys
781 psypdtrssc ssgddsvfsp dpmpyepclp qyphingsvk t (SEQ ID NO: 32)
```

FIG. 17A

```
MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQAPGREKEITASPDYLEIAIYCIGVFLIACMVVTVILCRMKNTTKKPDFSSQPAVHKLT
KRIPLRRQVTVSAESSSSMNSNTPLVRITTRLSSTADTPMLAGVSEYELPEDPKWEFPRD
KLTLGKPLGEGCFGQVVMAEAVGIDKDKPKEAVTVAVKMLKDDATEKDLSDLVSEMEMMK
MIGKHKNIINLLGACTQDGPLYVIVEYASKGNLREYLRARRPPGMEYSYDINRVPEEQMT
FKDLVSCTYQLARGMEYLASQKCIHRDLAARNVLVTENNVMKIADFGLARDINNIDYYKK
TTNGRLPVKWMAPEALFDRVYTHQSDVWSFGVLMWEIFTLGGSPYPGIPVEELFKLLKEG
HRMDKPANCTNELYMMMRDCWHAVPSQRPTFKQLVEDLDRILTLTTNEEYLDLSQPLEQY
SPSYPDTRSSCSSGDDSVFSPDPMPYEPCLPQYPHINGSVKT (SEQ ID NO: 21)
```

FIG. 17B

```
ATGGTCAGCTGGGGTCGTTTCATCTGCCTGGTCGTGGTCACCATGGCAACCTTGTCCCTGGCCCGGCCCTCCTTCA
GTTTAGTTGAGGATACCACATTAGAGCCAGAAGAGCCACCAACCAAATACCAAATCTCTCAACCAGAAGTGTACGT
GGCTGCGCCAGGGGAGTCGCTAGAGGTGCGCTGCCTGTTGAAAGATGCCGCCGTGATCAGTTGGACTAAGGATGGG
GTGCACTTGGGGCCCAACAATAGGACAGTGCTTATTGGGGAGTACTTGCAGATAAAGGGCGCCACGCCTAGAGACT
CCGGCCTCTATGCTTGTACTGCCAGTAGGACTGTAGACAGTGAAACTTGGTACTTCATGGTGAATGTCACAGATGC
CATCTCATCCGGAGATGATGAGGATGACACCGATGGTGCGGAAGATTTTGTCAGTGAGAACAGTAACAACAAGAGA
GCACCATACTGGACCAACACAGAAAAGATGGAAAAGCGGCTCCATGCTGTGCCTGCGGCCAACACTGTCAAGTTTC
GCTGCCCAGCCGGGGGGAACCCAATGCCAACCATGCGGTGGCTGAAAAACGGGAAGGAGTTTAAGCAGGAGCATCG
CATTGGAGGCTACAAGGTACGAAACCAGCACTGGAGCCTCATTATGGAAAGTGTGGTCCCATCTGACAAGGGAAAT
TATACCTGTGTAGTGGAGAATGAATACGGGTCCATCAATCACACGTACCACCTGGATGTTGTGGAGCGATCGCCTC
ACCGGCCCATCCTCCAAGCGGACTGCCGGCAAATGCCTCCACAGTGGTCGGAGGAGACGTAGAGTTTGTCTGCAA
GGTTTACAGTGATGCCCAGCCCCACATCCAGTGGATCAAGCACGTGGAAAAGAACGGCAGTAAATACGGGCCCGAC
GGGCTGCCCTACCTCAAGGTTCTCAAGCACTCGGGGATAAATAGTTCCAATGCAGAAGTGCTGGCTCTGTTCAATG
TGACCGAGGCGGATGCTGGGGAATATATATGTAAGGTCTCCAATTATATAGGGCAGGCCAACCAGTCTGCCTGGCT
CACTGTCCTGCCAAAACAGCAAGCGCCTGGAAGAGAAAGGAGATTACAGCTTCCCCAGACTACCTGGAGATAGCC
ATTTACTGCATAGGGGTCTTCTTAATCGCCTGTATGGTGGTAACAGTCATCCTGTGCCGAATGAAGAACACGACCA
AGAAGCCAGACTTCAGCAGCCAGCCGGCTGTGCACAAGCTGACCAAACGTATCCCCCTGCGGAGACAGGTAACAGT
TTCGGCTGAGTCCAGCTCCTCCATGAACTCCAACACCCCGCTGGTGAGGATAACAACACGCCTCTCTTCAACGGCA
GACACCCCCATGCTGGCAGGGGTCTCCGAGTATGAACTTCCAGAGGACCCAAAATGGGAGTTTCCAAGAGATAAGC
TGACACTGGGCAAGCCCCTGGGAGAAGGTTGCTTTGGGCAAGTGGTCATGGCGGAAGCAGTGGGAATTGACAAAGA
CAAGCCCAAGGAGGCGGTCACCGTGGCCGTGAAGATGTTGAAAGATGATGCCACAGAGAAAGACCTTTCTGATCTG
GTGTCAGAGATGGAGATGATGAAGATGATTGGGAAACACAAGAATATCATAAATCTTCTTGGAGCCTGCACACAGG
ATGGGCCTCTCTATGTCATAGTTGAGTATGCCTCTAAAGGCAACTCCGAGAATACCTCCGAGCCCGGAGGCCACC
CGGGATGGAGTACTCCTATGACATTAACCGTGTTCCTGAGGAGCAGATGACCTTCAAGGACTTGGTGTCATGCACC
TACCAGCTGGCCAGAGGCATGGAGTACTTGGCTTCCCAAAAATGTATTCATCGAGATTTAGCAGCCAGAAATGTTT
TGGTAACAGAAAACAATGTGATGAAAATAGCAGACTTTGGACTCGCCAGAGATATCAACAATATAGACTATTACAA
AAAGACCACCAATGGGCGGCTTCCAGTCAAGTGGATGGCTCCAGAAGCCCTGTTTGATAGAGTATACACTCATCAG
AGTGATGTCTGGTCCTTCGGGGTGTTAATGTGGGAGATCTTCACTTTAGGGGGCTCGCCCTACCCAGGGATTCCCG
TGGAGGAACTTTTTAAGCTGCTGAAGGAAGGACACAGAATGGATAAGCCAGCCAACTGCACCAACGAACTGTACAT
GATGATGAGGGACTGTTGGCATGCAGTGCCCTCCCAGAGACCAACGTTCAAGCAGTTGGTAGAAGACTTGGATCGA
ATTCCTCACTCTCACAACCAATGAGGAATACTTGGACCTCAGCCAACCTCTCGAACAGTATTCACCTAGTTACCCTG
ACACAAGAAGTTCTTGTTCTTCAGGAGATGATTCTGTTTTTTCTCCAGACCCCATGCCTTACGAACCATGCCTTCC
TCAGTATCCACACATAAACGGCAGTGTTAAAACATGA (SEQ ID NO: 63)
```

FIG. 17C

```
MVSWGRFICLVVVTMATLSLARPSFSLVEDTTLEPEDAISSGDDEDDTDGAEDFVSENSN
NKRAPYWTNTEKMEKRLHAVPAANTVKFRCPAGGNPMPTMRWLKNGKEFKQEHRIGGYKV
RNQHWSLIMESVVPSDKGNYTCVVENEYGSINHTYHLDVVERSPHRPILQAGLPANASTV
VGGDVEFVCKVYSDAQPHIQWIKHVEKNGSKYGPDGLPYLKVLKHSGINSSNAEVLALFN
VTEADAGEYICKVSNYIGQANQSAWLTVLPKQQAPGREKEITASPDYLEIAIYCIGVFLI
ACMVVTVILCRMKNTTKKPDFSSQPAVHKLTKRIPLRRQVSAESSSSMNSNTPLVRITTR
LSSTADTPMLAGVSEYELPEDPKWEFPRDKLTLGKPLGEGCFGQVVMAEAVGIDKDKPKE
AVTVAVKMLKDDATEKDLSDLVSEMEMMKMIGKHKNIINLLGACTQDGPLYVIVEYASKG
NLREYLRARRPPGMEYSYDINRVPEEQMTFKDLVSCTYQLARGMEYLASQKCIHRDLAAR
NVLVTENNVMKIADFGLARDINNIDYYKKTTNGRLPVKWMAPEALFDRVYTHQSDVWSFG
VLMWEIFTLGGSPYPGIPVEELFKLLKEGHRMDKPANCTNELYMMMRDCWHAVPSQRPTF
KQLVEDLDRIPPNPSLMSIFRK (SEQ ID NO: 22)
```

FIG. 17D

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQAPGREKEITASPDYLEIAIYCIGVFLIACMVVTVILCRMKNTTKKPDFSSQPAVHKLT
KRIPLRRQVTVSAESSSSMNSNTPLVRITTRLSSTADTPMLAGVSEYELPEDPKWEFPRD
KLTLGKPLGEGCFGQVVMAEAVGIDKDKPKEAVTVAVKMLKDDATEKDLSDLVSEMEMMK
MIGKHKNIINLLGACTQDGPLYVIVEYASKGNLREYLRARRPPGMEYSYDINRVPEEQMT
FKDLVSCTYQLARGMEYLASQKCIHRDLAARNVLVTENNVMKIADFGLARDINNIDYYKK
TTNGRLPVKWMAPEALFDRVYTHQSDVWSFGVLMWEIFTLGGSPYPGIPVEELFKLLKEG
HRMDKPANCTNELYMMMRDCWHAVPSQRPTFKQLVEDLDRILTLTTNERYKLLPCPDKHN
KRCKPEERGDLTEAGAAGSSRCVDSRKRVRQEKISTG (SEQ ID NO: 23)

FIG. 17E

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQAPGREKEITASPDYLEIAIYCIGVFLIACMVVTVILCRMKNTTKKPDFSSQPAVHKLT
KRIPLRRQVTVSAESSSSMNSNTPLVRITTRLSSTADTPMLAGVSEYELPEDPKWEFPRD
KLTLGKPLGEGCFGQVVMAEAVGIDKDKPKEAVTVAVKMLKDDATEKDLSDLVSEMEMMK
MIGKHKNIINLLGACTQDGPLYVIVEYASKGNLREYLRARRPPGMEYSYDINRVPEEQMT
FKDLVSCTYQLARGMEYLASQKCIHRDLAARNVLVTENNVMKIADFGLARDINNIDYYKK
TTNGRLPVKWMAPEALFDRVYTHQSDVWSFGVLMWEIFTLGGSPYPGIPVEELFKLLKEG
HRMDKPANCTNELYMMMRDCWHAVPSQRPTFKQLVEDLDRILTLTTNERILTLTTNENFQ
STSGREGTEIHALQCLRSEVTPAISCESPLADTGSKVPN (SEQ ID NO: 24)

FIG. 17F

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQAPGREKEITASPDYLEIAIYCIGVFLIACMVVTVILCRMKNTTKKPDFSSQPAVHKLT
KRIPLRRQVTVSAESSSSMNSNTPLVRITTRLSSTADTPMLAGVSEYELPEDPKWEFPRD
KLTLGKPLGEGCFGQVVMAEAVGIDKDKPKEAVTVAVKMLKDDATEKDLSDLVSEMEMMK
MIGKHKNIINLLGACTQDGPLYVIVEYASKGNLREYLRARRPPGMEYSYDINRVPEEQMT
FKDLVSCTYQLARGMEYLASQKCIHRDLAARNVLVTENNVMKIADFGLARDINNIDYYKK
TTNGRLPVKWMAPEALFDRVYTHQSDVWSFGVLMWEIFTLGGSPYPGIPVEELFKLLKEG
HRMDKPANCTNELYMMMRDCWHAVPSQRPTFKQLVEDLDRILTLTTNESFQSSLKSSSTG
IPGWPPGSEVFSEVAFRGILNYDIERPILCAGSKKIYDI (SEQ ID NO: 25)

FIG. 17G

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQAPGREKEITASPDYLEIAIYCIGVFLIACMVVTVILCRMKNTTKKPDFSSQPAVHKLT
KRIPLRRQVTVSAESSSSMNSNTPLVRITTRLSSTADTPMLAGVSEYELPEDPKWEFPRD
KLTLGKPLGEGCFGQVVMAEAVGIDKDKPKEAVTVAVKMLKDDATEKDLSDLVSEMEMMK
MIGKHKNIINLLGACTQDGPLYVIVEYASKGNLREYLRARRPPGMEYSYDINRVPEEQMT
FKDLVSCTYQLARGMEYLASQKCIHRDLAARNVLVTENNVMKIADFGLARDINNIDYYKK
TTNGRLPVKWMAPEALFDRVYTHQSDVWSFGVLMWEIFTLGGSPYPGIPVEELFKLLKEG
HRMDKPANCTNELYMMMRDCWHAVPSQRPTFKQLVEDLDRILTLTTNEGRLPAWASQEKE
NSQTSLFAISHVTLSSISKTRSSAKRDEKPGSSPHLALVRSQGLPQSVVP
(SEQ ID NO: 26)

FIG. 17H

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQAPGREKEITASPDYLEIAIYCIGVFLIACMVVTVILCRMKNTTKKPDFSSQPAVHKLT
KRIPLRRQVTVSAESSSSMNSNTPLVRITTRLSSTADTPMLAGVSEYELPEDPKWEFPRD
KLTLGKPLGEGCFGQVVMAEAVGIDKDKPKEAVTVAVKMLKDDATEKDLSDLVSEMEMMK
MIGKHKNIINLLGACTQDGPLYVIVEYASKGNLREYLRARRPPGMEYSYDINRVPEEQMT
FKDLVSCTYQLARGMEYLASQKCIHRDLAARNVLVTENNVMKIADFGLARDINNIDYYKK
TTNGRLPVKWMAPEALFDRVYTHQSDVWSFGVLMWEIFTLGGSPYPGIPVEELFKLLKEG
HRMDKPANCTNELYMMMRDCWHAVPSQRPTFKQLVEDLDRILTLTTNEPLS
(SEQ ID NO: 27)

FIG. 17I

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQAPGREKEITASPDYLEIAIYCIGVFLIACMVVTVILCRMKNTTKKPDFSSQPAVHKLT
KRIPLRRQVTVSAESSSSMNSNTPLVRITTRLSSTADTPMLAGVSEYELPEDPKWEFPRD
KLTLGKPLGEGCFGQVVMAEAVGIDKDKPKEAVTVAVKMLKDDATEKDLSDLVSEMEMMK
MIGKHKNIINLLGACTQDGPLYVIVEYASKGNLREYLRARRPPGMEYSYDINRVPEEQMT
FKDLVSCTYQLARGMEYLASQKCIHRDLAARNVLVTENNVMKIADFGLARDINNIDYYKK
TTNGRLPVKWMAPEALFDRVYTHQSDVWSFGVLMWEIFTLGGSPYPGIPVEELFKLLKEG
HRMDKPANCTNELYMMMRDCWHAVPSQRPTFKQLVEDLDRILTLTTNE
(SEQ ID NO: 28)

FIG. 17J

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVGSQGL (SEQ ID NO: 29)

FIG. 17K

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKVSAESSSSMNSNTPLVRITTRLSSTADTPMLAGVSEYELPEDPKWEF
PRDKLTLGKPLGEGCFGQVVMAEAVGIDKDKPKEAVTVAVKMLKDDATEKDLSDLVSEME
MMKMIGKHKNIINLLGACTQDGPLYVIVEYASKGNLREYLRARRPPGMEYSYDINRVPEE
QMTFKDLVSCTYQLARGMEYLASQKCIHRDLAARNVLVTENNVMKIADFGLARDINNIDY
YKKTTNGRLPVKWMAPEALFDRVYTHQSDVWSFGVLMWEIFTLGGSPYPGIPVEELFKLL
KEGHRMDKPANCTNELYMMMRDCWHAVPSQRPTFKQLVEDLDRILTLTTNEEYLDLSQPL
EQYSPSYPDTRSSCSSGDDSVFSPDPMPYEPCLPQYPHINGSVKT (SEQ ID NO: 30)

FIG. 17L

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQAPGREKEITASPDYLEIAIYCIGVFLIACMVVTVILCRMKNTTKKPDFSSQPAVHKLT
KRIPLRRQVTVSAESSSSMNSNTPLVRITTRLSSTADTPMLAGVSEYELPEDPKWEFPRD
KLTLGKPLGEGCFGQVVMAEAVGIDKDKPKEAVTVAVKMLKDDATEKDLSDLVSEMEMMK
MIGKHKNIINLLGACTQDGPLYVIVEYASKGNLREYLRARRPPGMEYSYDINRVPEEQMT
FKDLVSCTYQLARGMEYLASQKCIHRDLAARNVLVTENNVMKIADFGLARDINNIDYYKK
TTNGRLPVKWMAPEALFDRVYTHQSDVWSFGVLMWEIFTLGGSPYPGIPVEELFKLLKEG
HRMDKPANCTNELYMMMRDCWHAVPSQRPTFKQLVEDLDRILTLTTNEI
(SEQ ID NO: 31)

FIG. 17M

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQAPGREKEITASPDYLEIAIYCIGVFLIACMVVTVILCRMKNTTKKPDFSSQPAVHKLT
KRIPLRRQVSAESSSSMNSNTPLVRITTRLSSTADTPMLAGVSEYELPEDPKWEFPRDKL
TLGKPLGEGCFGQVVMAEAVGIDKDKPKEAVTVAVKMLKDDATEKDLSDLVSEMEMMKMI
GKHKNIINLLGACTQDGPLYVIVEYASKGNLREYLRARRPPGMEYSYDINRVPEEQMTFK
DLVSCTYQLARGMEYLASQKCIHRDLAARNVLVTENNVMKIADFGLARDINNIDYYKKTT
NGRLPVKWMAPEALFDRVYTHQSDVWSFGVLMWEIFTLGGSPYPGIPVEELFKLLKEGHR
MDKPANCTNELYMMMRDCWHAVPSQRPTFKQLVEDLDRILTLTTNEEYLDLSQPLEQYSP
SYPDTRSSCSSGDDSVFSPDPMPYEPCLPQYPHINGSVKT (SEQ ID NO: 52)

FIG. 17N

MVSWGRFICLVVVTMATLSLARPSFSLVEDTTLEPEEPPTKYQISQPEVYVAAPGESLEV
RCLLKDAAVISWTKDGVHLGPNNRTVLIGEYLQIKGATPRDSGLYACTASRTVDSETWYF
MVNVTDAISSGDDEDDTDGAEDFVSENSNNKRAPYWTNTEKMEKRLHAVPAANTVKFRCP
AGGNPMPTMRWLKNGKEFKQEHRIGGYKVRNQHWSLIMESVVPSDKGNYTCVVENEYGSI
NHTYHLDVVERSPHRPILQAGLPANASTVVGGDVEFVCKVYSDAQPHIQWIKHVEKNGSK
YGPDGLPYLKVLKHSGINSSNAEVLALFNVTEADAGEYICKVSNYIGQANQSAWLTVLPK
QQGRRC (SEQ ID NO: 53)

FIG. 17O

```
  1 mwswkcllfw avlvtatlct arpsptlpeq aqpwgapvev esflvhpgdl lqlrcrlrdd
 61 vqsinwlrdg vqlaesnrtr itgeevevqd svpadsglya cvtsspsgsd ttyfsvnvsd
121 alpssedddd dddssseeke tdntkpnrmp vapywtspek mekklhavpa aktvkfkcps
181 sgtpnptlrw lkngkefkpd hriggykvry atwsiimdsv vpsdkgnytc iveneygsin
241 htyqldvver sphrpilqag lpanktvalg snvefmckvy sdpqphiqwl khievngski
301 gpdnlpyvqi lktagvnttd kemevlhlrn vsfedageyt clagnsigls hhsawltvle
361 aleerpavmt splyleiiiy ctgafliscm vgsvivykmk sgtkksdfhs qmavhklaks
421 iplrrqvtvs adssasmnsg vllvrpsrls ssgtpmlagv seyelpedpr welprdrlvl
481 gkplgegcfg qvvlaeaigl dkdkpnrvtk vavkmlksda tekdlsdlis ememmkmigk
541 hkniinllga ctqdgplyvi veyaskgnlr eylqarrppg leycynpshn peeqlsskdl
601 vscayqvarg meylaskkci hrdlaarnvl vtednvmkia dfglardihh idyykkttng
661 rlpvkwmape alfdriythq sdvwsfgvll weiftlggsp ypgvpveelf kllkeghrmd
721 kpsnctnely mmmrdcwhav psqrptfkql vedldrival tsnqeyldls mpldqyspsf
781 pdtrsstcss gedsvfshep lpeepclprh paqlangglk rr (SEQ ID NO: 33)
```

FIG. 18A

MWSWKCLLFWAVLVTATLCTARPSPTLPEQAQPWGAPVEVESFLVHPGDLLQLRCRLRDD
VQSINWLRDGVQLAESNRTRITGEEVEVQDSVPADSGLYACVTSSPSGSDTTYFSVNVSD
ALPSSEDDDDDDSSSEEKETDNTKPNRMPVAPYWTSPEKMEKKLHAVPAAKTVKFKCPS
SGTPNPTLRWLKNGKEFKPDHRIGGYKVRYATWSIIMDSVVPSDKGNYTCIVENEYGSIN
HTYQLDVVERSPHRPILQAGLPANKTVALGSNVEFMCKVYSDPQPHIQWLKHIEVNGSKI
GPDNLPYVQILKTAGVNTTDKEMEVLHLRNVSFEDAGEYTCLAGNSIGLSHHSAWLTVLE
ALEERPAVMTSPLYLEIIYCTGAFLISCMVGSVIVYKMKSGTKKSDFHSQMAVHKLAKS
IPLRRQVTVSADSSASMNSGVLLVRPSRLSSSGTPMLAGVSEYELPEDPRWELPRDRLVL
GKPLGEGCFGQVVLAEAIGLDKDKPNRVTKVAVKMLKSDATEKDLSDLISEMEMMKMIGK
HKNIINLLGACTQDGPLYVIVEYASKGNLREYLQARRPPGLEYCYNPSHNPEEQLSSKDL
VSCAYQVARGMEYLASKKCIHRDLAARNVLVTEDNVMKIADFGLARDIHHIDYYKKTTNG
RLPVKWMAPEALFDRIYTHQSDVWSFGVLLWEIFTLGGSPYPGVPVEELFKLLKEGHRMD
KPSNCTNELYMMMRDCWHAVPSQRPTFKQLVEDLDRIVALTSNQEYLDLSMPLDQYSPSF
PDTRSSTCSSGEDSVFSHEPLPEEPCLPRHPAQLANGGLKRR (SEQ ID NO: 38)

FIG. 18B

MWSWKCLLFWAVLVTATLCTARPSPTLPEQAQPWGAPVEVESFLVHPGDLLQLRCRLRDD
VQSINWLRDGVQLAESNRTRITGEEVEVQDSVPADSGLYACVTSSPSGSDTTYFSVNVSD
ALPSSEDDDDDDSSSEEKETDNTKPNRMPVAPYWTSPEKMEKKLHAVPAAKTVKFKCPS
SGTPNPTLRWLKNGKEFKPDHRIGGYKVRYATWSIIMDSVVPSDKGNYTCIVENEYGSIN
HTYQLDVVERSPHRPILQAGLPANKTVALGSNVEFMCKVYSDPQPHIQWLKHIEVNGSKI
GPDNLPYVQILKTAGVNTTDKEMEVLHLRNVSFEDAGEYTCLAGNSIGLSHHSAWLTVLE
ALEERPAVMTSPLYLEIIYCTGAFLISCMVGSVIVYKMKSGTKKSDFHSQMAVHKLAKS
IPLRRQVSADSSASMNSGVLLVRPSRLSSSGTPMLAGVSEYELPEDPRWELPRDRLVLGK
PLGEGCFGQVVLAEAIGLDKDKPNRVTKVAVKMLKSDATEKDLSDLISEMEMMKMIGKHK
NIINLLGACTQDGPLYVIVEYASKGNLREYLQARRPPGLEYCYNPSHNPEEQLSSKDLVS
CAYQVARGMEYLASKKCIHRDLAARNVLVTEDNVMKIADFGLARDIHHIDYYKKTTNGRL
PVKWMAPEALFDRIYTHQSDVWSFGVLLWEIFTLGGSPYPGVPVEELFKLLKEGHRMDKP
SNCTNELYMMMRDCWHAVPSQRPTFKQLVEDLDRIVALTSNQEYLDLSMPLDQYSPSFPD
TRSSTCSSGEDSVFSHEPLPEEPCLPRHPAQLANGGLKRR (SEQ ID NO: 39)

FIG. 18C

```
MWSWKCLLFWAVLVTATLCTARPSPTLPEQAQPWGAPVEVESFLVHPGDLLQLRCRLRDD
VQSINWLRDGVQLAESNRTRITGEEVEVQDSVPADSGLYACVTSSPSGSDTTYFSVNVSD
ALPSSEDDDDDDDSSSEEKETDNTKPNPVAPYWTSPEKMEKKLHAVPAAKTVKFKCPSSG
TPNPTLRWLKNGKEFKPDHRIGGYKVRYATWSIIMDSVVPSDKGNYTCIVENEYGSINHT
YQLDVVERSPHRPILQAGLPANKTVALGSNVEFMCKVYSDPQPHIQWLKHIEVNGSKIGP
DNLPYVQILKTAGVNTTDKEMEVLHLRNVSFEDAGEYTCLAGNSIGLSHHSAWLTVLEAL
EERPAVMTSPLYLEIIIYCTGAFLISCMVGSVIVYKMKSGTKKSDFHSQMAVHKLAKSIP
LRRQVTVSADSSASMNSGVLLVRPSRLSSSGTPMLAGVSEYELPEDPRWELPRDRLVLGK
PLGEGCFGQVVLAEAIGLDKDKPNRVTKVAVKMLKSDATEKDLSDLISEMEMMKMIGKHK
NIINLLGACTQDGPLYVIVEYASKGNLREYLQARRPPGLEYCYNPSHNPEEQLSSKDLVS
CAYQVARGMEYLASKKCIHRDLAARNVLTEDNVMKIADFGLARDIHHIDYYKKTTNGRL
PVKWMAPEALFDRIYTHQSDVWSFGVLLWEIFTLGGSPYPGVPVEELFKLLKEGHRMDKP
SNCTNELYMMMRDCWHAVPSQRPTFKQLVEDLDRIVALTSNQEYLDLSMPLDQYSPSFPD
TRSSTCSSGEDSVFSHEPLPEEPCLPRHPAQLANGGLKRR (SEQ ID NO: 40)
```

FIG. 18D

```
MWSWKCLLFWAVLVTATLCTARPSPTLPEQAQPWGAPVEVESFLVHPGDLLQLRCRLRDD
VQSINWLRDGVQLAESNRTRITGEEVEVQDSVPADSGLYACVTSSPSGSDTTYFSVNVSA
CPDLQEAKWCSASFHSITPLPFGLGTRLSD (SEQ ID NO: 41)
```

FIG. 18E

```
MWSWKCLLFWAVLVTATLCTARPSPTLPEQDALPSSEDDDDDDDSSSEEKETDNTKPNRM
PVAPYWTSPEKMEKKLHAVPAAKTVKFKCPSSGTPNPTLRWLKNGKEFKPDHRIGGYKVR
YATWSIIMDSVVPSDKGNYTCIVENEYGSINHTYQLDVVERSPHRPILQAGLPANKTVAL
GSNVEFMCKVYSDPQPHIQWLKHIEVNGSKIGPDNLPYVQILKVIMAPVFVGQSTGKETT
VSGAQVPVGRLSCPRMGSFLTLQAHTLHLSRDLATSPRTSNRGHKVEVSWEQRAAGMGGA
GL (SEQ ID NO: 42)
```

FIG. 18F

```
MWSWKCLLFWAVLVTATLCTARPSPTLPEQACPDLQEAKSCSASFHSITPLPFGLGTRLS
D (SEQ ID NO: 43)
```

FIG. 18G

```
MWSWKCLLFWAVLVTATLCTARPSPTLPEQDALPSSEDDDDDDDSSSEEKETDNTKPNPV
APYWTSPEKMEKKLHAVPAAKTVKFKCPSSGTPNPTLRWLKNGKEFKPDHRIGGYKVRYA
TWSIIMDSVVPSDKGNYTCIVENEYGSINHTYQLDVVERSPHRPILQAGLPANKTVALGS
NVEFMCKVYSDPQPHIQWLKHIEVNGSKIGPDNLPYVQILKVIMAPVFVGQSTGKETTVS
GAQVPVGRLSCPRMGSFLTLQAHTLHLSRDLATSPRTSNRGHKVEVSWEQRAAGMGGAGL
(SEQ ID NO: 44)
```

FIG. 18H

```
   1 mellpplpqs flllllllpak paagedwqcp rtpyaasrdf dvkyvvpsfs agglvqamvt
  61 yegdrnesav fvairnrlhv lgpdlksvqs latgpagdpg cqtcaacgpg phgppgdtdt
 121 kvlvldpalp alvscgsslq grcflhdlep qgtavhlaap aclfsahhnr pddcpdcvas
 181 plgtrvtvve qgqasyfyva ssldaavags fsprsvsirr lkadasgfap gfvalsvlpk
 241 hlvsysieyv hsfhtgafvy fltvqpasvt ddpsalhtrl arlsatepel gdyrelvldc
 301 rfapkrrrrg apeggqpypv lqvahsapvg aqlatelsia egqevlfgvf vtgkdggpgv
 361 gpnsvvcafp idlldtlide qverccespv hpglrrgldf fqspsfcpnp pglealspnt
 421 scrhfpllvs ssfsrvdlfn gllgpvqvta lyvtrldnvt vahmgtmdgr ilqvelvrsl
 481 nyllyvsnfs lgdsgqpvqr dvsrlgdhll fasgdqvfqv pirgpgcrhf ltcgrclraw
 541 hfmgcgwcgn mcgqqkecpg swqqdhcppk ltefhphsgp lrgstrltlc gsnfylhpsg
 601 lvpegthqvt vgqspcrplp kdssklrpvp rkdfveefec eleplgtqav gptnvsltvt
 661 nmppgkhfrv dgtsvlrgfs fmepvliavq plfgpraggt cltlegqsls vgtsravlvn
 721 gtecllarvs egqllcatpp gatvasvpls lqvggaqvpg swtfqyredp vvlsispncg
 781 yinshiticg qhltsawhlv lsfhdglrav esrcerqlpe qqlcrlpeyv vrdpqgwvag
 841 nlsargdgaa gftlpgfrfl ppphppsanl vplkpeehai kfeyiglgav adcvginvtv
 901 ggescqhefr gdmvvcplpp slqlgqdgap lqvcvdgech ilgrvvrpgp dgvpqstllg
 961 illplllva alatalvfsy wwrrkqlvlp pnlndlasld qtagatplpi lysgsdyrsg
1021 lalpaidgld sttcvhgasf sdsedescvp llrkesiqlr dldsallaev kdvlipherv
1081 vthsdrvigk ghfgvvyhge yidqaqnriq caikslsrit emqqveaflr egllmrglnh
1141 pnvlaligim lppeglphvl lpymchgdll qfirspqrnp tvkdlisfgl qvargmeyla
1201 eqkfvhrdla arncmldesf tvkvadfgla rdildreyys vqqhrharlp vkwmaleslq
1261 tyrfttksdv wsfgvllwel ltrgappyrh idpfdlthfl aqgrrlpqpe ycpdslyqvm
1321 qqcweadpav rptfrvlvge veqivsallg dhyvqlpaty mnlgpstshe mnvrpeqpqf
1381 spmpgnvrrp rplsepprpt (SEQ ID NO: 34)
```

FIG. 19A

```
MELLPPLPQSFLLLLLLPAKPAAGEDWQCPRTPYAASRDFDVKYVVPSFSAGGLVQAMVT
YEGDRNESAVFVAIRNRLHVLGPDLKSVQSLATGPAGDPGCQTCAACGPGPHGPPGDTDT
KVLVLDPALPALVSCGSSLQGRCFLHDLEPQGTAVHLAAPACLFSAHHNRPDDCPDCVAS
PLGTRVTVVEQGQASYFYVASSLDAAVAGSFSPRSVSIRRLKADASGFAPGFVALSVLPK
HLVSYSIEYVHSFHTGAFVYFLTVQPASVTDDPSALHTRLARLSATEPELGDYRELVLDC
RFAPKRRRRGAPEGGQPYPVLQVAHSAPVGAQLATELSIAEGQEVLFGVFVTGKDGGPGV
GPNSVVCAFPIDLLDTLIDEGVERCCESPVHPGLRRGLDFFQSPSFCPNPPGLEALSPNT
SCRHFPLLVSSSFSRVDLFNGLLGPVQVTALYVTRLDNVTVAHMGTMDGRILQVELVRSL
NYLLYVSNFSLGDSGQPVQRDVSRLGDHLLFASGDQVFQVPIRGPGCRHFLTCGRCLRAW
HFMGCGWCGNMCGQQKECPGSWQQDHCPPKLTEFHPHSGPLRGSTRLTLCGSNFYLHPSG
LVPEGTHQVTVGQSPCRPLPKDSSKLRPVPRKDFVEEFECELEPLGTQAVGPTNVSLTVT
NMPPGKHFRVDGTSVLRGFSFMEPVLIAVQPLFGPRAGGTCLTLEGQSLSVGTSRAVLVN
GTECLLARVSEGQLLCATPPGATVASVPLSLQVGGAQVPGSWTFQYREDPVVLSISPNCG
YINSHITICGQHLTSAWHLVLSFHDGLRAVESRCERQLPEQQLCRLPEYVVRDPQGWVAG
NLSARGDGAAGFTLPGFRFLPPPHPPSANLVPLKPEEHAIKFEYIGLGAVADCVGINVTV
GGESCQHEFRGDMVVCPLPPSLQLGQDGAPLQVCVDGECHILGRVVRPGPDGVPQSTLLG
ILLPLLLLVAALATALVFSYWWRRKQLVLPPNLNDLASLDQTAGATPLPILYSGSDYRSG
LALPAIDGLDSTTCVHGASFSDSEDESCVPLLRKESIQLRDLDSALLAEVKDVLIPHERV
VTHSDRVIGKGHFGVVYHGEYIDQAQNRIQCAIKSLSRITEMQQVEAFLREGLLMRGLNH
PNVLALIGIMLPPEGLPHVLLPYMCHGDLLQFIRSPQRNPTVKDLISFGLQVARGMEYLA
EQKFVHRDLAARNCMLDESFTVKVADFGLARDILDREYYSVQQHRHARLPVKWMALESLQ
TYRFTTKSDVWSFGVLLWELLTRGAPPYRHIDPFDLTHFLAQGRRLPQPEYCPDSLYQVM
QQCWEADPAVRPTFRVLVGEVEQIVSALLGDHYVQLPATYMNLGPSTSHEMNVRPEQPQF
SPMPGNVRRPRPLSEPPRPT (SEQ ID NO: 45)
```

FIG. 19B

```
  1 mrgargawdf lcvlllllrv qtgssqpsvs pgepsppsih pgksdlivrv gdeirllctd
 61 pgfvkwtfei ldetnenkqn ewitekaeat ntgkytctnk hglsnsiyvf vrdpaklflv
121 drslygkedn dtlvrcpltd pevtnyslkg cqgkplpkdl rfipdpkagi miksvkrayh
181 rlclhcsvdq egksvlsekf ilkvrpafka vpvvsvskas yllregeeft vtctikdvss
241 svystwkren sqtklqekyn swhhgdfnye rqatltissa rvndsgvfmc yanntfgsan
301 vtttlevvdk gfinifpmin ttvfvndgen vdliveyeaf pkpehqqwiy mnrtftdkwe
361 dypksenesn iryvselhlt rlkgteggty tflvsnsdvn aaiafnvyvn tkpeiltydr
421 lvngmlqcva agfpeptidw yfcpgteqrc sasvlpvdvq tlnssgppfg klvvqssids
481 safkhngtve ckayndvgkt sayfnfafkg nnkeqihpht lftplligfv ivagmmciiv
541 miltykylqk pmyevqwkvv eeingnnyvy idptqlpydh kwefprnrls fgktlgagaf
601 gkvveatayg liksdaamtv avkmlkpsah lterealmse lkvlsylgnh mnivnllgac
661 tiggptlvit eyccygdlln flrrkrdsfi cskqedhaea alyknllhsk esscsdstne
721 ymdmkpgvsy vvptkadkrr svrigsyier dvtpaimedd elaldledll sfsyqvakgm
781 aflaskncih rdlaarnill thgritkicd fglardiknd snyvvkgnar lpvkwmapes
841 ifncvytfes dvwsygiflw elfslgsspy pgmpvdskfy kmikegfrml spehapaemy
901 dimktcwdad plkrptfkqi vqliekqise stnhiysnla ncspnrqkpv vdhsvrinsv
961 gstasssqpl lvhddv (SEQ ID NO: 35)
```

FIG. 20A

```
  1 MRGARGAWDF LCVLLLLLRV QTGSSQPSVS PGEPSPPSIH PGKSDLIVRV GDEIRLLCTD    60
 61 PGFVKWTFEI LDETNENKQN EWITEKAEAT NTGKYTCTNK HGLSNSIYVF VRDPAKLFLV   120
121 DRSLYGKEDN DTLVRCPLTD PEVTNYSLKG CQGKPLPKDL RFIPDPKAGI MIKSVKRAYH   180
181 RLCLHCSVDQ EGKSVLSEKF ILKVRPAFKA VPVVSVSKAS YLLREGEEFT VTCTIKDVSS   240
241 SVYSTWKREN SQTKLQEKYN SWHHGDFNYE RQATLTISSA RVNDSGVFMC YANNTFGSAN   300
301 VTTTLEVVDK GFINIFPMIN TTVFVNDGEN VDLIVEYEAF PKPEHQQWIY MNRTFTDKWE   360
361 DYPKSENESN IRYVSELHLT RLKGTEGGTY TFLVSNSDVN AAIAFNVYVN TKPEILTYDR   420
421 LVNGMLQCVA AGFPEPTIDW YFCPGTEQRC SASVLPVDVQ TLNSSGPPFG KLVVQSSIDS   480
481 SAFKHNGTVE CKAYNDVGKT SAYFNFAFKG NNKEQIHPHT LFTPLLIGFV IVAGMMCIIV   540
541 MILTYKYLQV VEEINGNNYV YIDPTQLPYD HKWEFPRNRL SFGKTLGAGA FGKVVEATAY   600
601 GLIKSDAAMT VAVKMLKPSA HLTEREALMS ELKVLSYLGN HMNIVNLLGA CTIGGPTLVI   660
661 TEYCCYGDLL NFLRRKRDSF ICSKQEDHAE AALYKNLLHS KESSCSDSTN EYMDMKPGVS   720
721 YVVPTKADKR RSVRIGSYIE RDVTPAIMED DELALDLEDL LSFSYQVAKG MAFLASKNCI   780
781 HRDLAARNIL LTHGRITKIC DFGLARDIKN DSNYVVKGNA RLPVKWMAPE SIFNCVYTFE   840
841 SDVWSYGIFL WELFSLGSSP YPGMPVDSKF YKMIKEGFRM LSPEHAPAEM YDIMKTCWDA   900
901 DPLKRPTFKQ IVQLIEKQIS ESTNHIYSNL ANCSPNRQKP VVDHSVRINS VGSTASSSQP   960
961 LLVHDDV (SEQ ID NO: 46)
```

FIG. 20B

```
  1 mrgargawdf lcvlllllrv qtgssqpsvs pgepsppsih pgksdlivrv gdeirllctd
 61 pgfvkwtfei ldetnenkqn ewitekaeat ntgkytctnk hglsnsiyvf vrdpaklflv
121 drslygkedn dtlvrcpltd pevtnyslkg cqgkplpkdl rfipdpkagi miksvkrayh
181 rlclhcsvdq egksvlsekf ilkvrpafka vpvvsvskas yllregeeft vtctikdvss
241 svystwkren sqtklqekyn swhhgdfnye rqatltissa rvndsgvfmc yanntfgsan
301 vtttlevvdk gfinifpmin ttvfvndgen vdliveyeaf pkpehqqwiy mnrtftdkwe
361 dypksenesn iryvselhlt rlkgteggty tflvsnsdvn aaiafnvyvn tkpeiltydr
421 lvngmlqcva agfpeptidw yfcpgteqrc sasvlpvdvq tlnssgppfg klvvqssids
481 safkhngtve ckayndvgkt sayfnfafkg nnkeqihpht lftplligfv ivagmmciiv
541 miltykylqk pmyevqwkvv eeingnnyvy idptqlpydh kwefprnrls fgktlgagaf
601 gkvveatayg liksdaamtv avkmlkpsah lterealmse lkvlsylgnh mnivnllgac
661 tiggptlvit eyccygdlln flrrkrdsfi cskqedhaea alyknllhsk esscsdstne
721 ymdmkpgvsy vvptkadkrr svrigsyier dvtpaimedd elaldledll sfsyqvakgm
781 aflaskncih rdlaarnill thgritkicd fglardiknd snyvvkgnar lpvkwmapes
841 ifncvytfes dvwsygiflw elfslgsspy pgmpvdskfy kmikegfrml spehapaemy
901 dimktcwdad plkrptfkqi vqliekqise stnhiysnla ncspnrqkpv vdhsvrinsv
961 gstasssqpl lvhddv (SEQ ID NO: 47)
```

FIG. 20C

```
  1 mrtlacllll gcgylahvla eeaeiprevi erlarsqihs irdlqrllei dsvgsedsld
 61 tslrahgvha tkhvpekrpl pirrkrsiee avpavcktrt viyeiprsqv dptsanfliw
121 ppcvevkrct gccntssvkc qpsrvhhrsv kvakveyvrk kpklkevqvr leehlecaca
181 ttslnpdyre edtgrpresg kkrkrkrlkp t (SEQ ID NO: 36)
```

FIG. 21A

MRTLACLLLLGCGYLAHVLAEEAEIPREVIERLARSQIHSIRDLQRLLEIDSVGSEDSLD
TSLRAHGVHATKHVPEKRPLPIRRKRSIEEAVPAVCKTRTVIYEIPRSQVDPTSANFLIW
PPCVEVKRCTGCCNTSSVKCQPSRVHHRSVKVAKVEYVRKKPKLKEVQVRLEEHLECACA
TTSLNPDYREEDTDVR (SEQ ID NO: 48)

FIG. 21B

MRTLACLLLLGCGYLAHVLAEEAEIPREVIERLARSQIHSIRDLQRLLEIDSVGSEDSLD
TSLRAHGVHATKHVPEKRPLPIRRKRSIEEAVPAVCKTRTVIYEIPRSQVDPTSANFLIW
PPCVEVKRCTGCCNTSSVKCQPSRVHHRSVKVAKVEYVRKKPKLKEVQVRLEEHLECACA
TTSLNPDYREEDTGRPRESGKKRKRKRLKPT (SEQ ID NO: 49)

FIG. 21C

```
   1  mgtshpaflv  lgclltglsl  ilcqlslpsi  lpnenekvvq  lnssfslrcf  gesevswqyp
  61  mseeessdve  irneennsgl  fvtvlevssa  saahtglytc  yynhtqteen  elegrhiyiy
 121  vpdpdvafvp  lgmtdylviv  edddsaiipc  rttdpetpvt  lhnsegvvpa  sydsrqgfng
 181  tftvgpyice  atvkgkkfqt  ipfnvyalka  tseldlemea  lktvyksget  ivvtcavfnn
 241  evvdlqwtyp  gevkgkgitm  leeikvpsik  lvytltvpea  tvkdsgdyec  aarqatrevk
 301  emkkvtisvh  ekgfieikpt  fsqleavnlh  evkhfvvevr  ayppppriswl knnltlienl
 361  teittdveki  qeiryrsklk  lirakeedsg  hytivaqned  avksytfell  tqvpssildl
 421  vddhhgstgg  qtvrctaegt  plpdiewmic  kdikkcnnet  swtilannvs  niiteihsrd
 481  rstvegrvtf  akveetiavr  claknllgae  nrelklvapt  lrseltvaaa  vlvllvivii
 541  slivlvviwk  qkpryeirwr  viesispdgh  eyiyvdpmql  pydsrwefpr  dglvlgrvlg
 601  sgafgkvveg  tayglsrsqp  vmkvavkmlk  ptarssekqa  lmselkimth  lgphlnivnl
 661  lgactksgpi  yiiteycfyg  dlvnylhknr  dsflshhpek  pkkeldifgl  npadestrsy
 721  vilsfenngd  ymdmkqadtt  qyvpmlerke  vskysdiqrs  lydrpasykk  ksmldsevkn
 781  llsddnsegl  tlldllsfty  qvargmefla  skncvhrdla  arnvllaqgk  ivkicdfgla
 841  rdimhdsnyv  skgstflpvk  wmapesifdn  lyttlsdvws  ygillweifs  lggtpypgmm
 901  vdstfynkik  sgyrmakpdh  atsevyeimv  kcwnsepekr  psfyhlseiv  enllpgqykk
 961  syekihldfl  ksdhpavarm  rvdsdnayig  vtykneedkl  kdweggldeq  rlsadsgyii
1021  plpdidpvpe  eedlgkrnrh  ssqtseesai  etgsssstfi  kredetiedi  dmmddigids
1081  sdlvedsfl  (SEQ ID NO: 37)
```

FIG. 22A

MGTSHPAFLVLGCLLTGLSLILCQLSLPSILPNENEKVVQLNSSFSLRCFGESEVSWQYP
MSEEESSDVEIRNEENNSGLFVTVLEVSSASAAHTGLYTCYYNHTQTEENELEGRHIYIY
VPDPDVAFVPLGMTDYLVIVEDDDSAIIPCRTTDPETPVTLHNSEGVVPASYDSRQGFNG
TFTVGPYICEATVKGKKFQTIPFNVYALKATSELDLEMEALKTVYKSGETIVVTCAVFNN
EVVDLQWTYPGEVKGKGITMLEEIKVPSIKLVYTLTVPEATVKDSGDYECAARQATREVK
EMKKVTISVHEKGFIEIKPTFSQLEAVNLHEVKHFVVEVRAYPPPRISWLKNNLTLIENL
TEITTDVEKIQEIRYRSKLKLIRAKEEDSGHYTIVAQNEDAVKSYTFELLTQVPSSILDL
VDDHHGSTGGQTVRCTAEGTPLPDIEWMICKDIKKCNNETSWTILANNVSNIITEIHSRD
RSTVEGRVTFAKVEETIAVRCLAKNLLGAENRELKLVAPTLRSELTVAAAVLVLLVIVII
SLIVLVVIWKQKPRYEIRWRVIESISPDGHEYIYVDPMQLPYDSRWEFPRDGLVLGRVLG
SGAFGKVVEGTAYGLSRSQPVMKVAVKMLKPTARSSEKQALMSELKIMTHLGPHLNIVNL
LGACTKSGPIYIITEYCFYGDLVNYLHKNRDSFLSHHPEKPKKELDIFGLNPADESTRSY
VILSFENNGDYMDMKQADTTQYVPMLERKEVSKYSDIQRSLYDRPASYKKKSMLDSEVKN
LLSDDNSEGLTLLDLLSFTYQVARGMEFLASKNCVHRDLAARNVLLAQGKIVKICDFGLA
RDIMHDSNYVSKGSTFLPVKWMAPESIFDNLYTTLSDVWSYGILLWEIFSLGGTPYPGMM
VDSTFYNKIKSGYRMAKPDHATSEVYEIMVKCWNSEPEKRPSFYHLSEIVENLLPGQYKK
SYEKIHLDFLKSDHPAVARMRVDSDNAYIGVTYKNEEDKLKDWEGGLDEQRLSADSGYII
PLPDIDPVPEEEDLGKRNRHSSQTSEESAIETGSSSSTFIKREDETIEDIDMMDDIGIDS
SDLVEDSFL (SEQ ID NO: 50)

FIG. 22B

```
MGTSHPAFLVLGCLLTGLSLILCQLSLPSILPNENEKVVQLNSSFSLRCFGESEVSWQYP
MSEEESSDVEIRNEENNSGLFVTVLEVSSASAAHTGLYTCYYNHTQTEENELEGRHIYIY
VPDPDVAFVPLGMTDYLVIVEDDDSAIIPCRTTDPETPVTLHNSEGVVPASYDSRQGFNG
TFTVGPYICEATVKGKKFQTIPFNVYALKATSELDLEMEALKTVYKSGETIVVTCAVFNN
EVVDLQWIYPGEVKGKGITMLEEIKVPSIKLVYTLTVPEATVKDSGDYECAARQATREVK
EMKKVTISVHEKGFIEIKPTFSQLEAVNLHEVKHFVVEVRAYPPPRISWLKNNLTLIENL
TEITTDVEKIQEIRNNETSWTILANNVSNIITEIHSRDRSTVEGRVTFAKVEETIAVRCL
AKNLLGAENRELKLVAPTLRSELTVAAAVLVLLVIVIISLIVLVVIWKQKPRYEIRWRVI
ESISPDGHEYIYVDPMQLPYDSRWEFPRDGLVLGRVLGSGAFGKVVEGTAYGLSRSQPVM
KVAVKMLKPTARSSEKQALMSELKIMTHLGPHLNIVNLLGACTKSGPIYIITEYCFYGDL
VNYLHKNRDSFLSHHPEKPKKELDIFGLNPADESTRSYVILSFENNGDYMDMKQADTTQY
VPMLERKEVSKYSDIQRSLYDRPASYKKKSMLDSEVKNLLSDDNSEGLTLLDLLSFTYQV
ARGMEFLASKNCVHRDLAARNVLLAQGKIVKICDFGLARDIMHDSNYVSKGSTFLPVKWM
APESIFDNLYTTLSDVWSYGILLWEIFSLGGTPYPGMMVDSTFYNKIKSGYRMAKPDHAT
SEVYEIMVKCWNSEPEKRPSFYHLSEIVENLLPGQYKKSYEKIHLDFLKSDHPAVARMRV
DSDNAYIGVTYKNEEDKLKDWEGGLDEQRLSADSGYIIPLPDIDPVPEEEDLGKRNRHSS
QTSEESAIETGSSSSTFIKREDETIEDIDMMDDIGIDSSDLVEDSFL(SEQ ID NO: 51)
```

FIG. 22C

```
  1 atgggcagcc cccgctccgc gctgagctgc ctgctgttgc acttgctggt cctctgcctc
 61 caagcccagg taactgttca gtcctcacct aatttacac agcatgtgag ggagcagagc
121 ctggtgacgg atcagctcag ccgccgcctc atccggacct accaactcta cagccgcacc
181 agcgggaagc acgtgcaggt cctggccaac aagcgcatca acgccatggc agaggacggc
241 gacccctccg caaagctcat cgtggagacg gacacctttg aagcagagt tcgagtccga
301 ggagccgaga cgggcctcta catctgcatg aacaagaagg ggaagctgat cgccaagagc
361 aacggcaaag gcaaggactg cgtcttcacg gagattgtgc tggagaacaa ctacacagcg
421 ctgcagaatg ccaagtacga gggctggtac atggccttca cccgcaaggg ccggccccgc
481 aagggctcca agacgcggca gcaccagcgt gaggtccact tcatgaagcg gctgccccgg
541 ggccaccaca ccaccgagca gagcctgcgc ttcgagttcc tcaactaccc gcccttcacg
601 cgcagcctgc gcggcagcca gaggacttgg gccccgagc ccgatag
(SEQ ID NO: 66)
```

FIG. 23

| | FGFR2IIIb | FGFR2IIIc |
|---|---|---|
| B7 | 0.073 | 0.892 |
| B8 | 0.081 | 0.828 |
| C5 | 0.085 | 1.004 |
| C8 | 0.082 | 0.835 |
| D2 | 0.081 | 0.536 |
| D5 | 0.088 | 0.623 |
| D10 | 0.089 | 0.494 |
| D11 | 0.069 | 0.631 |
| E3 | 0.064 | 0.987 |
| E4 | 0.087 | 0.875 |
| E8 | 0.061 | 0.489 |
| E9 | 0.063 | 0.720 |
| F3 | 0.092 | 0.822 |
| F9 | 0.086 | 0.915 |
| F10 | 0.105 | 0.690 |
| G8 | 0.083 | 0.522 |
| G9 | 0.087 | 0.628 |
| POSITIVE CTRL SERUM(1:2000) | 1.678 | |

| | FGFR2IIIc(128aa-mFc) | OA | Fer |
|---|---|---|---|
| Clone1 | 0.166±0.002 | 0.000±0.000 | 0.006±0.001 |
| Clone2 | 0.493±0.002 | 0.003±0.002 | 0.005±0.001 |
| Clone3 | 0.538±0.003 | 0.002±0.001 | 0.002±0.001 |
| Clone4 | 0.513±0.001 | 0.020±0.002 | 0.023±0.003 |
| Clone5 | 0.511±0.002 | 0.002±0.003 | 0.006±0.001 |
| Clone6 | 0.106±0.001 | 0.018±0.002 | 0.006±0.003 |
| Clone7 | 0.135±0.002 | 0.005±0.001 | 0.006±0.001 |
| Clone8 | 0.215±0.001 | 0.020±0.001 | 0.011±0.002 |

| | IIIc(hFc) | IIIb(hFc) | OA |
|---|---|---|---|
| Clone1 | 0.671±0.002 | 0.005±0.001 | 0.004±0.001 |
| Clone2 | 0.480±0.002 | 0.003±0.001 | 0.005±0.001 |
| Clone3 | 0.530±0.002 | 0.530±0.001 | 0.025±0.002 |
| Clone4 | 0.576±0.004 | 0.543±0.002 | 0.006±0.003 |
| Clone5 | 0.605±0.002 | 0.565±0.003 | 0.007±0.001 |
| Clone6 | 0.571±0.003 | 0.012±0.002 | 0.015±0.001 |
| Clone7 | 0.291±0.002 | 0.008±0.001 | 0.005±0.002 |
| Clone8 | 0.800±0.004 | 0.003±0.001 | 0.028±0.002 |

```
                              VL-CDR-1                    VL-CDR-2
Clon6  1   QSVLTQPPSVSAAPGQKVTISCSGSSSNIGNNYVSWYQQLPGTAPKLLIYDNNKRPSGIP  60
           QSVLTQPPSVSAAPGQKVTISCSGSSSNIGNNYVSWYQQLPGTAPKLLIYDNNKRPSGIP
Clon8  1   QSVLTQPPSVSAAPGQKVTISCSGSSSNIGNNYVSWYQQLPGTAPKLLIYDNNKRPSGIP  60

VL-CDR-3
Clon6  61  DRFSDSKSGTSATLGITGLQTGDEADYYCGTWDSSLSAVVFGGGTKLTVLGSGGSTITSY  120
           DRFS SKSGTSATL I+GLQ+ DEADYYC  WD SL+ VVFGGGTKLTVLGSGGSTITSY
Clon8  61  DRFSGSKSGTSATLAISGLQSEDEADYYCAAWDDSLNGVVFGGGTKLTVLGSGGSTITSY  120

VH-CDR-1
Clon6  121 NVYYTKLSSSGTEVQLVQSGAEVKKPGSSVKVSCKASGGTFSSYAISWVRQAPGQGLEWM  180
           NVYYTKLSSSGT+VQLVQSGAEVKKPGSSVKVSCKASGGTFSSYAISWVRQAPGQGLEWM
Clon8  121 NVYYTKLSSSGTQVQLVQSGAEVKKPGSSVKVSCKASGGTFSSYAISWVRQAPGQGLEWM  180

VH-CDR-2                           VH-CDR-3
Clon6  181 GRIIPILGIANYAQKFQGRVTITADKSTSTAYMELSSLRSEDTAVYYCARDPLLWS-YFD  239
           GRIIPT G ANYAQKFQGRVTITAD+STSTAYMEL+SLRSEDTAVYYCARD   W+  FD
Clon8  181 GRIIPIFGTANYAQKFQGRVTITADESTSTAYMELNSLRSEDTAVYYCARDRWDWNDAFD  240

Clon6  240 YWGQGTLVTVSS  251
            WGQGT+VTVSS
Clon8  241 IWGQGTMVTVSS  252
```

FIG. 28

CAGTCTGTGCTGACGCAGCCGCCCTCAGTGTCTCTGGGCCCCAGGACAGAAGGTCACCATCTCCTGCTCTGGAAGCAGCTC
CAACATTGGGAATAATTATGTATCCTGGTACCAGCAGCTCCCAGGAACAGCCCCCAAACTCCTCATATATGACAATAATA
AGCGACCCTCAGGGATTCCTGACCGATTCTCTGGCTCCAAGTCTGGCACGTCAGCCTCCACCCTGGCCATCAGTGGCTCCAG
TCTGAGGATGAGGCTGATTATTACTGTGCAGCAGATGACAGCCTGAATGGTGTGGTATTCGGCGGAGGACCAAGCT
GACCGTCCTAGGTTCCGGAGGGTCGACCATAACTTCGTATAATGTATACTATACGAAGTTATCCTGAGCGGTACCCAGG
TCCAGCTGGTGCAGTCTGGGGCTGAGGTGAAGAAGCCTGGGGTCCTGACAAGGCCCCTGGTGAAGGTCTCCTGCAAGG
TTCAGCAGCTATGCTATCAGCTGGGTGCGACAGGCCCCTGAGAGTCACGAGGCTTGAGTGGATGGGAAGGATCATCCTATCTT
TGGTACACAGCAAACTACGCAGAAGTTCCAGGGCAGAGTCACGATTACCGCGGACACAGTCCACAGCCTACATGG
AGCTGAACAGCCTGAGATCTGAGGACACGGCCGTGTATTACTGTGCGAGAGATCGATGGGACTGAACGACGCTTTTGAT
ATCTGGGGCCAAGGGACAATGGTCACCGTCTCCTCA

FIG. 29A

QSVLTQPPSV SAAPGQKVTI SCSGSGSSSNIG NNYVSWYQQL PGTAPKLLIY DNNKRPSGIP DRFSGSKSGT
SATLAISGLQ SEDEADYYCA AWDDSLNGVV FGGGTKLTVL G|SGGSTITSY NVYYTKLSSS GT|QVQLVQSG
AEVKKPGSSV KVSCKASGGT FSSYAISWVR QAPGQGLEWM GRIIPIFGTA NYAQKFQGRV TITADESTST
AYMELNSLRS EDTAVYYCAR DRWDWNDAFD IWGQGTMVTV SS

FIG. 29B

CAGTCTGTGCTGACGCAGCCGCCCTCAGTGTCTGCGGCCCCAGGACAGAAGGTCACCATCTCCTGCTCTGGAAGCAGCTC
CAACATTGGGAATAATTATGTATCCTGGTACCAGCAGCTCCCAGGAACAGCCCCCAAACTCCTCATATATGACAATAATA
AGCGACCCTCAGGGATTCCTGACCGATTCTCTGGCTCCAAGTCTGGCACCTCAGCCTCCCTGGCCATCAGTGGGCTCCAG
TCTGAGGATGAGGCTGATTATTACTGTGCAGCATGGGATGACAGCCTGAATGGTGTGGTATTCGGCGGAGGGACCAAGCT
GACCGTCCTAGGT

FIG. 29C

QSVLTQPPSV    SAAPGQKVTI    SCSGSSSNIG    NNYVSWYQQL    PGTAPKLLIY    DNNKRPSGIP    DRFSGSKSGT
SATLAISGLQ    SEDEADYYCA    AWDDSLNGVV    FGGGTKLTVL    G

FIG. 29D

CAGGTCCAGCTGGTGCAGTCTGGGGCTGAGGTGAAGAAGCCTGGGGCTTCCTGCAAGGCTTCTGGAGG
CACCTTCAGCAGCTATGCTATCAGCTGGGTGCGACAGGCCCCTGGACAAGGGCTTGAGTGGATGGGAAGGATCATCCCTA
TCTTTGGTACAGCAAACTACGCACAGAAGTTCCAGGGCAGAGTCACGATTACCGCGGACGAATCCACGAGCACAGCCTAC
ATGGAGCTGAACAGCCTGAGATCTGAGGACACGGCCGTGTATTACTGTGCGAGAGATCGATGGGACTGGAACGACGCTTT
TGATATCTGGGGCCAAGGGACAATGGTCACCGTCTCCTCA

FIG. 29E

QVQLVQSGAE VKKPGSSVKV SCKASGGTFS SYAISWVRQA PGQGLEWMGR IIPIFGTANY AQKFQGRVTI
TADESTSTAY MELNSLRSED TAVYYCARDR WDWNDAFDIW GQGTMVTVSS

FIG. 29F

CAGTCTGTGCTGACGCAGCCGCCCTCGGTGTCTGCGGCCCCAGGACAGAAGGTCACCATCTCCTGCTCTGGAAGCAGCTC
CAACATTGGGAATAATTATGTATCCTGGTACCAGCAGCTCCCAGGAACAGCCCCCAAACTCCTCATTTATGACAATAATA
AGCGACCCTCAGGGATTCCTGACCGATTCACTGCGAACATGGCAGACCTGAGTGCTGTTGTATACTATACGAAGTCTCCAG
ACTGGGACGAGCCGATTATTACTGCGAACATGGCAGACCTGAGTGCTGTTGTATACTATACGAAGTTATCCTCGAGCGGTACCGAGG
CACCGTCCTAGGTTCCGGAGGGTCGACCATAACTTCGTATAATGTATACTATACGAAGTTATCCTCGAGCGGTACCGAGG
TGCAGCTGGTGCAGTCTGGGGCTGAGGTGAAGAAGCCTGGGGTCCTCGGTGAAGGTCTCCTGCAAGGCTTCTGGAGGCACC
TTCAGCAGCTATGCTATCAGCTGGGTGCGACAGGCCCCTGGACAAGGGCTTGAGTGGATGGGAAGGATCATCCCTATCCT
TGGTATAGCAAACTACGCCCAGAAGTTCCAGGGCAGAGTCACGATTACCGCGGACAAATCCACGAGCACAGCCTACATGG
AGCTGAGCAGCCTGAGATCTGAGGACACGGCCGTGTATTACTGTGCGAGAGATCCGCTATTGTGGTCTTACTTTGACTAC
TGGGGCCAGGGAACCCCTGGTCACTGTCTCTTCA

FIG. 30A

QSVLTQPPSV SAAPGQKVTI SCSGSGSSNIG NNYVSWYQQL PGTAPKLLIY DNNKRPSGIP
DRFSDSKSGT SATLGITGLQ TGDEADYYCG TWDSSLSAVV FGGGTKLTVL GSGGSTITSY
NVYYTKLSSS GTEVQLVQSG AEVKKPGSSV KVSCKASGGT FSSYAISWVR QAPGQGLEWM
GRIIPILGIA NYAQKFQGRV TITADKSTST AYMELSSLRS EDTAVYYCAR DPLLWSYFDY
WGQGTLVTVS S

FIG. 30B

CAGTCTGTGCTGACGCAGCCGCCCTCGGTGTCTGCGGCCCCAGGACAGAAGGTCACCATCTCCTGCTCTGGAAGCAGCTC
CAACATTGGGAATAATTATGTATCCTGGTACCAGCAGCTCCCAGGAACAGCCCCCAAACTCCTCATTTATGACAATAATA
AGCGACCCTCAGGGATTCCTGACCGATTCTCTGACTCCAAGTCTGGCACGTCAGCCACCCTGGGCATCACCGGACTCCAG
ACTGGGGACGAGGCCGATTATTACTGCGAACATGGGATAGCAGCCTGAGTGCTGTGGTATTCGGCGGAGGGACCAAGCT
CACCGTCCTAGGT

FIG. 30C

QSVLTQPPSV SAAPGQKVTI SCSGSSSNIG NNYVSWYQQL PGTAPKLLIY DNNKRPSGIP
DRFSDSKSGT SATLGITGLQ TGDEADYYCG TWDSSLSAVV FGGGTKLTVL G

FIG. 30D

GAGGTGCAGCTGGTGCAGTCTGGGGCTGAGGTGAAGAAGCCTGGGGCTGAGGTCTCCTGCAAGGCTTCT
GGAGGCACCTTCAGCAGCTATGCTATCAGCTGGGTGCGACAAGCCCCTGGACAAGGGCTTGAGTGGATGGGAAGG
ATCATCCCTATCCTTGGTATAGCAAACTACGCACAGAAGTTCCAGGGCAGAGTCACGATTACCGCGGACAAATCC
ACGAGCACAGCCTACATGGAGCTGAGCAGCCTGAGATCTGAGGACACGGCCGTGTATTACTGTGCGAGAGATCCG
CTATTGTGGTCTTACTTTGACTACTGGGGCCAGGGAACCCTGGTCACTGTCTCTTCA

FIG. 30E

EVQLVQSGAE VKKPGSSVKV SCKASGGTFS SYAISWVRQA PGQGLEWMGR IIPILGIANY
AQKFQGRVTI TADKSTSTAY MELSSLRSED TAVYYCARDP LLWSYFDYWG QGTLVTVSS

FIG. 30F

| Round of panning | Input CFU | Eluted CFU | Yield |
| --- | --- | --- | --- |
| 1 | $1.53 \times 10^{13}$ | $6.95 \times 10^{4}$ | $5.54 \times 10^{-9}$ |
| 2 | $1.20 \times 10^{13}$ | $1.24 \times 10^{5}$ | $1.03 \times 10^{-8}$ |
| 3 | $2.18 \times 10^{13}$ | $4.67 \times 10^{6}$ | $2.14 \times 10^{-7}$ |
| 4 | $1.50 \times 10^{13}$ | $6.30 \times 10^{7}$ | $4.20 \times 10^{-6}$ | gaggtccagctgcagcagtctggggctgagctggcaagacctggggcttcagtgaagt
tgtcctgcaagacttctggctacacctttactagctactggatgcagtggttaaaaca
gaggcctggacagggtctggaatggattggggctattcatcctggagatggtgatact
aggtatactcagaagtttaagggcaaggccacattgactgcagataaatcctccagca
cagcctacatgcaactcagcagcttggcatctgaggactctgcggtctattactgtgc
aagatcggataccggccgttactatggtttggactactggggtcaaggaacctcagtc
accgtctcc (SEQ ID NO: 87)

FIG. 34A gacatccagatgaaccagtctccagccaccctgtctgtgactccaggagagacagtcagt
ctttcctgtagggccagccagagtatttacaagaacctacactggtatcaacagaaatca
catcggtctccaaggcttctcatcaagtctacttctgattccatctctgggatcccctcc
aggttcactggcagtggatcagggactgattacactctcagtatcaacagtgtgaagccc
gaagatgaagggatatattactgtcttcaaggttacagcacaccgtacacgttcggaggg
Gggaccaagctggaaataaaacg (SEQ ID NO: 89)

FIG. 34B

```
              FR1                    CDR1        FR2
21-LC: DIQMNQSPATLSVTPGETVSLSCRAS  QSIYKN  LHWYQQKSHRSPRLLIK
       CDR2                  FR3
       STS  DSISGIPSRFTGSGSGTDYTLSINSVKPEDEGIYYC
          CDR3         FR4
       LQGYSTPYT  FGGGTKLEIKR
```
(SEQ ID NO: 90)

```
              FR1                    CDR1        FR2
21-HC: EVQLQQSGAELARPGASVKLSCKTS  GYTFTSYW  MQWLKQRPGQGLEWIGA
          CDR2                 FR3
       IHPGDGDT  RYTQKFKGKATLTADKSSSTAYMQLSSLASEDSAVYYC
           CDR3         FR4
       ARSDTGRYYGLDY  WGQGTSVTVS
```
(SEQ ID NO: 88)

FIG. 35

```
                1                                                  50
21HC      (1)   EVQLQQSGAELARPGASVKLSCKTSGYTFTSYWMQWLKQRPGQGLEWIGA
subject   (1)   QVQLQQSGAELARPGASVKLSCKASGYTFTSYWMQWVKQRPGQGLEWIGA
Consensus (1)    VQLQQSGAELARPGASVKLSCK SGYTFTSYWMQWLKQRPGQGLEWIGA 51                                                 100
21HC     (51)   IHPGDGDTRYTQKFKGKATLTADKSSSTAYMQLSSLASEDSAVYYCARSD
subject  (51)   IYPGDGDTRYTQKFKGKATLTADKSSSTAYMQLSSLASEDSAVYYCARAS
Consensus(51)   IHPGDGDTRYTQKFKGKATLTADKSSSTAYMQLSSLASEDSAVYYCARA 101       119
21HC     (101)  TGRYYGLDYWGQGTSVTVS    (SEQ ID NO: 88)
subject  (101)  TAPYYAMDYWGQGTSVTVS    (SEQ ID NO: 142)
Consensus(101)  TA YYALDYWGQGTSVTVS
```

FIG. 36A

```
                1                                                  50
21LC      (1)   DIQMNQSPATLSVTPGETVSLSCRASQSIYKNLHWYQQKSHRSPRLLIKS
subject   (1)   DIQLTQSPAILSVTPGETVSLSCRASQTIYKNLHWYQQKSHRSPRLLIKY
Consensus (1)   DIQL QSPA LSVTPGETVSLSCRASQSIYKNLHWYQQKSHRSPRLLIK 51                                                 100
21LC     (51)   TSDSISGIPSRFTGSGSGTDYTLSINSVKPEDEGIYYCLQGYSTPYTFGG
subject  (51)   GSDSISGIPSRFTGSGSGTDYTLNINSVKPEDEGIYYCLQGYSTPWTFGG
Consensus(51)    SDSISGIPSRFTGSGSGTDYTL INSVKPEDEGIYYCLQGYSTPWTFGG 101
21L C    (101)  GTKLEI   (RESIDUES 1-106 OF SEQ ID NO: 90)
subject  (101)  GTKLEI   (SEQ ID NO: 143)
Consensus(101)  GTKLEI
```

FIG. 36B

QSVLTQPPSASGTPGQRVTISC<u>SGSSSNIGSNTVN</u>WYQQLPGTAPKLLIY<u>SNNQRPSGV</u>
PDRFSGSKSGTSASLAISGLQSEDEADYYC<u>AAWDDSLNGVVF</u>GGGTKLTVLGSGGSTVT
SYNVYYTKLSSSGTQVQLVQSGAEVKKPGSSVKVSCKASGGTF<u>SSYAIS</u>WVRQAPGQGL
EWMG<u>RIIPIFGTANYAQKFQGR</u>VIITADESTSTAYMELNSLRSEDTAVYYCAR<u>DRWDWN</u>
<u>DAFDI</u>WGQGTMVTVSS (SEQ ID NO: 190)

FIG. 37A

```
1    CAGTCTGTGC TGACGCAGCC ACCCTCAGCG TCTGGGACCC CCGGGCAGAG
51   GGTCACCATC TCTTGTTCTG GAAGCAGCTC CAACATCGGA AGTAATACTG
101  TAAACTGGTA CCAGCAGCTC CCAGGAACGG CCCCCAAACT CCTCATCTAT
151  AGTAATAATC AGCGGCCCTC AGGGGTCCCT GACCGATTCT CTGGCTCCAA
201  GTCTGGCACC TCAGCCTCCC TGGCCATCAG TGGGCTCCAG TCTGAGGATG
251  AGGCTGATTA TTACTGTGCA GCATGGATG ACAGCCTGAA TGGTGTGGTA
301  TTCGGCGGAG GGACCAAGCT GACCGTCCTA GGTTCCGGAG GGTCGACCGT
351  AACTTCGTAT AATGTATACT ATACGAAGTT ATCCTCGAGC GGTACCCAGG
401  TCCAGCTGGT GCAGTCTGGG GCTGAGGTGA AGAAGCCTGG GTCCTCGGTG
451  AAGGTCTCCT GCAAGGCTTC TGGAGGCACC TTCAGCAGCT ATGCTATCAG
501  CTGGGTGCGA CAGGCCCCTG ACAAGGGCT TGAGTGGATG GGAAGGATCA
551  TCCCTATCTT TGGTACAGCA AACTACGCAC AGAAGTTCCA GGGCAGAGTC
601  ACGATTACCG CGGACGAATC CACGAGCACA GCCTACATGG AGCTGAACAG
651  CCTGAGATCT GAGGACACGG CCGTGTATTA CTGTGCGAGA GATCGATGGG
701  ACTGGAACGA CGCTTTTGAT ATCTGGGGCC AAGGGACAAT GGTCACCGTC
751  TCCTCA  (SEQ ID NO: 191)
```

FIG. 37B

```
                            VL-CDR-1                                          VL-CDR-2
ScFv1   1   QSVLTQPPSASGTPGQRVTISCSGSSSNIGSNTVNWYQQLPGTAPKLLIYSNNQRPSGVP   60
            QSVLTQPPS S  PGQ+VTISCSGSSSNIG+N V+WYQQLPGTAPKLLIY NN+RPSG+P
ScFv6   1   QSVLTQPPSVSAAPGQKVTISCSGSSSNIGNNYVSWYQQLPGTAPKLLIYDNNKRPSGIP   60

VL-CDR-3
ScFv1  61   DRFSGSKSGTSASLAISGLQSEDEADYYCAAWDDSLNGVFGGGTKLTVLGSGGSTVTSY  120
            DRFS SKSGTSA+L I+GLQ+ DEADYYC  WD SL+ VFGGGTKLTVLGSGGST+TSY
ScFv6  61   DRFSDSKSGTSATLGITGLQTGDEADYYCGTWDSSLSAVVFGGGTKLTVLGSGGSTITSY  120

VH-CDR-1
ScFv1 121   NVYYTKLSSSGTQVQLVQSGAEVKKPGSSVKVSCKASGGTFSSYAISWVRQAPGQGLEWM  180
            NVYYTKLSSSGT+VQLVQSGAEVKKPGSSVKVSCKASGGTFSSYAISWVRQAPGQGLEWM
ScFv6 121   NVYYTKLSSSGTEVQLVQSGAEVKKPGSSVKVSCKASGGTFSSYAISWVRQAPGQGLEWM  180

VH-CDR-2                                      VH-CDR-3
ScFv1 181   GRIIPIFGTANYAQKFQGRVTITADESTSTAYMELNSLRSEDTAVYYCARDRWDWNDAFD  240
            GRIIPI G ANYAQKFQGRVTITAD+STSTAYMEL+SLRSEDTAVYYCARD  W+   FD
ScFv6 181   GRIIPILGIANYAQKFQGRVTITADKSTSTAYMELSSLRSEDTAVYYCARDPLLWS-YFD  239

ScFv1 241   IWGQGTMVTVSS  252
            WGQGT+VTVSS
ScFv6 240   YWGQGTLVTVSS  251
```

FIG. 38

```
                           VL-CDR-1                              VL-CDR-2
ScFv1   1  QSVLTQPPSASGTPGQRVTISCSGSSSNIGSNTVNWYQQLPGTAPKLLIYSNNQRPSGVP  60
           QSVLTQPPS S  PGQ+VTISCSGSSSNIG+N V+WYQQLPGTAPKLLIY NN+RPSG+P
ScFv8   1  QSVLTQPPSVSAAPGQKVTISCSGSSSNIGNNYVSWYQQLPGTAPKLLIYDNNKRPSGIP  60

VL-CDR-3
ScFv1  61  DRFSGSKSGTSASLAISGLQSEDEADYYCAAWDDSLNGVFGGGTKLTVLGSGGSTVTSY  120
           DRFSGSKSGTSA+LAISGLQSEDEADYYCAAWDDSLNGVFGGGTKLTVLGSGGST+TSY
ScFv8  61  DRFSGSKSGTSATLAISGLQSEDEADYYCAAWDDSLNGVFGGGTKLTVLGSGGSTITSY  120

VH-CDR-1
ScFv1 121  NVYYTKLSSSGTQVQLVQSGAEVKKPGSSVKVSCKASGGTFSSYAISWVRQAPGQGLEWM  180
           NVYYTKLSSSSTQVQLVQSGAEVKKPGSSVKVSCKASGGTFSSYAISWVRQAPGQGLEWM
ScFv8 121  NVYYTKLSSSSTQVQLVQSGAEVKKPGSSVKVSCKASGGTFSSYAISWVRQAPGQGLEWM  180

VH-CDR-2                              VH-CDR-3
ScFv1 181  GRIIPIFGTANYAQKFQGRVTITADESTSTAYMELNSLRSEDTAVYYCARDRWDWNDAFD  240
           GRIIPIFGTANYAQKFQGRVTITADESTSTAYMELNSLRSEDTAVYYCARDRWDWNDAFD
ScFv8 181  GRIIPIFGTANYAQKFQGRVTITADESTSTAYMELNSLRSEDTAVYYCARDRWDWNDAFD  240

ScFv1 241  IWGQGTMVTVSS  252
           IWGQGTMVTVSS
ScFv8 241  IWGQGTMVTVSS  252
```

FIG. 39

| Clone | VL-CDR1 | SEQ ID NO | VL-CDR2 | SEQ ID NO | VL-CDR3 | SEQ ID NO |
|---|---|---|---|---|---|---|
| scFv-1 | SGSSSNIGSNTVN | 144 | SNNQRPSGV | 145 | AAWDDSLNGVV | 146 |
| scFv-6 | SGSSSSNIGMNYVS | 155 | DNNKRPSGI | 156 | GTWDSSLSAVV | 157 |
| scFv-8 | SGSSSSNIGMNYVS | 155 | DNNKRPSGI | 156 | AAWDDSLNGVV | 146 |
| Clone | VH-CDR1 | | VH-CDR2 | | VH-CDR3 | |
| scFv-1 | SSYAIS | 147 | RIIPIFGTANYAQKFQGR | 148 | RDRWDWNDAFDI | 149 |
| scFv-6 | SSYAIS | 147 | RIIPILGIANYAQKFQGR | 158 | RDPLLWS-YFDY | 159 |
| scFv-8 | SSYAIS | 147 | RIIPIFGTANYAQKFQGR | 148 | RDRWDWNDAFDI | 149 |

FIG. 40

| Round of panning | Input phage (CFU) | Eluted phage (CFU) | Recovery rate (%) |
| --- | --- | --- | --- |
| 1 | $1.53 \times 10^{13}$ | $6.95 \times 10^{4}$ | $5.54 \times 10^{-7}$ |
| 2 | $1.2 \times 10^{13}$ | $1.24 \times 10^{5}$ | $1.03 \times 10^{-6}$ |
| 3 | $2.18 \times 10^{13}$ | $4.67 \times 10^{6}$ | $2.14 \times 10^{-5}$ |
| 4 | $1.5 \times 10^{13}$ | $6.3 \times 10^{7}$ | $4.2 \times 10^{-4}$ |

FIG. 46

(phage-displayed: Phage-scFv; secreted: Soluble scFv; bivalent soluble: Fc-fusion dcFv)

| | Ab Binding to Transient CHO | | | | | |
|---|---|---|---|---|---|---|
| | IIIb | IIIc | IIIb | IIIc | IIIb | IIIc |
| Clone No. | Phage-scFv | | Soluble scFv | | Fc-fusion dcFv | |
| NegCtr | - | - | - | - | n.a. | n.a. |
| 1 | - | ++ | - | ++ | - | ++ |
| 2 | ++ | +++ | + | +++ | ++ | ++ |
| 3 | + | ++ | - | +++ | n.a. | n.a. |
| 4 | + | +++ | - | - | n.a. | n.a. |
| 5 | + | ++ | - | +++ | n.a. | n.a. |
| 6 | + | + | + | ++ | n.a. | n.a. |
| 8 | - | + | - | + | - | + |

- = no binding
+ = positive binding
n.a. = not applied

FIG. 48

| | VL-CDR1 | VL-CDR2 | VL-CDR3 | VH-CDR1 | VH-CDR2 | VH-CDR3 |
|---|---|---|---|---|---|---|
| scFv-1 | SGSSSNIG<u>SNT</u>.<u>N</u> | <u>SNNQRPSGV</u> | AAWDDSLNGVV | SSYAIS | RIIPIFGTANYAQKFQGR | RDRWDWNDAFDI |
| scFv-6 | ........N.Y.S | D..K....I | GT..S..SA.. | ...... | .....L.I.......... | ..PLL.S-Y..Y |
| scFv-8 | ........N.Y.S | D..K....I | ............ | ...... | .................. | ............ |

Dash line = a space in the sequence

FIG. 49

```
                        SEQUENCE LISTING

<160> NUMBER OF SEQ ID NOS: 198

<210> SEQ ID NO 1
<211> LENGTH: 180
<212> TYPE: DNA
<213> ORGANISM: Homo sapiens

<400> SEQUENCE: 1
tacgggcccg acgggctgcc ctacctcaag gttctcaagg ccgccggtgt taacaccacg      60
gacaaagaga ttgaggttct ctatattcgg aatgtaactt ttgaggacgc tggggaatat    120
acgtgcttgg cgggtaattc tattgggata tcctttcact ctgcatggtt gacagttctg    180

<210> SEQ ID NO 2
<211> LENGTH: 60
<212> TYPE: PRT
<213> ORGANISM: Homo sapiens

<400> SEQUENCE: 2

Tyr Gly Pro Asp Gly Leu Pro Tyr Leu Lys Val Leu Lys Ala Ala Gly
1               5                   10                  15

Val Asn Thr Thr Asp Lys Glu Ile Glu Val Leu Tyr Ile Arg Asn Val
            20                  25                  30

Thr Phe Glu Asp Ala Gly Glu Tyr Thr Cys Leu Ala Gly Asn Ser Ile
```

```
                35                  40                  45
Gly Ile Ser Phe His Ser Ala Trp Leu Thr Val Leu
        50                  55                  60

<210> SEQ ID NO 3
<211> LENGTH: 33
<212> TYPE: DNA
<213> ORGANISM: Homo sapiens
<220> FEATURE:
<221> NAME/KEY: CDS
<222> LOCATION: (1)..(33)

<400> SEQUENCE: 3 gcc gcc ggt gtt aac acc acg gac aaa gag att            33
Ala Ala Gly Val Asn Thr Thr Asp Lys Glu Ile
1               5                  10

<210> SEQ ID NO 4
<211> LENGTH: 11
<212> TYPE: PRT
<213> ORGANISM: Homo sapiens

<400> SEQUENCE: 4

Ala Ala Gly Val Asn Thr Thr Asp Lys Glu Ile
1               5                  10

<210> SEQ ID NO 5
<211> LENGTH: 30
<212> TYPE: DNA
<213> ORGANISM: Homo sapiens
<220> FEATURE:
<221> NAME/KEY: CDS
<222> LOCATION: (1)..(30)

<400> SEQUENCE: 5 tat att cgg aat gta act ttt gag gac gct                30
Tyr Ile Arg Asn Val Thr Phe Glu Asp Ala
1               5                  10

<210> SEQ ID NO 6
<211> LENGTH: 10
<212> TYPE: PRT
<213> ORGANISM: Homo sapiens

<400> SEQUENCE: 6

Tyr Ile Arg Asn Val Thr Phe Glu Asp Ala
1               5                  10

<210> SEQ ID NO 7
<211> LENGTH: 12
<212> TYPE: DNA
<213> ORGANISM: Homo sapiens
<220> FEATURE:
<221> NAME/KEY: CDS
<222> LOCATION: (1)..(12)

<400> SEQUENCE: 7 ata tcc ttt cac                                        12
Ile Ser Phe His
1

<210> SEQ ID NO 8
<211> LENGTH: 4
<212> TYPE: PRT
<213> ORGANISM: Homo sapiens

<400> SEQUENCE: 8
```

Ile Ser Phe His
1

<210> SEQ ID NO 9
<211> LENGTH: 90
<212> TYPE: DNA
<213> ORGANISM: Homo sapiens
<220> FEATURE:
<221> NAME/KEY: CDS
<222> LOCATION: (1)..(90)

<400> SEQUENCE: 9

```
aat ggc aaa gaa ttc aaa cct gac cac aga att gga ggc tac aag act    48
Asn Gly Lys Glu Phe Lys Pro Asp His Arg Ile Gly Gly Tyr Lys Thr
1               5                   10                  15 gct gga gtt aat acc acc gac aaa gag atg gag gtg ctt cac             90
Ala Gly Val Asn Thr Thr Asp Lys Glu Met Glu Val Leu His
            20                  25                  30
```

<210> SEQ ID NO 10
<211> LENGTH: 30
<212> TYPE: PRT
<213> ORGANISM: Homo sapiens

<400> SEQUENCE: 10

Asn Gly Lys Glu Phe Lys Pro Asp His Arg Ile Gly Gly Tyr Lys Thr
1               5                   10                  15

Ala Gly Val Asn Thr Thr Asp Lys Glu Met Glu Val Leu His
            20                  25                  30

<210> SEQ ID NO 11
<211> LENGTH: 90
<212> TYPE: DNA
<213> ORGANISM: Homo sapiens
<220> FEATURE:
<221> NAME/KEY: CDS
<222> LOCATION: (1)..(90)

<400> SEQUENCE: 11

```
cct ggc tcc tgg caa cag gac cac tgc cca cct aag ctt act gag gag    48
Pro Gly Ser Trp Gln Gln Asp His Cys Pro Pro Lys Leu Thr Glu Glu
1               5                   10                  15 cca gtg ctg ata gca gtg caa ccc ctc ttt ggc cca cgg gca             90
Pro Val Leu Ile Ala Val Gln Pro Leu Phe Gly Pro Arg Ala
            20                  25                  30
```

<210> SEQ ID NO 12
<211> LENGTH: 30
<212> TYPE: PRT
<213> ORGANISM: Homo sapiens

<400> SEQUENCE: 12

Pro Gly Ser Trp Gln Gln Asp His Cys Pro Pro Lys Leu Thr Glu Glu
1               5                   10                  15

Pro Val Leu Ile Ala Val Gln Pro Leu Phe Gly Pro Arg Ala
            20                  25                  30

<210> SEQ ID NO 13
<211> LENGTH: 90
<212> TYPE: DNA
<213> ORGANISM: Homo sapiens
<220> FEATURE:
<221> NAME/KEY: CDS
<222> LOCATION: (1)..(90)

<400> SEQUENCE: 13

```
atg atg tgc att att gtg atg att ctg acc tac aaa tat tta cag gtt    48
Met Met Cys Ile Ile Val Met Ile Leu Thr Tyr Lys Tyr Leu Gln Val
1               5                   10                  15 gtt gag gag ata aat gga aac aat tat gtt tac ata gac cca            90
Val Glu Glu Ile Asn Gly Asn Asn Tyr Val Tyr Ile Asp Pro
            20                  25                  30
```

<210> SEQ ID NO 14
<211> LENGTH: 30
<212> TYPE: PRT
<213> ORGANISM: Homo sapiens

<400> SEQUENCE: 14

Met Met Cys Ile Ile Val Met Ile Leu Thr Tyr Lys Tyr Leu Gln Val
1               5                   10                  15

Val Glu Glu Ile Asn Gly Asn Asn Tyr Val Tyr Ile Asp Pro
            20                  25                  30

<210> SEQ ID NO 15
<211> LENGTH: 54
<212> TYPE: DNA
<213> ORGANISM: Homo sapiens
<220> FEATURE:
<221> NAME/KEY: CDS
<222> LOCATION: (1)..(54)

<400> SEQUENCE: 15

```
tgc gcg acc aca agc ctg aat ccg gat tat cgg gaa gag gac acg gat    48
Cys Ala Thr Thr Ser Leu Asn Pro Asp Tyr Arg Glu Glu Asp Thr Asp
1               5                   10                  15 gtg agg                                                            54
Val Arg
```

<210> SEQ ID NO 16
<211> LENGTH: 18
<212> TYPE: PRT
<213> ORGANISM: Homo sapiens

<400> SEQUENCE: 16

Cys Ala Thr Thr Ser Leu Asn Pro Asp Tyr Arg Glu Glu Asp Thr Asp
1               5                   10                  15

Val Arg

<210> SEQ ID NO 17
<211> LENGTH: 90
<212> TYPE: DNA
<213> ORGANISM: Homo sapiens
<220> FEATURE:
<221> NAME/KEY: CDS
<222> LOCATION: (1)..(90)

<400> SEQUENCE: 17

```
ctc act gag atc acc act gat gtg gaa aag att cag gaa ata agg aat    48
Leu Thr Glu Ile Thr Thr Asp Val Glu Lys Ile Gln Glu Ile Arg Asn
1               5                   10                  15 aat gaa act tcc tgg act att ttg gcc aac aat gtc tca aac            90
Asn Glu Thr Ser Trp Thr Ile Leu Ala Asn Asn Val Ser Asn
            20                  25                  30
```

<210> SEQ ID NO 18
<211> LENGTH: 30
<212> TYPE: PRT
<213> ORGANISM: Homo sapiens

<400> SEQUENCE: 18

Leu Thr Glu Ile Thr Thr Asp Val Glu Lys Ile Gln Glu Ile Arg Asn
1               5                   10                  15

Asn Glu Thr Ser Trp Thr Ile Leu Ala Asn Asn Val Ser Asn
            20                  25                  30

<210> SEQ ID NO 19
<211> LENGTH: 821
<212> TYPE: PRT
<213> ORGANISM: Homo sapiens

<400> SEQUENCE: 19

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

```
Ala Gly Glu Tyr Thr Cys Leu Ala Gly Asn Ser Ile Gly Ile Ser Phe
            340                 345                 350
His Ser Ala Trp Leu Thr Val Leu Pro Ala Pro Gly Arg Glu Lys Glu
            355                 360                 365
Ile Thr Ala Ser Pro Asp Tyr Leu Glu Ile Ala Ile Tyr Cys Ile Gly
370                 375                 380
Val Phe Leu Ile Ala Cys Met Val Val Thr Val Ile Leu Cys Arg Met
385                 390                 395                 400
Lys Asn Thr Thr Lys Lys Pro Asp Phe Ser Ser Gln Pro Ala Val His
            405                 410                 415
Lys Leu Thr Lys Arg Ile Pro Leu Arg Arg Gln Val Thr Val Ser Ala
            420                 425                 430
Glu Ser Ser Ser Ser Met Asn Ser Asn Thr Pro Leu Val Arg Ile Thr
            435                 440                 445
Thr Arg Leu Ser Ser Thr Ala Asp Thr Pro Met Leu Ala Gly Val Ser
450                 455                 460
Glu Tyr Glu Leu Pro Glu Asp Pro Lys Trp Glu Phe Pro Arg Asp Lys
465                 470                 475                 480
Leu Thr Leu Gly Lys Pro Leu Gly Glu Gly Cys Phe Gly Gln Val Val
            485                 490                 495
Met Ala Glu Ala Val Gly Ile Asp Lys Asp Lys Pro Lys Glu Ala Val
            500                 505                 510
Thr Val Ala Val Lys Met Leu Lys Asp Asp Ala Thr Glu Lys Asp Leu
            515                 520                 525
Ser Asp Leu Val Ser Glu Met Glu Met Met Lys Met Ile Gly Lys His
            530                 535                 540
Lys Asn Ile Ile Asn Leu Leu Gly Ala Cys Thr Gln Asp Gly Pro Leu
545                 550                 555                 560
Tyr Val Ile Val Glu Tyr Ala Ser Lys Gly Asn Leu Arg Glu Tyr Leu
                565                 570                 575
Arg Ala Arg Arg Pro Pro Gly Met Glu Tyr Ser Tyr Asp Ile Asn Arg
            580                 585                 590
Val Pro Glu Glu Gln Met Thr Phe Lys Asp Leu Val Ser Cys Thr Tyr
            595                 600                 605
Gln Leu Ala Arg Gly Met Glu Tyr Leu Ala Ser Gln Lys Cys Ile His
            610                 615                 620
Arg Asp Leu Ala Ala Arg Asn Val Leu Val Thr Glu Asn Asn Val Met
625                 630                 635                 640
Lys Ile Ala Asp Phe Gly Leu Ala Arg Asp Ile Asn Asn Ile Asp Tyr
                645                 650                 655
Tyr Lys Lys Thr Thr Asn Gly Arg Leu Pro Val Lys Trp Met Ala Pro
            660                 665                 670
Glu Ala Leu Phe Asp Arg Val Tyr Thr His Gln Ser Asp Val Trp Ser
            675                 680                 685
Phe Gly Val Leu Met Trp Glu Ile Phe Thr Leu Gly Gly Ser Pro Tyr
            690                 695                 700
Pro Gly Ile Pro Val Glu Glu Leu Phe Lys Leu Leu Lys Glu Gly His
705                 710                 715                 720
Arg Met Asp Lys Pro Ala Asn Cys Thr Asn Glu Leu Tyr Met Met Met
                725                 730                 735
Arg Asp Cys Trp His Ala Val Pro Ser Gln Arg Pro Thr Phe Lys Gln
            740                 745                 750
```

```
Leu Val Glu Asp Leu Asp Arg Ile Leu Thr Leu Thr Thr Asn Glu Glu
            755                 760                 765
Tyr Leu Asp Leu Ser Gln Pro Leu Glu Gln Tyr Ser Pro Ser Tyr Pro
        770                 775                 780
Asp Thr Arg Ser Ser Cys Ser Ser Gly Asp Asp Ser Val Phe Ser Pro
785                 790                 795                 800
Asp Pro Met Pro Tyr Glu Pro Cys Leu Pro Gln Tyr Pro His Ile Asn
                805                 810                 815
Gly Ser Val Lys Thr
            820

<210> SEQ ID NO 20
<211> LENGTH: 2466
<212> TYPE: DNA
<213> ORGANISM: Homo sapiens

<400> SEQUENCE: 20
atggtcagct ggggtcgttt catctgcctg gtcgtggtca ccatggcaac cttgtccctg      60
gcccggccct ccttcagttt agttgaggat accacattag agccagaaga gccaccaacc     120
aaataccaaa tctctcaacc agaagtgtac gtggctgcac caggggagtc gctagaggtg     180
cgctgcctgt tgaaagatgc cgccgtgatc agttggacta aggatggggt gcacttgggg     240
cccaacaata ggacagtgct tattggggag tacttgcaga taagggcgc cacgcctaga     300 gactccggcc tctatgcttg tactgccagt aggactgtag acagtgaaac ttggtacttc     360
atggtgaatg tcacagatgc catctcatcc ggagatgatg aggatgacac cgatggtgcg     420
gaagattttg tcagtgagaa cagtaacaac aagagagcac catactggac caacacagaa     480
aagatggaaa agcggctcca tgctgtgcct gcggccaaca ctgtcaagtt cgctgccca     540 gccgggggga acccaatgcc aaccatgcgg tggctgaaaa acgggaagga gtttaagcag     600
gagcatcgca ttgaggcta caaggtacga aaccagcact ggagcctcat tatggaaagt     660
gtggtcccat ctgacaaggg aaattatacc tgtgtggtgg agaatgaata cgggtccatc     720
aatcacacgt accacctgga tgttgtggag cgatcgcctc accggcccat cctccaagcc     780
ggactgccgg caaatgcctc cacagtggtc ggaggagacg tagagtttgt ctgcaaggtt     840
tacagtgatg cccagcccca catccagtgg atcaagcacg tggaaaagaa cggcagtaaa     900
tacgggcccg acgggctgcc ctacctcaag gttctcaagg ccgccggtgt aacaccacg     960 gacaaagaga ttgaggttct ctatattcgg aatgtaactt ttgaggacgc tgggg aatat    1020 acgtgcttgg cgggtaattc tattgggata tcctttcact ctgcatggtt gacagttctg    1080
ccagcgcctg gaagagaaaa ggagattaca gcttccccag actacctgga gatagccatt    1140
tactgcatag gggtcttctt aatcgcctgt atggtggtaa cagtcatcct gtgccgaatg    1200
aagaacacga ccaagaagcc agacttcagc agccagccgg ctgtgcacaa gctgaccaaa    1260 cgtatcccc tgcggagaca ggtaacagtt tcggctgagt ccagctcctc catgaactcc    1320 aacacccgc tggtgaggat aacaacacgc ctctcttcaa cggcagacac ccccatgctg    1380 gcagggg tct ccgagtatga acttccagag acccaaaat gggagtttcc aagagataag    1440
ctgacactgg gcaagcccct gggagaaggt tgctttgggc aagtggtcat ggcggaagca    1500
gtgggaattg acaaagacaa gcccaaggag gcggtcaccg tggccgtgaa gatgttgaaa    1560
gatgatgcca cagagaaaga cctttctgat ctggtgtcag agatggagat gatgaagatg    1620
attgggaaac acaagaatat cataaatctt cttggagcct gcacacagga tgggcctctc    1680
```

-continued

```
tatgtcatag ttgagtatgc ctctaaaggc aacctccgag aatacctccg agcccggagg    1740
ccacccggga tggagtactc ctatgacatt aaccgtgttc ctgaggagca gatgaccttc    1800
aaggacttgg tgtcatgcac ctaccagctg ccagaggca tggagtactt ggcttcccaa    1860
aaatgtattc atcgagattt agcagccaga aatgttttgg taacagaaaa caatgtgatg    1920
aaaatagcag actttggact cgccagagat atcaacaata tagactatta caaaaagacc    1980
accaatgggc ggcttccagt caagtggatg gctccagaag ccctgtttga tagagtatac    2040
actcatcaga gtgatgtctg gtccttcggg gtgttaatgt gggagatctt cactttaggg    2100
ggctcgccct acccagggat tcccgtggag gaacttttta agctgctgaa ggaaggacac    2160
agaatggata agccagccaa ctgcaccaac gaactgtaca tgatgatgag ggactgttgg    2220
catgcagtgc cctcccagag accaacgttc aagcagttgg tagaagactt ggatcgaatt    2280
ctcactctca caaccaatga ggaatacttg gacctcagcc aacctctcga acagtattca    2340
cctagttacc ctgacacaag aagttcttgt tcttcaggag atgattctgt tttttctcca    2400
gaccccatgc cttacgaacc atgccttcct cagtatccac ataaacggg cagtgttaaa    2460 acatga                                                              2466
```

<210> SEQ ID NO 21
<211> LENGTH: 822
<212> TYPE: PRT
<213> ORGANISM: Homo sapiens

<400> SEQUENCE: 21

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
```

```
                225                 230                 235                 240
Asn His Thr Tyr His Leu Asp Val Val Glu Arg Ser Pro His Arg Pro
                    245                 250                 255
Ile Leu Gln Ala Gly Leu Pro Ala Asn Ala Ser Thr Val Val Gly Gly
                    260                 265                 270
Asp Val Glu Phe Val Cys Lys Val Tyr Ser Asp Ala Gln Pro His Ile
                    275                 280                 285
Gln Trp Ile Lys His Val Glu Lys Asn Gly Ser Lys Tyr Gly Pro Asp
    290                 295                 300
Gly Leu Pro Tyr Leu Lys Val Leu Lys His Ser Gly Ile Asn Ser Ser
305                 310                 315                 320
Asn Ala Glu Val Leu Ala Leu Phe Asn Val Thr Glu Ala Asp Ala Gly
                    325                 330                 335
Glu Tyr Ile Cys Lys Val Ser Asn Tyr Ile Gly Gln Ala Asn Gln Ser
                    340                 345                 350
Ala Trp Leu Thr Val Leu Pro Lys Gln Gln Ala Pro Gly Arg Glu Lys
                    355                 360                 365
Glu Ile Thr Ala Ser Pro Asp Tyr Leu Glu Ile Ala Ile Tyr Cys Ile
    370                 375                 380
Gly Val Phe Leu Ile Ala Cys Met Val Val Thr Val Ile Leu Cys Arg
385                 390                 395                 400
Met Lys Asn Thr Thr Lys Lys Pro Asp Phe Ser Ser Gln Pro Ala Val
                    405                 410                 415
His Lys Leu Thr Lys Arg Ile Pro Leu Arg Arg Gln Val Thr Val Ser
                    420                 425                 430
Ala Glu Ser Ser Ser Ser Met Asn Ser Asn Thr Pro Leu Val Arg Ile
                    435                 440                 445
Thr Thr Arg Leu Ser Ser Thr Ala Asp Thr Pro Met Leu Ala Gly Val
    450                 455                 460
Ser Glu Tyr Glu Leu Pro Glu Asp Pro Lys Trp Glu Phe Pro Arg Asp
465                 470                 475                 480
Lys Leu Thr Leu Gly Lys Pro Leu Gly Glu Gly Cys Phe Gly Gln Val
                    485                 490                 495
Val Met Ala Glu Ala Val Gly Ile Asp Lys Asp Lys Pro Lys Glu Ala
                    500                 505                 510
Val Thr Val Ala Val Lys Met Leu Lys Asp Asp Ala Thr Glu Lys Asp
                    515                 520                 525
Leu Ser Asp Leu Val Ser Glu Met Glu Met Met Lys Met Ile Gly Lys
    530                 535                 540
His Lys Asn Ile Ile Asn Leu Leu Gly Ala Cys Thr Gln Asp Gly Pro
545                 550                 555                 560
Leu Tyr Val Ile Val Glu Tyr Ala Ser Lys Gly Asn Leu Arg Glu Tyr
                    565                 570                 575
Leu Arg Ala Arg Arg Pro Pro Gly Met Glu Tyr Ser Tyr Asp Ile Asn
                    580                 585                 590
Arg Val Pro Glu Glu Gln Met Thr Phe Lys Asp Leu Val Ser Cys Thr
                    595                 600                 605
Tyr Gln Leu Ala Arg Gly Met Glu Tyr Leu Ala Ser Gln Lys Cys Ile
                    610                 615                 620
His Arg Asp Leu Ala Ala Arg Asn Val Leu Val Thr Glu Asn Asn Val
625                 630                 635                 640
Met Lys Ile Ala Asp Phe Gly Leu Ala Arg Asp Ile Asn Asn Ile Asp
                    645                 650                 655
```

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Lys Glu Gly
705                 710                 715                 720

His Arg Met Asp Lys Pro Ala Asn Cys Thr Asn Glu Leu Tyr Met Met
            725                 730                 735

Met Arg Asp Cys Trp His Ala Val Pro Ser Gln Arg Pro Thr Phe Lys
        740                 745                 750

Gln Leu Val Glu Asp Leu Asp Arg Ile Leu Thr Leu Thr Thr Asn Glu
        755                 760                 765

Glu Tyr Leu Asp Leu Ser Gln Pro Leu Glu Gln Tyr Ser Pro Ser Tyr
770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
            805                 810                 815

Asn Gly Ser Val Lys Thr
            820

<210> SEQ ID NO 22
<211> LENGTH: 682
<212> TYPE: PRT
<213> ORGANISM: Homo sapiens

<400> SEQUENCE: 22

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Thr
        35                  40                  45

Asp Gly Ala Glu Asp Phe Val Ser Glu Asn Ser Asn Asn Lys Arg Ala
    50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn

```
              195                 200                 205
Gly Ser Lys Tyr Gly Pro Asp Gly Leu Pro Tyr Leu Lys Val Leu Lys
210                 215                 220

His Ser Gly Ile Asn Ser Ser Asn Ala Glu Val Leu Ala Leu Phe Asn
225                 230                 235                 240

Val Thr Glu Ala Asp Ala Gly Glu Tyr Ile Cys Lys Val Ser Asn Tyr
                245                 250                 255

Ile Gly Gln Ala Asn Gln Ser Ala Trp Leu Thr Val Leu Pro Lys Gln
                260                 265                 270

Gln Ala Pro Gly Arg Glu Lys Glu Ile Thr Ala Ser Pro Asp Tyr Leu
            275                 280                 285

Glu Ile Ala Ile Tyr Cys Ile Gly Val Phe Leu Ile Ala Cys Met Val
        290                 295                 300

Val Thr Val Ile Leu Cys Arg Met Lys Asn Thr Thr Lys Lys Pro Asp
305                 310                 315                 320

Phe Ser Ser Gln Pro Ala Val His Lys Leu Thr Lys Arg Ile Pro Leu
                325                 330                 335

Arg Arg Gln Val Ser Ala Glu Ser Ser Ser Ser Met Asn Ser Asn Thr
                340                 345                 350

Pro Leu Val Arg Ile Thr Thr Arg Leu Ser Ser Thr Ala Asp Thr Pro
            355                 360                 365

Met Leu Ala Gly Val Ser Glu Tyr Glu Leu Pro Glu Asp Pro Lys Trp
370                 375                 380

Glu Phe Pro Arg Asp Lys Leu Thr Leu Gly Lys Pro Leu Gly Glu Gly
385                 390                 395                 400

Cys Phe Gly Gln Val Val Met Ala Glu Ala Val Gly Ile Asp Lys Asp
                405                 410                 415

Lys Pro Lys Glu Ala Val Thr Val Ala Val Lys Met Leu Lys Asp Asp
            420                 425                 430

Ala Thr Glu Lys Asp Leu Ser Asp Leu Val Ser Glu Met Glu Met Met
        435                 440                 445

Lys Met Ile Gly Lys His Lys Asn Ile Ile Asn Leu Leu Gly Ala Cys
    450                 455                 460

Thr Gln Asp Gly Pro Leu Tyr Val Ile Val Glu Tyr Ala Ser Lys Gly
465                 470                 475                 480

Asn Leu Arg Glu Tyr Leu Arg Ala Arg Arg Pro Pro Gly Met Glu Tyr
                485                 490                 495

Ser Tyr Asp Ile Asn Arg Val Pro Glu Glu Gln Met Thr Phe Lys Asp
            500                 505                 510

Leu Val Ser Cys Thr Tyr Gln Leu Ala Arg Gly Met Glu Tyr Leu Ala
        515                 520                 525

Ser Gln Lys Cys Ile His Arg Asp Leu Ala Ala Arg Asn Val Leu Val
    530                 535                 540

Thr Glu Asn Asn Val Met Lys Ile Ala Asp Phe Gly Leu Ala Arg Asp
545                 550                 555                 560

Ile Asn Asn Ile Asp Tyr Tyr Lys Lys Thr Thr Asn Gly Arg Leu Pro
                565                 570                 575

Val Lys Trp Met Ala Pro Glu Ala Leu Phe Asp Arg Val Tyr Thr His
            580                 585                 590

Gln Ser Asp Val Trp Ser Phe Gly Val Leu Met Trp Glu Ile Phe Thr
        595                 600                 605

Leu Gly Gly Ser Pro Tyr Pro Gly Ile Pro Val Glu Glu Leu Phe Lys
610                 615                 620
```

```
Leu Leu Lys Glu Gly His Arg Met Asp Lys Pro Ala Asn Cys Thr Asn
625                 630                 635                 640

Glu Leu Tyr Met Met Met Arg Asp Cys Trp His Ala Val Pro Ser Gln
            645                 650                 655

Arg Pro Thr Phe Lys Gln Leu Val Glu Asp Leu Asp Arg Ile Pro Pro
                660                 665                 670

Asn Pro Ser Leu Met Ser Ile Phe Arg Lys
            675                 680

<210> SEQ ID NO 23
<211> LENGTH: 817
<212> TYPE: PRT
<213> ORGANISM: Homo sapiens

<400> SEQUENCE: 23

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
```

```
                305                 310                 315                 320
Asn Ala Glu Val Leu Ala Leu Phe Asn Val Thr Glu Ala Asp Ala Gly
                325                 330                 335
Glu Tyr Ile Cys Lys Val Ser Asn Tyr Ile Gly Gln Ala Asn Gln Ser
                340                 345                 350
Ala Trp Leu Thr Val Leu Pro Lys Gln Gln Ala Pro Gly Arg Glu Lys
                355                 360                 365
Glu Ile Thr Ala Ser Pro Asp Tyr Leu Glu Ile Ala Ile Tyr Cys Ile
                370                 375                 380
Gly Val Phe Leu Ile Ala Cys Met Val Val Thr Val Ile Leu Cys Arg
385                 390                 395                 400
Met Lys Asn Thr Thr Lys Lys Pro Asp Phe Ser Ser Gln Pro Ala Val
                405                 410                 415
His Lys Leu Thr Lys Arg Ile Pro Leu Arg Arg Gln Val Thr Val Ser
                420                 425                 430
Ala Glu Ser Ser Ser Ser Met Asn Ser Asn Thr Pro Leu Val Arg Ile
                435                 440                 445
Thr Thr Arg Leu Ser Ser Thr Ala Asp Thr Pro Met Leu Ala Gly Val
                450                 455                 460
Ser Glu Tyr Glu Leu Pro Glu Asp Pro Lys Trp Glu Phe Pro Arg Asp
465                 470                 475                 480
Lys Leu Thr Leu Gly Lys Pro Leu Gly Glu Gly Cys Phe Gly Gln Val
                485                 490                 495
Val Met Ala Glu Ala Val Gly Ile Asp Lys Asp Lys Pro Lys Glu Ala
                500                 505                 510
Val Thr Val Ala Val Lys Met Leu Lys Asp Asp Ala Thr Glu Lys Asp
                515                 520                 525
Leu Ser Asp Leu Val Ser Glu Met Glu Met Met Lys Met Ile Gly Lys
                530                 535                 540
His Lys Asn Ile Ile Asn Leu Leu Gly Ala Cys Thr Gln Asp Gly Pro
545                 550                 555                 560
Leu Tyr Val Ile Val Glu Tyr Ala Ser Lys Gly Asn Leu Arg Glu Tyr
                565                 570                 575
Leu Arg Ala Arg Arg Pro Pro Gly Met Glu Tyr Ser Tyr Asp Ile Asn
                580                 585                 590
Arg Val Pro Glu Glu Gln Met Thr Phe Lys Asp Leu Val Ser Cys Thr
                595                 600                 605
Tyr Gln Leu Ala Arg Gly Met Glu Tyr Leu Ala Ser Gln Lys Cys Ile
                610                 615                 620
His Arg Asp Leu Ala Ala Arg Asn Val Leu Val Thr Glu Asn Asn Val
625                 630                 635                 640
Met Lys Ile Ala Asp Phe Gly Leu Ala Arg Asp Ile Asn Asn Ile Asp
                645                 650                 655
Tyr Tyr Lys Lys Thr Thr Asn Gly Arg Leu Pro Val Lys Trp Met Ala
                660                 665                 670
Pro Glu Ala Leu Phe Asp Arg Val Tyr Thr His Gln Ser Asp Val Trp
                675                 680                 685
Ser Phe Gly Val Leu Met Trp Glu Ile Phe Thr Leu Gly Gly Ser Pro
                690                 695                 700
Tyr Pro Gly Ile Pro Val Glu Glu Leu Phe Lys Leu Leu Lys Glu Gly
705                 710                 715                 720
His Arg Met Asp Lys Pro Ala Asn Cys Thr Asn Glu Leu Tyr Met Met
                725                 730                 735
```

```
Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Arg Tyr Lys Leu Leu Pro Cys Pro Asp Lys His Asn Lys Arg Cys Lys
770                 775                 780

Pro Glu Glu Arg Gly Asp Leu Thr Glu Ala Gly Ala Ala Gly Ser Ser
785                 790                 795                 800

Arg Cys Val Asp Ser Arg Lys Arg Val Arg Gln Glu Lys Ile Ser Thr
                    805                 810                 815

Gly

<210> SEQ ID NO 24
<211> LENGTH: 819
<212> TYPE: PRT
<213> ORGANISM: Homo sapiens

<400> SEQUENCE: 24

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285
```

-continued

```
Gln Trp Ile Lys His Val Glu Lys Asn Gly Ser Lys Tyr Gly Pro Asp
    290                 295                 300
Gly Leu Pro Tyr Leu Lys Val Leu Lys His Ser Gly Ile Asn Ser Ser
305                 310                 315                 320
Asn Ala Glu Val Leu Ala Leu Phe Asn Val Thr Glu Ala Asp Ala Gly
                325                 330                 335
Glu Tyr Ile Cys Lys Val Ser Asn Tyr Ile Gly Gln Ala Asn Gln Ser
                340                 345                 350
Ala Trp Leu Thr Val Leu Pro Lys Gln Gln Ala Pro Gly Arg Glu Lys
            355                 360                 365
Glu Ile Thr Ala Ser Pro Asp Tyr Leu Glu Ile Ala Ile Tyr Cys Ile
370                 375                 380
Gly Val Phe Leu Ile Ala Cys Met Val Val Thr Val Ile Leu Cys Arg
385                 390                 395                 400
Met Lys Asn Thr Thr Lys Lys Pro Asp Phe Ser Ser Gln Pro Ala Val
                405                 410                 415
His Lys Leu Thr Lys Arg Ile Pro Leu Arg Arg Gln Val Thr Val Ser
                420                 425                 430
Ala Glu Ser Ser Ser Met Asn Ser Asn Thr Pro Leu Val Arg Ile
            435                 440                 445
Thr Thr Arg Leu Ser Ser Thr Ala Asp Thr Pro Met Leu Ala Gly Val
450                 455                 460
Ser Glu Tyr Glu Leu Pro Glu Asp Pro Lys Trp Glu Phe Pro Arg Asp
465                 470                 475                 480
Lys Leu Thr Leu Gly Lys Pro Leu Gly Glu Gly Cys Phe Gly Gln Val
                485                 490                 495
Val Met Ala Glu Ala Val Gly Ile Asp Lys Asp Lys Pro Lys Glu Ala
            500                 505                 510
Val Thr Val Ala Val Lys Met Leu Lys Asp Asp Ala Thr Glu Lys Asp
            515                 520                 525
Leu Ser Asp Leu Val Ser Glu Met Glu Met Met Lys Met Ile Gly Lys
530                 535                 540
His Lys Asn Ile Ile Asn Leu Leu Gly Ala Cys Thr Gln Asp Gly Pro
545                 550                 555                 560
Leu Tyr Val Ile Val Glu Tyr Ala Ser Lys Gly Asn Leu Arg Glu Tyr
                565                 570                 575
Leu Arg Ala Arg Arg Pro Pro Gly Met Glu Tyr Ser Tyr Asp Ile Asn
            580                 585                 590
Arg Val Pro Glu Glu Gln Met Thr Phe Lys Asp Leu Val Ser Cys Thr
            595                 600                 605
Tyr Gln Leu Ala Arg Gly Met Glu Tyr Leu Ala Ser Gln Lys Cys Ile
            610                 615                 620
His Arg Asp Leu Ala Ala Arg Asn Val Leu Val Thr Glu Asn Asn Val
625                 630                 635                 640
Met Lys Ile Ala Asp Phe Gly Leu Ala Arg Asp Ile Asn Asn Ile Asp
                645                 650                 655
Tyr Tyr Lys Lys Thr Thr Asn Gly Arg Leu Pro Val Lys Trp Met Ala
                660                 665                 670
Pro Glu Ala Leu Phe Asp Arg Val Tyr Thr His Gln Ser Asp Val Trp
            675                 680                 685
Ser Phe Gly Val Leu Met Trp Glu Ile Phe Thr Leu Gly Gly Ser Pro
690                 695                 700
```

```
Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Arg Ile Leu Thr Leu Thr Thr Asn Glu Asn Phe Gln Ser Thr Ser Gly
    770                 775                 780

Arg Glu Gly Thr Glu Ile His Ala Leu Gln Cys Leu Arg Ser Glu Val
785                 790                 795                 800

Thr Pro Ala Ile Ser Cys Glu Ser Pro Leu Ala Asp Thr Gly Ser Lys
                805                 810                 815

Val Pro Asn

<210> SEQ ID NO 25
<211> LENGTH: 819
<212> TYPE: PRT
<213> ORGANISM: Homo sapiens

<400> SEQUENCE: 25

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
        50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255
```

```
Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
```

```
                    675                 680                 685
Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
            725                 730                 735

Met Arg Asp Cys Trp His Ala Val Pro Ser Gln Arg Pro Thr Phe Lys
        740                 745                 750

Gln Leu Val Glu Asp Leu Asp Arg Ile Leu Thr Leu Thr Thr Asn Glu
    755                 760                 765

Ser Phe Gln Ser Ser Leu Lys Ser Ser Thr Gly Ile Pro Gly Trp
770                 775                 780

Pro Pro Gly Ser Glu Val Phe Ser Glu Val Ala Phe Arg Gly Ile Leu
785                 790                 795                 800

Asn Tyr Asp Ile Glu Arg Pro Ile Leu Cys Ala Gly Ser Lys Lys Ile
            805                 810                 815

Tyr Asp Ile

<210> SEQ ID NO 26
<211> LENGTH: 830
<212> TYPE: PRT
<213> ORGANISM: Homo sapiens

<400> SEQUENCE: 26

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
```

```
            225                 230                 235                 240
Asn His Thr Tyr His Leu Asp Val Val Glu Arg Ser Pro His Arg Pro
                    245                 250                 255

Ile Leu Gln Ala Gly Leu Pro Ala Asn Ala Ser Thr Val Val Gly Gly
                    260                 265                 270

Asp Val Glu Phe Val Cys Lys Val Tyr Ser Asp Ala Gln Pro His Ile
                    275                 280                 285

Gln Trp Ile Lys His Val Glu Lys Asn Gly Ser Lys Tyr Gly Pro Asp
                    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                    325                 330                 335

Glu Tyr Ile Cys Lys Val Ser Asn Tyr Ile Gly Gln Ala Asn Gln Ser
                    340                 345                 350

Ala Trp Leu Thr Val Leu Pro Lys Gln Gln Ala Pro Gly Arg Glu Lys
                    355                 360                 365

Glu Ile Thr Ala Ser Pro Asp Tyr Leu Glu Ile Ala Ile Tyr Cys Ile
                    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                    405                 410                 415

His Lys Leu Thr Lys Arg Ile Pro Leu Arg Arg Gln Val Thr Val Ser
                    420                 425                 430

Ala Glu Ser Ser Ser Ser Met Asn Ser Asn Thr Pro Leu Val Arg Ile
                    435                 440                 445

Thr Thr Arg Leu Ser Ser Thr Ala Asp Thr Pro Met Leu Ala Gly Val
                    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                    485                 490                 495

Val Met Ala Glu Ala Val Gly Ile Asp Lys Asp Lys Pro Lys Glu Ala
                    500                 505                 510

Val Thr Val Ala Val Lys Met Leu Lys Asp Asp Ala Thr Glu Lys Asp
                    515                 520                 525

Leu Ser Asp Leu Val Ser Glu Met Glu Met Met Lys Met Ile Gly Lys
                    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                    565                 570                 575

Leu Arg Ala Arg Arg Pro Pro Gly Met Glu Tyr Ser Tyr Asp Ile Asn
                    580                 585                 590

Arg Val Pro Glu Glu Gln Met Thr Phe Lys Asp Leu Val Ser Cys Thr
                    595                 600                 605

Tyr Gln Leu Ala Arg Gly Met Glu Tyr Leu Ala Ser Gln Lys Cys Ile
                    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                    645                 650                 655
```

-continued

```
Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Gly Arg Leu Pro Ala Trp Ala Ser Gln Glu Lys Glu Asn Ser Gln Thr
770                 775                 780

Ser Leu Phe Ala Ile Ser His Val Thr Leu Ser Ser Ile Ser Lys Thr
785                 790                 795                 800

Arg Ser Ser Ala Lys Arg Asp Glu Lys Pro Gly Ser Ser Pro His Leu
                805                 810                 815

Ala Leu Val Arg Ser Gln Gly Leu Pro Gln Ser Val Val Pro
            820                 825                 830

<210> SEQ ID NO 27
<211> LENGTH: 771
<212> TYPE: PRT
<213> ORGANISM: Homo sapiens

<400> SEQUENCE: 27

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
```

-continued

```
            195                 200                 205
Val Arg Asn Gln His Trp Ser Leu Ile Met Glu Ser Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                    245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
                340                 345                 350

Ala Trp Leu Thr Val Leu Pro Lys Gln Gln Ala Pro Gly Arg Glu Lys
            355                 360                 365

Glu Ile Thr Ala Ser Pro Asp Tyr Leu Glu Ile Ala Ile Tyr Cys Ile
370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
                420                 425                 430

Ala Glu Ser Ser Ser Ser Met Asn Ser Asn Thr Pro Leu Val Arg Ile
            435                 440                 445

Thr Thr Arg Leu Ser Ser Thr Ala Asp Thr Pro Met Leu Ala Gly Val
450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
                500                 505                 510

Val Thr Val Ala Val Lys Met Leu Lys Asp Asp Ala Thr Glu Lys Asp
            515                 520                 525

Leu Ser Asp Leu Val Ser Glu Met Glu Met Met Lys Met Ile Gly Lys
530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
                580                 585                 590

Arg Val Pro Glu Glu Gln Met Thr Phe Lys Asp Leu Val Ser Cys Thr
            595                 600                 605

Tyr Gln Leu Ala Arg Gly Met Glu Tyr Leu Ala Ser Gln Lys Cys Ile
610                 615                 620
```

```
His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
            645                 650                 655

Tyr Tyr Lys Lys Thr Thr Asn Gly Arg Leu Pro Val Lys Trp Met Ala
        660                 665                 670

Pro Glu Ala Leu Phe Asp Arg Val Tyr Thr His Gln Ser Asp Val Trp
    675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Pro Leu Ser
    770

<210> SEQ ID NO 28
<211> LENGTH: 768
<212> TYPE: PRT
<213> ORGANISM: Homo sapiens

<400> SEQUENCE: 28

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
    115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
```

```
                 210                 215                 220
Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
                275                 280                 285

Gln Trp Ile Lys His Val Glu Lys Asn Gly Ser Lys Tyr Gly Pro Asp
        290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
                340                 345                 350

Ala Trp Leu Thr Val Leu Pro Lys Gln Gln Ala Pro Gly Arg Glu Lys
                355                 360                 365

Glu Ile Thr Ala Ser Pro Asp Tyr Leu Glu Ile Ala Ile Tyr Cys Ile
        370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
                420                 425                 430

Ala Glu Ser Ser Ser Ser Met Asn Ser Asn Thr Pro Leu Val Arg Ile
                435                 440                 445

Thr Thr Arg Leu Ser Ser Thr Ala Asp Thr Pro Met Leu Ala Gly Val
        450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
                500                 505                 510

Val Thr Val Ala Val Lys Met Leu Lys Asp Asp Ala Thr Glu Lys Asp
                515                 520                 525

Leu Ser Asp Leu Val Ser Glu Met Glu Met Met Lys Met Ile Gly Lys
        530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
                580                 585                 590

Arg Val Pro Glu Glu Gln Met Thr Phe Lys Asp Leu Val Ser Cys Thr
                595                 600                 605

Tyr Gln Leu Ala Arg Gly Met Glu Tyr Leu Ala Ser Gln Lys Cys Ile
        610                 615                 620

His Arg Asp Leu Ala Ala Arg Asn Val Leu Val Thr Glu Asn Asn Val
625                 630                 635                 640
```

```
Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

<210> SEQ ID NO 29
<211> LENGTH: 254
<212> TYPE: PRT
<213> ORGANISM: Homo sapiens

<400> SEQUENCE: 29

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Gly Ser Gln Gly Leu
```

<210> SEQ ID NO 30
<211> LENGTH: 705
<212> TYPE: PRT
<213> ORGANISM: Homo sapiens

<400> SEQUENCE: 30

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
 50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Val Ser Ala Glu Ser Ser Ser
305                 310                 315                 320

Ser Met Asn Ser Asn Thr Pro Leu Val Arg Ile Thr Thr Arg Leu Ser
                325                 330                 335

Ser Thr Ala Asp Thr Pro Met Leu Ala Gly Val Ser Glu Tyr Glu Leu
            340                 345                 350

Pro Glu Asp Pro Lys Trp Glu Phe Pro Arg Asp Lys Leu Thr Leu Gly
        355                 360                 365
```

```
Lys Pro Leu Gly Glu Gly Cys Phe Gly Gln Val Val Met Ala Glu Ala
    370                 375                 380

Val Gly Ile Asp Lys Asp Lys Pro Lys Glu Ala Val Thr Val Ala Val
385                 390                 395                 400

Lys Met Leu Lys Asp Asp Ala Thr Glu Lys Asp Leu Ser Asp Leu Val
                405                 410                 415

Ser Glu Met Glu Met Met Lys Met Ile Gly Lys His Lys Asn Ile Ile
            420                 425                 430

Asn Leu Leu Gly Ala Cys Thr Gln Asp Gly Pro Leu Tyr Val Ile Val
        435                 440                 445

Glu Tyr Ala Ser Lys Gly Asn Leu Arg Glu Tyr Leu Arg Ala Arg Arg
450                 455                 460

Pro Pro Gly Met Glu Tyr Ser Tyr Asp Ile Asn Arg Val Pro Glu Glu
465                 470                 475                 480

Gln Met Thr Phe Lys Asp Leu Val Ser Cys Thr Tyr Gln Leu Ala Arg
                485                 490                 495

Gly Met Glu Tyr Leu Ala Ser Gln Lys Cys Ile His Arg Asp Leu Ala
            500                 505                 510

Ala Arg Asn Val Leu Val Thr Glu Asn Asn Val Met Lys Ile Ala Asp
        515                 520                 525

Phe Gly Leu Ala Arg Asp Ile Asn Asn Ile Asp Tyr Tyr Lys Lys Thr
530                 535                 540

Thr Asn Gly Arg Leu Pro Val Lys Trp Met Ala Pro Glu Ala Leu Phe
545                 550                 555                 560

Asp Arg Val Tyr Thr His Gln Ser Asp Val Trp Ser Phe Gly Val Leu
                565                 570                 575

Met Trp Glu Ile Phe Thr Leu Gly Gly Ser Pro Tyr Pro Gly Ile Pro
            580                 585                 590

Val Glu Glu Leu Phe Lys Leu Leu Lys Glu Gly His Arg Met Asp Lys
        595                 600                 605

Pro Ala Asn Cys Thr Asn Glu Leu Tyr Met Met Met Arg Asp Cys Trp
610                 615                 620

His Ala Val Pro Ser Gln Arg Pro Thr Phe Lys Gln Leu Val Glu Asp
625                 630                 635                 640

Leu Asp Arg Ile Leu Thr Leu Thr Thr Asn Glu Glu Tyr Leu Asp Leu
                645                 650                 655

Ser Gln Pro Leu Glu Gln Tyr Ser Pro Ser Tyr Pro Asp Thr Arg Ser
            660                 665                 670

Ser Cys Ser Ser Gly Asp Asp Ser Val Phe Ser Pro Asp Pro Met Pro
        675                 680                 685

Tyr Glu Pro Cys Leu Pro Gln Tyr Pro His Ile Asn Gly Ser Val Lys
    690                 695                 700

Thr
705

<210> SEQ ID NO 31
<211> LENGTH: 769
<212> TYPE: PRT
<213> ORGANISM: Homo sapiens

<400> SEQUENCE: 31

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30
```

```
Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
 50                  55                  60

Lys Asp Ala Ala Val Ile Ser Trp Thr Lys Asp Gly Val His Leu Gly
 65                  70                  75                  80

Pro Asn Asn Arg Thr Val Leu Ile Gly Glu Tyr Leu Gln Ile Lys Gly
                 85                  90                  95

Ala Thr Pro Arg Asp Ser Gly Leu Tyr Ala Cys Thr Ala Ser Arg Thr
                100                 105                 110

Val Asp Ser Glu Thr Trp Tyr Phe Met Val Asn Val Thr Asp Ala Ile
            115                 120                 125

Ser Ser Gly Asp Asp Glu Asp Asp Thr Asp Gly Ala Glu Asp Phe Val
        130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
                340                 345                 350

Ala Trp Leu Thr Val Leu Pro Lys Gln Gln Ala Pro Gly Arg Glu Lys
            355                 360                 365

Glu Ile Thr Ala Ser Pro Asp Tyr Leu Glu Ile Ala Ile Tyr Cys Ile
        370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445
```

```
Thr Thr Arg Leu Ser Ser Thr Ala Asp Thr Pro Met Leu Ala Gly Val
    450                 455                 460
Ser Glu Tyr Glu Leu Pro Glu Asp Pro Lys Trp Glu Phe Pro Arg Asp
465                 470                 475                 480
Lys Leu Thr Leu Gly Lys Pro Leu Gly Glu Gly Cys Phe Gly Gln Val
                485                 490                 495
Val Met Ala Glu Ala Val Gly Ile Asp Lys Asp Lys Pro Lys Glu Ala
            500                 505                 510
Val Thr Val Ala Val Lys Met Leu Lys Asp Asp Ala Thr Glu Lys Asp
                515                 520                 525
Leu Ser Asp Leu Val Ser Glu Met Glu Met Met Lys Met Ile Gly Lys
    530                 535                 540
His Lys Asn Ile Ile Asn Leu Leu Gly Ala Cys Thr Gln Asp Gly Pro
545                 550                 555                 560
Leu Tyr Val Ile Val Glu Tyr Ala Ser Lys Gly Asn Leu Arg Glu Tyr
                565                 570                 575
Leu Arg Ala Arg Arg Pro Pro Gly Met Glu Tyr Ser Tyr Asp Ile Asn
            580                 585                 590
Arg Val Pro Glu Glu Gln Met Thr Phe Lys Asp Leu Val Ser Cys Thr
                595                 600                 605
Tyr Gln Leu Ala Arg Gly Met Glu Tyr Leu Ala Ser Gln Lys Cys Ile
    610                 615                 620
His Arg Asp Leu Ala Ala Arg Asn Val Leu Val Thr Glu Asn Asn Val
625                 630                 635                 640
Met Lys Ile Ala Asp Phe Gly Leu Ala Arg Asp Ile Asn Asn Ile Asp
                645                 650                 655
Tyr Tyr Lys Lys Thr Thr Asn Gly Arg Leu Pro Val Lys Trp Met Ala
            660                 665                 670
Pro Glu Ala Leu Phe Asp Arg Val Tyr Thr His Gln Ser Asp Val Trp
                675                 680                 685
Ser Phe Gly Val Leu Met Trp Glu Ile Phe Thr Leu Gly Gly Ser Pro
    690                 695                 700
Tyr Pro Gly Ile Pro Val Glu Glu Leu Phe Lys Leu Lys Glu Gly
705                 710                 715                 720
His Arg Met Asp Lys Pro Ala Asn Cys Thr Asn Glu Leu Tyr Met Met
                725                 730                 735
Met Arg Asp Cys Trp His Ala Val Pro Ser Gln Arg Pro Thr Phe Lys
            740                 745                 750
Gln Leu Val Glu Asp Leu Asp Arg Ile Leu Thr Leu Thr Thr Asn Glu
    755                 760                 765
Ile

<210> SEQ ID NO 32
<211> LENGTH: 821
<212> TYPE: PRT
<213> ORGANISM: Homo sapiens

<400> SEQUENCE: 32

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45
```

-continued

```
Val Tyr Val Ala Ala Pro Gly Glu Ser Leu Glu Val Arg Cys Leu Leu
    50              55                  60
Lys Asp Ala Ala Val Ile Ser Trp Thr Lys Asp Gly Val His Leu Gly
 65              70                  75                      80
Pro Asn Asn Arg Thr Val Leu Ile Gly Glu Tyr Leu Gln Ile Lys Gly
                 85                  90                  95
Ala Thr Pro Arg Asp Ser Gly Leu Tyr Ala Cys Thr Ala Ser Arg Thr
                100                 105                 110
Val Asp Ser Glu Thr Trp Tyr Phe Met Val Asn Val Thr Asp Ala Ile
                115                 120                 125
Ser Ser Gly Asp Asp Glu Asp Thr Asp Gly Ala Glu Asp Phe Val
    130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
                180                 185                 190
Lys Asn Gly Lys Glu Phe Lys Gln Glu His Arg Ile Gly Gly Tyr Lys
                195                 200                 205
Val Arg Asn Gln His Trp Ser Leu Ile Met Glu Ser Val Val Pro Ser
    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
Ile Leu Gln Ala Gly Leu Pro Ala Asn Ala Ser Thr Val Val Gly Gly
                260                 265                 270
Asp Val Glu Phe Val Cys Lys Val Tyr Ser Asp Ala Gln Pro His Ile
                275                 280                 285
Gln Trp Ile Lys His Val Glu Lys Asn Gly Ser Lys Tyr Gly Pro Asp
    290                 295                 300
Gly Leu Pro Tyr Leu Lys Val Leu Lys Ala Ala Gly Val Asn Thr Thr
305                 310                 315                 320
Asp Lys Glu Ile Glu Val Leu Tyr Ile Arg Asn Val Thr Phe Glu Asp
                325                 330                 335
Ala Gly Glu Tyr Thr Cys Leu Ala Gly Asn Ser Ile Gly Ile Ser Phe
                340                 345                 350
His Ser Ala Trp Leu Thr Val Leu Pro Ala Pro Gly Arg Glu Lys Glu
                355                 360                 365
Ile Thr Ala Ser Pro Asp Tyr Leu Glu Ile Ala Ile Tyr Cys Ile Gly
                370                 375                 380
Val Phe Leu Ile Ala Cys Met Val Val Thr Val Ile Leu Cys Arg Met
385                 390                 395                 400
Lys Asn Thr Thr Lys Lys Pro Asp Phe Ser Ser Gln Pro Ala Val His
                405                 410                 415
Lys Leu Thr Lys Arg Ile Pro Leu Arg Arg Gln Val Thr Val Ser Ala
                420                 425                 430
Glu Ser Ser Ser Ser Met Asn Ser Asn Thr Pro Leu Val Arg Ile Thr
                435                 440                 445
Thr Arg Leu Ser Ser Thr Ala Asp Thr Pro Met Leu Ala Gly Val Ser
450                 455                 460
Glu Tyr Glu Leu Pro Glu Asp Pro Lys Trp Glu Phe Pro Arg Asp Lys
```

```
                465                 470                 475                 480
Leu Thr Leu Gly Lys Pro Leu Gly Glu Gly Cys Phe Gly Gln Val Val
                    485                 490                 495

Met Ala Glu Ala Val Gly Ile Asp Lys Asp Lys Pro Lys Glu Ala Val
                500                 505                 510

Thr Val Ala Val Lys Met Leu Lys Asp Asp Ala Thr Glu Lys Asp Leu
            515                 520                 525

Ser Asp Leu Val Ser Glu Met Glu Met Met Lys Met Ile Gly Lys His
        530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
                580                 585                 590

Val Pro Glu Glu Gln Met Thr Phe Lys Asp Leu Val Ser Cys Thr Tyr
            595                 600                 605

Gln Leu Ala Arg Gly Met Glu Tyr Leu Ala Ser Gln Lys Cys Ile His
        610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
                660                 665                 670

Glu Ala Leu Phe Asp Arg Val Tyr Thr His Gln Ser Asp Val Trp Ser
            675                 680                 685

Phe Gly Val Leu Met Trp Glu Ile Phe Thr Leu Gly Gly Ser Pro Tyr
        690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
                740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
        770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 33
<211> LENGTH: 822
<212> TYPE: PRT
<213> ORGANISM: Homo sapiens

<400> SEQUENCE: 33

Met Trp Ser Trp Lys Cys Leu Leu Phe Trp Ala Val Leu Val Thr Ala
1               5                   10                  15
```

-continued

```
Thr Leu Cys Thr Ala Arg Pro Ser Pro Thr Leu Pro Glu Gln Ala Gln
         20                  25                  30

Pro Trp Gly Ala Pro Val Glu Val Glu Ser Phe Leu Val His Pro Gly
     35                  40                  45

Asp Leu Leu Gln Leu Arg Cys Arg Leu Arg Asp Asp Val Gln Ser Ile
 50                  55                  60

Asn Trp Leu Arg Asp Gly Val Gln Leu Ala Glu Ser Asn Arg Thr Arg
 65                  70                  75                  80

Ile Thr Gly Glu Glu Val Glu Val Gln Asp Ser Val Pro Ala Asp Ser
                 85                  90                  95

Gly Leu Tyr Ala Cys Val Thr Ser Ser Pro Ser Gly Ser Asp Thr Thr
                100                 105                 110

Tyr Phe Ser Val Asn Val Ser Asp Ala Leu Pro Ser Ser Glu Asp Asp
             115                 120                 125

Asp Asp Asp Asp Asp Ser Ser Ser Glu Glu Lys Glu Thr Asp Asn Thr
 130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                 165                 170                 175

Lys Cys Pro Ser Ser Gly Thr Pro Asn Pro Thr Leu Arg Trp Leu Lys
                 180                 185                 190

Asn Gly Lys Glu Phe Lys Pro Asp His Arg Ile Gly Gly Tyr Lys Val
             195                 200                 205

Arg Tyr Ala Thr Trp Ser Ile Ile Met Asp Ser Val Val Pro Ser Asp
 210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                 245                 250                 255

Leu Gln Ala Gly Leu Pro Ala Asn Lys Thr Val Ala Leu Gly Ser Asn
                 260                 265                 270

Val Glu Phe Met Cys Lys Val Tyr Ser Asp Pro Gln Pro His Ile Gln
             275                 280                 285

Trp Leu Lys His Ile Glu Val Asn Gly Ser Lys Ile Gly Pro Asp Asn
 290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                 325                 330                 335

Gly Glu Tyr Thr Cys Leu Ala Gly Asn Ser Ile Gly Leu Ser His His
                 340                 345                 350

Ser Ala Trp Leu Thr Val Leu Glu Ala Leu Glu Glu Arg Pro Ala Val
             355                 360                 365

Met Thr Ser Pro Leu Tyr Leu Glu Ile Ile Ile Tyr Cys Thr Gly Ala
 370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                 405                 410                 415

Leu Ala Lys Ser Ile Pro Leu Arg Arg Gln Val Thr Val Ser Ala Asp
                 420                 425                 430

Ser Ser Ala Ser Met Asn Ser Gly Val Leu Leu Val Arg Pro Ser Arg
```

```
                435                 440                 445
Leu Ser Ser Gly Thr Pro Met Leu Ala Gly Val Ser Glu Tyr Glu
450                 455                 460
Leu Pro Glu Asp Pro Arg Trp Glu Leu Pro Arg Asp Arg Leu Val Leu
465                 470                 475             480
Gly Lys Pro Leu Gly Glu Gly Cys Phe Gly Gln Val Val Leu Ala Glu
                485                 490                 495
Ala Ile Gly Leu Asp Lys Asp Lys Pro Asn Arg Val Thr Lys Val Ala
                500                 505                 510
Val Lys Met Leu Lys Ser Asp Ala Thr Glu Lys Asp Leu Ser Asp Leu
            515                 520                 525
Ile Ser Glu Met Glu Met Met Lys Met Ile Gly Lys His Lys Asn Ile
            530                 535                 540
Ile Asn Leu Leu Gly Ala Cys Thr Gln Asp Gly Pro Leu Tyr Val Ile
545                 550                 555                 560
Val Glu Tyr Ala Ser Lys Gly Asn Leu Arg Glu Tyr Leu Gln Ala Arg
                565                 570                 575
Arg Pro Pro Gly Leu Glu Tyr Cys Tyr Asn Pro Ser His Asn Pro Glu
                580                 585                 590
Glu Gln Leu Ser Ser Lys Asp Leu Val Ser Cys Ala Tyr Gln Val Ala
            595                 600                 605
Arg Gly Met Glu Tyr Leu Ala Ser Lys Lys Cys Ile His Arg Asp Leu
            610                 615                 620
Ala Ala Arg Asn Val Leu Val Thr Glu Asp Asn Val Met Lys Ile Ala
625                 630                 635                 640
Asp Phe Gly Leu Ala Arg Asp Ile His His Ile Asp Tyr Tyr Lys Lys
                645                 650                 655
Thr Thr Asn Gly Arg Leu Pro Val Lys Trp Met Ala Pro Glu Ala Leu
                660                 665                 670
Phe Asp Arg Ile Tyr Thr His Gln Ser Asp Val Trp Ser Phe Gly Val
            675                 680                 685
Leu Leu Trp Glu Ile Phe Thr Leu Gly Gly Ser Pro Tyr Pro Gly Val
            690                 695                 700
Pro Val Glu Glu Leu Phe Lys Leu Leu Lys Glu Gly His Arg Met Asp
705                 710                 715             720
Lys Pro Ser Asn Cys Thr Asn Glu Leu Tyr Met Met Met Arg Asp Cys
                725                 730                 735
Trp His Ala Val Pro Ser Gln Arg Pro Thr Phe Lys Gln Leu Val Glu
                740                 745                 750
Asp Leu Asp Arg Ile Val Ala Leu Thr Ser Asn Gln Glu Tyr Leu Asp
            755                 760                 765
Leu Ser Met Pro Leu Asp Gln Tyr Ser Pro Ser Phe Pro Asp Thr Arg
            770                 775                 780
Ser Ser Thr Cys Ser Ser Gly Glu Asp Ser Val Phe Ser His Glu Pro
785                 790                 795                 800
Leu Pro Glu Glu Pro Cys Leu Pro Arg His Pro Ala Gln Leu Ala Asn
                805                 810                 815
Gly Gly Leu Lys Arg Arg
                820

<210> SEQ ID NO 34
<211> LENGTH: 1400
<212> TYPE: PRT
<213> ORGANISM: Homo sapiens
```

<400> SEQUENCE: 34

| | | | | | | | | | | | | | | |
|---|---|---|---|---|---|---|---|---|---|---|---|---|---|---|
| Met | Glu | Leu | Leu | Pro | Pro | Leu | Pro | Gln | Ser | Phe | Leu | Leu | Leu | Leu |
| 1 | | | | 5 | | | | | 10 | | | | | 15 |
| Leu | Pro | Ala | Lys | Pro | Ala | Ala | Gly | Glu | Asp | Trp | Gln | Cys | Pro | Arg | Thr |
| | | | 20 | | | | | 25 | | | | | 30 | | |
| Pro | Tyr | Ala | Ala | Ser | Arg | Asp | Phe | Asp | Val | Lys | Tyr | Val | Val | Pro | Ser |
| | | | 35 | | | | 40 | | | | | 45 | | | |
| Phe | Ser | Ala | Gly | Gly | Leu | Val | Gln | Ala | Met | Val | Thr | Tyr | Glu | Gly | Asp |
| | 50 | | | | | 55 | | | | | 60 | | | | |
| Arg | Asn | Glu | Ser | Ala | Val | Phe | Val | Ala | Ile | Arg | Asn | Arg | Leu | His | Val |
| 65 | | | | 70 | | | | | 75 | | | | | 80 | |
| Leu | Gly | Pro | Asp | Leu | Lys | Ser | Val | Gln | Ser | Leu | Ala | Thr | Gly | Pro | Ala |
| | | | | 85 | | | | | 90 | | | | | 95 | |
| Gly | Asp | Pro | Gly | Cys | Gln | Thr | Cys | Ala | Ala | Cys | Gly | Pro | Gly | Pro | His |
| | | | 100 | | | | | 105 | | | | | 110 | | |
| Gly | Pro | Pro | Gly | Asp | Thr | Asp | Thr | Lys | Val | Leu | Val | Leu | Asp | Pro | Ala |
| | | | 115 | | | | | 120 | | | | | 125 | | |
| Leu | Pro | Ala | Leu | Val | Ser | Cys | Gly | Ser | Ser | Leu | Gln | Gly | Arg | Cys | Phe |
| | 130 | | | | | 135 | | | | | 140 | | | | |
| Leu | His | Asp | Leu | Glu | Pro | Gln | Gly | Thr | Ala | Val | His | Leu | Ala | Ala | Pro |
| 145 | | | | | 150 | | | | | 155 | | | | | 160 |
| Ala | Cys | Leu | Phe | Ser | Ala | His | His | Asn | Arg | Pro | Asp | Asp | Cys | Pro | Asp |
| | | | | 165 | | | | | 170 | | | | | 175 | |
| Cys | Val | Ala | Ser | Pro | Leu | Gly | Thr | Arg | Val | Thr | Val | Glu | Gln | Gly | |
| | | | 180 | | | | | 185 | | | | | 190 | | |
| Gln | Ala | Ser | Tyr | Phe | Tyr | Val | Ala | Ser | Ser | Leu | Asp | Ala | Ala | Val | Ala |
| | | | 195 | | | | | 200 | | | | | 205 | | |
| Gly | Ser | Phe | Ser | Pro | Arg | Ser | Val | Ser | Ile | Arg | Arg | Leu | Lys | Ala | Asp |
| | 210 | | | | | 215 | | | | | 220 | | | | |
| Ala | Ser | Gly | Phe | Ala | Pro | Gly | Phe | Val | Ala | Leu | Ser | Val | Leu | Pro | Lys |
| 225 | | | | | 230 | | | | | 235 | | | | | 240 |
| His | Leu | Val | Ser | Tyr | Ser | Ile | Glu | Tyr | Val | His | Ser | Phe | His | Thr | Gly |
| | | | | 245 | | | | | 250 | | | | | 255 | |
| Ala | Phe | Val | Tyr | Phe | Leu | Thr | Val | Gln | Pro | Ala | Ser | Val | Thr | Asp | Asp |
| | | | 260 | | | | | 265 | | | | | 270 | | |
| Pro | Ser | Ala | Leu | His | Thr | Arg | Leu | Ala | Arg | Leu | Ser | Ala | Thr | Glu | Pro |
| | | | 275 | | | | | 280 | | | | | 285 | | |
| Glu | Leu | Gly | Asp | Tyr | Arg | Glu | Leu | Val | Leu | Asp | Cys | Arg | Phe | Ala | Pro |
| | 290 | | | | | 295 | | | | | 300 | | | | |
| Lys | Arg | Arg | Arg | Arg | Gly | Ala | Pro | Glu | Gly | Gly | Gln | Pro | Tyr | Pro | Val |
| 305 | | | | | 310 | | | | | 315 | | | | | 320 |
| Leu | Gln | Val | Ala | His | Ser | Ala | Pro | Val | Gly | Ala | Gln | Leu | Ala | Thr | Glu |
| | | | | 325 | | | | | 330 | | | | | 335 | |
| Leu | Ser | Ile | Ala | Glu | Gly | Gln | Glu | Val | Leu | Phe | Gly | Val | Phe | Val | Thr |
| | | | 340 | | | | | 345 | | | | | 350 | | |
| Gly | Lys | Asp | Gly | Gly | Pro | Gly | Val | Gly | Pro | Asn | Ser | Val | Val | Cys | Ala |
| | | | 355 | | | | | 360 | | | | | 365 | | |
| Phe | Pro | Ile | Asp | Leu | Leu | Asp | Thr | Leu | Ile | Asp | Glu | Gly | Val | Glu | Arg |
| | 370 | | | | | 375 | | | | | 380 | | | | |
| Cys | Cys | Glu | Ser | Pro | Val | His | Pro | Gly | Leu | Arg | Arg | Gly | Leu | Asp | Phe |
| 385 | | | | | 390 | | | | | 395 | | | | | 400 |
| Phe | Gln | Ser | Pro | Ser | Phe | Cys | Pro | Asn | Pro | Pro | Gly | Leu | Glu | Ala | Leu |

-continued

```
                405                 410                 415
Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830
```

```
Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
850                 855                 860

Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
                900                 905                 910

Met Val Val Cys Pro Leu Pro Ser Leu Gln Leu Gly Gln Asp Gly
        915                 920                 925

Ala Pro Leu Gln Val Cys Val Asp Gly Glu Cys His Ile Leu Gly Arg
        930                 935                 940

Val Val Arg Pro Gly Pro Asp Gly Val Pro Gln Ser Thr Leu Leu Gly
945                 950                 955                 960

Ile Leu Leu Pro Leu Leu Leu Val Ala Ala Leu Ala Thr Ala Leu
                965                 970                 975

Val Phe Ser Tyr Trp Trp Arg Arg Lys Gln Leu Val Leu Pro Pro Asn
        980                 985                 990

Leu Asn Asp Leu Ala Ser Leu Asp Gln Thr Ala Gly Ala Thr Pro Leu
        995                 1000                1005

Pro Ile Leu Tyr Ser Gly Ser Asp Tyr Arg Ser Gly Leu Ala Leu
        1010                1015                1020

Pro Ala Ile Asp Gly Leu Asp Ser Thr Thr Cys Val His Gly Ala
        1025                1030                1035

Ser Phe Ser Asp Ser Glu Asp Glu Ser Cys Val Pro Leu Leu Arg
        1040                1045                1050

Lys Glu Ser Ile Gln Leu Arg Asp Leu Asp Ser Ala Leu Leu Ala
        1055                1060                1065

Glu Val Lys Asp Val Leu Ile Pro His Glu Arg Val Val Thr His
        1070                1075                1080

Ser Asp Arg Val Ile Gly Lys Gly His Phe Gly Val Val Tyr His
        1085                1090                1095

Gly Glu Tyr Ile Asp Gln Ala Gln Asn Arg Ile Gln Cys Ala Ile
        1100                1105                1110

Lys Ser Leu Ser Arg Ile Thr Glu Met Gln Gln Val Glu Ala Phe
        1115                1120                1125

Leu Arg Glu Gly Leu Leu Met Arg Gly Leu Asn His Pro Asn Val
        1130                1135                1140

Leu Ala Leu Ile Gly Ile Met Leu Pro Pro Glu Gly Leu Pro His
        1145                1150                1155

Val Leu Leu Pro Tyr Met Cys His Gly Asp Leu Leu Gln Phe Ile
        1160                1165                1170

Arg Ser Pro Gln Arg Asn Pro Thr Val Lys Asp Leu Ile Ser Phe
        1175                1180                1185

Gly Leu Gln Val Ala Arg Gly Met Glu Tyr Leu Ala Glu Gln Lys
        1190                1195                1200

Phe Val His Arg Asp Leu Ala Ala Arg Asn Cys Met Leu Asp Glu
        1205                1210                1215

Ser Phe Thr Val Lys Val Ala Asp Phe Gly Leu Ala Arg Asp Ile
        1220                1225                1230
```

Leu Asp Arg Glu Tyr Tyr Ser Val Gln Gln His Arg His Ala Arg
    1235                1240                1245

Leu Pro Val Lys Trp Met Ala Leu Glu Ser Leu Gln Thr Tyr Arg
    1250                1255                1260

Phe Thr Thr Lys Ser Asp Val Trp Ser Phe Gly Val Leu Leu Trp
    1265                1270                1275

Glu Leu Leu Thr Arg Gly Ala Pro Pro Tyr Arg His Ile Asp Pro
    1280                1285                1290

Phe Asp Leu Thr His Phe Leu Ala Gln Gly Arg Arg Leu Pro Gln
    1295                1300                1305

Pro Glu Tyr Cys Pro Asp Ser Leu Tyr Gln Val Met Gln Gln Cys
    1310                1315                1320

Trp Glu Ala Asp Pro Ala Val Arg Pro Thr Phe Arg Val Leu Val
    1325                1330                1335

Gly Glu Val Glu Gln Ile Val Ser Ala Leu Leu Gly Asp His Tyr
    1340                1345                1350

Val Gln Leu Pro Ala Thr Tyr Met Asn Leu Gly Pro Ser Thr Ser
    1355                1360                1365

His Glu Met Asn Val Arg Pro Glu Gln Pro Gln Phe Ser Pro Met
    1370                1375                1380

Pro Gly Asn Val Arg Arg Pro Arg Pro Leu Ser Glu Pro Pro Arg
    1385                1390                1395

Pro Thr
    1400

<210> SEQ ID NO 35
<211> LENGTH: 976
<212> TYPE: PRT
<213> ORGANISM: Homo sapiens

<400> SEQUENCE: 35

Met Arg Gly Ala Arg Gly Ala Trp Asp Phe Leu Cys Val Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
            115                 120                 125

Asp Asn Asp Thr Leu Val Arg Cys Pro Leu Thr Asp Pro Glu Val Thr
        130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

```
Lys Ser Val Leu Ser Glu Lys Phe Ile Leu Lys Val Arg Pro Ala Phe
            195                 200                 205

Lys Ala Val Pro Val Val Ser Val Ser Lys Ala Ser Tyr Leu Leu Arg
        210                 215                 220

Glu Gly Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
            245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
            275                 280                 285

Met Cys Tyr Ala Asn Asn Thr Phe Gly Ser Ala Asn Val Thr Thr Thr
        290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
        370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
        450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
            485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
        530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
            565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605
```

```
Tyr Gly Leu Ile Lys Ser Asp Ala Ala Met Thr Val Ala Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
            645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                    725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                    805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                    885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                    965                 970                 975

<210> SEQ ID NO 36
<211> LENGTH: 211
<212> TYPE: PRT
<213> ORGANISM: Homo sapiens

<400> SEQUENCE: 36

Met Arg Thr Leu Ala Cys Leu Leu Leu Leu Gly Cys Gly Tyr Leu Ala
1               5                   10                  15
```

His Val Leu Ala Glu Ala Glu Ile Pro Arg Val Ile Glu Arg
         20                  25                  30

Leu Ala Arg Ser Gln Ile His Ser Ile Arg Asp Leu Gln Arg Leu Leu
     35                  40                  45

Glu Ile Asp Ser Val Gly Ser Glu Asp Ser Leu Asp Thr Ser Leu Arg
 50                  55                  60

Ala His Gly Val His Ala Thr Lys His Val Pro Glu Lys Arg Pro Leu
 65                  70                  75                  80

Pro Ile Arg Arg Lys Arg Ser Ile Glu Glu Ala Val Pro Ala Val Cys
                 85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
        195                 200                 205

Lys Pro Thr
    210

<210> SEQ ID NO 37
<211> LENGTH: 1089
<212> TYPE: PRT
<213> ORGANISM: Homo sapiens

<400> SEQUENCE: 37

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln

```
                165                 170                 175
Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590
```

```
Leu Val Leu Gly Arg Val Leu Ser Gly Ala Phe Gly Lys Val Val
            595                 600                 605
Glu Gly Thr Ala Tyr Gly Leu Ser Arg Ser Gln Pro Val Met Lys Val
610                 615                 620
Ala Val Lys Met Leu Lys Pro Thr Ala Arg Ser Ser Glu Lys Gln Ala
625                 630                 635                 640
Leu Met Ser Glu Leu Lys Ile Met Thr His Leu Gly Pro His Leu Asn
                645                 650                 655
Ile Val Asn Leu Leu Gly Ala Cys Thr Lys Ser Gly Pro Ile Tyr Ile
                660                 665                 670
Ile Thr Glu Tyr Cys Phe Tyr Gly Asp Leu Val Asn Tyr Leu His Lys
                675                 680                 685
Asn Arg Asp Ser Phe Leu Ser His His Pro Glu Lys Pro Lys Lys Glu
            690                 695                 700
Leu Asp Ile Phe Gly Leu Asn Pro Ala Asp Glu Ser Thr Arg Ser Tyr
705                 710                 715                 720
Val Ile Leu Ser Phe Glu Asn Asn Gly Asp Tyr Met Asp Met Lys Gln
                725                 730                 735
Ala Asp Thr Thr Gln Tyr Val Pro Met Leu Glu Arg Lys Glu Val Ser
            740                 745                 750
Lys Tyr Ser Asp Ile Gln Arg Ser Leu Tyr Asp Arg Pro Ala Ser Tyr
            755                 760                 765
Lys Lys Lys Ser Met Leu Asp Ser Glu Val Lys Asn Leu Leu Ser Asp
            770                 775                 780
Asp Asn Ser Glu Gly Leu Thr Leu Leu Asp Leu Leu Ser Phe Thr Tyr
785                 790                 795                 800
Gln Val Ala Arg Gly Met Glu Phe Leu Ala Ser Lys Asn Cys Val His
                805                 810                 815
Arg Asp Leu Ala Ala Arg Asn Val Leu Leu Ala Gln Gly Lys Ile Val
                820                 825                 830
Lys Ile Cys Asp Phe Gly Leu Ala Arg Asp Ile Met His Asp Ser Asn
            835                 840                 845
Tyr Val Ser Lys Gly Ser Thr Phe Leu Pro Val Lys Trp Met Ala Pro
            850                 855                 860
Glu Ser Ile Phe Asp Asn Leu Tyr Thr Thr Leu Ser Asp Val Trp Ser
865                 870                 875                 880
Tyr Gly Ile Leu Leu Trp Glu Ile Phe Ser Leu Gly Gly Thr Pro Tyr
                885                 890                 895
Pro Gly Met Met Val Asp Ser Thr Phe Tyr Asn Lys Ile Lys Ser Gly
            900                 905                 910
Tyr Arg Met Ala Lys Pro Asp His Ala Thr Ser Glu Val Tyr Glu Ile
            915                 920                 925
Met Val Lys Cys Trp Asn Ser Glu Pro Glu Lys Arg Pro Ser Phe Tyr
            930                 935                 940
His Leu Ser Glu Ile Val Glu Asn Leu Leu Pro Gly Gln Tyr Lys Lys
945                 950                 955                 960
Ser Tyr Glu Lys Ile His Leu Asp Phe Leu Lys Ser Asp His Pro Ala
                965                 970                 975
Val Ala Arg Met Arg Val Asp Ser Asp Asn Ala Tyr Ile Gly Val Thr
            980                 985                 990
Tyr Lys Asn Glu Glu Asp Lys Leu Lys Asp Trp Glu Gly Gly Leu Asp
            995                 1000                1005
```

```
Glu Gln Arg Leu Ser Ala Asp Ser Gly Tyr Ile Ile Pro Leu Pro
    1010                1015                1020

Asp Ile Asp Pro Val Pro Glu Glu Glu Asp Leu Gly Lys Arg Asn
    1025                1030                1035

Arg His Ser Ser Gln Thr Ser Glu Glu Ser Ala Ile Glu Thr Gly
    1040                1045                1050

Ser Ser Ser Ser Thr Phe Ile Lys Arg Glu Asp Glu Thr Ile Glu
    1055                1060                1065

Asp Ile Asp Met Met Asp Asp Ile Gly Ile Asp Ser Ser Asp Leu
    1070                1075                1080

Val Glu Asp Ser Phe Leu
    1085

<210> SEQ ID NO 38
<211> LENGTH: 822
<212> TYPE: PRT
<213> ORGANISM: Homo sapiens

<400> SEQUENCE: 38

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285
```

```
Trp Leu Lys His Ile Glu Val Asn Gly Ser Lys Ile Gly Pro Asp Asn
            290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
                340                 345                 350

Ser Ala Trp Leu Thr Val Leu Glu Ala Leu Glu Glu Arg Pro Ala Val
            355                 360                 365

Met Thr Ser Pro Leu Tyr Leu Glu Ile Ile Tyr Cys Thr Gly Ala
            370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
                420                 425                 430

Ser Ser Ala Ser Met Asn Ser Gly Val Leu Leu Val Arg Pro Ser Arg
            435                 440                 445

Leu Ser Ser Ser Gly Thr Pro Met Leu Ala Gly Val Ser Glu Tyr Glu
450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
            530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
                580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
                660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
            690                 695                 700
```

```
Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Arg Asp Cys
            725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
            770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
            805                 810                 815

Gly Gly Leu Lys Arg Arg
            820

<210> SEQ ID NO 39
<211> LENGTH: 820
<212> TYPE: PRT
<213> ORGANISM: Homo sapiens

<400> SEQUENCE: 39

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
            50                  55                  60

Asn Trp Leu Arg Asp Gly Val Gln Leu Ala Glu Ser Asn Arg Thr Arg
65              70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
            115                 120                 125

Asp Asp Asp Asp Asp Ser Ser Ser Glu Glu Lys Glu Thr Asp Asn Thr
            130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
            195                 200                 205

Arg Tyr Ala Thr Trp Ser Ile Ile Met Asp Ser Val Val Pro Ser Asp
            210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255
```

```
Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
                340                 345                 350

Ser Ala Trp Leu Thr Val Leu Glu Ala Leu Glu Glu Arg Pro Ala Val
            355                 360                 365

Met Thr Ser Pro Leu Tyr Leu Glu Ile Ile Ile Tyr Cys Thr Gly Ala
        370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Ser Ala Asp Ser Ser
                420                 425                 430

Ala Ser Met Asn Ser Gly Val Leu Leu Val Arg Pro Ser Arg Leu Ser
            435                 440                 445

Ser Ser Gly Thr Pro Met Leu Ala Gly Val Ser Glu Tyr Glu Leu Pro
        450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
                500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
        530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
                580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
        610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
                660                 665                 670
```

```
Arg Ile Tyr Thr His Gln Ser Asp Val Trp Ser Phe Gly Val Leu Leu
            675                 680                 685

Trp Glu Ile Phe Thr Leu Gly Gly Ser Pro Tyr Pro Gly Val Pro Val
690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 40
<211> LENGTH: 820
<212> TYPE: PRT
<213> ORGANISM: Homo sapiens

<400> SEQUENCE: 40

Met Trp Ser Trp Lys Cys Leu Leu Phe Trp Ala Val Leu Val Thr Ala
1                   5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
210                 215                 220
```

```
Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
            245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
            275                 280                 285

Lys His Ile Glu Val Asn Gly Ser Lys Ile Gly Pro Asp Asn Leu Pro
            290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
            325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365

Ser Pro Leu Tyr Leu Glu Ile Ile Ile Tyr Cys Thr Gly Ala Phe Leu
370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
            405                 410                 415

Lys Ser Ile Pro Leu Arg Arg Gln Val Thr Val Ser Ala Asp Ser Ser
            420                 425                 430

Ala Ser Met Asn Ser Gly Val Leu Leu Val Arg Pro Ser Arg Leu Ser
        435                 440                 445

Ser Ser Gly Thr Pro Met Leu Ala Gly Val Ser Glu Tyr Glu Leu Pro
450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
            485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
            530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
            565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
            610                 615                 620

Arg Asn Val Leu Val Thr Glu Asp Asn Val Met Lys Ile Ala Asp Phe
625                 630                 635                 640
```

```
Gly Leu Ala Arg Asp Ile His His Ile Asp Tyr Tyr Lys Lys Thr Thr
            645                 650                 655

Asn Gly Arg Leu Pro Val Lys Trp Met Ala Pro Glu Ala Leu Phe Asp
        660                 665                 670

Arg Ile Tyr Thr His Gln Ser Asp Val Trp Ser Phe Gly Val Leu Leu
            675                 680                 685

Trp Glu Ile Phe Thr Leu Gly Gly Ser Pro Tyr Pro Gly Val Pro Val
690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
            725                 730                 735

Ala Val Pro Ser Gln Arg Pro Thr Phe Lys Gln Leu Val Glu Asp Leu
        740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
            805                 810                 815

Leu Lys Arg Arg
        820

<210> SEQ ID NO 41
<211> LENGTH: 150
<212> TYPE: PRT
<213> ORGANISM: Homo sapiens

<400> SEQUENCE: 41

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Ala Cys Pro Asp Leu Gln Glu Ala Lys
        115                 120                 125

Trp Cys Ser Ala Ser Phe His Ser Ile Thr Pro Leu Pro Phe Gly Leu
    130                 135                 140

Gly Thr Arg Leu Ser Asp
145                 150

<210> SEQ ID NO 42
<211> LENGTH: 302
<212> TYPE: PRT
<213> ORGANISM: Homo sapiens
```

```
<400> SEQUENCE: 42

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
            20                  25                  30

Leu Pro Ser Ser Glu Asp Asp Asp Asp Asp Asp Ser Ser Glu
        35                  40                  45

Glu Lys Glu Thr Asp Asn Thr Lys Pro Asn Arg Met Pro Val Ala Pro
50                  55                  60

Tyr Trp Thr Ser Pro Glu Lys Met Glu Lys Lys Leu His Ala Val Pro
65                  70                  75                  80

Ala Ala Lys Thr Val Lys Phe Lys Cys Pro Ser Ser Gly Thr Pro Asn
                85                  90                  95

Pro Thr Leu Arg Trp Leu Lys Asn Gly Lys Glu Phe Lys Pro Asp His
            100                 105                 110

Arg Ile Gly Gly Tyr Lys Val Arg Tyr Ala Thr Trp Ser Ile Ile Met
        115                 120                 125

Asp Ser Val Val Pro Ser Asp Lys Gly Asn Tyr Thr Cys Ile Val Glu
130                 135                 140

Asn Glu Tyr Gly Ser Ile Asn His Thr Tyr Gln Leu Asp Val Val Glu
145                 150                 155                 160

Arg Ser Pro His Arg Pro Ile Leu Gln Ala Gly Leu Pro Ala Asn Lys
                165                 170                 175

Thr Val Ala Leu Gly Ser Asn Val Glu Phe Met Cys Lys Val Tyr Ser
            180                 185                 190

Asp Pro Gln Pro His Ile Gln Trp Leu Lys His Ile Glu Val Asn Gly
        195                 200                 205

Ser Lys Ile Gly Pro Asp Asn Leu Pro Tyr Val Gln Ile Leu Lys Val
    210                 215                 220

Ile Met Ala Pro Val Phe Val Gly Gln Ser Thr Gly Lys Glu Thr Thr
225                 230                 235                 240

Val Ser Gly Ala Gln Val Pro Val Gly Arg Leu Ser Cys Pro Arg Met
                245                 250                 255

Gly Ser Phe Leu Thr Leu Gln Ala His Thr Leu His Leu Ser Arg Asp
            260                 265                 270

Leu Ala Thr Ser Pro Arg Thr Ser Asn Arg Gly His Lys Val Glu Val
        275                 280                 285

Ser Trp Glu Gln Arg Ala Ala Gly Met Gly Gly Ala Gly Leu
    290                 295                 300

<210> SEQ ID NO 43
<211> LENGTH: 61
<212> TYPE: PRT
<213> ORGANISM: Homo sapiens

<400> SEQUENCE: 43

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Cys
            20                  25                  30

Pro Asp Leu Gln Glu Ala Lys Ser Cys Ser Ala Ser Phe His Ser Ile
        35                  40                  45

Thr Pro Leu Pro Phe Gly Leu Gly Thr Arg Leu Ser Asp
        50                  55                  60
```

<210> SEQ ID NO 44
<211> LENGTH: 300
<212> TYPE: PRT
<213> ORGANISM: Homo sapiens

<400> SEQUENCE: 44

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
            20                  25                  30

Leu Pro Ser Ser Glu Asp Asp Asp Asp Asp Asp Ser Ser Ser Ser Glu
        35                  40                  45

Glu Lys Glu Thr Asp Asn Thr Lys Pro Asn Pro Val Ala Pro Tyr Trp
    50                  55                  60

Thr Ser Pro Glu Lys Met Glu Lys Lys Leu His Ala Val Pro Ala Ala
65                  70                  75                  80

Lys Thr Val Lys Phe Lys Cys Pro Ser Ser Gly Thr Pro Asn Pro Thr
                85                  90                  95

Leu Arg Trp Leu Lys Asn Gly Lys Glu Phe Lys Pro Asp His Arg Ile
            100                 105                 110

Gly Gly Tyr Lys Val Arg Tyr Ala Thr Trp Ser Ile Ile Met Asp Ser
        115                 120                 125

Val Val Pro Ser Asp Lys Gly Asn Tyr Thr Cys Ile Val Glu Asn Glu
    130                 135                 140

Tyr Gly Ser Ile Asn His Thr Tyr Gln Leu Asp Val Val Glu Arg Ser
145                 150                 155                 160

Pro His Arg Pro Ile Leu Gln Ala Gly Leu Pro Ala Asn Lys Thr Val
                165                 170                 175

Ala Leu Gly Ser Asn Val Glu Phe Met Cys Lys Val Tyr Ser Asp Pro
            180                 185                 190

Gln Pro His Ile Gln Trp Leu Lys His Ile Glu Val Asn Gly Ser Lys
        195                 200                 205

Ile Gly Pro Asp Asn Leu Pro Tyr Val Gln Ile Leu Lys Val Ile Met
    210                 215                 220

Ala Pro Val Phe Val Gly Gln Ser Thr Gly Lys Glu Thr Thr Val Ser
225                 230                 235                 240

Gly Ala Gln Val Pro Val Gly Arg Leu Ser Cys Pro Arg Met Gly Ser
                245                 250                 255

Phe Leu Thr Leu Gln Ala His Thr Leu His Leu Ser Arg Asp Leu Ala
            260                 265                 270

Thr Ser Pro Arg Thr Ser Asn Arg Gly His Lys Val Glu Val Ser Trp
        275                 280                 285

Glu Gln Arg Ala Ala Gly Met Gly Gly Ala Gly Leu
    290                 295                 300
```

<210> SEQ ID NO 45
<211> LENGTH: 1400
<212> TYPE: PRT
<213> ORGANISM: Homo sapiens

<400> SEQUENCE: 45

```
Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30
```

```
Pro Tyr Ala Ala Ser Arg Asp Phe Asp Val Lys Tyr Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
                100                 105                 110

Gly Pro Pro Gly Asp Thr Asp Thr Lys Val Leu Val Leu Asp Pro Ala
            115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445
```

Thr Ala Leu Tyr Val Thr Arg Leu Asp Asn Val Thr Val Ala His Met
450             455                 460

Gly Thr Met Asp Gly Arg Ile Leu Gln Val Glu Leu Val Arg Ser Leu
465             470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
            515                 520                 525

His Phe Leu Thr Cys Gly Arg Cys Leu Arg Ala Trp His Phe Met Gly
530             535                 540

Cys Gly Trp Cys Gly Asn Met Cys Gly Gln Gln Lys Glu Cys Pro Gly
545             550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
                595                 600                 605

Val Thr Val Gly Gln Ser Pro Cys Arg Pro Leu Pro Lys Asp Ser Ser
610             615                 620

Lys Leu Arg Pro Val Pro Arg Lys Asp Phe Val Glu Phe Glu Cys
625             630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
            675                 680                 685

Val Gln Pro Leu Phe Gly Pro Arg Ala Gly Gly Thr Cys Leu Thr Leu
            690                 695                 700

Glu Gly Gln Ser Leu Ser Val Gly Thr Ser Arg Ala Val Leu Val Asn
705             710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
            755                 760                 765

Asp Pro Val Val Leu Ser Ile Ser Pro Asn Cys Gly Tyr Ile Asn Ser
770             775                 780

His Ile Thr Ile Cys Gly Gln His Leu Thr Ser Ala Trp His Leu Val
785             790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
            835                 840                 845

Ala Ala Gly Phe Thr Leu Pro Gly Phe Arg Phe Leu Pro Pro His
850             855                 860

Pro Pro Ser Ala Asn Leu Val Pro Leu Lys Pro Glu Glu His Ala Ile

-continued

```
                865                 870                 875                 880
Lys Phe Glu Tyr Ile Gly Leu Gly Ala Val Ala Asp Cys Val Gly Ile
                    885                 890                 895
Asn Val Thr Val Gly Gly Glu Ser Cys Gln His Glu Phe Arg Gly Asp
                900                 905                 910
Met Val Val Cys Pro Leu Pro Ser Leu Gln Leu Gly Gln Asp Gly
                915                 920                 925
Ala Pro Leu Gln Val Cys Val Asp Gly Glu Cys His Ile Leu Gly Arg
            930                 935                 940
Val Val Arg Pro Gly Pro Asp Gly Val Pro Gln Ser Thr Leu Leu Gly
945                 950                 955                 960
Ile Leu Leu Pro Leu Leu Leu Val Ala Ala Leu Ala Thr Ala Leu
                    965                 970                 975
Val Phe Ser Tyr Trp Trp Arg Arg Lys Gln Leu Val Leu Pro Pro Asn
                980                 985                 990
Leu Asn Asp Leu Ala Ser Leu Asp Gln Thr Ala Gly Ala Thr Pro Leu
                995                 1000                1005
Pro Ile Leu Tyr Ser Gly Ser Asp Tyr Arg Ser Gly Leu Ala Leu
            1010                1015                1020
Pro Ala Ile Asp Gly Leu Asp Ser Thr Thr Cys Val His Gly Ala
            1025                1030                1035
Ser Phe Ser Asp Ser Glu Asp Glu Ser Cys Val Pro Leu Leu Arg
            1040                1045                1050
Lys Glu Ser Ile Gln Leu Arg Asp Leu Asp Ser Ala Leu Leu Ala
            1055                1060                1065
Glu Val Lys Asp Val Leu Ile Pro His Glu Arg Val Val Thr His
            1070                1075                1080
Ser Asp Arg Val Ile Gly Lys Gly His Phe Gly Val Val Tyr His
            1085                1090                1095
Gly Glu Tyr Ile Asp Gln Ala Gln Asn Arg Ile Gln Cys Ala Ile
            1100                1105                1110
Lys Ser Leu Ser Arg Ile Thr Glu Met Gln Gln Val Glu Ala Phe
            1115                1120                1125
Leu Arg Glu Gly Leu Leu Met Arg Gly Leu Asn His Pro Asn Val
            1130                1135                1140
Leu Ala Leu Ile Gly Ile Met Leu Pro Pro Glu Gly Leu Pro His
            1145                1150                1155
Val Leu Leu Pro Tyr Met Cys His Gly Asp Leu Leu Gln Phe Ile
            1160                1165                1170
Arg Ser Pro Gln Arg Asn Pro Thr Val Lys Asp Leu Ile Ser Phe
            1175                1180                1185
Gly Leu Gln Val Ala Arg Gly Met Glu Tyr Leu Ala Glu Gln Lys
            1190                1195                1200
Phe Val His Arg Asp Leu Ala Ala Arg Asn Cys Met Leu Asp Glu
            1205                1210                1215
Ser Phe Thr Val Lys Val Ala Asp Phe Gly Leu Ala Arg Asp Ile
            1220                1225                1230
Leu Asp Arg Glu Tyr Tyr Ser Val Gln Gln His Arg His Ala Arg
            1235                1240                1245
Leu Pro Val Lys Trp Met Ala Leu Glu Ser Leu Gln Thr Tyr Arg
            1250                1255                1260
Phe Thr Thr Lys Ser Asp Val Trp Ser Phe Gly Val Leu Leu Trp
            1265                1270                1275
```

```
Glu Leu Leu Thr Arg Gly Ala Pro Pro Tyr Arg His Ile Asp Pro
    1280                1285                1290

Phe Asp Leu Thr His Phe Leu Ala Gln Gly Arg Arg Leu Pro Gln
    1295                1300                1305

Pro Glu Tyr Cys Pro Asp Ser Leu Tyr Gln Val Met Gln Gln Cys
    1310                1315                1320

Trp Glu Ala Asp Pro Ala Val Arg Pro Thr Phe Arg Val Leu Val
    1325                1330                1335

Gly Glu Val Glu Gln Ile Val Ser Ala Leu Leu Gly Asp His Tyr
    1340                1345                1350

Val Gln Leu Pro Ala Thr Tyr Met Asn Leu Gly Pro Ser Thr Ser
    1355                1360                1365

His Glu Met Asn Val Arg Pro Glu Gln Pro Gln Phe Ser Pro Met
    1370                1375                1380

Pro Gly Asn Val Arg Arg Pro Arg Pro Leu Ser Glu Pro Pro Arg
    1385                1390                1395

Pro Thr
    1400

<210> SEQ ID NO 46
<211> LENGTH: 967
<212> TYPE: PRT
<213> ORGANISM: Homo sapiens

<400> SEQUENCE: 46

Met Arg Gly Ala Arg Gly Ala Trp Asp Phe Leu Cys Val Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
```

```
            225                 230                 235                 240
        Ser Val Tyr Ser Thr Trp Lys Arg Glu Asn Ser Gln Thr Lys Leu Gln
                        245                 250                 255

Glu Lys Tyr Asn Ser Trp His His Gly Asp Phe Asn Tyr Glu Arg Gln
                        260                 265                 270

Ala Thr Leu Thr Ile Ser Ser Ala Arg Val Asn Asp Ser Gly Val Phe
                        275                 280                 285

Met Cys Tyr Ala Asn Asn Thr Phe Gly Ser Ala Asn Val Thr Thr Thr
                        290                 295                 300

Leu Glu Val Val Asp Lys Gly Phe Ile Asn Ile Phe Pro Met Ile Asn
        305                 310                 315                 320

Thr Thr Val Phe Val Asn Asp Gly Glu Asn Val Asp Leu Ile Val Glu
                        325                 330                 335

Tyr Glu Ala Phe Pro Lys Pro Glu His Gln Gln Trp Ile Tyr Met Asn
                        340                 345                 350

Arg Thr Phe Thr Asp Lys Trp Glu Asp Tyr Pro Lys Ser Glu Asn Glu
                        355                 360                 365

Ser Asn Ile Arg Tyr Val Ser Glu Leu His Leu Thr Arg Leu Lys Gly
                        370                 375                 380

Thr Glu Gly Gly Thr Tyr Thr Phe Leu Val Ser Asn Ser Asp Val Asn
        385                 390                 395                 400

Ala Ala Ile Ala Phe Asn Val Tyr Val Asn Thr Lys Pro Glu Ile Leu
                        405                 410                 415

Thr Tyr Asp Arg Leu Val Asn Gly Met Leu Gln Cys Val Ala Ala Gly
                        420                 425                 430

Phe Pro Glu Pro Thr Ile Asp Trp Tyr Phe Cys Pro Gly Thr Glu Gln
                        435                 440                 445

Arg Cys Ser Ala Ser Val Leu Pro Val Asp Val Gln Thr Leu Asn Ser
                        450                 455                 460

Ser Gly Pro Pro Phe Gly Lys Leu Val Val Gln Ser Ser Ile Asp Ser
        465                 470                 475                 480

Ser Ala Phe Lys His Asn Gly Thr Val Glu Cys Lys Ala Tyr Asn Asp
                        485                 490                 495

Val Gly Lys Thr Ser Ala Tyr Phe Asn Phe Ala Phe Lys Gly Asn Asn
                        500                 505                 510

Lys Glu Gln Ile His Pro His Thr Leu Phe Thr Pro Leu Leu Ile Gly
                        515                 520                 525

Phe Val Ile Val Ala Gly Met Met Cys Ile Ile Val Met Ile Leu Thr
                        530                 535                 540

Tyr Lys Tyr Leu Gln Val Val Glu Glu Ile Asn Gly Asn Asn Tyr Val
        545                 550                 555                 560

Tyr Ile Asp Pro Thr Gln Leu Pro Tyr Asp His Lys Trp Glu Phe Pro
                        565                 570                 575

Arg Asn Arg Leu Ser Phe Gly Lys Thr Leu Gly Ala Gly Ala Phe Gly
                        580                 585                 590

Lys Val Val Glu Ala Thr Ala Tyr Gly Leu Ile Lys Ser Asp Ala Ala
                        595                 600                 605

Met Thr Val Ala Val Lys Met Leu Lys Pro Ser Ala His Leu Thr Glu
                        610                 615                 620

Arg Glu Ala Leu Met Ser Glu Leu Lys Val Leu Ser Tyr Leu Gly Asn
        625                 630                 635                 640

His Met Asn Ile Val Asn Leu Leu Gly Ala Cys Thr Ile Gly Gly Pro
                        645                 650                 655
```

```
Thr Leu Val Ile Thr Glu Tyr Cys Cys Tyr Gly Asp Leu Leu Asn Phe
                660             665                 670

Leu Arg Arg Lys Arg Asp Ser Phe Ile Cys Ser Lys Gln Glu Asp His
            675                 680                 685

Ala Glu Ala Ala Leu Tyr Lys Asn Leu Leu His Ser Lys Glu Ser Ser
690                 695                 700

Cys Ser Asp Ser Thr Asn Glu Tyr Met Asp Met Lys Pro Gly Val Ser
705                 710                 715                 720

Tyr Val Val Pro Thr Lys Ala Asp Lys Arg Arg Ser Val Arg Ile Gly
                725                 730                 735

Ser Tyr Ile Glu Arg Asp Val Thr Pro Ala Ile Met Glu Asp Asp Glu
            740                 745                 750

Leu Ala Leu Asp Leu Glu Asp Leu Leu Ser Phe Ser Tyr Gln Val Ala
        755                 760                 765

Lys Gly Met Ala Phe Leu Ala Ser Lys Asn Cys Ile His Arg Asp Leu
    770                 775                 780

Ala Ala Arg Asn Ile Leu Leu Thr His Gly Arg Ile Thr Lys Ile Cys
785                 790                 795                 800

Asp Phe Gly Leu Ala Arg Asp Ile Lys Asn Asp Ser Asn Tyr Val Val
                805                 810                 815

Lys Gly Asn Ala Arg Leu Pro Val Lys Trp Met Ala Pro Glu Ser Ile
            820                 825                 830

Phe Asn Cys Val Tyr Thr Phe Glu Ser Asp Val Trp Ser Tyr Gly Ile
        835                 840                 845

Phe Leu Trp Glu Leu Phe Ser Leu Gly Ser Ser Pro Tyr Pro Gly Met
    850                 855                 860

Pro Val Asp Ser Lys Phe Tyr Lys Met Ile Lys Glu Gly Phe Arg Met
865                 870                 875                 880

Leu Ser Pro Glu His Ala Pro Ala Glu Met Tyr Asp Ile Met Lys Thr
                885                 890                 895

Cys Trp Asp Ala Asp Pro Leu Lys Arg Pro Thr Phe Lys Gln Ile Val
            900                 905                 910

Gln Leu Ile Glu Lys Gln Ile Ser Glu Ser Thr Asn His Ile Tyr Ser
        915                 920                 925

Asn Leu Ala Asn Cys Ser Pro Asn Arg Gln Lys Pro Val Val Asp His
    930                 935                 940

Ser Val Arg Ile Asn Ser Val Gly Ser Thr Ala Ser Ser Ser Gln Pro
945                 950                 955                 960

Leu Leu Val His Asp Asp Val
                965

<210> SEQ ID NO 47
<211> LENGTH: 976
<212> TYPE: PRT
<213> ORGANISM: Homo sapiens

<400> SEQUENCE: 47

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
```

```
            50                  55                  60
Lys Trp Thr Phe Glu Ile Leu Asp Glu Thr Asn Glu Asn Lys Gln Asn
 65                  70                  75                  80

Glu Trp Ile Thr Glu Lys Ala Glu Ala Thr Asn Thr Gly Lys Tyr Thr
                 85                  90                  95

Cys Thr Asn Lys His Gly Leu Ser Asn Ser Ile Tyr Val Phe Val Arg
                100                 105                 110

Asp Pro Ala Lys Leu Phe Leu Val Asp Arg Ser Leu Tyr Gly Lys Glu
                115                 120                 125

Asp Asn Asp Thr Leu Val Arg Cys Pro Leu Thr Asp Pro Glu Val Thr
130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
                180                 185                 190

Lys Ser Val Leu Ser Glu Lys Phe Ile Leu Lys Val Arg Pro Ala Phe
                195                 200                 205

Lys Ala Val Pro Val Val Ser Val Ser Lys Ala Ser Tyr Leu Leu Arg
210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
                260                 265                 270

Ala Thr Leu Thr Ile Ser Ser Ala Arg Val Asn Asp Ser Gly Val Phe
                275                 280                 285

Met Cys Tyr Ala Asn Asn Thr Phe Gly Ser Ala Asn Val Thr Thr Thr
                290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
                340                 345                 350

Arg Thr Phe Thr Asp Lys Trp Glu Asp Tyr Pro Lys Ser Glu Asn Glu
                355                 360                 365

Ser Asn Ile Arg Tyr Val Ser Glu Leu His Leu Thr Arg Leu Lys Gly
370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
                420                 425                 430

Phe Pro Glu Pro Thr Ile Asp Trp Tyr Phe Cys Pro Gly Thr Glu Gln
                435                 440                 445

Arg Cys Ser Ala Ser Val Leu Pro Val Asp Val Gln Thr Leu Asn Ser
                450                 455                 460

Ser Gly Pro Pro Phe Gly Lys Leu Val Val Gln Ser Ser Ile Asp Ser
465                 470                 475                 480
```

```
Ser Ala Phe Lys His Asn Gly Thr Val Glu Cys Lys Ala Tyr Asn Asp
            485                 490                 495
Val Gly Lys Thr Ser Ala Tyr Phe Asn Phe Ala Phe Lys Gly Asn Asn
                500                 505                 510
Lys Glu Gln Ile His Pro His Thr Leu Phe Thr Pro Leu Leu Ile Gly
            515                 520                 525
Phe Val Ile Val Ala Gly Met Met Cys Ile Ile Val Met Ile Leu Thr
        530                 535                 540
Tyr Lys Tyr Leu Gln Lys Pro Met Tyr Glu Val Gln Trp Lys Val Val
545                 550                 555                 560
Glu Glu Ile Asn Gly Asn Asn Tyr Val Tyr Ile Asp Pro Thr Gln Leu
                565                 570                 575
Pro Tyr Asp His Lys Trp Glu Phe Pro Arg Asn Arg Leu Ser Phe Gly
            580                 585                 590
Lys Thr Leu Gly Ala Gly Ala Phe Gly Lys Val Val Glu Ala Thr Ala
        595                 600                 605
Tyr Gly Leu Ile Lys Ser Asp Ala Ala Met Thr Val Ala Val Lys Met
        610                 615                 620
Leu Lys Pro Ser Ala His Leu Thr Glu Arg Glu Ala Leu Met Ser Glu
625                 630                 635                 640
Leu Lys Val Leu Ser Tyr Leu Gly Asn His Met Asn Ile Val Asn Leu
                645                 650                 655
Leu Gly Ala Cys Thr Ile Gly Gly Pro Thr Leu Val Ile Thr Glu Tyr
            660                 665                 670
Cys Cys Tyr Gly Asp Leu Leu Asn Phe Leu Arg Arg Lys Arg Asp Ser
        675                 680                 685
Phe Ile Cys Ser Lys Gln Glu Asp His Ala Glu Ala Ala Leu Tyr Lys
        690                 695                 700
Asn Leu Leu His Ser Lys Glu Ser Ser Cys Ser Asp Ser Thr Asn Glu
705                 710                 715                 720
Tyr Met Asp Met Lys Pro Gly Val Ser Tyr Val Val Pro Thr Lys Ala
                725                 730                 735
Asp Lys Arg Arg Ser Val Arg Ile Gly Ser Tyr Ile Glu Arg Asp Val
            740                 745                 750
Thr Pro Ala Ile Met Glu Asp Asp Glu Leu Ala Leu Asp Leu Glu Asp
        755                 760                 765
Leu Leu Ser Phe Ser Tyr Gln Val Ala Lys Gly Met Ala Phe Leu Ala
        770                 775                 780
Ser Lys Asn Cys Ile His Arg Asp Leu Ala Ala Arg Asn Ile Leu Leu
785                 790                 795                 800
Thr His Gly Arg Ile Thr Lys Ile Cys Asp Phe Gly Leu Ala Arg Asp
                805                 810                 815
Ile Lys Asn Asp Ser Asn Tyr Val Val Lys Gly Asn Ala Arg Leu Pro
            820                 825                 830
Val Lys Trp Met Ala Pro Glu Ser Ile Phe Asn Cys Val Tyr Thr Phe
        835                 840                 845
Glu Ser Asp Val Trp Ser Tyr Gly Ile Phe Leu Trp Glu Leu Phe Ser
        850                 855                 860
Leu Gly Ser Ser Pro Tyr Pro Gly Met Pro Val Asp Ser Lys Phe Tyr
865                 870                 875                 880
Lys Met Ile Lys Glu Gly Phe Arg Met Leu Ser Pro Glu His Ala Pro
                885                 890                 895
```

```
Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Gln Pro Leu Leu Val His Asp Asp Val
                965                 970                 975

<210> SEQ ID NO 48
<211> LENGTH: 196
<212> TYPE: PRT
<213> ORGANISM: Homo sapiens

<400> SEQUENCE: 48

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Asp Val Arg
        195

<210> SEQ ID NO 49
<211> LENGTH: 211
<212> TYPE: PRT
<213> ORGANISM: Homo sapiens

<400> SEQUENCE: 49

Met Arg Thr Leu Ala Cys Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45
```

```
Glu Ile Asp Ser Val Gly Ser Glu Asp Ser Leu Asp Thr Ser Leu Arg
 50                  55                  60
Ala His Gly Val His Ala Thr Lys His Val Pro Glu Lys Arg Pro Leu
 65                  70                  75                  80
Pro Ile Arg Arg Lys Arg Ser Ile Glu Glu Ala Val Pro Ala Val Cys
                 85                  90                  95
Lys Thr Arg Thr Val Ile Tyr Glu Ile Pro Arg Ser Gln Val Asp Pro
                100                 105                 110
Thr Ser Ala Asn Phe Leu Ile Trp Pro Pro Cys Val Glu Val Lys Arg
            115                 120                 125
Cys Thr Gly Cys Cys Asn Thr Ser Ser Val Lys Cys Gln Pro Ser Arg
130                 135                 140
Val His His Arg Ser Val Lys Val Ala Lys Val Glu Tyr Val Arg Lys
145                 150                 155                 160
Lys Pro Lys Leu Lys Glu Val Gln Val Arg Leu Glu Glu His Leu Glu
                165                 170                 175
Cys Ala Cys Ala Thr Thr Ser Leu Asn Pro Asp Tyr Arg Glu Glu Asp
            180                 185                 190
Thr Gly Arg Pro Arg Glu Ser Gly Lys Lys Arg Lys Arg Lys Arg Leu
            195                 200                 205
Lys Pro Thr
210

<210> SEQ ID NO 50
<211> LENGTH: 1089
<212> TYPE: PRT
<213> ORGANISM: Homo sapiens

<400> SEQUENCE: 50

Met Gly Thr Ser His Pro Ala Phe Leu Val Leu Gly Cys Leu Leu Thr
  1               5                  10                  15
Gly Leu Ser Leu Ile Leu Cys Gln Leu Ser Leu Pro Ser Ile Leu Pro
                 20                  25                  30
Asn Glu Asn Glu Lys Val Val Gln Leu Asn Ser Ser Phe Ser Leu Arg
             35                  40                  45
Cys Phe Gly Glu Ser Glu Val Ser Trp Gln Tyr Pro Met Ser Glu Glu
 50                  55                  60
Glu Ser Ser Asp Val Glu Ile Arg Asn Glu Glu Asn Ser Ser Gly Leu
 65                  70                  75                  80
Phe Val Thr Val Leu Glu Val Ser Ser Ala Ser Ala Ala His Thr Gly
                 85                  90                  95
Leu Tyr Thr Cys Tyr Tyr Asn His Thr Gln Thr Glu Glu Asn Glu Leu
                100                 105                 110
Glu Gly Arg His Ile Tyr Ile Tyr Val Pro Asp Pro Asp Val Ala Phe
            115                 120                 125
Val Pro Leu Gly Met Thr Asp Tyr Leu Val Ile Val Glu Asp Asp Asp
130                 135                 140
Ser Ala Ile Ile Pro Cys Arg Thr Thr Asp Pro Glu Thr Pro Val Thr
145                 150                 155                 160
Leu His Asn Ser Glu Gly Val Val Pro Ala Ser Tyr Asp Ser Arg Gln
                165                 170                 175
Gly Phe Asn Gly Thr Phe Thr Val Gly Pro Tyr Ile Cys Glu Ala Thr
            180                 185                 190
Val Lys Gly Lys Lys Phe Gln Thr Ile Pro Phe Asn Val Tyr Ala Leu
            195                 200                 205
```

```
Lys Ala Thr Ser Glu Leu Asp Leu Glu Met Glu Ala Leu Lys Thr Val
    210                 215                 220
Tyr Lys Ser Gly Glu Thr Ile Val Val Thr Cys Ala Val Phe Asn Asn
225                 230                 235                 240
Glu Val Val Asp Leu Gln Trp Thr Tyr Pro Gly Glu Val Lys Gly Lys
                245                 250                 255
Gly Ile Thr Met Leu Glu Glu Ile Lys Val Pro Ser Ile Lys Leu Val
                260                 265                 270
Tyr Thr Leu Thr Val Pro Glu Ala Thr Val Lys Asp Ser Gly Asp Tyr
            275                 280                 285
Glu Cys Ala Ala Arg Gln Ala Thr Arg Glu Val Lys Glu Met Lys Lys
        290                 295                 300
Val Thr Ile Ser Val His Glu Lys Gly Phe Ile Glu Ile Lys Pro Thr
305                 310                 315                 320
Phe Ser Gln Leu Glu Ala Val Asn Leu His Glu Val Lys His Phe Val
                325                 330                 335
Val Glu Val Arg Ala Tyr Pro Pro Arg Ile Ser Trp Leu Lys Asn
                340                 345                 350
Asn Leu Thr Leu Ile Glu Asn Leu Thr Glu Ile Thr Thr Asp Val Glu
            355                 360                 365
Lys Ile Gln Glu Ile Arg Tyr Arg Ser Lys Leu Lys Leu Ile Arg Ala
370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp Asp His His Gly Ser Thr Gly Gly Gln Thr
            420                 425                 430
Val Arg Cys Thr Ala Glu Gly Thr Pro Leu Pro Asp Ile Glu Trp Met
        435                 440                 445
Ile Cys Lys Asp Ile Lys Lys Cys Asn Asn Glu Thr Ser Trp Thr Ile
        450                 455                 460
Leu Ala Asn Asn Val Ser Asn Ile Ile Thr Glu Ile His Ser Arg Asp
465                 470                 475                 480
Arg Ser Thr Val Glu Gly Arg Val Thr Phe Ala Lys Val Glu Glu Thr
                485                 490                 495
Ile Ala Val Arg Cys Leu Ala Lys Asn Leu Leu Gly Ala Glu Asn Arg
            500                 505                 510
Glu Leu Lys Leu Val Ala Pro Thr Leu Arg Ser Glu Leu Thr Val Ala
        515                 520                 525
Ala Ala Val Leu Val Leu Leu Val Ile Val Ile Ile Ser Leu Ile Val
        530                 535                 540
Leu Val Val Ile Trp Lys Gln Lys Pro Arg Tyr Glu Ile Arg Trp Arg
545                 550                 555                 560
Val Ile Glu Ser Ile Ser Pro Asp Gly His Glu Tyr Ile Tyr Val Asp
                565                 570                 575
Pro Met Gln Leu Pro Tyr Asp Ser Arg Trp Glu Phe Pro Arg Asp Gly
                580                 585                 590
Leu Val Leu Gly Arg Val Leu Gly Ser Gly Ala Phe Gly Lys Val Val
            595                 600                 605
Glu Gly Thr Ala Tyr Gly Leu Ser Arg Ser Gln Pro Val Met Lys Val
        610                 615                 620
```

```
Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
            645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu  Lys Asp Trp Glu Gly  Gly Leu Asp
        995                 1000                1005

Glu Gln  Arg Leu Ser Ala Asp  Ser Gly Tyr Ile Ile  Pro Leu Pro
        1010                1015                1020

Asp Ile Asp Pro Val Pro Glu  Glu Asp Leu Gly  Lys Arg Asn
        1025                1030                1035

Arg His  Ser Ser Gln Thr Ser  Glu Glu Ser Ala Ile  Glu Thr Gly
```

```
                    1040                1045                1050

Ser Ser Ser Ser Thr Phe Ile Lys Arg Glu Asp Glu Thr Ile Glu
        1055                1060                1065

Asp Ile Asp Met Met Asp Asp Ile Gly Ile Asp Ser Ser Asp Leu
        1070                1075                1080

Val Glu Asp Ser Phe Leu
        1085

<210> SEQ ID NO 51
<211> LENGTH: 1007
<212> TYPE: PRT
<213> ORGANISM: Homo sapiens

<400> SEQUENCE: 51

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320
```

```
                    -continued

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Asn Asn Glu Thr Ser Trp Thr Ile Leu Ala
        370                 375                 380

Asn Asn Val Ser Asn Ile Ile Thr Glu Ile His Ser Arg Asp Arg Ser
385                 390                 395                 400

Thr Val Glu Gly Arg Val Thr Phe Ala Lys Val Glu Glu Thr Ile Ala
                405                 410                 415

Val Arg Cys Leu Ala Lys Asn Leu Leu Gly Ala Glu Asn Arg Glu Leu
            420                 425                 430

Lys Leu Val Ala Pro Thr Leu Arg Ser Glu Leu Thr Val Ala Ala Ala
        435                 440                 445

Val Leu Val Leu Leu Val Ile Ile Ser Leu Ile Val Leu Val
                450                 455                 460

Val Ile Trp Lys Gln Lys Pro Arg Tyr Glu Ile Arg Trp Arg Val Ile
465                 470                 475                 480

Glu Ser Ile Ser Pro Asp Gly His Glu Tyr Ile Tyr Val Asp Pro Met
                485                 490                 495

Gln Leu Pro Tyr Asp Ser Arg Trp Glu Phe Pro Arg Asp Gly Leu Val
            500                 505                 510

Leu Gly Arg Val Leu Gly Ser Gly Ala Phe Gly Lys Val Val Glu Gly
        515                 520                 525

Thr Ala Tyr Gly Leu Ser Arg Ser Gln Pro Val Met Lys Val Ala Val
        530                 535                 540

Lys Met Leu Lys Pro Thr Ala Arg Ser Ser Glu Lys Gln Ala Leu Met
545                 550                 555                 560

Ser Glu Leu Lys Ile Met Thr His Leu Gly Pro His Leu Asn Ile Val
                565                 570                 575

Asn Leu Leu Gly Ala Cys Thr Lys Ser Gly Pro Ile Tyr Ile Ile Thr
            580                 585                 590

Glu Tyr Cys Phe Tyr Gly Asp Leu Val Asn Tyr Leu His Lys Asn Arg
        595                 600                 605

Asp Ser Phe Leu Ser His His Pro Glu Lys Pro Lys Lys Glu Leu Asp
        610                 615                 620

Ile Phe Gly Leu Asn Pro Ala Asp Glu Ser Thr Arg Ser Tyr Val Ile
625                 630                 635                 640

Leu Ser Phe Glu Asn Asn Gly Asp Tyr Met Asp Met Lys Gln Ala Asp
                645                 650                 655

Thr Thr Gln Tyr Val Pro Met Leu Glu Arg Lys Glu Val Ser Lys Tyr
            660                 665                 670

Ser Asp Ile Gln Arg Ser Leu Tyr Asp Arg Pro Ala Ser Tyr Lys Lys
        675                 680                 685

Lys Ser Met Leu Asp Ser Glu Val Lys Asn Leu Leu Ser Asp Asp Asn
690                 695                 700

Ser Glu Gly Leu Thr Leu Leu Asp Leu Leu Ser Phe Thr Tyr Gln Val
705                 710                 715                 720

Ala Arg Gly Met Glu Phe Leu Ala Ser Lys Asn Cys Val His Arg Asp
                725                 730                 735

Leu Ala Ala Arg Asn Val Leu Leu Ala Gln Gly Lys Ile Val Lys Ile
```

```
                    740                 745                 750
Cys Asp Phe Gly Leu Ala Arg Asp Ile Met His Asp Ser Asn Tyr Val
            755                 760                 765
Ser Lys Gly Ser Thr Phe Leu Pro Val Lys Trp Met Ala Pro Glu Ser
        770                 775                 780
Ile Phe Asp Asn Leu Tyr Thr Thr Leu Ser Asp Val Trp Ser Tyr Gly
785                 790                 795                 800
Ile Leu Leu Trp Glu Ile Phe Ser Leu Gly Gly Thr Pro Tyr Pro Gly
                805                 810                 815
Met Met Val Asp Ser Thr Phe Tyr Asn Lys Ile Lys Ser Gly Tyr Arg
            820                 825                 830
Met Ala Lys Pro Asp His Ala Thr Ser Glu Val Tyr Glu Ile Met Val
        835                 840                 845
Lys Cys Trp Asn Ser Glu Pro Glu Lys Arg Pro Ser Phe Tyr His Leu
    850                 855                 860
Ser Glu Ile Val Glu Asn Leu Leu Pro Gly Gln Tyr Lys Lys Ser Tyr
865                 870                 875                 880
Glu Lys Ile His Leu Asp Phe Leu Lys Ser Asp His Pro Ala Val Ala
                885                 890                 895
Arg Met Arg Val Asp Ser Asp Asn Ala Tyr Ile Gly Val Thr Tyr Lys
            900                 905                 910
Asn Glu Glu Asp Lys Leu Lys Asp Trp Glu Gly Gly Leu Asp Glu Gln
        915                 920                 925
Arg Leu Ser Ala Asp Ser Gly Tyr Ile Ile Pro Leu Pro Asp Ile Asp
    930                 935                 940
Pro Val Pro Glu Glu Glu Asp Leu Gly Lys Arg Asn Arg His Ser Ser
945                 950                 955                 960
Gln Thr Ser Glu Glu Ser Ala Ile Glu Thr Gly Ser Ser Ser Ser Thr
                965                 970                 975
Phe Ile Lys Arg Glu Asp Glu Thr Ile Glu Asp Ile Asp Met Met Asp
            980                 985                 990
Asp Ile Gly Ile Asp Ser Ser Asp Leu Val Glu Asp Ser Phe Leu
        995                 1000                1005

<210> SEQ ID NO 52
<211> LENGTH: 820
<212> TYPE: PRT
<213> ORGANISM: Homo sapiens

<400> SEQUENCE: 52

Met Val Ser Trp Gly Arg Phe Ile Cys Leu Val Val Thr Met Ala
1               5                   10                  15
Thr Leu Ser Leu Ala Arg Pro Ser Phe Ser Leu Val Glu Asp Thr Thr
            20                  25                  30
Leu Glu Pro Glu Glu Pro Pro Thr Lys Tyr Gln Ile Ser Gln Pro Glu
        35                  40                  45
Val Tyr Val Ala Ala Pro Gly Glu Ser Leu Glu Val Arg Cys Leu Leu
    50                  55                  60
Lys Asp Ala Ala Val Ile Ser Trp Thr Lys Asp Gly Val His Leu Gly
65                  70                  75                  80
Pro Asn Asn Arg Thr Val Leu Ile Gly Glu Tyr Leu Gln Ile Lys Gly
                85                  90                  95
Ala Thr Pro Arg Asp Ser Gly Leu Tyr Ala Cys Thr Ala Ser Arg Thr
            100                 105                 110
```

-continued

Val Asp Ser Glu Thr Trp Tyr Phe Met Val Asn Val Thr Asp Ala Ile
        115                 120                 125

Ser Ser Gly Asp Glu Asp Asp Thr Asp Gly Ala Glu Asp Phe Val
        130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
                180                 185                 190

Lys Asn Gly Lys Glu Phe Lys Gln Glu His Arg Ile Gly Gly Tyr Lys
                195                 200                 205

Val Arg Asn Gln His Trp Ser Leu Ile Met Glu Ser Val Val Pro Ser
        210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
        290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
                340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
        370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Ser Ala Glu
                420                 425                 430

Ser Ser Ser Ser Met Asn Ser Asn Thr Pro Leu Val Arg Ile Thr Thr
        435                 440                 445

Arg Leu Ser Ser Thr Ala Asp Thr Pro Met Leu Ala Gly Val Ser Glu
        450                 455                 460

Tyr Glu Leu Pro Glu Asp Pro Lys Trp Glu Phe Pro Arg Asp Lys Leu
465                 470                 475                 480

Thr Leu Gly Lys Pro Leu Gly Glu Gly Cys Phe Gly Gln Val Val Met
                485                 490                 495

Ala Glu Ala Val Gly Ile Asp Lys Asp Lys Pro Lys Glu Ala Val Thr
                500                 505                 510

Val Ala Val Lys Met Leu Lys Asp Asp Ala Thr Glu Lys Asp Leu Ser
        515                 520                 525

Asp Leu Val Ser Glu Met Glu Met Met Lys Met Ile Gly Lys His Lys

```
                530                 535                 540
Asn Ile Ile Asn Leu Leu Gly Ala Cys Thr Gln Asp Gly Pro Leu Tyr
545                 550                 555                 560

Val Ile Val Glu Tyr Ala Ser Lys Gly Asn Leu Arg Glu Tyr Leu Arg
                565                 570                 575

Ala Arg Arg Pro Pro Gly Met Glu Tyr Ser Tyr Asp Ile Asn Arg Val
                580                 585                 590

Pro Glu Glu Gln Met Thr Phe Lys Asp Leu Val Ser Cys Thr Tyr Gln
            595                 600                 605

Leu Ala Arg Gly Met Glu Tyr Leu Ala Ser Gln Lys Cys Ile His Arg
        610                 615                 620

Asp Leu Ala Ala Arg Asn Val Leu Val Thr Glu Asn Asn Val Met Lys
625                 630                 635                 640

Ile Ala Asp Phe Gly Leu Ala Arg Asp Ile Asn Asn Ile Asp Tyr Tyr
                645                 650                 655

Lys Lys Thr Thr Asn Gly Arg Leu Pro Val Lys Trp Met Ala Pro Glu
                660                 665                 670

Ala Leu Phe Asp Arg Val Tyr Thr His Gln Ser Asp Val Trp Ser Phe
            675                 680                 685

Gly Val Leu Met Trp Glu Ile Phe Thr Leu Gly Gly Ser Pro Tyr Pro
        690                 695                 700

Gly Ile Pro Val Glu Glu Leu Phe Lys Leu Leu Lys Glu Gly His Arg
705                 710                 715                 720

Met Asp Lys Pro Ala Asn Cys Thr Asn Glu Leu Tyr Met Met Met Arg
                725                 730                 735

Asp Cys Trp His Ala Val Pro Ser Gln Arg Pro Thr Phe Lys Gln Leu
            740                 745                 750

Val Glu Asp Leu Asp Arg Ile Leu Thr Leu Thr Thr Asn Glu Glu Tyr
        755                 760                 765

Leu Asp Leu Ser Gln Pro Leu Glu Gln Tyr Ser Pro Ser Tyr Pro Asp
770                 775                 780

Thr Arg Ser Ser Cys Ser Ser Gly Asp Asp Ser Val Phe Ser Pro Asp
785                 790                 795                 800

Pro Met Pro Tyr Glu Pro Cys Leu Pro Gln Tyr Pro His Ile Asn Gly
                805                 810                 815

Ser Val Lys Thr
            820

<210> SEQ ID NO 53
<211> LENGTH: 366
<212> TYPE: PRT
<213> ORGANISM: Homo sapiens

<400> SEQUENCE: 53

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
        50                  55                  60

Lys Asp Ala Ala Val Ile Ser Trp Thr Lys Asp Gly Val His Leu Gly
65                  70                  75                  80
```

```
Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Gly Arg Arg Cys
        355                 360                 365

<210> SEQ ID NO 54
<211> LENGTH: 1476
<212> TYPE: DNA
<213> ORGANISM: Homo sapiens

<400> SEQUENCE: 54
atggtcagct ggggtcgttt catctgcctg gtcgtggtca ccatggcaac cttgtccctg      60
gcccggccct ccttcagttt agttgaggat accacattag agccagaagg agcaccatac     120
tggaccaaca cagaaaagat ggaaaagcgg ctccatgctg tgcctgcggc caacactgtc     180
aagtttcgct gcccagccgg ggggaaccca atgccaacca tgcggtggct gaaaaacggg     240
aaggagttta gcaggagcat tcgcattgga ggctacaagg tacgaaacca gcactggagc     300
ctcattatgg aaagtgtggt cccatctgac aagggaaatt atacctgtgt ggtggagaat     360
gaatacgggt ccatcaatca cacgtaccac ctggatgttg tggagcgatc gcctcaccgg     420
cccatcctcc aagccggact gccggcaaat gcctccacag tggtcggagg agacgtagag     480
tttgtctgca aggtttacag tgatgcccag ccccacatcc agtggatcaa gcacgtggaa     540
```

-continued

```
aagaacggca gtaaatacgg gcccgacggg ctgccctacc tcaaggttct caaggccgcc    600
ggtgttaaca ccacggacaa agagattgag gttctctata ttcggaatgt aacttttgag    660
gacgctgggg aatatacgtg cttggcgggt aattctattg ggatatcctt tcactctgca    720
tggttgacag ttctgccagc gcctggaaga gaaaaggaga ttacagcttc cccagactac    780
ctggagagat ctgacaaaac tcacacatgc ccaccgtgcc cagcacctga actcctgggg    840
ggaccgtcag tcttcctctt cccccaaaa cccaaggaca ccctctacat cacccgggaa    900
cctgaggtca catgcgtggt ggtggacgtg agccacgaag accctgaggt caagttcaac    960
tggtacgtgg acggcgtgga ggtgcataat gccaagacaa agccgcggga ggagcagtac   1020
aacagcacgt accgtgtggt cagcgtcctc accgtcctgc accaggactg gctgaatggc   1080
aaggagtaca agtgcaaggt ctccaacaaa gccctcccag cccccatcga aaaaccatc    1140 tccaaagcca aagggcagcc ccgagaacca caggtgtaca ccctgccccc atcccgggag   1200
gagatgacca agaaccaggt cagcctgacc tgcctggtca aaggcttcta tcccagcgac   1260
atcgccgtgg agtgggagag caatgggcag ccggagaaca actacaagac cacgcctccc   1320
gtgctggact ccgacggctc cttcttcctc tacagcaagc tcaccgtgga caagagcagg   1380
tggcagcagg ggaacgtctt ctcatgctcc gtgatgcatg aggctctgaa gttccactac   1440
acgcagaaga gcctctccct gtctccgggt aaatga                              1476
```

<210> SEQ ID NO 55
<211> LENGTH: 491
<212> TYPE: PRT
<213> ORGANISM: Homo sapiens

<400> SEQUENCE: 55

```
Met Val Ser Trp Gly Arg Phe Ile Cys Leu Val Val Thr Met Ala
1               5                  10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys Ala Ala Gly Val Asn Thr Thr Asp Lys Glu
        195                 200                 205
```

```
Ile Glu Val Leu Tyr Ile Arg Asn Val Thr Phe Glu Asp Ala Gly Glu
    210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
                245                 250                 255

Ser Pro Asp Tyr Leu Glu Arg Ser Asp Lys Thr His Thr Cys Pro Pro
                260                 265                 270

Cys Pro Ala Pro Glu Leu Leu Gly Gly Pro Ser Val Phe Leu Phe Pro
            275                 280                 285

Pro Lys Pro Lys Asp Thr Leu Tyr Ile Thr Arg Glu Pro Glu Val Thr
        290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
                340                 345                 350

Leu His Gln Asp Trp Leu Asn Gly Lys Glu Tyr Lys Cys Lys Val Ser
            355                 360                 365

Asn Lys Ala Leu Pro Ala Pro Ile Glu Lys Thr Ile Ser Lys Ala Lys
        370                 375                 380

Gly Gln Pro Arg Glu Pro Gln Val Tyr Thr Leu Pro Pro Ser Arg Glu
385                 390                 395                 400

Glu Met Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
                420                 425                 430

Asn Asn Tyr Lys Thr Thr Pro Pro Val Leu Asp Ser Asp Gly Ser Phe
            435                 440                 445

Phe Leu Tyr Ser Lys Leu Thr Val Asp Lys Ser Arg Trp Gln Gln Gly
        450                 455                 460

Asn Val Phe Ser Cys Ser Val Met His Glu Ala Leu Lys Phe His Tyr
465                 470                 475                 480

Thr Gln Lys Ser Leu Ser Leu Ser Pro Gly Lys
                485                 490

<210> SEQ ID NO 56
<211> LENGTH: 38
<212> TYPE: PRT
<213> ORGANISM: Homo sapiens

<400> SEQUENCE: 56

His Ser Gly Ile Asn Ser Ser Asn Ala Glu Val Leu Ala Leu Phe Asn
1               5                   10                  15

Val Thr Glu Ala Asp Ala Gly Glu Tyr Ile Cys Lys Val Ser Asn Tyr
                20                  25                  30

Ile Gly Gln Ala Asn Gln
        35

<210> SEQ ID NO 57
<211> LENGTH: 15
<212> TYPE: PRT
<213> ORGANISM: Homo sapiens

<400> SEQUENCE: 57
```

His Ser Gly Ile Asn Ser Ser Asn Ala Glu Val Leu Ala Leu Phe
1               5                   10                  15

<210> SEQ ID NO 58
<211> LENGTH: 12
<212> TYPE: PRT
<213> ORGANISM: Homo sapiens

<400> SEQUENCE: 58

Cys Lys Val Ser Asn Tyr Ile Gly Gln Ala Asn Gln
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Gly Gly Gly Ser Gly Gly Gly Gly Ser
1               5                   10

<210> SEQ ID NO 60
<211> LENGTH: 114
<212> TYPE: DNA
<213> ORGANISM: Homo sapiens

<400> SEQUENCE: 60
cactcgggga taaatagttc caatgcagaa gtgctggctc tgttcaatgt gaccgaggcg      60
gatgctgggg aatatatatg taaggtctcc aattatatag ggcaggccaa ccag           114

<210> SEQ ID NO 61
<211> LENGTH: 45
<212> TYPE: DNA
<213> ORGANISM: Homo sapiens

<400> SEQUENCE: 61
cactcgggga taaatagttc caatgcagaa gtgctggctc tgttc                      45

<210> SEQ ID NO 62
<211> LENGTH: 36
<212> TYPE: DNA
<213> ORGANISM: Homo sapiens

<400> SEQUENCE: 62
tgtaaggtct ccaattatat agggcaggcc aaccag                                36

<210> SEQ ID NO 63
<211> LENGTH: 2469
<212> TYPE: DNA
<213> ORGANISM: Homo sapiens

<400> SEQUENCE: 63
atggtcagct ggggtcgttt catctgcctg gtcgtggtca ccatggcaac cttgtccctg      60
gcccggccct ccttcagttt agttgaggat accacattag agccagaaga gccaccaacc     120
aaataccaaa tctctcaacc agaagtgtac gtggctgcgc agggggagtc gctagaggtg     180
cgctgcctgt tgaaagatgc cgccgtgatc agttggacta aggatggggt gcacttgggg     240
cccaacaata ggacagtgct tattggggag tacttgcaga taaagggcgc cacgcctaga     300

```
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagc actcggggat aaatagttcc    960
aatgcagaag tgctggctct gttcaatgtg accgaggcgg atgctgggga atatatatgt    1020
aaggtctcca attatatagg gcaggccaac cagtctgcct ggctcactgt cctgccaaaa    1080
cagcaagcgc ctggaagaga aaaggagatt acagcttccc cagactacct ggagatagcc    1140
atttactgca taggggtctt cttaatcgcc tgtatggtgg taacagtcat cctgtgccga    1200
atgaagaaca cgaccaagaa gccagacttc agcagccagc cggctgtgca caagctgacc    1260
aaacgtatcc ccctgcggag acaggtaaca gtttcggctg agtccagctc ctccatgaac    1320
tccaacaccc cgctggtgag gataacaaca cgcctctctt caacggcaga caccccatg    1380
ctggcagggg tctccgagta tgaacttcca gaggacccaa atgggagtt tccaagagat    1440
aagctgacac tgggcaagcc cctgggagaa ggttgctttg ggcaagtggt catggcggaa    1500
gcagtggaa ttgacaaaga caagcccaag gaggcggtca ccgtggccgt gaagatgttg    1560
aaagatgatg ccacagagaa agaccttctt gatctggtgt cagagatgga gatgatgaag    1620
atgattggga acacaagaa tatcataaat cttcttggag cctgcacaca ggatgggcct    1680
ctctatgtca tagttgagta tgcctctaaa ggcaacctcc gagaatacct ccgagcccgg    1740
aggccaccg ggatggagta ctcctatgac attaaccgtg ttcctgagga gcagatgacc    1800
ttcaaggact tggtgtcatg cacctaccag ctggccagag gcatggagta cttggcttcc    1860
caaaaatgta ttcatcgaga tttagcagcc agaaatgttt tggtaacaga aaacaatgtg    1920
atgaaaatag cagactttgg actcgccaga gatatcaaca atatagacta ttacaaaaag    1980
accaccaatg gcggcttcc agtcaagtgg atggctccag aagccctgtt tgatagagta    2040
tacactcatc agagtgatgt ctggtccttc ggggtgttaa tgtgggagat cttcacttta    2100
gggggctcgc cctacccagg gattcccgtg gaggaacttt ttaagctgct gaaggaagga    2160
cacagaatgg ataagccagc caactgcacc aacgaactgt acatgatgat gagggactgt    2220
tggcatgcag tgcccctccca gagaccaacg ttcaagcagt tggtagaaga cttggatcga    2280
attctcactc tcacaaccaa tgaggaatac ttggacctca gccaacctct cgaacagtat    2340
tcacctagtt accctgacac aagaagttct tgttcttcag gagatgattc tgtttttttct    2400
ccagacccca tgccttacga accatgcctt cctcagtatc cacacataaa cggcagtgtt    2460
aaaacatga                                                            2469

<210> SEQ ID NO 64
<211> LENGTH: 174
<212> TYPE: DNA
<213> ORGANISM: Homo sapiens
```

<400> SEQUENCE: 64

```
tacgggcccg acgggctgcc ctacctcaag gttctcaagc actcggggat aaatagttcc      60
aatgcagaag tgctggctct gttcaatgtg accgaggcgg atgctgggga atatatatgt     120
aaggtctcca attatatagg gcaggccaac cagtctgcct ggctcactgt cctg           174
```

<210> SEQ ID NO 65
<211> LENGTH: 58
<212> TYPE: PRT
<213> ORGANISM: Homo sapiens

<400> SEQUENCE: 65

```
Tyr Gly Pro Asp Gly Leu Pro Tyr Leu Lys Val Leu Lys His Ser Gly
1               5                   10                  15

Ile Asn Ser Ser Asn Ala Glu Val Leu Ala Leu Phe Asn Val Thr Glu
            20                  25                  30

Ala Asp Ala Gly Glu Tyr Ile Cys Lys Val Ser Asn Tyr Ile Gly Gln
        35                  40                  45

Ala Asn Gln Ser Ala Trp Leu Thr Val Leu
    50                  55
```

<210> SEQ ID NO 66
<211> LENGTH: 648
<212> TYPE: DNA
<213> ORGANISM: Homo sapiens

<400> SEQUENCE: 66

```
atgggcagcc ccgctccgc gctgagctgc ctgctgttgc acttgctggt cctctgcctc       60
caagcccagg taactgttca gtcctcacct aattttacac agcatgtgag ggagcagagc     120
ctggtgacgg atcagctcag ccgccgcctc atccggacct accaactcta cagccgcacc     180
agcgggaagc acgtgcaggt cctggccaac aagcgcatca cgccatggc agaggacggc      240 gaccccttcg caaagctcat cgtggagacg acacctttg gaagcagagt tcgagtccga      300
ggagccgaga cgggcctcta catctgcatg aacaagaagg ggaagctgat cgccaagagc     360
aacggcaaag gcaaggactg cgtcttcacg gagattgtgc tggagaacaa ctacacagcg     420
ctgcagaatg ccaagtacga gggctggtac atggccttca cccgcaaggg ccggccccgc     480
aagggctcca gacgcggca gcaccagcgt gaggtccact tcatgaagcg gctgccccgg     540
ggccaccaca ccaccgagca gagcctgcgc ttcgagttcc tcaactaccc gcccttcacg     600
cgcagcctgc gcggcagcca gaggacttgg gcccccgagc ccgatag                   648
```

<210> SEQ ID NO 67
<211> LENGTH: 48
<212> TYPE: PRT
<213> ORGANISM: Rattus sp.

<400> SEQUENCE: 67

```
Leu Pro Tyr Leu Lys Val Leu Lys Ala Ala Gly Val Asn Thr Thr Asp
1               5                   10                  15

Lys Glu Ile Glu Val Leu Tyr Ile Arg Asn Val Thr Phe Glu Asp Ala
            20                  25                  30

Gly Glu Tyr Thr Cys Leu Ala Gly Asn Ser Ile Gly Ile Ser Phe His
        35                  40                  45
```

<210> SEQ ID NO 68
<211> LENGTH: 46

<212> TYPE: PRT
<213> ORGANISM: Rattus sp.

<400> SEQUENCE: 68

Leu Pro Tyr Leu Lys Val Leu Lys His Ser Gly Ile Asn Ser Ser Asn
1               5                   10                  15

Ala Glu Val Leu Ala Leu Phe Asn Val Thr Glu Met Asp Ala Gly Glu
            20                  25                  30

Tyr Ile Cys Lys Val Ser Asn Tyr Ile Gly Gln Ala Asn Gln
        35                  40                  45

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggttctcaag cactcgggga                                               20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gccaggcaga ctggttggcc                                               20

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aggttctcaa ggccgccggt gt                                            22

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
caaccatgca gagtgaaagg a                                             21

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Gly Gly Gly Gly
1               5

```
<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Gly Gly Gly Gly Ser Gly Gly Gly Gly
1               5                   10

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Gly Gly Gly Gly Ser Gly Gly Gly Gly Ser Gly Gly Gly Gly
1               5                   10                  15

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Gly Gly Gly Gly Ser Gly Gly Gly Gly Ser Gly Gly Gly Gly Ser
1               5                   10                  15

Gly Gly Gly Gly
            20

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Gly Gly Gly Gly Ser Gly Gly Gly Gly Ser Gly Gly Gly Gly Ser
1               5                   10                  15

Gly Gly Gly Gly Ser Gly Gly Gly Gly
            20                  25

<210> SEQ ID NO 78
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly
            20                  25                  30
```

<210> SEQ ID NO 79
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
                20                  25                  30

Gly Gly Gly
        35

<210> SEQ ID NO 80
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
                20                  25                  30

Gly Gly Gly Ser Gly Gly Gly Gly
        35                  40

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 81

His His His His His His
1               5

<210> SEQ ID NO 82
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Arg Thr Glu Arg Ser Pro His Arg Pro Ile Leu Gln Ala Gly Leu Pro
1               5                   10                  15

Ala Asn Ala Ser Thr Val Val Gly Gly Asp Val Glu Phe Val Cys Lys
                20                  25                  30

Val Tyr Ser Asp Ala Gln Pro His Ile Gln Trp Ile Lys His Val Glu
                35                  40                  45

Lys Asn Gly Ser Lys Tyr Gly Pro Asp Gly Leu Pro Tyr Leu Lys Val
            50                  55                  60

Leu Lys Ala Ala Gly Val Asn Thr Thr Asp Lys Glu Ile Glu Val Leu

```
                65                  70                  75                  80
Tyr Ile Arg Asn Val Thr Phe Glu Asp Ala Gly Glu Tyr Thr Cys Leu
                    85                  90                  95

Ala Gly Asn Ser Ile Gly Ile Ser Phe His Ser Ala Trp Leu Thr Val
                100                 105                 110

Leu Pro Ala Pro Gly Arg Glu Lys Glu Ile Thr Ala Ser Pro Asp Tyr
            115                 120                 125

Leu Glu
    130

<210> SEQ ID NO 83
<211> LENGTH: 120
<212> TYPE: DNA
<213> ORGANISM: Homo sapiens

<400> SEQUENCE: 83
gccgccggtg ttaacaccac ggacaaagag attgaggttc tctatattcg gaatgtaact      60
tttgaggacg ctggggaata tacgtgcttg gcgggtaatt ctattgggat atcctttcac    120

<210> SEQ ID NO 84
<211> LENGTH: 40
<212> TYPE: PRT
<213> ORGANISM: Homo sapiens

<400> SEQUENCE: 84

Ala Ala Gly Val Asn Thr Thr Asp Lys Glu Ile Glu Val Leu Tyr Ile
1               5                   10                  15

Arg Asn Val Thr Phe Glu Asp Ala Gly Glu Tyr Thr Cys Leu Ala Gly
            20                  25                  30

Asn Ser Ile Gly Ile Ser Phe His
        35                  40

<210> SEQ ID NO 85
<211> LENGTH: 39
<212> TYPE: DNA
<213> ORGANISM: Homo sapiens

<400> SEQUENCE: 85
acgtgcttgg cgggtaattc tattgggata tcctttcac                             39

<210> SEQ ID NO 86
<211> LENGTH: 13
<212> TYPE: PRT
<213> ORGANISM: Homo sapiens

<400> SEQUENCE: 86

Thr Cys Leu Ala Gly Asn Ser Ile Gly Ile Ser Phe His
1               5                   10

<210> SEQ ID NO 87
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gaggtccagc tgcagcagtc tggggctgag ctggcaagac ctggggcttc agtgaagttg      60
tcctgcaaga cttctggcta cacctttact agctactgga tgcagtggtt aaaacagagg    120
```

```
cctggacagg gtctggaatg gattggggct attcatcctg agatggtga tactaggtat    180 actcagaagt ttaagggcaa ggccacattg actgcagata atcctccag cacagcctac    240 atgcaactca gcagcttggc atctgaggac tctgcggtct attactgtgc aagatcggat    300
accggccgtt actatggttt ggactactgg ggtcaaggaa cctcagtcac cgtctcc      357
```

<210> SEQ ID NO 88
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Glu Val Gln Leu Gln Gln Ser Gly Ala Glu Leu Ala Arg Pro Gly Ala
1               5                   10                  15

Ser Val Lys Leu Ser Cys Lys Thr Ser Gly Tyr Thr Phe Thr Ser Tyr
            20                  25                  30

Trp Met Gln Trp Leu Lys Gln Arg Pro Gly Gln Gly Leu Glu Trp Ile
        35                  40                  45

Gly Ala Ile His Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Ser Asp Thr Gly Arg Tyr Tyr Gly Leu Asp Tyr Trp Gly Gln
            100                 105                 110

Gly Thr Ser Val Thr Val Ser
        115
```

<210> SEQ ID NO 89
<211> LENGTH: 323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
gacatccaga tgaaccagtc tccagccacc ctgtctgtga ctccaggaga cagtcagt     60 ctttcctgta gggccagcca gagtatttac aagaacctac actggtatca acagaaatca   120
catcggtctc caaggcttct catcaagtct acttctgatt ccatctctgg gatcccctcc   180
aggttcactg gcagtggatc agggactgat tacactctca gtatcaacag tgtgaagccc   240
gaagatgaag ggatatatta ctgtcttcaa ggttacagca caccgtacac gttcggaggg   300
gggaccaagc tggaaataaa acg                                           323
```

<210> SEQ ID NO 90
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Asp Ile Gln Met Asn Gln Ser Pro Ala Thr Leu Ser Val Thr Pro Gly
1               5                   10                  15
```

```
Glu Thr Val Ser Leu Ser Cys Arg Ala Ser Gln Ser Ile Tyr Lys Asn
             20                  25                  30

Leu His Trp Tyr Gln Gln Lys Ser His Arg Ser Pro Arg Leu Leu Ile
         35                  40                  45

Lys Ser Thr Ser Asp Ser Ile Ser Gly Ile Pro Ser Arg Phe Thr Gly
 50                  55                  60

Ser Gly Ser Gly Thr Asp Tyr Thr Leu Ser Ile Asn Ser Val Lys Pro
 65                  70                  75                  80

Glu Asp Glu Gly Ile Tyr Tyr Cys Leu Gln Gly Tyr Ser Thr Pro Tyr
                 85                  90                  95

Thr Phe Gly Gly Gly Thr Lys Leu Glu Ile Lys Arg
            100                 105
```

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 91
ggctacacct ttactagcta ctgg                                          24

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

```
Gly Tyr Thr Phe Thr Ser Tyr Trp
 1               5
```

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
attcatcctg gagatggtga tact                                          24

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

```
Ile His Pro Gly Asp Gly Asp Thr
 1               5
```

<210> SEQ ID NO 95
<211> LENGTH: 39
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 95
gcaagatcgg ataccggccg ttactatggt ttggactac                                 39

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Arg Ser Asp Thr Gly Arg Tyr Tyr Gly Leu Asp Tyr
1               5                   10

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
agggccagcc agagtattta caagaac                                              27

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Ser Ile Tyr Lys Asn
1               5

<210> SEQ ID NO 99
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99 tctacttct                                                                   9

<210> SEQ ID NO 100
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Thr Ser
1

<210> SEQ ID NO 101
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 101
cttcaaggtt acagcacacc gtacacg                                           27

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Leu Gln Gly Tyr Ser Thr Pro Tyr Thr
1               5

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ataggatcct tgccgccggt gttaac                                            26

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gcggaattcg tgaaaggata tccc                                              24

<210> SEQ ID NO 105
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ataggatcct tgccgccggt gttaac                                            26

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gcggaattcg tgaaaggata tccc                                              24

<210> SEQ ID NO 107
<211> LENGTH: 128
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 107

Glu Arg Ser Pro His Arg Pro Ile Leu Gln Ala Gly Leu Pro Ala Asn
1               5                   10                  15

Ala Ser Thr Val Val Gly Gly Asp Val Glu Phe Val Cys Lys Val Tyr
            20                  25                  30

Ser Asp Ala Gln Pro His Ile Gln Trp Ile Lys His Val Glu Lys Asn
        35                  40                  45

Gly Ser Lys Tyr Gly Pro Asp Gly Leu Pro Tyr Leu Lys Val Leu Lys
    50                  55                  60

Ala Ala Gly Val Asn Thr Thr Asp Lys Glu Ile Glu Val Leu Tyr Ile
65                  70                  75                  80

Arg Asn Val Thr Phe Glu Asp Ala Gly Glu Tyr Thr Cys Leu Ala Gly
                85                  90                  95

Asn Ser Ile Gly Ile Ser Phe His Ser Ala Trp Leu Thr Val Leu Pro
            100                 105                 110

Ala Pro Gly Arg Glu Lys Glu Ile Thr Ala Ser Pro Tyr Leu Glu
        115                 120                 125

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
gagcgatcgc ctcaccggcc                                           20

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
ctccaggtag tctggggaag ct                                        22

<210> SEQ ID NO 110
<211> LENGTH: 227
<212> TYPE: PRT
<213> ORGANISM: Homo sapiens

<400> SEQUENCE: 110

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

```
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Glu Glu Met Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu Lys Phe His Tyr Thr Gln Lys Ser Leu Ser Leu Ser
    210                 215                 220
Pro Gly Lys
225

<210> SEQ ID NO 111
<211> LENGTH: 262
<212> TYPE: PRT
<213> ORGANISM: Homo sapiens

<400> SEQUENCE: 111

Met Val Ser Trp Gly Arg Phe Ile Cys Leu Val Val Thr Met Ala
1               5                   10                  15
Thr Leu Ser Leu Ala Arg Pro Ser Phe Ser Leu Val Glu Asp Thr Thr
                20                  25                  30
Leu Glu Pro Glu Gly Ala Pro Tyr Trp Thr Asn Thr Glu Lys Met Glu
            35                  40                  45
Lys Arg Leu His Ala Val Pro Ala Ala Asn Thr Val Lys Phe Arg Cys
        50                  55                  60
Pro Ala Gly Gly Asn Pro Met Pro Thr Met Arg Trp Leu Lys Asn Gly
65                  70                  75                  80
Lys Glu Phe Lys Gln Glu His Arg Ile Gly Gly Tyr Lys Val Arg Asn
                85                  90                  95
Gln His Trp Ser Leu Ile Met Glu Ser Val Val Pro Ser Asp Lys Gly
            100                 105                 110
Asn Tyr Thr Cys Val Val Glu Asn Glu Tyr Gly Ser Ile Asn His Thr
        115                 120                 125
Tyr His Leu Asp Val Val Glu Arg Ser Pro His Arg Pro Ile Leu Gln
130                 135                 140
Ala Gly Leu Pro Ala Asn Ala Ser Thr Val Val Gly Gly Asp Val Glu
145                 150                 155                 160
Phe Val Cys Lys Val Tyr Ser Asp Ala Gln Pro His Ile Gln Trp Ile
                165                 170                 175
Lys His Val Glu Lys Asn Gly Ser Lys Tyr Gly Pro Asp Gly Leu Pro
            180                 185                 190
Tyr Leu Lys Val Leu Lys Ala Ala Gly Val Asn Thr Thr Asp Lys Glu
        195                 200                 205
Ile Glu Val Leu Tyr Ile Arg Asn Val Thr Phe Glu Asp Ala Gly Glu
```

```
              210                 215                 220
Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
                245                 250                 255

Ser Pro Asp Tyr Leu Glu
            260

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agagaattcg cggccctcct tcagtttagt                                              30

<210> SEQ ID NO 113
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gtgagatctc tccaggtagt ctggggaagc t                                            31

<210> SEQ ID NO 114
<211> LENGTH: 258
<212> TYPE: PRT
<213> ORGANISM: Homo sapiens

<400> SEQUENCE: 114

Thr Leu Glu Pro Glu Asp Ala Ile Ser Ser Gly Asp Asp Glu Asp Asp
1               5                   10                  15

Thr Asp Gly Ala Glu Asp Phe Val Ser Glu Asn Ser Asn Asn Lys Arg
            20                  25                  30

Ala Pro Tyr Trp Thr Asn Thr Glu Lys Met Glu Lys Arg Leu His Ala
        35                  40                  45

Val Pro Ala Ala Asn Thr Val Lys Phe Arg Cys Pro Ala Gly Gly Asn
    50                  55                  60

Pro Met Pro Thr Met Arg Trp Leu Lys Asn Gly Lys Glu Phe Lys Gln
65                  70                  75                  80

Glu His Arg Ile Gly Gly Tyr Lys Val Arg Asn Gln His Trp Ser Leu
                85                  90                  95

Ile Met Glu Ser Val Val Pro Ser Asp Lys Gly Asn Tyr Thr Cys Val
            100                 105                 110

Val Glu Asn Glu Tyr Gly Ser Ile Asn His Thr Tyr His Leu Asp Val
        115                 120                 125

Val Glu Arg Ser Pro His Arg Pro Val Leu Gln Ala Gly Leu Pro Ala
    130                 135                 140

Asn Ala Ser Thr Val Val Gly Gly Asp Val Glu Phe Val Cys Lys Val
145                 150                 155                 160

Tyr Ser Asp Ala Gln Pro His Ile Gln Trp Ile Lys His Val Glu Lys
                165                 170                 175

Asn Gly Ser Lys Tyr Gly Pro Asp Gly Leu Pro Tyr Leu Lys Val Leu
```

```
            180                 185                 190
Lys His Ser Gly Ile Asn Ser Ser Asn Ala Glu Val Leu Ala Leu Phe
                195                 200                 205

Asn Val Thr Glu Ala Asp Ala Gly Glu Tyr Ile Cys Lys Val Ser Asn
    210                 215                 220

Tyr Ile Gly Gln Ala Asn Gln Ser Ala Trp Leu Thr Val Leu Pro Lys
225                 230                 235                 240

Gln Gln Ala Pro Gly Arg Glu Lys Glu Ile Thr Ala Ser Pro Asp Tyr
                245                 250                 255

Leu Glu

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
agagaattcg cggccctcct tcagtttagt                                    30

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gtgagatctc tccaggtagt ctggggaagc                                    30

<210> SEQ ID NO 117
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cgactagtcg accagggatc cagagttcca ag                                 32

<210> SEQ ID NO 118
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gcgccgtcta gaattaacac tcattcctgt tgaa                               34

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
```

```
saggtccagc tgcagcagyy tgg                                          23
```

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

```
gaggttcagc tgcagcagtc tgk                                          23
```

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121

```
gaggaaacgg tgaccgtggt                                              20
```

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122

```
gaggagactg tgagagtggt                                              20
```

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123

```
gcagagacag tgaccagagt                                              20
```

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124

```
gaggagacgg tgactgaggt                                              20
```

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125

```
gatgytktkv tgacccaaac tcc                                          23
```

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gatatccaga tgacacagac tac                                              23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
racattgtgc tgacmcaatc tcc                                              23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
saaawtgtkc tcwcccagtc tcc                                              23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gamatcmwga tgacccartc tcc                                              23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
rrcattgtga tgacccagwc tcm                                              23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gatattgtga tracbcaggy tgm                                              23

```
<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
ramattdtgw tgwcacagtc tay                                              23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gacatccaga tgacwcartc tyc                                              23

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gacatccaga tgammcagtc tcc                                              23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gayatystgm tracrcagtc tcc                                              23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gacattgtga tgactcagtc tcc                                              23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gaaacaactg tgacccagtc tcc                                              23
```

```
<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
acgtttgatt tccagcttgg                                               20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
acgttttatt tccagcttgg                                               20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
acgttttatt tccaactttg                                               20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
acgtttcagc tccagcttgg                                               20

<210> SEQ ID NO 142
<211> LENGTH: 119
<212> TYPE: PRT
<213> ORGANISM: Mus musculus

<400> SEQUENCE: 142
```

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Ala Ser Thr Ala Pro Tyr Tyr Ala Met Asp Tyr Trp Gly Gln
            100                 105                 110

```
Gly Thr Ser Val Thr Val Ser
            115

<210> SEQ ID NO 143
<211> LENGTH: 106
<212> TYPE: PRT
<213> ORGANISM: Mus musculus

<400> SEQUENCE: 143

Asp Ile Gln Leu Thr Gln Ser Pro Ala Ile Leu Ser Val Thr Pro Gly
1               5                   10                  15

Glu Thr Val Ser Leu Ser Cys Arg Ala Ser Gln Thr Ile Tyr Lys Asn
            20                  25                  30

Leu His Trp Tyr Gln Gln Lys Ser His Arg Ser Pro Arg Leu Leu Ile
        35                  40                  45

Lys Tyr Gly Ser Asp Ser Ile Ser Gly Ile Pro Ser Arg Phe Thr Gly
    50                  55                  60

Ser Gly Ser Gly Thr Asp Tyr Thr Leu Asn Ile Asn Ser Val Lys Pro
65                  70                  75                  80

Glu Asp Glu Gly Ile Tyr Tyr Cys Leu Gln Gly Tyr Ser Thr Pro Trp
                85                  90                  95

Thr Phe Gly Gly Gly Thr Lys Leu Glu Ile
            100                 105

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ser Gly Ser Ser Ser Asn Ile Gly Ser Asn Thr Val Asn
1               5                   10

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Asn Asn Gln Arg Pro Ser Gly Val
1               5

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Ala Trp Asp Asp Ser Leu Asn Gly Val Val
1               5                   10

<210> SEQ ID NO 147
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 147

Ser Ser Tyr Ala Ile Ser
1               5

<210> SEQ ID NO 148
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ile Ile Pro Ile Phe Gly Thr Ala Asn Tyr Ala Gln Lys Phe Gln
1               5                   10                  15

Gly Arg

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Asp Arg Trp Asp Trp Asn Asp Ala Phe Asp Ile
1               5                   10

<210> SEQ ID NO 150
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ser or Asn
<220> FEATURE:
<221> NAME/KEY: MOD_RES
<222> LOCATION: (11)..(11)
<223> OTHER INFORMATION: Thr or Tyr
<220> FEATURE:
<221> NAME/KEY: MOD_RES
<222> LOCATION: (13)..(13)
<223> OTHER INFORMATION: Ser or Asn

<400> SEQUENCE: 150

Ser Gly Ser Ser Ser Asn Ile Gly Xaa Asn Xaa Val Xaa
1               5                   10

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asp
<220> FEATURE:
```

```
<221> NAME/KEY: MOD_RES
<222> LOCATION: (4)..(4)
<223> OTHER INFORMATION: Gln or Lys
<220> FEATURE:
<221> NAME/KEY: MOD_RES
<222> LOCATION: (9)..(9)
<223> OTHER INFORMATION: Val or Ile

<400> SEQUENCE: 151

Xaa Asn Asn Xaa Arg Pro Ser Gly Xaa
1               5

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala or Gly
<220> FEATURE:
<221> NAME/KEY: MOD_RES
<222> LOCATION: (2)..(2)
<223> OTHER INFORMATION: Ala or Thr
<220> FEATURE:
<221> NAME/KEY: MOD_RES
<222> LOCATION: (5)..(5)
<223> OTHER INFORMATION: Asp or Ser
<220> FEATURE:
<221> NAME/KEY: MOD_RES
<222> LOCATION: (8)..(8)
<223> OTHER INFORMATION: Asn or Ser
<220> FEATURE:
<221> NAME/KEY: MOD_RES
<222> LOCATION: (9)..(9)
<223> OTHER INFORMATION: Gly or Ala

<400> SEQUENCE: 152

Xaa Xaa Trp Asp Xaa Ser Leu Xaa Xaa Val Val
1               5                   10

<210> SEQ ID NO 153
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phe or Leu
<220> FEATURE:
<221> NAME/KEY: MOD_RES
<222> LOCATION: (8)..(8)
<223> OTHER INFORMATION: Thr or Ile

<400> SEQUENCE: 153

Arg Ile Ile Pro Ile Xaa Gly Xaa Ala Asn Tyr Ala Gln Lys Phe Gln
1               5                   10                  15

Gly Arg

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Arg or Pro
<220> FEATURE:
<221> NAME/KEY: MOD_RES
<222> LOCATION: (4)..(4)
<223> OTHER INFORMATION: Trp or Leu
<220> FEATURE:
<221> NAME/KEY: MOD_RES
<222> LOCATION: (5)..(5)
<223> OTHER INFORMATION: Asp or Leu
<220> FEATURE:
<221> NAME/KEY: MOD_RES
<222> LOCATION: (7)..(7)
<223> OTHER INFORMATION: Asn or Ser
<220> FEATURE:
<221> NAME/KEY: MOD_RES
<222> LOCATION: (8)..(8)
<223> OTHER INFORMATION: Asp or absent
<220> FEATURE:
<221> NAME/KEY: MOD_RES
<222> LOCATION: (9)..(9)
<223> OTHER INFORMATION: Ala or Tyr
<220> FEATURE:
<221> NAME/KEY: MOD_RES
<222> LOCATION: (12)..(12)
<223> OTHER INFORMATION: Ile or Tyr

<400> SEQUENCE: 154

Arg Asp Xaa Xaa Xaa Trp Xaa Xaa Xaa Phe Asp Xaa
1               5                   10

<210> SEQ ID NO 155
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Gly Ser Ser Ser Asn Ile Gly Asn Asn Tyr Val Ser
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Asn Asn Lys Arg Pro Ser Gly Ile
1               5

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Thr Trp Asp Ser Ser Leu Ser Ala Val Val
1               5                   10

<210> SEQ ID NO 158
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Ile Ile Pro Ile Leu Gly Ile Ala Asn Tyr Ala Gln Lys Phe Gln
1               5                   10                  15

Gly Arg

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Asp Pro Leu Leu Trp Ser Tyr Phe Asp Tyr
1               5                   10

<210> SEQ ID NO 160
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Asp Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly Ser
            100                 105                 110

Gly Gly Ser Thr Ile Thr Ser Tyr Asn Val Tyr Tyr Thr Lys Leu Ser
        115                 120                 125

Ser Ser Gly Thr Glu Val Gln Leu Val Gln Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Arg Ile Ile Pro Ile Leu Gly Ile Ala Asn Tyr
            180                 185                 190

Ala Gln Lys Phe Gln Gly Arg Val Thr Ile Thr Ala Asp Lys Ser Thr
        195                 200                 205

Ser Thr Ala Tyr Met Glu Leu Ser Ser Leu Arg Ser Glu Asp Thr Ala
    210                 215                 220
```

```
Val Tyr Tyr Cys Ala Arg Asp Pro Leu Leu Trp Ser Tyr Phe Asp Tyr
225                 230                 235                 240

Trp Gly Gln Gly Thr Leu Val Thr Val Ser Ser
                245                 250
```

<210> SEQ ID NO 161
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly Ser
            100                 105                 110

Gly Gly Ser Thr Ile Thr Ser Tyr Asn Val Tyr Tyr Thr Lys Leu Ser
        115                 120                 125

Ser Ser Gly Thr Gln Val Gln Leu Val Gln Ser Gly Ala Glu Val Lys
130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Arg Ile Ile Pro Ile Phe Gly Thr Ala Asn Tyr
            180                 185                 190

Ala Gln Lys Phe Gln Gly Arg Val Thr Ile Thr Ala Asp Glu Ser Thr
        195                 200                 205

Ser Thr Ala Tyr Met Glu Leu Asn Ser Leu Arg Ser Glu Asp Thr Ala
210                 215                 220

Val Tyr Tyr Cys Ala Arg Asp Arg Trp Asp Trp Asn Asp Ala Phe Asp
225                 230                 235                 240

Ile Trp Gly Gln Gly Thr Met Val Thr Val Ser Ser
                245                 250
```

<210> SEQ ID NO 162
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162

```
cagtctgtgc tgacgcagcc gccctcagtg tctgcggccc caggacagaa ggtcaccatc      60
```

```
tcctgctctg gaagcagctc caacattggg aataattatg tatcctggta ccagcagctc    120
ccaggaacag cccccaaact cctcatatat gacaataata agcgaccctc agggattcct    180
gaccgattct ctggctccaa gtctggcacg tcagccaccc tggccatcag tgggctccag    240
tctgaggatg aggctgatta ttactgtgca gcatgggatg acagcctgaa tggtgtggta    300
ttcggcggag ggaccaagct gaccgtccta ggttccggag ggtcgaccat aacttcgtat    360
aatgtatact atacgaagtt atcctcgagc ggtacccagg tccagctggt gcagtctggg    420
gctgaggtga agaagcctgg gtcctcggtg aaggtctcct gcaaggcttc tggaggcacc    480
ttcagcagct atgctatcag ctgggtgcga caggcccctg acaagggct tgagtggatg    540 ggaaggatca tccctatctt tggtacagca aactacgcac agaagttcca gggcagagtc    600
acgattaccg cggacgaatc cacgagcaca gcctacatgg agctgaacag cctgagatct    660
gaggacacgg ccgtgtatta ctgtgcgaga gatcgatggg actggaacga cgcttttgat    720
atctggggcc aagggacaat ggtcaccgtc tcctca                              756
```

```
<210> SEQ ID NO 163
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
                100                 105                 110
```

```
<210> SEQ ID NO 164
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
cagtctgtgc tgacgcagcc gccctcagtg tctgcggccc caggacagaa ggtcaccatc    60
tcctgctctg gaagcagctc caacattggg aataattatg tatcctggta ccagcagctc    120
ccaggaacag cccccaaact cctcatatat gacaataata agcgaccctc agggattcct    180
gaccgattct ctggctccaa gtctggcacg tcagccaccc tggccatcag tgggctccag    240
tctgaggatg aggctgatta ttactgtgca gcatgggatg acagcctgaa tggtgtggta    300
ttcggcggag ggaccaagct gaccgtccta ggt                                 333
```

<210> SEQ ID NO 165
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 165

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Arg Asp Arg Trp Asp Trp Asn Asp Ala Phe Asp Ile Trp Gly Gln
            100                 105                 110

Gly Thr Met Val Thr Val Ser Ser
        115                 120

<210> SEQ ID NO 166
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166
caggtccagc tggtgcagtc tggggctgag gtgaagaagc ctgggtcctc ggtgaaggtc      60
tcctgcaagg cttctggagg cacctteage agetatgeta tcagetgggt gcgacaggcc     120 cctggacaag ggcttgagtg gatgggaagg atcatccecta tctttggtac agcaaactac     180
gcacagaagt tccagggcag agtcacgatt accgcggacg aatccacgag cacagcctac     240
atggagctga acagcctgag atctgaggac acggccgtgt attactgtgc gagagatcga     300
tgggactgga acgacgcttt tgatatctgg ggccaaggga caatggtcac cgtctcctca     360

<210> SEQ ID NO 167
<211> LENGTH: 753
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 167
cagtctgtgc tgacgcagcc gccctcggtg tctgcggccc caggacagaa ggtcaccatc      60
tcctgctctg gaagcagctc caacattggg aataattatg tatcctggta ccagcagctc     120
ccaggaacag cccccaaact cctcatttat gacaataata gcgaccctc agggattcct     180 gaccgattct ctgactccaa gtctggcacg tcagccaccc tgggcatcac cggactccag     240
actggggacg aggccgatta ttactgcgga acatgggata gcagcctgag tgctgtggta     300

```
ttcggcggag ggaccaagct caccgtccta ggttccggag ggtcgaccat aacttcgtat       360
aatgtatact atacgaagtt atcctcgagc ggtaccgagg tgcagctggt gcagtctggg       420
gctgaggtga agaagcctgg gtcctcggtg aaggtctcct gcaaggcttc tggaggcacc       480
ttcagcagct atgctatcag ctgggtgcga caagcccctg acaagggct tgagtggatg        540 ggaaggatca tccctatcct tggtatagca aactacgcac agaagttcca gggcagagtc       600
acgattaccg cggacaaatc cacgagcaca gcctacatgg agctgagcag cctgagatct       660
gaggacacgg ccgtgtatta ctgtgcgaga gatccgctat tgtggtctta ctttgactac       720
tggggccagg gaaccctggt cactgtctct tca                                    753
```

<210> SEQ ID NO 168
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

```
Gln Ser Val Leu Thr Gln Pro Pro Ser Val Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Asp Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly
            100                 105                 110
```

<210> SEQ ID NO 169
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169

```
cagtctgtgc tgacgcagcc gccctcggtg tctgcggccc caggacagaa ggtcaccatc       60
tcctgctctg gaagcagctc caacattggg aataattatg tatcctggta ccagcagctc      120
ccaggaacag cccccaaact cctcatttat gacaataata gcgaccctc agggattcct       180 gaccgattct ctgactccaa gtctggcacg tcagccaccc tgggcatcac ggactccag       240 actggggacg aggccgatta ttactgcgga acatgggata gcagcctgag tgctgtggta      300
ttcggcggag ggaccaagct caccgtccta ggt                                    333
```

<210> SEQ ID NO 170
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Leu Leu Trp Ser Tyr Phe Asp Tyr Trp Gly Gln Gly
            100                 105                 110

Thr Leu Val Thr Val Ser Ser
        115

<210> SEQ ID NO 171
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171
gaggtgcagc tggtgcagtc tggggctgag gtgaagaagc ctgggtcctc ggtgaaggtc      60
tcctgcaagg cttctggagg cacctcagc agctatgcta tcagctgggt gcgacaagcc     120
cctggacaag ggcttgagtg gatgggaagg atcatcccta tccttggtat agcaaactac    180
gcacagaagt tccagggcag agtcacgatt accgcggaca aatccacgag cacagcctac    240
atggagctga gcagcctgag atctgaggac acggccgtgt attactgtgc gagagatccg    300
ctattgtggt cttactttga ctactggggc cagggaaccc tggtcactgt ctcttca       357

<210> SEQ ID NO 172
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tctggaagca gctccaacat cggaagtaat actgtaaac                             39

<210> SEQ ID NO 173
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
agtaataatc agcggccctc agggtc                                           27

<210> SEQ ID NO 174
<211> LENGTH: 33

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gcagcatggg atgacagcct gaatggtgtg gta                             33

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
agcagctatg ctatcagc                                              18

<210> SEQ ID NO 176
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
aggatcatcc ctatctttgg tacagcaaac tacgcacaga agttccaggg caga      54

<210> SEQ ID NO 177
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
agagatcgat gggactggaa cgacgctttt gatatc                          36

<210> SEQ ID NO 178
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
tctggaagca gctccaacat tgggaataat tatgtatcc                       39

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gacaataata agcgaccctc agggatt                                    27

<210> SEQ ID NO 180
<211> LENGTH: 33
<212> TYPE: DNA

<210> SEQ ID NO 181
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 180
ggaacatggg atagcagcct gagtgctgtg gta                33

<210> SEQ ID NO 181
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 181
agctatgcta tcagc                15

<210> SEQ ID NO 182
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 182
aggatcatcc ctatccttgg tatagcaaac tacgcacaga agttccaggg c                51

<210> SEQ ID NO 183
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 183
agagatccgc tattgtggtc ttactttgac tac                33

<210> SEQ ID NO 184
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 184
tctggaagca gctccaacat tgggaataat tatgtatcc                39

<210> SEQ ID NO 185
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 185
gacaataata agcgaccctc agggatt                27

<210> SEQ ID NO 186
<211> LENGTH: 33
<212> TYPE: DNA
<213> ORGANISM: Artificial Sequence
<210> SEQ ID NO 187
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gcagcatggg atgacagcct gaatggtgtg gta                                  33

<210> SEQ ID NO 187
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
agctatgcta tcagc                                                      15

<210> SEQ ID NO 188
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
aggatcatcc ctatctttgg tacagcaaac tacgcacaga gttccaggg caga            54

<210> SEQ ID NO 189
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
agagatcgat gggactggaa cgacgctttt gatatc                               36

<210> SEQ ID NO 190
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly Ser
            100                 105                 110

Gly Gly Ser Thr Val Thr Ser Tyr Asn Val Tyr Tyr Thr Lys Leu Ser
            115                 120                 125

Ser Ser Gly Thr Gln Val Gln Leu Val Gln Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Arg Ile Ile Pro Ile Phe Gly Thr Ala Asn Tyr
            180                 185                 190

Ala Gln Lys Phe Gln Gly Arg Val Thr Ile Thr Ala Asp Glu Ser Thr
        195                 200                 205

Ser Thr Ala Tyr Met Glu Leu Asn Ser Leu Arg Ser Glu Asp Thr Ala
    210                 215                 220

Val Tyr Tyr Cys Ala Arg Asp Arg Trp Asp Trp Asn Asp Ala Phe Asp
225                 230                 235                 240

Ile Trp Gly Gln Gly Thr Met Val Thr Val Ser Ser
                245                 250

<210> SEQ ID NO 191
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
cagtctgtgc tgacgcagcc accctcagcg tctgggaccc ccgggcagag ggtcaccatc      60
tcttgttctg gaagcagctc caacatcgga agtaatactg taaactggta ccagcagctc     120
ccaggaacgg ccccccaaact cctcatctat agtaataatc agcggccctc agggctccct     180
gaccgattct ctggctccaa gtctggcacc tcagcctccc tggccatcag tgggctccag     240
tctgaggatg aggctgatta ttactgtgca gcatgggatg acagcctgaa tggtgtggta     300
ttcggcggag ggaccaagct gaccgtccta ggttccggag gtcgaccgt aacttcgtat     360
aatgtatact atacgaagtt atcctcgagc ggtacccagg tccagctggt gcagtctggg     420
gctgaggtga agaagcctgg gtcctcggtg aaggtctcct gcaaggcttc tggaggcacc     480
ttcagcagct atgctatcag ctgggtgcga caggcccctg gacaagggct tgagtggatg     540
ggaaggatca tccctatctt tggtacagca aactacgcac agaagttcca gggcagagtc     600
acgattaccg cggacgaatc cacgagcaca gcctacatgg agctgaacag cctgagatct     660
gaggacacgg ccgtgtatta ctgtgcgaga gatcgatggg actggaacga cgcttttgat     720
atctggggcc aagggacaat ggtcaccgtc tcctca                                756

<210> SEQ ID NO 192
<211> LENGTH: 739
<212> TYPE: PRT
<213> ORGANISM: Homo sapiens

<400> SEQUENCE: 192

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Asp Thr

-continued

```
                35                  40                  45
Asp Gly Ala Glu Asp Phe Val Ser Glu Asn Ser Asn Asn Lys Arg Ala
 50                  55                  60
Pro Tyr Trp Thr Asn Thr Glu Lys Met Glu Lys Arg Leu His Ala Val
 65                  70                  75                  80
Pro Ala Ala Asn Thr Val Lys Phe Arg Cys Pro Ala Gly Gly Asn Pro
                 85                  90                  95
Met Pro Thr Met Arg Trp Leu Lys Asn Gly Lys Glu Phe Lys Gln Glu
                100                 105                 110
His Arg Ile Gly Gly Tyr Lys Val Arg Asn Gln His Trp Ser Leu Ile
                115                 120                 125
Met Glu Ser Val Val Pro Ser Asp Lys Gly Asn Tyr Thr Cys Val Val
                130                 135                 140
Glu Asn Glu Tyr Gly Ser Ile Asn His Thr Tyr His Leu Asp Val Val
145                 150                 155                 160
Glu Arg Ser Pro His Arg Pro Val Leu Gln Ala Gly Leu Pro Ala Asn
                165                 170                 175
Ala Ser Thr Val Val Gly Gly Asp Val Glu Phe Val Cys Lys Val Tyr
                180                 185                 190
Ser Asp Ala Gln Pro His Ile Gln Trp Ile Lys His Val Glu Lys Asn
                195                 200                 205
Gly Ser Lys Tyr Gly Pro Asp Gly Leu Pro Tyr Leu Lys Val Leu Lys
                210                 215                 220
His Ser Gly Ile Asn Ser Ser Asn Ala Glu Val Leu Ala Leu Phe Asn
225                 230                 235                 240
Val Thr Glu Ala Asp Ala Gly Glu Tyr Ile Cys Lys Val Ser Asn Tyr
                245                 250                 255
Ile Gly Gln Ala Asn Gln Ser Ala Trp Leu Thr Val Leu Pro Lys Gln
                260                 265                 270
Gln Ala Pro Gly Arg Glu Lys Glu Ile Thr Ala Ser Pro Asp Tyr Leu
                275                 280                 285
Glu Ile Ala Ile Tyr Cys Ile Gly Val Phe Leu Ile Ala Cys Met Val
                290                 295                 300
Val Thr Val Ile Leu Cys Arg Met Lys Asn Thr Thr Lys Lys Pro Asp
305                 310                 315                 320
Phe Ser Ser Gln Pro Ala Val His Lys Leu Thr Lys Arg Ile Pro Leu
                325                 330                 335
Arg Arg Gln Val Ser Ala Glu Ser Ser Ser Ser Met Asn Ser Asn Thr
                340                 345                 350
Pro Leu Val Arg Ile Thr Thr Arg Leu Ser Ser Thr Ala Asp Thr Pro
                355                 360                 365
Met Leu Ala Gly Val Ser Glu Tyr Glu Leu Pro Glu Asp Pro Lys Trp
                370                 375                 380
Glu Phe Pro Arg Asp Lys Leu Thr Leu Gly Lys Pro Leu Gly Glu Gly
385                 390                 395                 400
Cys Phe Gly Gln Val Val Met Ala Glu Ala Val Gly Ile Asp Lys Asp
                405                 410                 415
Lys Pro Lys Glu Ala Val Thr Val Ala Val Lys Met Leu Lys Asp Asp
                420                 425                 430
Ala Thr Glu Lys Asp Leu Ser Asp Leu Val Ser Glu Met Glu Met Met
                435                 440                 445
Lys Met Ile Gly Lys His Lys Asn Ile Ile Asn Leu Leu Gly Ala Cys
                450                 455                 460
```

```
Thr Gln Asp Gly Pro Leu Tyr Val Ile Val Glu Tyr Ala Ser Lys Gly
465                 470                 475                 480

Asn Leu Arg Glu Tyr Leu Arg Ala Arg Arg Pro Pro Gly Met Glu Tyr
            485                 490                 495

Ser Tyr Asp Ile Asn Arg Val Pro Glu Glu Gln Met Thr Phe Lys Asp
        500                 505                 510

Leu Val Ser Cys Thr Tyr Gln Leu Ala Arg Gly Met Glu Tyr Leu Ala
    515                 520                 525

Ser Gln Lys Cys Ile His Arg Asp Leu Ala Ala Arg Asn Val Leu Val
530                 535                 540

Thr Glu Asn Asn Val Met Lys Ile Ala Asp Phe Gly Leu Ala Arg Asp
545                 550                 555                 560

Ile Asn Asn Ile Asp Tyr Tyr Lys Lys Thr Thr Asn Gly Arg Leu Pro
                565                 570                 575

Val Lys Trp Met Ala Pro Glu Ala Leu Phe Asp Arg Val Tyr Thr His
            580                 585                 590

Gln Ser Asp Val Trp Ser Phe Gly Val Leu Met Trp Glu Ile Phe Thr
        595                 600                 605

Leu Gly Gly Ser Pro Tyr Pro Gly Ile Pro Val Glu Glu Leu Phe Arg
    610                 615                 620

Leu Leu Lys Glu Gly His Arg Met Asp Lys Pro Ala Asn Cys Thr Asn
625                 630                 635                 640

Glu Leu Tyr Met Met Met Arg Asp Cys Trp His Ala Val Pro Ser Gln
                645                 650                 655

Arg Pro Thr Phe Lys Gln Leu Val Glu Asp Leu Asp Arg Ile Leu Thr
            660                 665                 670

Leu Thr Thr Asn Glu Glu Tyr Leu Asp Leu Ser Gln Pro Leu Glu Gln
        675                 680                 685

Tyr Ser Pro Ser Tyr Pro Asp Thr Arg Ser Ser Cys Ser Ser Gly Asp
    690                 695                 700

Asp Ser Val Phe Ser Pro Asp Pro Met Pro Tyr Glu Pro Cys Leu Pro
705                 710                 715                 720

Gln Tyr Pro His Ile Asn Gly Ser Val Lys Thr Met Thr Val Ser Ala
                725                 730                 735

Cys Pro Gln

<210> SEQ ID NO 193
<211> LENGTH: 2254
<212> TYPE: DNA
<213> ORGANISM: Homo sapiens

<400> SEQUENCE: 193
atggaagagg accggggatt ggtaccgtaa ccatggtcag ctggggtcgt tcatctgcc      60 tggtcgtggt caccatggca accttgtccc tggcccggcc ctccttcagt ttagttgagg    120
ataccacatt agagccagaa gatgccatct catccggaga tgatgaggat gacaccgatg    180
gtgcggaaga ttttgtcagt gagaacagta ataacaagag agcaccatac tggaccaaca    240
cagaaaagat ggaaaagcgg ctccatgctg tgcctgcggc caacactgtc aagtttcgct    300
gcccagccgg ggggaaccca tgccaacca tgcggtggct gaaaaacggg aaggagttta    360
agcaggagca tcgcattgga ggctacaagg tacgaaacca gcactggagc ctcattatgg    420
aaagtgtggt cccatctgac aagggaaatt atacctgtgt ggtggagaat gaatacgggt    480
ccatcaatca cacgtaccac ctggatgttg tggagcgatc gcctcaccgg ccgtcctcc    540
```

-continued

```
aagccggact gccggcaaat gcctccacag tggtcggagg agacgtagag tttgtctgca    600
aggtttacag tgatgcccag ccccacatcc agtggatcaa gcacgtggaa agaacggca     660 gtaaatacgg gcccgacggg ctgccctacc tcaaggttct caagcactcg gggataaata    720
gttccaatgc agaagtgctg gctctgttca atgtgaccga gcggatgct ggggaatata     780 tatgtaaggt ctccaattat atagggcagg ccaaccagtc tgcctggctc actgtcctgc    840
caaaacagca agcgcctgga agagaaaagg agattacagc ttccccagac tacctggaga    900
tagccattta ctgcataggg gtcttcttaa tcgcctgtat ggtggtaaca gtcatcctgt    960
gccgaatgaa gaacacgacc aagaagccag acttcagcag ccagccggct gtgcacaagc   1020
tgaccaaacg tatcccctg cggagacagg tttcggctga gtccagctcc tccatgaact    1080
ccaacacccc gctggtgagg ataacaacac gcctctcttc aacggcagac accccatgc    1140 tggcaggggt ctccgagtat gaacttccag aggacccaaa atgggagttt ccaagagata   1200
agctgacact gggcaagccc ctgggagaag gttgctttgg gcaagtggtc atggcggaag   1260
cagtgggaat tgacaaagac aagcccaagg aggcggtcac cgtggccgtg aagatgttga   1320
aagatgatgc cacagagaaa gaccttctct atctggtgtc agagatggag atgatgaaga   1380
tgattgggaa acacaagaat atcataaatc ttcttggagc ctgcacacag gatgggcctc   1440
tctatgtcat agttgagtat gcctctaaag gcaacctccg agaatacctc cgagcccgga   1500
ggccacccgg gatggagtac tcctatgaca ttaaccgtgt tcctgaggag cagatgacct   1560
tcaaggactt ggtgtcatgc acctaccagc tggccagagg catggagtac ttggcttccc   1620
aaaaatgtat tcatcgagat ttagcagcca gaaatgtttt ggtaacagaa acaatgtga    1680 tgaaaatagc agactttgga ctcgccagag atatcaacaa tatagactat tacaaaaaga   1740
ccaccaatgg gcggcttcca gtcaagtgga tggctccaga agccctgttt gatagagtat   1800
acactcatca gagtgatgtc tggtccttcg gggtgttaat gtgggagatc ttcactttag   1860
ggggctcgcc ctacccaggg attcccgtgg aggaactttt taggctgctg aaggaaggac   1920
acagaatgga taagccagcc aactgcacca cgaactgta catgatgatg agggactgtt   1980
ggcatgcagt gccctcccag agaccaacgt tcaagcagtt ggtagaagac ttggatcgaa   2040
ttctcactct cacaaccaat gaggaatact tggacctcag ccaacctctc gaacagtatt   2100
cacctagtta ccctgacaca agaagttctt gttcttcagg agatgattct gttttttctc   2160
cagaccccat gccttacgaa ccatgccttc ctcagtatcc acacataaac ggcagtgtta   2220
aaacatgaat gactgtgtct gcctgtcccc aaac                               2254
```

<210> SEQ ID NO 194
<211> LENGTH: 19
<212> TYPE: PRT
<213> ORGANISM: Artificial Sequence
<220> FEATURE:
<223> OTHER INFORMATION: synthetic MT polypeptide

<400> SEQUENCE: 194

Asp Gln Val His Phe Gln Pro Leu Pro Pro Ala Val Val Lys Leu Ser
1               5                   10                  15

Asp Ala Leu

<210> SEQ ID NO 195
<211> LENGTH: 450
<212> TYPE: DNA
<213> ORGANISM: Artificial Sequence
<220> FEATURE:
<223> OTHER INFORMATION: Synthetic pGEX-128AA-MT

<400> SEQUENCE: 195

```
gagcgatcgc ctcaccggcc catcctccaa gccggactgc cggcaaatgc ctccacagtg      60
gtcggaggag acgtagagtt tgtctgcaag gtttacagtg atgcccagcc ccacatccag     120
tggatcaagc acgtggaaaa gaacggcagt aaatacgggc ccgacgggct gccctacctc     180
aaggttctca aggccgccgg tgttaacacc acggacaaag agattgaggt tctctatatt     240
cggaatgtaa cttttgagga cgctggggaa tatacgtgct tggcgggtaa ttctattggg     300
atatcctttc actctgcatg gttgacagtt ctgccagcgc ctggaagaga aaaggagatt     360
acagcttccc cagactacct ggagatcgat gaccaggttc acttccagcc gctgccgccg     420
gctgttgtta aactgtctga cgctctgtaa                                      450
```

<210> SEQ ID NO 196
<211> LENGTH: 149
<212> TYPE: PRT
<213> ORGANISM: Artificial Sequence
<220> FEATURE:
<223> OTHER INFORMATION: Sythetic pGEX-128AA-MT

<400> SEQUENCE: 196

```
Glu Arg Ser Pro His Arg Pro Ile Leu Gln Ala Gly Leu Pro Ala Asn
1               5                   10                  15

Ala Ser Thr Val Val Gly Gly Asp Val Glu Phe Val Cys Lys Val Tyr
            20                  25                  30

Ser Asp Ala Gln Pro His Ile Gln Trp Ile Lys His Val Glu Lys Asn
        35                  40                  45

Gly Ser Lys Tyr Gly Pro Asp Gly Leu Pro Tyr Leu Lys Val Leu Lys
    50                  55                  60

Ala Ala Gly Val Asn Thr Thr Asp Lys Glu Ile Glu Val Leu Tyr Ile
65                  70                  75                  80

Arg Asn Val Thr Phe Glu Asp Ala Gly Glu Tyr Thr Cys Leu Ala Gly
                85                  90                  95

Asn Ser Ile Gly Ile Ser Phe His Ser Ala Trp Leu Thr Val Leu Pro
            100                 105                 110

Ala Pro Gly Arg Glu Lys Glu Ile Thr Ala Ser Pro Asp Tyr Leu Glu
        115                 120                 125

Ile Asp Asp Gln Val His Phe Gln Pro Leu Pro Pro Ala Val Val Lys
    130                 135                 140

Leu Ser Asp Ala Leu
145
```

<210> SEQ ID NO 197
<211> LENGTH: 1089
<212> TYPE: DNA
<213> ORGANISM: Artificial Sequence
<220> FEATURE:
<223> OTHER INFORMATION: Synthetic pFUS-128AA-mFc

<400> SEQUENCE: 197

```
gagcgatcgc ctcaccggcc catcctccaa gccggactgc cggcaaatgc ctccacagtg      60
gtcggaggag acgtagagtt tgtctgcaag gtttacagtg atgcccagcc ccacatccag     120
tggatcaagc acgtggaaaa gaacggcagt aaatacgggc ccgacgggct gccctacctc     180
aaggttctca aggccgccgg tgttaacacc acggacaaag agattgaggt tctctatatt     240
```

```
cggaatgtaa cttttgagga cgctggggaa tatacgtgct tggcgggtaa ttctattggg    300 atatccttc  actctgcatg gttgacagtt ctgccagcgc ctggaagaga aaggagatt     360 acagcttccc cagactacct ggagagatct cccagagggc cacaatcaa  gccctgtcct    420 ccatgcaaat gcccagcacc taacctcgag ggtggaccat ccgtcttcat cttccctcca    480
aagatcaagg atgtactcat gatctccctg agccccatag tcacatgtgt ggtggtggat    540
gtgagcgagg atgacccaga tgtccagatc agctggtttg tgaacaacgt ggaagtacac    600
acagctcaga cacaaaccca tagagaggat tacaacagta ctctccgggt ggtcagtgcc    660
ctccccatcc agcaccagga ctggatgagt ggcaaggcgt tcgcatgcgc ggtcaacaac    720
aaagacctcc cagcgcccat cgagagaacc atctcaaaac ccaagggtc  agtaagagct    780 ccacaggtat atgtcttgcc tccaccagaa gaagagatga ctaagaaaca ggtcactctg    840
acctgcatgg tcacagactt catgcctgaa gacatttacg tggagtggac caacaacggg    900
aaaacagagc taaactacaa gaacactgaa ccagtcctgg actctgatgg ttcttacttc    960
atgtacagca agctgagagt ggaaaagaag aactgggtgg aaagaaatag ctactcctgt   1020
tcagtggtcc acgagggtct gcacaatcac cacacgacta agagcttctc ccggactccg   1080
ggtaaatga                                                           1089
```

<210> SEQ ID NO 198
<211> LENGTH: 362
<212> TYPE: PRT
<213> ORGANISM: Artificial Sequence
<220> FEATURE:
<223> OTHER INFORMATION: Synthetic pFUS-128AA-mFc

<400> SEQUENCE: 198

```
Glu Arg Ser Pro His Arg Pro Ile Leu Gln Ala Gly Leu Pro Ala Asn
1               5                   10                  15

Ala Ser Thr Val Val Gly Gly Asp Val Glu Phe Val Cys Lys Val Tyr
            20                  25                  30

Ser Asp Ala Gln Pro His Ile Gln Trp Ile Lys His Val Glu Lys Asn
        35                  40                  45

Gly Ser Lys Tyr Gly Pro Asp Gly Leu Pro Tyr Leu Lys Val Leu Lys
    50                  55                  60

Ala Ala Gly Val Asn Thr Thr Asp Lys Glu Ile Glu Val Leu Tyr Ile
65                  70                  75                  80

Arg Asn Val Thr Phe Glu Asp Ala Gly Glu Tyr Thr Cys Leu Ala Gly
                85                  90                  95

Asn Ser Ile Gly Ile Ser Phe His Ser Ala Trp Leu Thr Val Leu Pro
            100                 105                 110

Ala Pro Gly Arg Glu Lys Glu Ile Thr Ala Ser Pro Asp Tyr Leu Glu
        115                 120                 125

Arg Ser Pro Arg Gly Pro Thr Ile Lys Pro Cys Pro Pro Cys Lys Cys
    130                 135                 140

Pro Ala Pro Asn Leu Glu Gly Gly Pro Ser Val Phe Ile Phe Pro Pro
145                 150                 155                 160

Lys Ile Lys Asp Val Leu Met Ile Ser Leu Ser Pro Ile Val Thr Cys
                165                 170                 175

Val Val Val Asp Val Ser Glu Asp Asp Pro Asp Val Gln Ile Ser Trp
            180                 185                 190

Phe Val Asn Asn Val Glu Val His Thr Ala Gln Thr Gln Thr His Arg
        195                 200                 205
```

-continued

```
Glu Asp Tyr Asn Ser Thr Leu Arg Val Val Ser Ala Leu Pro Ile Gln
    210                 215                 220

His Gln Asp Trp Met Ser Gly Lys Ala Phe Ala Cys Ala Val Asn Asn
225                 230                 235                 240

Lys Asp Leu Pro Ala Pro Ile Glu Arg Thr Ile Ser Lys Pro Lys Gly
                245                 250                 255

Ser Val Arg Ala Pro Gln Val Tyr Val Leu Pro Pro Pro Glu Glu Glu
                260                 265                 270

Met Thr Lys Lys Gln Val Thr Leu Thr Cys Met Val Thr Asp Phe Met
            275                 280                 285

Pro Glu Asp Ile Tyr Val Glu Trp Thr Asn Asn Gly Lys Thr Glu Leu
    290                 295                 300

Asn Tyr Lys Asn Thr Glu Pro Val Leu Asp Ser Asp Gly Ser Tyr Phe
305                 310                 315                 320

Met Tyr Ser Lys Leu Arg Val Glu Lys Lys Asn Trp Val Glu Arg Asn
                325                 330                 335

Ser Tyr Ser Cys Ser Val Val His Glu Gly Leu His Asn His His Thr
                340                 345                 350

Thr Lys Ser Phe Ser Arg Thr Pro Gly Lys
            355                 360
```

ANTIBODY MOLECULES TO ONCOGENIC ISOFORMS OF FIBROBLAST GROWTH FACTOR RECEPTOR-2 AND USES THEREOF

CROSS REFERENCE TO RELATED APPLICATIONS

This application is a continuation-in-part application of U.S. Ser. No. 12/866,013, filed on Nov. 22, 2010, which is abandoned, which is a 371 U.S. National Phase of International Application No. PCT/US2009/033031, filed Feb. 4, 2009, published as International Publication No. WO 2009/100105 on Aug. 13, 2009, and which claims the benefit of priority to U.S. Ser. No. 61/025,947, filed on Feb. 4, 2008. This application is also a continuation-in-part of PCT/US2011/047650, filed Aug. 12, 2011, published as International Publication No. WO 2012/021841, which claims the benefit of priority to U.S. Provisional Application Ser. No. 61/373,072, filed Aug. 12, 2010. The contents of the aforementioned applications are hereby incorporated by reference in their entirety.

GOVERNMENT SUPPORT

The work described herein was carried out, at least in part, using funds from the United States government under contract number 1R43CA137929-01, from the National Institutes of Health (NIH). The U.S. government may therefore have certain rights in the invention.

SEQUENCE LISTING

The instant application contains a Sequence Listing which has been submitted in ASCII format via EFS-Web and is hereby incorporated by reference in its entirety. Said ASCII copy, created on Feb. 8, 2013, is named "A2049700130 Sequence Listing_ST25.txt" and is 302,262 bytes in size.

BACKGROUND

In spite of numerous advances in medical research, cancer remains a leading cause of death in the United States. Traditional modes of clinical care, such as surgical resection, radiotherapy and chemotherapy, have a significant failure rate, especially for solid tumors. Failure occurs either because the initial tumor is unresponsive, or because of recurrence due to re-growth at the original site and/or metastases. The etiology, diagnosis and ablation of cancer remain a central focus for medical research and development.

Since the probability of complete remission of cancer is, in most cases, greatly enhanced by early diagnosis, it is desirable for physicians to be able to identify cancerous tumors as early as possible. Identification of cancerous cells based on changes in gene expression is desirable because changes in gene expression are likely to occur prior to the histological changes that distinguish malignant cells from normal cells. Using biomarkers that identify such changes in gene expression, one can identify cancerous or pre-cancerous cells when changes in gene expression are apparent, and thereby effectively target individuals who would most likely benefit from adjuvant therapy. However, the development of methods and compositions that permit early, rapid, and accurate detection of many forms of cancers continues to challenge the medical community. Thus, a significant problem in the treatment of cancer remains detection and prognosis to enable appropriate therapeutic treatment and ablation of cancer.

For example, prostate cancer (CaP) is one of the most common malignancies in men, with an increasing incidence. In 2007, approximately 218,900 men were diagnosed and approximately 27,050 men died of the disease in the U.S. alone. Despite important progress in the early diagnosis of prostate malignancies through the measurement of PSA levels, about 10% of newly diagnosed patients have some evidence of locally advanced CaP and 5% already have distant metastasis at the time of diagnoses (Draisma et al., (2003) *J. Natl. Cancer Inst.* 95:868-878; Thompson et al., (2003) *N. Engl. J. Med.* 349, 215-224; Makinen et al., (2003) *Clin. Cancer Res.* 9, 2435-2439). Curative treatments for locally advanced CaP are available (Bolla et al., (2002) *Lancet* 360, 103-106; Messing et al., (1999) *N. Engl. J. Med.* 341, 1781-1788; D'Amico et al., (2004) *J. Am. Med. Assoc.* 292, 821-827). In contrast, patients with evidence of distant metastases have a very poor prognosis and limited curative treatment exists (Cheville et al., (2002) *Cancer* 95, 1028-1036). Tumor metastasis is the main cause for mortality associated with prostate cancer. Hormone-refractory prostate cancer (HRPC) is an example of an invasive type of prostate cancer.

Limited treatment modalities currently exist for prostate cancer once it has metastasized. For example, systemic therapy is limited to various forms of androgen deprivation. While most patients will demonstrate initial clinical improvement, virtually inevitably, androgen-independent cells develop. Endocrine therapy is thus palliative, not curative. In a study of 1,387 patients with metastatic disease detectable by imaging (e.g., bone or CT scan), the median time to objective disease progression (excluding biochemical/PSA progression) after initiation of hormonal therapy (i.e., development of androgen-independence) was 16-48 months (Eisenberger M. A., et al. (1998) *NEJM* 339:1036-42). Median overall survival in these patients was 28-52 months from the onset of hormonal treatment (Eisenberger M. A., et al. (1998) supra.). Subsequent to developing androgen-independence, there is no effective standard therapy and the median duration of survival is 9-12 months (Vollmer, R. T., et al. (1999) *Clin Can Res* 5: 831-7; Hudes G., et al., (1997) *Proc Am Soc Clin Oncol* 16:316a (abstract); Pienta K. J., et al., (1994) *J Clin Oncol* 12(10):2005-12; Pienta K. J., et al. (1997) *Urology* 50:401-7; Tannock I. F., et al., (1996) *J Clin Oncol* 14:1756-65; Kantoff P. W., et al., (1996) *J. Clin. Oncol.* 15 (Suppl):25:110-25). Cytotoxic chemotherapy is poorly tolerated in this age group and generally considered ineffective and/or impractical. In addition, prostate cancer is relatively resistant to cytotoxic agents. Thus, chemotherapeutic regimen has not demonstrated a significant survival benefit in this patient group. In view of the shortcomings of existing therapies and diagnostics, the need still exists for improved targeted modalities for preventing, treating and/or diagnosing cancers, such as prostate cancer.

SUMMARY

The present invention features, at least in part, isoform-specific inhibitors that inhibit or reduce one or more isoform-associated activities, wherein the isoform-specific inhibitors include but are not limited to, binding molecules (also referred to herein as "isoform-binding molecules") that specifically interact with, e.g., bind to, one or more isoforms (e.g., isoform polypeptides or nucleic acids encoding the same) that arise from, e.g., one or more of: alternative splicing, frameshifting, translational and/or post-translational events, thereby resulting in different transcription or translation products. In one embodiment, the isoform-specific inhibitors specifically bind to, and/or inhibit the activity of, one or more isoforms expressed and/or associated with oncogenic or malignant phenotypes (referred to herein as "oncogenic isoforms"). For example, the isoform-specific inhibitor can be an oncogenic isoform-binding molecule, e.g., an antibody molecule or a nucleic acid inhibitor that specifically interacts with, e.g., binds to, one or more oncogenic isoforms (e.g., oncogenic isoform polypeptides or nucleic acids encoding the same). In another embodiment, the isoform-specific inhibitor is a soluble receptor polypeptide or a fusion form thereof, or a peptide or a functional variant thereof that reduces or inhibits one or more isoform- (e.g., oncogenic isoform-) associated activities.

The oncogenic isoforms can arise from, e.g., alternative splicing, frameshifting, translational and/or post-translational events, of various proto-oncogene expression products in a cell, e.g., a hyperproliferative cell (e.g., a cancerous or tumor cell). The isoform-binding molecules described herein specifically bind to such oncogenic isoforms, and do not substantially bind to the proto-oncogene from which the isoform is derived. In certain embodiments, the isoform-binding molecule (e.g., an antibody molecule) specifically interacts with, e.g., binds to, an oncogenic isoform of fibroblast growth factor receptor 2 (FGFR2) (e.g., an oncogenic FGFR2 isoform IIIc). In other embodiments, the isoform-binding molecules described herein specifically bind to an oncogenic isoform of fibroblast growth factor receptor 1 (FGFR1) (e.g., an oncogenic FGFR1L); RON receptor tyrosine kinase (c-met-related tyrosine kinase) (e.g., an oncogenic RON receptor tyrosine kinase comprising a deletion of exons 5 and 6); KIT receptor tyrosine kinase (e.g., an oncogenic KIT receptor tyrosine kinase comprising a deletion in exon 11); platelet-derived growth factor (PDGF) (e.g., an oncogenic PDGF isoform having a deletion in exon 6); or PDGF-receptor alpha (e.g., an oncogenic PDGF-receptor alpha comprising a deletion of exons 7 and 8). Thus, the binding molecules that specifically bind to an oncogenic isoform provided herein can be used to identify cancerous or tumor cells associated with expression of the oncogenic isoform.

Accordingly, the present invention provides, in part, isoform-specific inhibitors (e.g., antibody molecules, soluble receptor polypeptides and fusion forms thereof, peptides and functional variants thereof, and nucleic acid inhibitors), pharmaceutical compositions thereof, as well as nucleic acids, recombinant expression vectors and host cells for making such isoform-binding molecules. In certain embodiments, the isoform-specific inhibitors selectively bind to and/or reduce, inhibit or otherwise block an interaction of an oncogenic isoform with a ligand or co-receptor, thereby reducing or inhibiting oncogenic activity. In some embodiments, the isoform-specific inhibitors compete for binding of a cognate ligand (e.g., FGF8b) to the isoform (e.g., FGFR2-IIIc). In other embodiments, the isoform-specific inhibitors act as dominant negative competitors, e.g., a dominant negative competitor that binds to the isoform but does not produce intracellular signal. In other embodiments, the isoform-binding molecules may selectively target a cytotoxic or cytostatic agent to a hyperproliferative cell, e.g., a cancer or tumor cell. The isoform-specific inhibitors disclosed herein can be used to treat, prevent and/or diagnose cancerous or malignant conditions and/or disorders, such as cancers or tumors (primary, recurring or metastasizing), including but not limited to, prostatic, bladder, breast, pancreatic, ovarian, brain (glioblastoma) and gastrointestinal cancers. Methods of using the isoform-binding molecules of the invention to detect oncogenic isoforms, to reduce the activity and/or or kill a hyperproliferative cell expressing an oncogenic isoform in vitro, ex vivo or in vivo are also encompassed by the invention. Diagnostic and/or screening methods and kits for evaluating the function or expression of an oncogenic isoform are also disclosed.

Accordingly, in one aspect, the invention features an isoform-specific inhibitor (e.g., an antibody molecule, a soluble receptor polypeptide or a fusion form thereof), which interacts with, or more preferably specifically binds to, one or more isoform polypeptides or fragments thereof. Typical isoform-binding molecules bind to one or more isoform polypeptides or fragments thereof, with high affinity, e.g., with an affinity constant of at least about $10^7$ $M^{-1}$, typically about $10^8$ $M^{-1}$, and more typically, about $10^9$ $M^{-1}$ to $10^{10}$ $M^{-1}$ or stronger; and reduce and/or inhibit one or more activities of the isoforms, e.g., oncogenic isoforms, in a hyperproliferative (e.g., cancerous or malignant) cell and/or tissue. For example, the binding molecule may selectively and specifically reduce or inhibit an oncogenic isoform-associated activity chosen from one or more of: (i) binding of a ligand or co-receptor (e.g., FGF ligand, e.g., FGF8b, FGF2, FGF17 or FGF18 to FGFR2 isoform IIIc); (ii) receptor dimerization (e.g., FGFR2 isoform IIIc dimerization); (iii) isoform signaling, e.g., FGFR2 isoform IIIc signaling; (iv) hyperproliferative (e.g., cancerous or tumor) cell proliferation, growth and/or survival, for example, by induction of apoptosis of the hyperproliferative cell; and/or (v) angiogenesis and/or vascularization of a tumor. In certain embodiments, the inhibitor may exert its effects directly in the hyperproliferative (e.g., cancerous or malignant) cell and/or tissue (e.g., inducing cell killing or apoptosis directly). In other embodiments, the inhibitor can exert its effects by acting on proximal cells, e.g., cells in the vicinity, of the hyperproliferative (e.g., cancerous or malignant) cell and/or tissue. For example, the inhibitor may reduce the angiogenesis and/or vascularization of a tumor tissue.

In one embodiment, the isoform-binding molecule is an antibody molecule that binds to a mammalian, e.g., human, isoform polypeptide or a fragment thereof. For example, the antibody molecule binds to an isoform polypeptide or fragment expressed and/or associated with a hyperproliferative cell, e.g., a cancerous or tumor cell. For example, the antibody molecule binds specifically to an epitope, e.g., a linear or conformational epitope, located or expressed primarily on the surface of a hyperproliferative cell, e.g., a cancerous or tumor cell. In embodiments, the epitope recognized by the antibody molecule is expressed or associated with a hyperproliferative disease, e.g., a cancerous or malignant disease. For example, the epitope recognized by the antibody molecule is expressed or associated with an exon sequence predominantly expressed or associated with one or more cancerous or tumor cells or disorders; the epitope may be located at the junctional region between two exons that are predominantly joined together in one or more cancerous or tumor cells or disorders, e.g., as a result of an in-frame exon deletion or the use of an alternatively spliced exon. Exemplary isoform polypeptides or fragments recognized by isoform-binding molecules of the invention include, but are not limited to, oncogenic isoforms of FGFR2, FGFR1, RON receptor tyrosine kinase, KIT receptor tyrosine kinase, PDGF and PDGF-receptor alpha.

In one embodiment, the antibody molecule binds to an isoform, e.g., an oncogenic isoform, of FGFR2, e.g., human FGFR2. The antibody molecule can bind specifically to FGFR2 isoform IIIc or a fragment thereof, e.g., does not substantially bind to other non-oncogenic isoforms of the FGF receptors, such as other alternative splice variants of FGFR2 (e.g., FGFR2 IIIb (SEQ ID NO: 21), FGFR2 isoform 4 (SEQ ID NO: 22), FGFR2 isoform 7 (SEQ ID NO: 23), FGFR2 isoform 9 (SEQ ID NO: 24), FGFR2 isoform 10 (SEQ ID NO: 25), FGFR2 isoform 11 (SEQ ID NO: 26), FGFR2 isoform 12 (SEQ ID NO: 27), FGFR2 isoform 13

(SEQ ID NO: 28), FGFR2 isoform 14 (SEQ ID NO: 29), FGFR2 isoform 15 (SEQ ID NO: 30), FGFR isoform 17 (SEQ ID NO: 31), FGFR2 isoform 18 (SEQ ID NO: 52), or FGFR2 isoform 19 (SEQ ID NO: 53)). For example, the antibody molecule binds preferentially to FGFR2 isoform IIIc or a fragment thereof, but does not substantially bind to (e.g., shows less than 10%, 8%, 5%, 4%, 3%, 2%, 1% cross-reactivity with) FGFR2 isoform IIIb, e.g., about amino acids 314 to 351 of human FGFR2 isoform IIIb (HSGINSSNAE-VLALFNVTEADAGEYICKVSNYIGQANQ; SEQ ID NO: 56); about amino acids 314 to 328 of human FGFR2 isoform IIIb (HSGINSSNAEVLALF; SEQ ID NO: 57); or about amino acids 340 to 351 of human FGFR2 isoform IIIb (CK-VSNYIGQANQ; SEQ ID NO: 58). In those embodiments, the antibody molecule binds specifically to at least one or more amino acids (e.g., at least one epitope) located in the alternative spliced form of Exon III, e.g., from about amino acids 301 to 360 of FGFR2-IIIc (SEQ ID NO:2); about amino acids 314 to 324 of FGFR2-IIIc (AAGVNTTDKEI, SEQ ID NO:4); about amino acids 328 to 337 of FGFR2-IIIc (YIRN-VTFEDA, SEQ ID NO:6); about amino acids 350 to 353 of FGFR2-IIIc (ISFH, SEQ ID NO:8); about amino acid residues 314-353 of FGFR2 IIIc (AAGVNTTDKEIEVL YIRNVTFEDAGEYTCLAGNSIGISFH(SEQ ID NO: 84)); or about amino acids 341 to 353 of FGFR2-IIIc (TCLA-GNSIGISFH (SEQ ID NO: 86), or an amino acid sequence encoded by a nucleotide sequence of SEQ ID NOs: 1, 3, 5, 7, 83, or 85; or an amino acid or nucleotide sequence substantially identical thereto. In one embodiment, the anti-FGFR2-IIIc antibody molecule binds to one, two, three, four, five, six, seven, eight, nine, ten, twelve, fourteen, sixteen, eighteen, twenty, twenty-two or more of: alanine at position 1, alanine at position 2, valine at position 4, threonine at position 6, threonine at position 7, aspartate at position 8, lysine at position 9, isoleucine at position 11, glutamate at position 12, valine at position 13, tyrosine at position 15, isoleucine at position 16, arginine at position 17, phenylalanine at position 21, glutamate at position 22, threonine at position 28, leucine at position 30, alanine at position 31, glycine at position 32, serine at position 34, isoleucine at position 37, serine at position 38, phenylalanine at position 39, or histidine at position 40 of SEQ ID NO: 84 (corresponding to the highlighted amino acid residues in AAGVNTTDKEIEVLYIRNVT FEDAGEYTCLAGNSIGISFH (SEQ ID NO: 84)); or one or more of: threonine at position 1, leucine at position 3, alanine at position 4, glycine at position 5, serine at position 7, isoleucine at position 10, serine at position 11, phenylalanine at position 12, or histidine at position 13 of SEQ ID NO: 86 (corresponding to the highlighted amino acid residues in TC LAGNSIGISFH; SEQ ID NO: 86).

Exemplary anti-FGFR2-IIIc antibody molecules within the scope of the invention are disclosed in Examples 8-15. In one embodiment, the anti-FGFR2-IIIc antibody molecule binds to, e.g., selectively binds to, mammalian, e.g., human FGFR2-IIIc (e.g., an epitope located in the extracellular domain of human FGFR2-IIIc at about amino acids 301 to 360 of FGFR2-IIIc (SEQ ID NO:2), or a sequence that is at least 85%, 90%, 95%, 99% or more identical thereto). In certain embodiments, the anti-FGFR2-IIIc antibody molecule binds to one or more amino acid residues chosen from (e.g., an epitope comprising amino acid residues) residues 314-353 (AAGVNTTDKEIEVLYIRNVTFEDAGEYT-CLAGNSIGISFH (SEQ ID NO: 84)); or amino acids TCLA-GNSIGISFH (SEQ ID NO:86), of human FGFR2-IIIc, or a modified form thereof (e.g., a fragment or substituted (e.g., conservatively substituted) form thereof). In one embodiment, the anti-FGFR2-IIIc antibody molecule binds to a synthetic, recombinant or native epitope on the extracellular domain of human FGFR2-IIIc. In certain embodiments, the anti-FGFR2-IIIc antibody molecule binds to the native FGFR2-IIIc present in a prostate cancer cell, e.g., a human prostate cancer cell (e.g., DU145 human prostate cancer cell line), or a rat prostate cancer cell line (e.g., AT3B-1 rat prostate cancer cell line).

In one embodiment, the anti-FGFR2-IIIc antibody molecule preferentially to FGFR2 isoform IIIc or a fragment thereof, but does not substantially bind to (e.g., shows less than 10%, 8%, 5%, 4%, 3%, 2%, 1% cross-reactivity with) FGFR2 isoform IIIb, e.g., the extracellular domain of human FGFR2 isoform IIIb (e.g., about amino acids 314 to 351 of human FGFR2 isoform IIIb (HSGINSSNAEVLALFN-VTEADAGEYICKVSNYIGQANQ; SEQ ID NO: 56); about amino acids 314 to 328 of human FGFR2 isoform IIIb (HS-GINSSNAEVLALF; SEQ ID NO: 57); or about amino acids 340 to 351 of human FGFR2 isoform IIIb (CKVS-NYIGQANQ; SEQ ID NO: 58).

In one embodiment, the anti-FGFR2-IIIc antibody molecule shows a preferential binding to human FGFR2-IIIc as any of the monoclonal antibodies shown in FIGS. 24A-24B, 25A-25B, 27A-27B, 28, 29A-29F, 30A-30F, 32-39, and 41-44. For example, the anti-FGFR2-IIIc antibody molecule shows the same or similar binding selectivity as any of clones B7 (also referred to herein as "Atto-MuMab-03"), C5, D2, D10, E3, E8, F3, F10 or G9 of FIG. 24A-24B or 32; or any of human clones 1 (also referred to herein as "Atto-HuMab-01"), 2, 6 (also referred to herein as "Atto-HuMab-06"), 7 or 8 (also referred to herein as "Atto-HuMab-08") of FIGS. 25A-25B, 27A-27B, 28, 29A-29F, 30A-30F, 37-39, and/or 41-44. In other embodiments, the anti-FGFR2-IIIc antibody molecule shows the same or similar binding selectivity as Atto-MuMab-01 or Atto-MuMab-02 (VH and VL shown in FIGS. 33, 34A-34B, 35, and 36A-36B). In yet another embodiment, the anti-FGFR2-IIIc antibody molecule shows the same or similar binding selectivity as human clones 1, 6 or 8 of FIGS. 25A-25B, 27A-27B, 28-29, 30A-30F, 37-39, and/or 41-44 (Atto-HuMab-01, Atto-HuMab-06, Atto-HuMab-08, respectively). In one embodiment, the FGFR2-IIIc antibody molecule binds specifically to human FGFR2-IIIc, and competitively inhibits the binding of a second antibody molecule to FGFR2-IIIc, wherein the second antibody molecule can be an antibody molecule chosen from, e.g., Atto-MuMab-01, Atto-MuMab-02, Atto-MuMab-03, Atto-HuMab-01, Atto-HuMab-06, or Atto-HuMab-08.

An amino acid sequence alignment of human scFv Clone-6 (Atto-HuMab-06) and Clone-8 (Atto-HuMab-08) is shown in FIG. 28. The locations of the complementarity determining regions (CDRs) of the light and heavy chain variable regions are underlined and labeled as VL-CDR-1, -2, and -3, and VH-CDR-1, -2, and -3, respectively.

An amino acid sequence alignment of human scFv Clone-1 (Atto-HuMab-01) and Clone-6 (Atto-HuMab-06) is shown in FIG. 38. The locations of the complementarity determining regions (CDRs) of the light and heavy chain variable regions are underlined and labeled as VL-CDR-1, -2, and -3, and VH-CDR-1, -2, and -3, respectively.

An amino acid sequence alignment of human scFv Clone-1 (Atto-HuMab-01) and Clone-8 (Atto-HuMab-08) is shown in FIG. 39. The locations of the complementarity determining regions (CDRs) of the light and heavy chain variable regions are underlined and labeled as VL-CDR-1, -2, and -3, and VH-CDR-1, -2, and -3, respectively.

The nucleotide and amino acid sequence for the full length coding region of the light chain variable domain and the heavy chain variable domain of human scFv Clone 8 (Atto- HuMab-08) is shown in FIGS. 29A-29B, respectively. The nucleotide and amino acid sequence of the light chain variable domain of the human scFv Clone 8 (Atto-HuMab-08) is shown in FIGS. 29C-29D, respectively. The nucleotide and amino acid sequence of the heavy chain variable domain of the human scFv Clone 8 (Atto-HuMab-08) is shown in FIGS. 29E-29F, respectively.

The nucleotide and amino acid sequence for the full length coding region of the light chain variable domain and the heavy chain variable domain of human scFv Clone 6 (Atto-HuMab-06) is shown in FIGS. 30A-30B, respectively. The nucleotide and amino acid sequence, respectively, of the light chain variable domain of the human scFv Clone 6 (Atto-HuMab-06) is shown in FIGS. 30C-30D. The nucleotide and amino acid sequence, respectively, of the heavy chain variable domain of the human scFv Clone 6 (Atto-HuMab-06) is shown in FIGS. 30E-30F. The relative location of the complementarity determining regions (CDRs) is underlined in the aforesaid Figures.

The amino acid sequence for the light and heavy chain variable domains of Atto-MuMab-02 is shown in FIG. 35 (SEQ ID NO: 90 and 88, respectively). The relative locations of the CDRs in the heavy and light chain variable regions are indicated in FIG. 35. The nucleotide sequences encoding the heavy and light chain variable domains of Atto-MuMab-02 are shown in FIGS. 34A and 34B (SEQ ID NO: 87 and 89), respectively.

The amino acid and nucleotide sequences for the full length coding region of the light chain variable domain and the heavy chain variable domain of human scFv Clone 1 (Atto-HuMab-01) are shown in FIGS. 37A-37B (SEQ ID NOs: 190-191), respectively. The amino acid sequence of the light chain variable domain of the human scFv Clone 1 (Atto-HuMab-01) is shown in FIGS. 38-39) (corresponding to amino acids 1-111 of the upper amino acid sequence, prior to the linker region). The amino acid sequence of the heavy chain variable domain of the human scFv Clone 1 (Atto-HuMab-01) is shown in FIGS. 38-39 (corresponding to amino acids 133-252 of the upper amino acid sequence, after the linker region). The relative location of the complementarity determining regions (CDRs) is underlined and indicated in the aforesaid Figures. FIG. 40 is a table depicting a comparison of the CDR regions (heavy and light chain CDRs) among Atto-HuMab-01, -06, and -08).

In yet other embodiments, the anti-FGFR2-IIIc antibody molecule has one or more biological properties of any of clones B7 (Atto-MuMab-03), C5, D2, D10, E3, E8, F3, F10 or G9 of FIG. 24A-24B or 32; or any of human clones 1 (Atto-HuMab-01), 2, 6 (Atto-HuMab-06), 7 or 8 (Atto-HuMab-08) of FIGS. 25A-25B, 27A-27B, 28-29, 30A-30F, 37-39, and/or 41-44, and in particular, antibodies Atto-MuMab-01, Atto-MuMab-02, Atto-MuMab-03, Atto-HuMab-01, Atto-HuMab-06, or Atto-HuMab-08, including but not limited to:

(i) the antibody molecule binds to the same or a similar epitope on human FGFR2-IIIc as antibody Atto-MuMab-01, Atto-MuMab-02, Atto-MuMab-03, Atto-HuMab-01, Atto-HuMab-06, or Atto-HuMab-08 (e.g., the anti-FGFR2-IIIc antibody molecule competes for binding with monoclonal antibodies Atto-MuMab-01, Atto-MuMab-02, Atto-MuMab-03, Atto-HuMab-01, Atto-HuMab-06, or Atto-HuMab-08);

(ii) binds to at least one amino acid residue of 314-353 of FGFR2 IIIc (AAGVNTTDKEIEVLYIRNVTFEDAGEYTCLAGNSIGISHUSEQ ID NO: 84)); or at least one amino acid residue of TCLAGNSIGISFH (SEQ ID NO: 86) of human FGFR2-IIIc;

(iii) binds preferentially to at least one amino acid residue present in human FGFR2-IIIc, but not in human FGFR2-IIIb (e.g., one, two, three, four, five, six, seven, eight, nine, ten, twelve, fourteen, sixteen, eighteen, twenty, twenty-two or more of: alanine at position 1, alanine at position 2, valine at position 4, threonine at position 6, threonine at position 7, aspartate at position 8, lysine at position 9, isoleucine at position 11, glutamate at position 12, valine at position 13, tyrosine at position 15, isoleucine at position 16, arginine at position 17, phenylalanine at position 21, glutamate at position 22, threonine at position 28, leucine at position 30, alanine at position 31, glycine at position 32, serine at position 34, isoleucine at position 37, serine at position 38, phenylalanine at position 39, or histidine at position 40 of SEQ ID NO: 84 (corresponding to the highlighted amino acid residues in AAGVNTTDKEIEVLYIRNVTFEDAGEYTCLAGNSIGISFH (SEQ ID NO: 84)); or one, two, three, four, five, six or more of: threonine at position 1, leucine at position 3, alanine at position 4, glycine at position 5, serine at position 7, isoleucine at position 10, serine at position 11, phenylalanine at position 12, or histidine at position 13 of SEQ ID NO: 86 (corresponding to the highlighted amino acid residues in TCLAGNSIGISFH; SEQ ID NO: 86);

(iv) binds to recombinant, synthetic or native human FGFR2-IIIc;

(v) binds to native FGFR2-IIIc present on a prostate or liver cancer cell, e.g., a human prostate cancer cell (e.g., DU145 human prostate cancer cell line), or liver cell line HepG2;

(vi) shows the same or similar binding selectivity to human FGFR2-IIIc as monoclonal antibody Atto-MuMab-01, Atto-MuMab-02, Atto-MuMab-03, Atto-HuMab-01, Atto-HuMab-06, or Atto-HuMab-08;

(vii) shows the same or similar binding affinity as monoclonal antibody Atto-MuMab-01, Atto-MuMab-02, Atto-MuMab-03, Atto-HuMab-01, Atto-HuMab-06, or Atto-HuMab-08; and/or (viii) shows the same or similar binding kinetics as monoclonal antibody Atto-MuMab-01, Atto-MuMab-02, Atto-MuMab-03, Atto-HuMab-01, Atto-HuMab-06, or Atto-HuMab-08.

In one embodiment, the anti-FGFR2-IIIc antibody molecule is the monoclonal antibody Atto-MuMab-01, Atto-MuMab-02, Atto-MuMab-03, Atto-HuMab-01, Atto-HuMab-06, or Atto-HuMab-08.

In one embodiment, the anti-FGFR2-IIIc antibody molecule binds to FGFR2-IIIc with high affinity, e.g., with a Kd less than $10^{-7}$ M, $10^{-8}$, $10^{-9}$, $10^{-10}$, $10^{-11}$M or better. In other embodiments, the anti-FGFR2-IIIc antibodies or fragments thereof can reduce one or more FGFR2-IIIc-associated activities with an IC50 of at least about $10^{-8}$, $10^{-9}$, $10^{-10}$, $10^{-11}$M or better. In other embodiments, the anti-FGFR2-IIIc antibodies or fragments thereof associate with human FGFR2-IIIc with kinetics in the range of $k_{off}$ of less than $1\times10$ $s^{-1}$ to $1\times10^{-6}$ $s^{-1}$ as determined by surface plasmon resonance (SPR), or a $k_{on}$ of between $10^3$ and $10^7$ $M^{-1}s^{-1}$ as determined by surface plasmon resonance (SPR). The affinity and binding kinetics of the anti-FGFR2-IIIc antibody or fragment thereof can be tested using, e.g., biosensor technology (BIA-CORE).

In one embodiment, the anti-FGFR2-IIIc antibody molecule is a full antibody or fragment thereof (e.g., a Fab, F(ab')$_2$, Fv, or a single chain Fv fragment (scFv)). In certain embodiments, the anti-FGFR2-IIIc antibody molecule is a monoclonal antibody or an antibody with single specificity. The anti-FGFR2-IIIc antibody molecule can also be a human, humanized, chimeric, camelid, shark, or in vitro-generated antibody molecules. In one embodiment, the anti-FGFR2-

IIIc antibody molecule thereof is a humanized antibody molecule. The heavy and light chains of the anti-FGFR2-IIIc antibody molecule can be full-length (e.g., an antibody can include at least one, and preferably two, complete heavy chains, and at least one, and preferably two, complete light chains) or can include an antigen-binding fragment (e.g., a Fab, F(ab')₂, Fv, a single chain Fv fragment, a single domain antibody, a diabody (dAb), a bivalent or bispecific antibody or fragment thereof, a single domain variant thereof, or a camelid antibody). In yet other embodiments, the antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG2 (e.g., human IgG1 or IgG2). In one embodiment, the heavy chain constant region is human IgG1. In another embodiment, the anti-FGFR2-IIIc antibody molecule has a light chain constant region chosen from, e.g., the light chain constant regions of kappa or lambda, preferably kappa (e.g., human kappa). In one embodiment, the constant region is altered, e.g., mutated, to modify the properties of the anti-FGFR2-IIIc antibody molecule (e.g., to increase or decrease one or more of: Fc receptor binding, antibody glycosylation, the number of cysteine residues, effector cell function, or complement function). For example, the constant region is mutated at positions 296 (M to Y), 298 (S to T), 300 (T to E), 477 (H to K) and 478 (N to F) of SEQ ID NO: 55 to alter Fc receptor binding.

In certain embodiments, the anti-FGFR2-IIIc is covalently linked to a cell-surface protein (e.g., phage) or soluble secreted form (e.g., scFv or fusion thereof). In other embodiment, the anti-FGFR2-IIIc is secreted as a single chain Fv or is fused to an Fc constant region (e.g., to form a monomeric or dimeric chain construct of a human IgG1 Fc fusion).

In another embodiment, the anti-FGFR2-IIIc antibody molecule comprises at least one antigen-binding region, e.g., a variable region, from an antibody chosen from, e.g., Atto-MuMab-01, Atto-MuMab-02, Atto-MuMab-03, Atto-HuMab-01, Atto-HuMab-06, or Atto-HuMab-08. In yet another embodiment, the anti-FGFR2-IIIc antibody molecule includes at least one, two, three or four variable regions from an antibody chosen from, e.g., Atto-MuMab-01, Atto-MuMab-02, Atto-MuMab-03, Atto-HuMab-01, Atto-HuMab-06, or Atto-HuMab-08. In another embodiment, the anti-FGFR2-IIIc antibody molecule includes at least one or two heavy chain variable regions from an antibody chosen from, e.g., Atto-MuMab-01, Atto-MuMab-02, Atto-MuMab-03, Atto-HuMab-01, Atto-HuMab-06, or Atto-HuMab-08. In another embodiment, the anti-FGFR2-IIIc antibody molecule includes at least one or two light chain variable regions from an antibody chosen from, e.g., Atto-MuMab-01, Atto-MuMab-02, Atto-MuMab-03, Atto-HuMab-01, Atto-HuMab-06, or Atto-HuMab-08. In yet another embodiment, the anti-FGFR2-IIIc antibody molecule includes at least one, two, or three complementarity determining regions (CDRs) from a heavy chain variable region of an antibody chosen from, e.g., Atto-MuMab-01, Atto-MuMab-02, Atto-MuMab-03, Atto-HuMab-01, Atto-HuMab-06, or Atto-HuMab-08, or at least particularly the amino acids from those CDRs that contact FGFR2-IIIc. In yet another embodiment, the anti-FGFR2-IIIc antibody molecule includes at least one, two, or three CDRs from a light chain variable region of an antibody chosen from, e.g., Atto-MuMab-01, Atto-MuMab-02, Atto-MuMab-03, Atto-HuMab-01, Atto-HuMab-06, or Atto-HuMab-08, or at least includes the amino acids from those CDRs that contact FGFR2-IIIc. In yet another embodiment, the anti-FGFR2-IIIc antibody molecule includes at least one, two, three, four, five, or six CDRs from the heavy and light chain variable regions of an antibody chosen from, e.g., Atto-MuMab-01, Atto-MuMab-02, Atto-MuMab-03, Atto-HuMab-01, Atto-HuMab-06, or Atto-HuMab-08.

In one embodiment, the anti-FGFR2-IIIc antibody molecule includes all six CDR's from Atto-MuMab-01, Atto-MuMab-02, Atto-MuMab-03, Atto-HuMab-01, Atto-HuMab-06, or Atto-HuMab-08, or closely related CDRs, e.g., CDRs which are identical or which have at least one amino acid alteration, but not more than two, three or four alterations (e.g., substitutions, deletions, or insertions, e.g., conservative substitutions). Optionally, the protein may include any CDR described herein.

In another embodiment, the anti-FGFR2-IIIc antibody molecule includes at least one, two, or three Chothia hypervariable loops from a heavy chain variable region of an antibody chosen from, e.g., Atto-MuMab-01, Atto-MuMab-02, Atto-MuMab-03, Atto-HuMab-01, Atto-HuMab-06, or Atto-HuMab-08, or at least particularly the amino acids from those hypervariable loops that contact FGFR2-IIIc. In yet another embodiment, the anti-FGFR2-IIIc antibody molecule includes at least one, two, or three hypervariable loops from a light chain variable region of an antibody chosen from, e.g., Atto-MuMab-01, Atto-MuMab-02, Atto-MuMab-03, Atto-HuMab-01, Atto-HuMab-06, or Atto-HuMab-08, or at least includes the amino acids from those hypervariable loops that contact FGFR2-IIIc. In yet another embodiment, the anti-FGFR2-IIIc antibody molecule includes at least one, two, three, four, five, or six hypervariable loops from the heavy and light chain variable regions of an antibody chosen from, e.g., Atto-MuMab-01, Atto-MuMab-02, Atto-MuMab-03, Atto-HuMab-01, Atto-HuMab-06, or Atto-HuMab-08.

In one embodiment, the anti-FGFR2-IIIc antibody molecule includes all six hypervariable loops from FGFR2-IIIc or closely related hypervariable loops, e.g., hypervariable loops which are identical or which have at least one amino acid alteration, but not more than two, three or four alterations (e.g., substitutions, deletions, or insertions, e.g., conservative substitutions). Optionally, the anti-FGFR2-IIIc antibody molecule may include any hypervariable loop described herein.

In still another embodiment, the anti-FGFR2-IIIc antibody molecule includes at least one, two, or three hypervariable loops that have the same canonical structures as the corresponding hypervariable loop of Atto-MuMab-01, Atto-MuMab-02, Atto-MuMab-03, Atto-HuMab-01, Atto-HuMab-06, or Atto-HuMab-08, e.g., the same canonical structures as at least loop 1 and/or loop 2 of the heavy and/or light chain variable domains of Atto-MuMab-01, Atto-MuMab-02, Atto-MuMab-03, Atto-HuMab-01, Atto-HuMab-06, or Atto-HuMab-08. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In one embodiment, the light or the heavy chain variable framework (e.g., the region encompassing at least FR1, FR2, FR3, and optionally FR4) of the anti-FGFR2-IIIc antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VH segment of a human germline gene.

In one embodiment, the heavy or light chain variable domain of the of the anti-FGFR2-IIIc antibody molecule includes an amino acid sequence, which is at least 80%, 85%, 90%, 92%, 95%, 97%, 98%, 99% or higher identical to a variable region of an antibody described herein, e.g., Atto-MuMab-01, Atto-MuMab-02, Atto-MuMab-03, Atto-HuMab-01, Atto-HuMab-06, or Atto-HuMab-08; or which differs at least 1 or 5 residues, but less than 40, 30, 20, or 10 residues, from a variable region of an antibody described herein, e.g., Atto-MuMab-01, Atto-MuMab-02, Atto-MuMab-03, Atto-HuMab-01, Atto-HuMab-06, or Atto-HuMab-08.

In one embodiment, the heavy or light chain variable region of the of the anti-FGFR2-IIIc antibody molecule includes an amino acid sequence encoded by a nucleic acid sequence described herein or a nucleic acid that hybridizes to a nucleic acid sequence described herein (e.g., a specific nucleic acid sequence or a nucleic acid sequence that encodes an amino acid sequence described herein) or its complement, e.g., under low stringency, medium stringency, or high stringency, or other hybridization condition described herein.

In another embodiment, the anti-FGFR2-IIIc antibody molecule comprises at least one, two, three, or four antigen-binding regions, e.g., variable regions, having an amino acid sequence as set forth in FIG. 28, 29B, 29D, 29F, 30B, 30D, 30F, 35, 36A, 36B, 37A, 38, or 39, or a sequence substantially identical thereto (e.g., a sequence at least about 85%, 90%, 95%, 99% or more identical thereto, or which differs by no more than 1, 2, 5, 10, or 15 amino acid residues from the sequences shown in FIG. 28, 29B, 29D, 29F, 30B, 30D, 30F, 35, 36A, 36B, 37A, 38, or 39. In another embodiment, the anti-FGFR2-IIIc antibody molecule includes a VH and/or VL domain encoded by a nucleic acid having a nucleotide sequence as set forth in FIG. 29A, 29C, 29E, 30A, 30C, 30E, 34A, 34B, or 37B, or a sequence substantially identical thereto (e.g., a sequence at least about 85%, 90%, 95%, 99% or more identical thereto, or which differs by no more than 3, 6, 15, 30, or 45 nucleotides from the sequences shown in FIG. 29A, 29C, 29E, 30A, 30C, 30E, 34A, 34B, or 37B.

In yet another embodiment, the anti-FGFR2-IIIc antibody molecule comprises at least one, two, or three CDRs from a heavy chain variable region having an amino acid sequence as set forth in FIG. 28, 29F, 30F, 35, or 38-40, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-FGFR2-IIIc antibody molecule comprises at least one, two, or three CDRs from a light chain variable region having an amino acid sequence as set forth in FIG. 28, 29D, 30D, 35, or 38-40, or a sequence substantially homologous thereto (e.g., a sequence at least about 85%, 90%, 95%, 99% or more identical thereto, and/or having one, two, three or more substitutions, insertions or deletions, e.g., conserved substitutions). In another embodiment, the anti-FGFR2-IIIc antibody molecule comprises at least one, two, three, four, five or six CDRs from heavy and light chain variable regions having an amino acid sequence as set forth in FIG. 28, 29D, 29F, 30D, 30F, 35, or 38-40), or a sequence substantially homologous thereto (e.g., a sequence at least about 85%, 90%, 95%, 99% or more identical thereto, and/or having one, two, three or more substitutions, insertions or deletions, e.g., conserved substitutions).

In one embodiment, the anti-FGFR2-IIIc antibody molecule comprises at least one, two, or three CDRs from a heavy chain variable region having an amino acid sequence of Atto-HuMab-01 (e.g., SEQ ID NOs:147-149, corresponding to CDRs 1-3, respectively), Atto-HuMab-06 (e.g., SEQ ID NOs: 147, 158,159, corresponding to CDRs 1-3, respectively), or Atto-HuMab-08 (e.g., SEQ ID NOs:147-149, corresponding to CDRs 1-3, respectively), as set forth in FIG. 40, or a sequence substantially homologous thereto (e.g., a sequence at least about 85%, 90%, 95%, 99% or more identical thereto, and/or having one, two, three or more substitutions, insertions or deletions, e.g., conserved substitutions). In one embodiment, the anti-FGFR2-IIIc antibody molecule comprises at least one, two, or three CDRs from a light chain variable region having an amino acid sequence of Atto-HuMab-01 (e.g., SEQ ID NOs:144-146, corresponding to CDRs 1-3, respectively), Atto-HuMab-06 (e.g., SEQ ID NOs:155-157, corresponding to CDRs 1-3, respectively), or Atto-HuMab-08 (e.g., SEQ ID NOs:155, 156, 146, corresponding to CDRs 1-3, respectively), as set forth in FIG. 40, or a sequence substantially homologous thereto (e.g., a sequence at least about 85%, 90%, 95%, 99% or more identical thereto, and/or having one, two, three or more substitutions, insertions or deletions, e.g., conserved substitutions).

In yet another embodiment, the anti-FGFR2-IIIc antibody molecule comprises at least one, two, or three CDRs from a heavy chain variable region having an amino acid sequence chosen from:

SSYAIS in CDR1, (SEQ ID NO: 147)

RIIPIX$_1$G X$_2$ANYAQKFQGR, wherein X$_1$ is F or L, and X$_2$ is T or I in CDR2 (SEQ ID NO:153), or RDX$_1$X$_2$X$_3$WX$_4$X$_5$X$_6$FDX$_7$ in CDR3, wherein X$_1$ is R or P, X$_2$ is W or L, X$_3$ is D or L, X$_4$ is N or S, X$_5$ is D or absent, X$_6$ is A or Y, and X$_7$ is I or Y (SEQ ID NO:154).

In yet another embodiment, the anti-FGFR2-IIIc antibody molecule comprises at least one, two, or three CDRs from a light chain variable region having an amino acid sequence chosen from:

SGSSSNIG X$_1$N X$_2$V X$_3$ in CDR1, wherein X$_1$ is S or N, X$_2$ is T or Y, and X$_3$ is S or N, (SEQ ID NO:150), X$_1$NN X$_2$RPSG X$_3$ in CDR2, wherein X$_1$ is S or D, X$_2$ is Q or K, and X$_3$ is V or I (SEQ ID NO:151), or X$_1$ X$_2$WD X$_3$SLX$_4$X$_5$VV, wherein X$_1$ is A or G, X$_2$ is A or T, X$_3$ is D or S, X$_4$ is N or S, and X$_5$ is G or A, in CDR3 (SEQ ID NO:152).

In yet another embodiment, the anti-FGFR2-IIIc antibody molecule comprises:

(i) at least one, two, or three CDRs from a heavy chain variable region having an amino acid sequence chosen from:

SSYAIS in CDR1, (SEQ ID NO: 147)

RIIPIX$_1$G X$_2$ANYAQKFQGR, wherein X$_1$ is F or L, and X$_2$ is T or I in CDR2 (SEQ ID NO:153), or RDX$_1$X$_2$X$_3$WX$_4$X$_5$X$_6$FDX$_7$ in CDR3, wherein X$_1$ is R or P, X$_2$ is W or L, X$_3$ is D or L, X$_4$ is N or S, X$_5$ is D or absent, X$_6$ is A or Y, and X$_7$ is I or Y (SEQ ID NO:154); and (ii) at least one, two, or three CDRs from a light chain variable region having an amino acid sequence chosen from:

SGSSSNIG X$_1$N X$_2$V X$_3$ in CDR1, wherein X$_1$ is S or N, X$_2$ is T or Y, and X$_3$ is S or N, (SEQ ID NO:150), X$_1$NN X$_2$RPSG X$_3$ in CDR2, wherein X$_1$ is S or D, X$_2$ is Q or K, and X$_3$ is V or I (SEQ ID NO:151), or X$_1$ X$_2$WD X$_3$SLX$_4$X$_5$VV, wherein X$_1$ is A or G, X$_2$ is A or T, X$_3$ is D or S, X$_4$ is N or S, and X$_5$ is G or A, in CDR3 (SEQ ID NO:152).

In one embodiment, the anti-FGFR2-IIIc antibody molecule comprises all six CDRs described herein, e.g., described in FIG. 40. The invention also features nucleic acids comprising nucleotide sequences that encode heavy and light chain variable regions and CDRs of the anti-FGFR2-IIIc antibody molecules, as described herein. For example, the invention features a first and second nucleic acid encoding heavy and light chain variable regions, respectively, of an anti-FGFR2-IIIc antibody molecule chosen from one or more of, e.g., Atto-MuMab-01, Atto-MuMab-02, Atto-MuMab-03, Atto-HuMab-01, Atto-HuMab-06, or Atto-HuMab-08, as described herein. For example, the nucleic acid can comprise a nucleotide sequence as set forth in FIG. 29A, 29C, 29E, 30A, 30C, 30E, 34A, 34B, or 37B, or a sequence substantially identical thereto (e.g., a sequence at least about 85%, 90%, 95%, 99% or more identical thereto, or which differs by no more than 3, 6, 15, 30, or 45 nucleotides from the sequences shown in FIG. 29A, 29C, 29E, 30A, 30C, 30E, 34A, 34B, or 37B. In certain embodiments, the nucleic acid can comprise a nucleotide sequence encoding at least one, two, or three CDRs from a heavy chain variable region having an amino acid sequence as set forth in FIG. 28, 29F, 30F, 35, or 38-40, or a sequence substantially homologous thereto (e.g., a sequence at least about 85%, 90%, 95%, 99% or more identical thereto, and/or having one, two, three or more substitutions, insertions or deletions, e.g., conserved substitutions). In another embodiment, the nucleic acid can comprise a nucleotide sequence encoding at least one, two, or three CDRs from a light chain variable region having an amino acid sequence as set forth in FIG. 28, 29D, 30D, 35, or 38-40, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the nucleic acid can comprise a nucleotide sequence encoding at least one, two, three, four, five, or six CDRs from heavy and light chain variable regions having an amino acid sequence as set forth in FIG. 28, 29D, 29F, 30D, 30F, 35, or 38-40, or a sequence substantially homologous thereto (e.g., a sequence at least about 85%, 90%, 95%, 99% or more identical thereto, and/or having one, two, three or more substitutions, insertions or deletions, e.g., conserved substitutions).

In another aspect, the application features host cells and vectors containing the nucleic acids described herein. The nucleic acids may be present in a single vector or separate vectors present in the same host cell or separate host cell.

The epitope of FGFR2-IIIc, e.g., human FGFR2-IIIc, recognized by one or more of, e.g., Atto-MuMab-01 or Atto-MuMab-02, is featured. In one embodiment, the epitope of the anti-FGFR2-IIIc antibody molecule includes at least one amino acid residue of 314-353 of FGFR2 IIIc (AAGVN TTDKEIEVLYIRNVTFEDAGEYTCLAGNSIGISFH (SEQ ID NO: 84)); or at least one amino acid residue of TCLAGNSIGISFH (SEQ ID NO: 86). In one embodiment, the epitope of human FGFR2-IIIc comprises one, two, three, four, five, six, seven, eight, nine, ten, twelve, fourteen, sixteen, eighteen, twenty, twenty-two or more of: alanine at position 1, alanine at position 2, valine at position 4, threonine at position 6, threonine at position 7, aspartate at position 8, lysine at position 9, isoleucine at position 11, glutamate at position 12, valine at position 13, tyrosine at position 15, isoleucine at position 16, arginine at position 17, phenylalanine at position 21, glutamate at position 22, threonine at position 28, leucine at position 30, alanine at position 31, glycine at position 32, serine at position 34, isoleucine at position 37, serine at position 38, phenylalanine at position 39, or histidine at position 40 of SEQ ID NO: 84 (corresponding to the highlighted amino acid residues in AAGVN TTDKEIEVLYIRNVTFEDAGEYTCLAGNSIGISFH (SEQ ID NO: 84)); or one or more of: threonine at position 1, leucine at position 3, alanine at position 4, glycine at position 5, serine at position 7, isoleucine at position 10, serine at position 11, phenylalanine at position 12, or histidine at position 13 of SEQ ID NO: 86 (corresponding to the highlighted amino acid residues in TCLAGNSIGISFH; SEQ ID NO: 86).

In embodiments, the antibody molecule inhibits, reduces or neutralizes one or more activities of the isoforms, e.g., oncogenic isoforms, in a hyperproliferative (e.g., cancerous or tumor) cell and/or tissue. For example, the antibody molecule may selectively and specifically reduce or inhibit an oncogenic isoform-associated activity chosen from one or more of: (i) binding of a ligand or co-receptor (e.g., FGF ligand (e.g., FGF8b, FGF2, FGF17 or FGF18)) to FGFR2 isoform IIIc); (ii) receptor dimerization (e.g., FGFR2 isoform IIIc dimerization); (iii) receptor signaling, e.g., FGFR2 isoform IIIc signaling; (iv) hyperproliferative (e.g., cancerous or tumor) cell proliferation, growth and/or survival, for example, by induction of apoptosis of the hyperproliferative cell; and/or (v) angiogenesis and/or vascularization of a tumor. In certain embodiments, the antibody molecule is conjugated to one or more cytotoxic or cytostatic agents or moieties, e.g., a therapeutic drug; a compound emitting radiation; molecules of plant, fungal, or bacterial origin, or a biological protein (e.g., a protein toxin); or a particle (e.g., a recombinant viral particle, e.g., via a viral coat protein). Upon binding of the conjugated antibody molecule to an epitope located on an exon sequence or a junctional region predominantly expressed and/or associated with one or more cancerous or tumor cells or disorders (e.g., an epitope as described herein), the conjugated antibody molecule selectively targets or delivers the cytotoxic or cytostatic agent to the hyperproliferative (e.g., cancerous or tumor) cell and/or tissue. In other embodiments, the antibody molecule can be used alone in unconjugated form to thereby reduce an activity (e.g., cell growth or proliferation) and/or kill the hyperproliferative (e.g., cancerous or tumor) cell and/or tissue by, e.g., antibody-dependent cell killing mechanisms, such as complement-mediated cell lysis and/or effector cell-mediated cell killing. In other embodiments, the antibody molecule can disrupt a cellular interaction, e.g., binding of the isoform, e.g., the oncogenic isoform, to a cognate receptor or ligand, thereby reducing or blocking the activity of the hyperproliferative (e.g., cancerous or tumor) cell and/or tissue. For example, the antibody molecule that selectively binds to exon IIIc of FGFR2 can reduce or inhibit the interaction of FGFR2 isoform IIIc to one or more of its ligands, e.g., one or more of: FGF8b, FGF2, FGF17 or FGF18, thus reducing the proliferation and/or survival of FGFR2 isoform IIIc-expressing cells.

It will be understood that the antibody molecules, soluble or fusion proteins, peptides, and nucleic acid inhibitors described herein can be functionally linked or derivatized (e.g., by chemical coupling, genetic fusion, non-covalent association or otherwise) to one or more other molecular entities, such as an antibody (e.g., a bispecific or a multispecific antibody), toxins, radioisotopes, cytotoxic or cytostatic agents, a label, among others. For example, the antibody molecules, soluble or fusion proteins, peptides, and nucleic acid inhibitors described herein can be coupled to a label, such as a fluorescent label, a biologically active enzyme label, a radioisotope (e.g., a radioactive ion), a nuclear magnetic resonance active label, a luminescent label, or a chromophore. In other embodiments, the antibody molecules, soluble or fusion proteins and peptides described herein can be coupled to a therapeutic agent, e.g., a cytotoxic moiety (e.g., a therapeutic drug; a radioisotope: molecules of plant, fungal, or bacterial origin: or biological proteins (e.g., protein toxins); or particles (e.g., recombinant viral particles, e.g., via a viral coat protein); or mixtures thereof. The therapeutic agent can be an intracellularly active drug or other agent, such as short-range radiation emitters, including, for example, short-rage, high-energy α-emitters, as described herein. In some preferred embodiments, the antibody molecules, soluble or fusion proteins and peptides described herein, can be coupled to a molecule of plant or bacterial origin (or derivative thereof), e.g., a maytansinoid, a taxane, or a calicheamicin. A radioisotope can be an α-, β-, or γ-emitter, or an β- and γ-emitter. Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I, indium ($^{111}$In) technetium ($^{99}$mTc), phosphorus ($^{32}$P), carbon ($^{14}$C), and tritium ($^{3}$H). The antibody molecules, soluble or fusion proteins and peptides described herein can also be linked to another antibody to form, e.g., a bispecific or a multispecific antibody.

In another aspect, the invention provides, compositions, e.g., pharmaceutical compositions, which include a pharmaceutically acceptable carrier, excipient or stabilizer, and at least one of the isoform-specific inhibitors described herein. In one embodiment, the isoform-specific inhibitor is conjugated to a label or a therapeutic agent. In one embodiment, the compositions, e.g., the pharmaceutical compositions, comprise a combination of two or more of the aforesaid the isoform-specific inhibitors, or different antibody molecules. For example, a composition, e.g., pharmaceutical composition, which comprises an isoform-specific inhibitor as described herein, in combination with other growth factor inhibitors, such as antibodies against FGF 1-23, FGF receptors 1-4, VEGF, EGF or EGF receptor, PSMA antibody, or Her-2/neu, etc. Combinations of an isoform-specific inhibitor and a drug, e.g., a therapeutic agent (e.g., a cytototoxic or cytostatic drug, e.g., DM1, calicheamicin, or taxanes, topoisomerase inhibitors, or an immunomodulatory agent, e.g., IL-1, 2, 4, 6, or 12, interferon alpha or gamma, or immune cell growth factors such as GM-CSF) are also within the scope of the invention.

The invention also features nucleic acid sequences that encode the isoform-binding molecules described herein described herein. For example, the invention features, a first and second nucleic acid encoding a modified heavy and light chain variable region, respectively, of an antibody molecule as described herein. In other embodiments, the invention provides nucleic acids comprising nucleotide sequences encoding the soluble receptors, fusions, peptides and functional analogs thereof described herein. In another aspect, the invention features host cells and vectors containing the nucleic acids of the invention. The host cell can be a eukaryotic cell, e.g., a mammalian cell, an insect cell, a yeast cell, or a prokaryotic cell, e.g., E. coli. For example, the mammalian cell can be a cultured cell or a cell line. Exemplary mammalian cells include lymphocytic cell lines (e.g., NS0), Chinese hamster ovary cells (CHO), COS cells, oocyte cells, and cells from a transgenic animal, e.g., mammary epithelial cell. For example, nucleic acids encoding the isoform binding molecule described herein can be expressed in a transgenic animal. In one embodiment, the nucleic acids are placed under the control of a tissue-specific promoter (e.g., a mammary specific promoter) and the antibody is produced in the transgenic animal. For example, the isoform binding molecule is secreted into the milk of the transgenic animal, such as a transgenic cow, pig, horse, sheep, goat or rodent.

In one aspect, the invention features a method of providing an isoform binding antibody molecule that specifically binds to an isoform (e.g., an oncogenic isoform) polypeptide. The method includes: providing a isoform-specific antigen (e.g., an antigen comprising at least a portion of an epitope as described herein); obtaining an antibody molecule that specifically binds to the isoform polypeptide; and evaluating if the antibody molecule specifically binds to the isoform polypeptide (e.g., evaluating if there is a decrease in binding between the antibody molecule and the isoform polypeptide in the present of one or more of the epitopes described herein), or evaluating efficacy of the antibody molecule in modulating, e.g., inhibiting, the activity of the isoform (e.g., an oncogenic isoform) polypeptide. The method can further include administering the antibody molecule to a subject, e.g., a human or non-human animal.

Isoform-specific epitopes, e.g., isolated epitopes, as described herein are also encompassed by the present invention. The epitopes can be linear or conformational protein of the isoform (e.g., oncogenic) isoform, e.g., from about 2 to 80, about 4 to 75, about 5 to 70, about 10 to 60, about 10 to 50, about 10 to 40, about 10 to 30, about 10 to 20, amino acid residues. In certain embodiments, the epitope consists of, or includes, an amino acid sequence located at the junctional region between two exons that are predominantly joined together in protein isoforms expressed or associated with one or more cancerous or tumor cells or disorders, e.g., as a result of an in-frame exon deletion or the use of an alternatively spliced exon. For example, the epitope can consist of, or include, an amino acid sequence identical to the alternative spliced form of Exon III, e.g., from about amino acids 301 to 360 of FGFR2-IIIc (SEQ ID NO:2); about amino acids 314 to 324 of FGFR2-IIIc (AAGVNTTDKEI, SEQ ID NO:4); about amino acids 328 to 337 of FGFR2-IIIc (YIRNVTFEDA, SEQ ID NO:6); about amino acids 350 to 353 of FGFR2-IIIc (ISFH, SEQ ID NO:8), or an amino acid sequence encoded by a nucleotide sequence of SEQ ID NOs: 1, 3, 5 or 7; or an amino acid or nucleotide sequence substantially identical thereto. In other embodiments, the epitope of FGFR2-IIIc, e.g., human FGFR2-IIIc, can include or consist of at least one amino acid residue of 314-353 of FGFR2 IIIc (AAGVNTTD-KEIEVLYIRNVTFEDAGEYTCLAGNSIGISFH (SEQ ID NO: 84)); or at least one amino acid residue of TCLAGNSIG-ISFH (SEQ ID NO: 86). In one embodiment, the epitope of human FGFR2-IIIc comprises one, two, three, four, five, six, seven, eight, nine, ten, twelve, fourteen, sixteen, eighteen, twenty, twenty-two or more of: alanine at position 1, alanine at position 2, valine at position 4, threonine at position 6, threonine at position 7, aspartate at position 8, lysine at position 9, isoleucine at position 11, glutamate at position 12, valine at position 13, tyrosine at position 15, isoleucine at position 16, arginine at position 17, phenylalanine at position 21, glutamate at position 22, threonine at position 28, leucine at position 30, alanine at position 31, glycine at position 32, serine at position 34, isoleucine at position 37, serine at position 38, phenylalanine at position 39, or histidine at position 40 of SEQ ID NO: 84 (corresponding to the highlighted amino acid residues in AAG<u>V</u>NT<u>T</u>DKE<u>I</u>EVL<u>Y</u>IRNVT FEDAGEY<u>T</u>CLAG<u>N</u>SIG<u>ISFH</u>(SEQ ID NO: 84)); or one or more of: threonine at position 1, leucine at position 3, alanine at position 4, glycine at position 5, serine at position 7, isoleucine at position 10, serine at position 11, phenylalanine at position 12, or histidine at position 13 of SEQ ID NO: 86 (corresponding to the highlighted amino acid residues in <u>TC</u> LAG<u>N</u>SIG<u>ISFH</u>; SEQ ID NO: 86).

The invention also features a method of reducing the activity (e.g., cell growth or proliferation), or inducing the killing (e.g., inducing apoptosis of), a hyperproliferative cell, e.g., a cancerous or tumor cell (e.g., a cancerous or tumor cell expressing an oncogenic isoform, such as FGFR2-IIIc and exon deleted-isoforms of FGFR1, RON, KIT, PDGF and PDGFR-alpha, as described herein). The method includes contacting the hyperproliferative cell, or a cell (e.g., a vascular cell) in proximity to the hyperproliferative cell, with one or more isoform-specific inhibitors as described herein, e.g., an isoform-specific antibody molecule described herein, in an amount sufficient to reduce the expression or activity of the isoform, e.g., the oncogenic isoform, thereby reducing the activity of, or killing, the hyperproliferative cell. The isoform-specific inhibitors as described herein can be used in conjugated or unconjugated form, alone as a monotherapy or in combination with one or more therapeutic agents, to thereby kill, or reduce the activity, e.g., inhibit cell growth of, the hyperproliferative cell.

In embodiments, the isoform-binding molecule is an antibody molecule that specifically binds to FGFR2-IIIc, e.g., an antibody molecule that specifically binds to an amino acid sequence identical to the alternative spliced form of Exon III, e.g., from about amino acids 301 to 360 of FGFR2-IIIc (SEQ ID NO:2); about amino acids 314 to 324 of FGFR2-IIIc (AAGVNTTDKEI, SEQ ID NO:4); about amino acids 328 to 337 of FGFR2-IIIc (YIRNVTFEDA, SEQ ID NO:6); about amino acids 350 to 353 of FGFR2-IIIc (ISFH, SEQ ID NO:8), or an amino acid sequence encoded by a nucleotide sequence of SEQ ID NOs: 1, 3, 5 or 7; or an amino acid or nucleotide sequence substantially identical thereto. In such embodiments, the hyperproliferative cell is a cancerous or tumor cell from the prostate, breast, pancreas, ovary, brain (glioblastoma), gastric cancers, lung squamous cell carcinoma, non-small cell lung carcinoma, thyroid cancer, endometrial carcinoma, hematopoietic cancers, and skeletal disorders, such as craniofacial dysostosis 1, Crouzon syndrome, Pfeiffer syndrome, Jackson-Weiss syndrome and Apert syndrome.

The methods can be used on cells in culture, e.g., in vitro or ex vivo. For example, hyperproliferative cells (e.g., cancerous or metastatic cells (e.g., prostatic, renal, urothelial (e.g., bladder), testicular, ovarian, breast, colon, rectal, lung (e.g., non-small cell lung carcinoma), liver, brain, neural (e.g., neuroendocrine), glial (e.g., glioblastoma), pancreatic, melanoma (e.g., malignant melanoma), or soft tissue sarcoma cancerous or metastatic cells) can be cultured in vitro in culture medium and the contacting step can be effected by adding the isoform binding molecule, to the culture medium. Alternatively, the method can be performed on hyperproliferative cells present in a subject, as part of an in vivo (e.g., therapeutic or prophylactic) protocol.

Methods of the invention can be used, for example, to treat or prevent a hyperproliferative disorder, e.g., a cancer (primary, recurring or metastasizing) of, e.g. prostate, breast, pancreas and brain (glioblastoma), by administering to a subject an isoform-specific inhibitor described herein, in an amount effective to treat or prevent such disorder. In one embodiment, the cancer is an adenocarcinoma or carcinoma of the prostate and/or testicular tumors. For example, the cancer is hormone-resistant or refractory prostate cancer. In one embodiment, the cancer is an androgen-resistant or refractory prostate cancer associated with elevated expression of FGFR2-IIIc. For example, the cancer shows elevated level or expression of FGFR2-IIIc protein or mRNA compared to a reference value (e.g., a non-cancerous prostatic tissue), optionally, accompanied by a reduction in one or more epithelial markers (e.g., reduction in the level or expression of epithelial cell surface adhesion molecules (Ep-CAM) and/or gain of mesenchymal markers. In certain embodiments, the cancer is a metastatic cancer showing elevated levels of prostate-derived circulating tumor cells (e.g., prostate-derived circulating FGFR2IIIc-expressing prostatic tumor cells). Methods and compositions disclosed herein are particularly useful for treating metastatic lesions associated with prostate cancer. In some embodiments, the patient will have undergone one or more of prostatectomy, chemotherapy, or other anti-tumor therapy and the primary or sole target will be metastatic lesions, e.g., metastases in the bone marrow or lymph nodes.

In other embodiments, the cancer treated with the isoform-specific inhibitor(s) described herein includes, but is not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), genitals and genitourinary tract (e.g., renal, urothelial, bladder cells), pharynx, CNS (e.g., brain, neural or glial cells), skin (e.g., melanoma), and pancreas, as well as adenocarcinomas which include malignancies such as most colon cancers, rectal cancer, renal-cell carcinoma, liver cancer, non-small cell-carcinoma of the lung, cancer of the small intestine and cancer of the esophagus. Methods and compositions disclosed herein are particularly useful for treating metastatic lesions associated with the aforementioned cancers. In some embodiments, the patient will have undergone one or more of surgical removal of a tissue, chemotherapy, or other anti-cancer therapy and the primary or sole target will be metastatic lesions, e.g., metastases in the bone marrow or lymph nodes. For example, a reduction in expression or activity of an FGFR2-IIIc oncogenic isoform can be used to prevent and/or treat hormone-refractory prostate cancer, breast cancer, bladder cancer, thyroid cancer, or other form of cancer.

In one embodiment, the subject is treated to prevent a hyperproliferative disorder, e.g., a hyperproliferative disorder as described herein. The subject can be a mammal, e.g., a primate, preferably a higher primate, e.g., a human (e.g., a patient having, or at risk of, a hyperproliferative disorder described herein, e.g., a prostatic cancer disorder). In one embodiment, the subject is a patient having prostate cancer (e.g., a patient suffering from recurrent or metastatic prostate cancer). The subject can be one at risk for the disorder, e.g., a subject having a relative afflicted with the disorder, e.g., a subject with one or more of a grandparent, parent, uncle or aunt, sibling, or child who has or had the disorder, or a subject having a genetic trait associated with risk for the disorder. In one embodiment, the subject can be symptomatic or asymptomatic. For example, the subject can suffer from symptomatic or asymptomatic prostatic cancer, e.g., hormone-resistant or refractory prostate cancer. In some embodiments, the subject suffers from metastatic prostate cancer. In some embodiments, the subject has elevated levels of prostate-derived circulating tumor cells (e.g., prostate-derived circulating FGFR2IIIc-expressing prostatic tumor cells). In other embodiments, the subject has abnormal levels of one or more markers for a cancer, e.g., prostatic cancer. For example, the subject has abnormal levels of prostate-specific antigen (PSA), prostate specific membrane antigen (PSMA), prostate stem cell antigen (PSCA), androgen receptor (AR), chromogranin, synaptophysin, MIB-1, and/or α-methylacyl-CoA racemase (AMACR).

The isoform-specific inhibitors described herein can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

The methods of the invention, e.g., methods of treatment or preventing, can further include the step of monitoring the subject, e.g., for a change (e.g., an increase or decrease) in one or more of: tumor size; levels of a cancer marker (e.g., level or expression of FGFR2IIIc; levels of circulating prostate-derived FGFR2IIIc-expressing cells, epithelial cell markers (Ep-CAM), FGF ligands (e.g., FGF8), stromal derived factor α (SDFα), VEGF (e.g., VEGF121), mesenchymal markers, PSA, PSMA, PSCA, AR, chromogranin, synaptophysin, MIB-1, AMACR, alkaline phosphatase, and/or serum hemoglobin for a patient with prostate cancer); the rate of appearance of new lesions, e.g., in a bone scan; the appearance of new disease-related symptoms; the size of soft tissue mass, e.g., a decreased or stabilization; quality of life, e.g., amount of disease associated pain, e.g., bone pain; or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same isoform-binding molecule or for additional treatment with additional agents. Generally, a decrease in one or more of the parameters described above is indicative of the improved condition of the subject, although with serum hemoglobin levels, an increase can be associated with the improved condition of the subject.

The methods of the invention can further include the step of analyzing a nucleic acid or protein from the subject, e.g., analyzing the genotype of the subject. In one embodiment, a nucleic acid encoding the isoform, e.g., the oncogenic isoform, and/or an upstream or downstream component(s) of the isoform signaling, e.g., an extracellular or intracellular activator or inhibitor of the isoform, is analyzed. The analysis can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response phenotype or genotype. The nucleic acid or protein can be analyzed at any stage of treatment, but preferably, prior to administration of the isoform-specific inhibitor to thereby determine appropriate dosage(s) and treatment regimen(s) of the isoform-specific inhibitor (e.g., amount per treatment or frequency of treatments) for prophylactic or therapeutic treatment of the subject.

The isoform-specific inhibitor (e.g., the isoform-specific binding agent) can be used alone in unconjugated form to thereby reduce the activity or induce the killing of the isoform-expressing hyperproliferative or cancerous cells by, e.g., antibody-dependent cell killing mechanisms such as complement-mediated cell lysis and/or effector cell-mediated cell killing. In other embodiments, the isoform-specific inhibitor can be bound to a substance, e.g., a cytotoxic agent or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the isoform-specific inhibitor can be coupled to a radioactive isotope such as an α-, β-, or γ-emitter, or a β- and γ-emitter. Examples of radioactive isotopes include iodine ($^{131}$I or $^{125}$I), yttrium ($^{90}$Y), lutetium ($^{177}$Lu), actinium ($^{225}$Ac), praseodymium, or bismuth ($^{212}$Bi or $^{213}$Bi). Alternatively, the isoform-binding molecule can be coupled to a biological protein, a molecule of plant or bacterial origin (or derivative thereof), e.g., a maytansinoid (e.g., maytansinol or DM1), as well as a taxane (e.g., Taxol® or taxotere), or calicheamicin. The maytansinoid can be, for example, maytansinol or a maytansinol analogue. Examples of maytansinol analogues include those having a modified aromatic ring (e.g., C-19-decloro, C-20-demethoxy, C-20-acyloxy) and those having modifications at other positions (e.g., C-9-CH, C-14-alkoxymethyl, C-14-hydroxymethyl or aceloxymethyl, C-15-hydroxy/acyloxy, C-15-methoxy, C-18-N-demethyl 4,5-deoxy). Maytansinol and maytansinol analogues are described, for example, in U.S. Pat. No. 6,333,410, the contents of which is incorporated herein by reference. The calicheamicin can be, for example, a bromo-complex calicheamicin (e.g., an alpha, beta or gamma bromo-complex), an iodo-complex calicheamicin (e.g., an alpha, beta or gamma iodo-complex), or analogs and mimics thereof. Bromo-complex calicheamicins include $\alpha_1$-BR, $\alpha_2$-BR, $\alpha_3$-BR, $\alpha_4$-BR, $\beta_1$-BR, $\beta_2$-BR and $\gamma_1$-BR. Iodo-complex calicheamicins include $\alpha_1$-I, $\alpha_2$-I, $\alpha_3$-I, $\beta_1$-I, $\beta_2$-I, $\delta_1$-I and $\gamma_1$-BR. Calicheamicin and mutants, analogs and mimics thereof are described, for example, in U.S. Pat. No. 4,970,198, issued Nov. 13, 1990, U.S. Pat. No. 5,264,586, issued Nov. 23, 1993, U.S. Pat. No. 5,550,246, issued Aug. 27, 1996, U.S. Pat. No. 5,712,374, issued Jan. 27, 1998, and U.S. Pat. No. 5,714,586, issued Feb. 3, 1998, the contents of which are incorporated herein by reference. Maytansinol can be coupled to antibodies using, e.g., an N-succinimidyl 3-(2-pyridyldithio)proprionate (also known as N-succinimidyl 4-(2-pyridyldithio)pentanoate or SPP), 4-succinimidyl-oxycarbonyl-a-(2-pyridyldithio)-toluene (SMPT), N-succinimidyl-3-(2-pyridyldithio)butyrate (SDPB), 2-iminothiolane, or S-acetylsuccinic anhydride.

The methods and compositions of the invention can be used in combination with other therapeutic modalities. In one embodiment, the methods of the invention include administering to the subject an isoform-specific inhibitor as described herein, in combination with a cytotoxic agent, in an amount effective to treat or prevent said disorder. The binding molecule and the cytotoxic agent can be administered simultaneously or sequentially. In other embodiments, the methods and compositions of the invention are used in combination with surgical and/or radiation procedures. In yet other embodiments, the methods can be used in combination with immunodulatory agents, e.g., IL-1, 2, 4, 6, or 12, or interferon alpha or gamma, or immune cell growth factors such as GM-CSF. Exemplary cytotoxic agents that can be administered in combination with the isoform-specific inhibitor include anti-microtubule agents, topoisomerase inhibitors, antimetabolites, mitotic inhibitors, alkylating agents, intercalating agents, agents capable of interfering with a signal transduction pathway, agents that promote apoptosis and radiation.

In therapies of prostatic disorders, e.g., prostate cancer, the isoform-specific inhibitor can be used in combination with existing therapeutic modalities, e.g., prostatectomy (partial or radical), radiation therapy, hormonal therapy, androgen ablation therapy, and cytotoxic chemotherapy. Typically, hormonal therapy works to reduce the levels of androgens in a patient, and can involve administering a leuteinizing hormone-releasing hormone (LHRH) analog or agonist (e.g., Lupron, Zoladex, leuprolide, buserelin, or goserelin), as well as antagonists (e.g., Abarelix). Non-steroidal anti-androgens, e.g., flutamide, bicalutimade, or nilutamide, can also be used in hormonal therapy, as well as steroidal anti-androgens (e.g., cyproterone acetate or megastrol acetate), estrogens (e.g., diethylstilbestrol), surgical castration, PROSCAR®, secondary or tertiary hormonal manipulations (e.g., involving corticosteroids (e.g., hydrocortisone, prednisone, or dexamethasone), ketoconazole, and/or aminogluthethimide), inhibitors of 5a-reductase (e.g., finisteride), herbal preparations (e.g., PC-SPES), hypophysectomy, and adrenalectomy. Furthermore, hormonal therapy can be performed intermittently or using combinations of any of the above treatments, e.g., combined use of leuprolide and flutamide.

Any combination and sequence of isoform-specific inhibitor and other therapeutic modalities can be used. The isoform-specific inhibitor and other therapeutic modalities can be administered during periods of active disorder, or during a period of remission or less active disease. The isoform-specific inhibitor and other therapeutic modalities can be administered before treatment, concurrently with treatment, post-treatment, or during remission of the disorder.

In another aspect, the invention features methods for detecting the presence of an isoform (e.g., an oncogenic isoform as described herein) polypeptide or gene expression product in a sample in vitro (e.g., a biological sample, e.g., serum, semen or urine, or a tissue biopsy, e.g., from a hyperproliferative or cancerous lesion). The subject method can be used to evaluate (e.g., monitor treatment or progression of, diagnose and/or stage a disorder described herein, e.g., a hyperproliferative or cancerous disorder, in a subject). The method includes: (i) contacting the sample (and optionally, a reference, e.g., a control sample) with an isoform binding molecule (e.g., an antibody molecule), as described herein, under conditions that allow interaction of the isoform binding molecule and the polypeptide or gene expression product to occur, and (ii) detecting formation of a complex between the isoform binding molecule, and the sample (and optionally, the reference, e.g., control, sample). Formation of the complex is indicative of the presence of the polypeptide or gene expression product, and can indicate the suitability or need for a treatment described herein. For example, a statistically significant change in the formation of the complex in the sample relative to the reference sample, e.g., the control sample, is indicative of the presence of the isoform, e.g., the oncogenic isoform, in the sample. In some embodiments, the methods can include the use of more than one isoform-binding molecules, e.g., two antibody molecules that bind to different epitopes on the same oncogenic isoform (e.g., FGFR2 isoform IIIc) or different oncogenic isoform. For example, the method can involve an immunohistochemistry, immunocytochemistry, FACS, antibody molecule complexed magnetic beads, ELISA assays, PCR-techniques (e.g., RT-PCR), e.g., as described in the appended Examples.

In yet another aspect, the invention provides a method for detecting the presence of an isoform (e.g., an oncogenic isoform as described herein) polypeptide or gene expression product in vivo (e.g., in vivo imaging in a subject). The method can be used to evaluate (e.g., monitor treatment or progression of, diagnose and/or stage a disorder described herein, e.g., a hyperproliferative or cancerous disorder), in a subject, e.g., a mammal, e.g., a primate, e.g., a human. The method includes: (i) administering to a subject an isoform binding molecule (e.g., an antibody molecule as described herein), under conditions that allow interaction of the isoform binding molecule and the polypeptide or gene expression product to occur; and (ii) detecting formation of a complex between the isoform binding molecule and the polypeptide or gene expression product. A statistically significant change in the formation of the complex in the subject relative to the reference, e.g., the control subject or subject's baseline, is indicative of the presence of the polypeptide or gene expression product.

In other embodiments, a method of evaluating (e.g., monitoring treatment or progression of, diagnosing and/or staging a hyperproliferative or cancerous disorder as described herein, in a subject, is provided. The method includes: (i) identifying a subject having, or at risk of having, the disorder, (ii) obtaining a sample of a tissue or cell affected with the disorder, (iii) contacting said sample or a control sample with an isoform binding molecule as described herein, e.g., an antibody molecule as described herein, under conditions that allow an interaction of the binding molecule and the isoform polypeptide or gene product to occur, and (iv) detecting formation of a complex. A statistically significant increase in the formation of the complex with respect to a reference sample, e.g., a control sample, is indicative of the disorder or the stage of the disorder.

Typically, the isoform binding molecule used in the in vivo and in vitro diagnostic methods is directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials. In some embodiments, the isoform binding molecule is coupled to a radioactive ion, e.g., indium ($^{111}$In) iodine ($^{131}$I or $^{125}$I), yttrium ($^{90}$Y) lutetium ($^{177}$Lu), actinium ($^{225}$Ac), bismuth ($^{212}$Bi or $^{213}$Bi), sulfur ($^{35}$S), carbon ($^{14}$C), tritium ($^{3}$H), rhodium ($^{188}$Rh), technetium ($^{99m}$Tc), praseodymium, or phosphorous ($^{32}$P).

The detection/diagnostic methods described herein can further include the step of monitoring the subject, e.g., for a change (e.g., an increase or decrease) in one or more of: tumor size; levels of a cancer marker (e.g., level or expression of FGFR2IIIc; levels of circulating prostate-derived FGFR2IIIc-expressing cells, epithelial cell markers (Ep-CAM), FGF ligands (e.g., FGF8), stromal derived factor alpha (SDFalpha, VEGF (e.g., VEGF121), mesenchymal markers, PSA, PSMA, PSCA, AR, chromogranin, synaptophysin, MIB-1, AMACR, alkaline phosphatase, and/or serum hemoglobin for a patient with prostate cancer); the rate of appearance of new lesions, e.g., in a bone scan; the appearance of new disease-related symptoms; the size of soft tissue mass, e.g., a decreased or stabilization; quality of life, e.g., amount of disease associated pain, e.g., bone pain; or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same isoform-binding molecule or for additional treatment with additional agents. Generally, a decrease in one or more of the parameters described above is indicative of the improved condition of the subject, although with serum hemoglobin levels, an increase can be associated with the improved condition of the subject.

In another aspect, the invention features diagnostic or therapeutic kits that include the isoform-specific inhibitors described herein and instructions for use.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

The terms "proteins" and "polypeptides" are used interchangeably herein.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

All publications, patent applications, patents, and other references mentioned herein are incorporated by reference in their entirety.

Other features, objects, and advantages of the invention will be apparent from the description and drawings, and from the claims.

BRIEF DESCRIPTION OF DRAWINGS

FIG. 2 depicts the sequence alignment of IIIc (SEQ ID NO: 2) and IIIb isoforms (SEQ ID NO: 65).

FIG. 3A depicts the amino acid sequence of human FGFR2 IIIc (SEQ ID NO: 19).

FIG. 3B depicts the nucleotide sequence of human FGFR2 IIIc (SEQ ID NO: 20).

FIG. 4A depicts the nucleotide sequence of FGFR2 Exon-IIIc (SEQ ID NO: 1).

FIG. 4B depicts the nucleotide sequence of FGFR2 Exon-IIIb (SEQ ID NO: 64).

FIG. 5A depicts the amino acid (SEQ ID NO: 4) and nucleotide (SEQ ID NO: 3) sequences of peptide IIIc-314.

FIG. 5B depicts the amino acid (SEQ ID NO: 6) and nucleotide (SEQ ID NO: 5) sequences of peptide IIIc-328.

FIG. 5C depicts the amino acid (SEQ ID NO: 8) and nucleotide (SEQ ID NO: 7) sequences of peptide IIIc-350.

FIG. 6A depicts the amino acid (SEQ ID NO: 56) and nucleotide (SEQ ID NO: 60) sequences of IIIb (Loop3-C') fragment: amino acids 314-351.

FIG. 6B depicts the amino acid (SEQ ID NO: 57) and nucleotide (SEQ ID NO: 61) sequences of IIIb epitope: amino acids 314-328.

FIG. 6C depicts the amino acid (SEQ ID NO: 58) and nucleotide (SEQ ID NO: 62) sequences of IIIb epitope: amino acids 340-351.

FIG. 9 depicts the nucleotide (SEQ ID NO: 11) and amino acid (SEQ ID NO: 12) sequences of RONΔ160 epitope at the junction between exon 4 and exon 7.

FIG. 10 depicts the nucleotide (SEQ ID NO: 13) and amino acid (SEQ ID NO: 14) sequences of the epitope designed for antibody targeting KIT isoform.

FIG. 11 depicts the nucleotide (SEQ ID NO: 15) and amino acid (SEQ ID NO: 16) sequences of the epitope designed for antibody targeting PDGF isoform.

FIG. 12 depicts the nucleotide (SEQ ID NO: 17) and amino acid (SEQ ID NO: 18) sequences of the epitope of PDGFR-alpha isoform.

FIG. 13A depicts the structure of the soluble FGFR2 IIIc-Fc fusion protein.

FIG. 13B depicts the nucleotide sequence (SEQ ID NO: 54) of the soluble FGFR2 IIIc-Fc fusion protein.

FIG. 13C depicts the amino acid sequence (SEQ ID NO: 55) of the soluble FGFR2 IIIc-Fc fusion protein. The signal peptide corresponds to amino acids 1 to 21 of SEQ ID NO: 55.

FIG. 13D depicts a Western blot of SDS-PAGE analysis of CHO stable cell lines expressing the recombinant fusion protein of soluble FGFR2 IIIc-Fc.

FIG. 14 depicts sequence alignments of FGFR2 receptor Ig-like loop-3 regions from human and rat. The C-terminal half of loop-3 is encoded by either exon-8 to give rise to IIIc (shown in bold) (residues 6-53 of SEQ ID NO: 2 and SEQ ID NO: 67), or exon-9 to give rise to IIIb (italic) (residues 6-51 of SEQ ID NO: 65 and SEQ ID NO: 68). Human and rat sequences are 100% identical in these regions.

FIG. 17A depicts the amino acid sequence of human FGFR2 gene (SEQ ID NO: 32).

FIGS. 17B-17C depict the amino acid (SEQ ID NO: 21) and nucleotide sequences (SEQ ID NO: 63) of human FGFR2 IIIb, respectively.

FIGS. 17D-17O depict the amino acid sequence of human FGFR2 isoform 4 (SEQ ID NO: 22), isoform 7 (SEQ ID NO: 23), isoform 9 (SEQ ID NO: 24), isoform 10 (SEQ ID NO: 25), isoform 11 (SEQ ID NO: 26), isoform 12 (SEQ ID NO: 27), isoform 13 (SEQ ID NO: 28), isoform 14 (SEQ ID NO: 29), isoform 15 (SEQ ID NO: 30), isoform 17 (SEQ ID NO: 31), isoform 18 (SEQ ID NO: 52), and isoform 19 (SEQ ID NO: 53), respectively.

FIG. 18A depicts the amino acid sequence of human FGFR1 gene (SEQ ID NO: 33).

FIGS. 18B-18H depict the amino acid sequences of human FGFR1 isoform 1 (SEQ ID NO: 38), isoform 4 (SEQ ID NO: 39), isoform 14 (SEQ ID NO: 40), isoform 16 (SEQ ID NO: 41), isoform 17 (SEQ ID NO: 42), isoform 3 (SEQ ID NO: 43), and isoform 18 (SEQ ID NO: 44), respectively.

FIG. 19A depicts the amino acid sequence of human RON gene (SEQ ID NO: 34).

FIG. 19B depicts the amino acid sequence of human non-oncogenic RON isoform (SEQ ID NO: 45).

FIG. 20A depicts the amino acid sequence of human KIT gene (SEQ ID NO: 35).

FIG. 20B depicts the amino acid sequence of human KIT variant with deletion in exon 11 (SEQ ID NO: 46).

FIG. 20C depict the amino acid sequence of full-length human KIT (SEQ ID NO: 47).

FIG. 21A depicts the amino acid sequence of human PDGF gene (SEQ ID NO: 36).

FIG. 21B depicts the amino acid sequence of human PDGF isoform 2 (SEQ ID NO: 48).

FIG. 21C depict the amino acid sequence of full-length human PDGF (SEQ ID NO: 49).

FIG. 22A depicts the amino acid sequence of human PDGFR alpha gene (SEQ ID NO: 37).

FIG. 22B depicts the amino acid sequence of human PDGFR alpha isoform 1 (SEQ ID NO: 50).

FIG. 22C depict the amino acid sequence of human PDGFR alpha isoform with deletion in exons 7-8 (SEQ ID NO: 51).

FIG. 23 depicts the amino acid sequence of human FGF8 (SEQ ID NO: 66).

FIG. 28 depicts an amino acid sequence alignment of human scFv Clone-6 (SEQ ID NO: 160) and Clone-8 (SEQ ID NO: 161). The locations of the complementarity determining regions (CDRs) of the light and heavy chain variable regions are underlined and labeled as VL-CDR-1, -2, and -3, and VH-CDR-1, -2, and -3, respectively. The linker sequence is shaded. Clone-6 and Clone-8 are also referred to herein as "Atto-HuMab-06" and "Atto-HuMab-08," respectively.

FIGS. 29A-29B depict the nucleotide (SEQ ID NO: 162) and amino acid (SEQ ID NO: 161) sequence, respectively, for the full length coding region of the light chain variable domain and the heavy chain variable domain of human scFv Clone 8 (Atto-HuMab-08). The linker sequence is shaded.

FIGS. 29C-29D depict the nucleotide (SEQ ID NO: 164) and amino acid (SEQ ID NO: 163) sequence, respectively, of the light chain variable domain of the human scFv Clone 8 (Atto-HuMab-08). The CDR sequences (SEQ ID NOS: 184-186, corresponding to the nucleotide sequences of CDRs 1-3, respectively; SEQ ID NOS: 155, 156 and 146, corresponding to the amino acid sequences of CDRs 1-3, respectively) are underlined.

FIGS. 29E-29F depict the nucleotide (SEQ ID NO: 166) and amino acid (SEQ ID NO: 165) sequence, respectively, of the heavy chain variable domain of the human scFv Clone 8 (Atto-HuMab-08). The CDR sequences (SEQ ID NOS: 187-189, corresponding to the nucleotide sequences of CDRs 1-3, respectively; SEQ ID NOS: 147-149, corresponding to the amino acid sequences of CDRs 1-3, respectively) are underlined.

FIGS. 30A-30B depict the nucleotide (SEQ ID NO: 167) and amino acid (SEQ ID NO: 160) sequence, respectively, for the full length coding region of the light chain variable domain and the heavy chain variable domain of human scFv Clone 6 (Atto-HuMab-06). The linker sequence is shaded.

FIGS. 30C-30D depict the nucleotide (SEQ ID NO: 169) and amino acid (SEQ ID NO: 168) sequence, respectively, of the light chain variable domain of the human scFv Clone 6 (Atto-HuMab-06). The CDR sequences (SEQ ID NOS: 178-180, corresponding to the nucleotide sequences of CDRs 1-3, respectively; SEQ ID NOS: 155-157, corresponding to the amino acid sequences of CDRs 1-3, respectively) are underlined.

FIGS. 30E-30F depict the nucleotide (SEQ ID NO: 171) and amino acid (SEQ ID NO: 170) sequence, respectively, of the heavy chain variable domain of the human scFv Clone 6 (Atto-HuMab-06). The CDR sequences (SEQ ID NOS: 181-183, corresponding to the nucleotide sequences of CDRs 1-3, respectively; SEQ ID NOS: 147, 158 and 159, corresponding to the amino acid sequences of CDRs 1-3, respectively) are underlined.

FIG. 34A depicts the nucleotide sequence of Atto-MuMab-02 heavy chain variable region (SEQ ID NO: 87; 358 bp). The nucleotide sequences of CDRs (SEQ ID NOS: 91, 93 and 95, corresponding to CDRs 1-3, respectively) and framework regions are shown as underlined and in italic, respectively.

FIG. 34B depicts the nucleotide sequence of Atto-MuMab-02 light chain variable region (SEQ ID NO: 89; 324 bp). The nucleotide sequences of CDRs (SEQ ID NOS: 97, 99 and 101, corresponding to CDRs 1-3, respectively) and framework regions are shown as underlined and in italic, respectively.

FIG. 35 depicts the amino acid sequences of Atto-MuMab-02 light chain variable region (SEQ ID NO: 90; 21-LC) and heavy chain variable region (SEQ ID NO: 88; 21-HC). SEQ ID NOS: 98, 100 and 102 correspond to VL CDRs 1-3, respectively. SEQ ID NOS: 92, 94 and 96 correspond to VH CDRs 1-3, respectively.

FIG. 36A depicts the amino acid sequence alignment of Atto-MuMab-02 heavy chain variable region with mouse immunoglobulin mu chain. 21HC: Atto-MuMab-02 immunoglobulin heavy chain variable region (SEQ ID NO: 88); subject: immunoglobulin mu chain [*Mus musculus*] (SEQ ID NO: 142; GenBank: AAA88255.1).

FIG. 36B depicts the amino acid sequence alignment of Atto-MuMab-02 light chain variable region with mouse anti-human melanoma immunoglobulin light chain. 21LC: Atto-MuMab-02 immunoglobulin light chain variable region (residues 1-106 of SEQ ID NO: 90); subject: anti-human melanoma immunoglobulin light chain [*Mus musculus*] (SEQ ID NO: 143; GenBank: AAO49727.1).

FIGS. 37A-37B depicts the amino acid (SEQ ID NO: 190) and nucleotide (SEQ ID NO: 191) sequences, respectively, for the full length coding region of the light chain variable domain and the heavy chain variable domain of human scFv Clone 1 (scFv-1, also referred to herein as "Atto-HuMab-01"). The linker sequence is shaded. The CDR sequences are underlined. SEQ ID NOS: 144-146 correspond to the amino acid sequences of VL CDRs 1-3, respectively. SEQ ID NOS: 147-149 correspond to the amino acid sequences of VH CDRs 1-3, respectively. SEQ ID NOS: 172-174 correspond to the nucleotide sequences of VL CDRs 1-3, respectively. SEQ ID NOS: 175-177 correspond to the nucleotide sequences of VH CDRs 1-3, respectively.

FIG. 38 depicts an amino acid sequence alignment of human scFv Clone 1 (scFv-1, SEQ ID NO: 142) and Clone 6 (scFv-6, SEQ ID NO: 160). The locations of the complementarity determining regions (CDRs) of the light and heavy chain variable regions are underlined and labeled as VL-CDR-1, -2, and -3, and VH-CDR-1, -2, and -3, respectively. The linker sequence is shaded. Clone-1 and Clone-6 are also referred to herein as "Atto-HuMab-01" and "Atto-HuMab-06," respectively.

FIG. 39 depicts an amino acid sequence alignment of human scFv Clone 1 (scFv-1, SEQ ID NO: 142) and Clone 8 (scFv-8; SEQ ID NO: 161). The locations of the complementarity determining regions (CDRs) of the light and heavy chain variable regions are underlined and labeled as VL-CDR-1, -2, and -3, and VH-CDR-1, -2, and -3, respectively. The linker sequence is shaded. Clone-1 and Clone-8 are also referred to herein as "Atto-HuMab-01" and "Atto-HuMab-08," respectively.

FIG. 40 is a table depicting a comparison of the CDR region homology among human scFv clones scFv-1, scFv-6 and scFv-8. Unique amino acid residues are underlined. Amino acid residues that share sequence homology among two of the three clones are shown in italics. Amino acid residues homologous among all three clones are shown in regular font.

FIG. 46 is a table depicting a summary of library panning and enrichment results.

FIG. 48 is a table depicting antibody binding to transient CHO cells (phage-displayed: Phage-scFv; secreted: Soluble scFv; bivalent soluble: Fc-fusion dcFv).

FIG. 49 is a table depicting exemplary CDR region homology comparison among scFv vlones. A dashed line=a space in the sequence.

DETAILED DESCRIPTION

Figure 1:
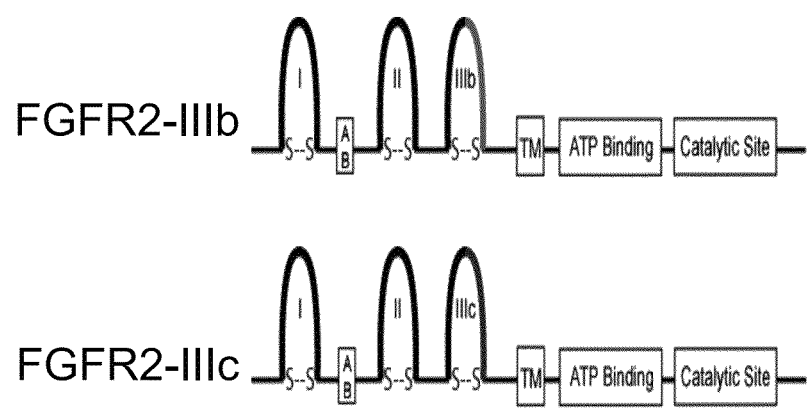
FIG. 1 depicts the isoform structure of FGFR2 receptor tyrosine kinase. Top: Isoform IIIb is expressed on normal prostate epithelial cells. Bottom: Isoform IIIc is expressed in hormone-refractory prostate cancer. TM=Transmembrane; AB=Acid box; I, II, or III=Ig-like loop I, II, or III.

The present invention provides, at least in part, isoform-specific inhibitors that inhibit or reduce one or more isoform-associated activities. In certain embodiments, the isoforms (e.g., polypeptide or nucleic acid isoforms) are expressed and/or are associated with oncogenic or malignant phenotypes (referred to herein as "oncogenic isoforms"). For example, the isoforms can arise from, e.g., one or more of: alternative splicing, frameshifting, translational and/or post-translational events, thereby resulting in different transcription or translation products. In one embodiment, the isoform-specific inhibitor is an isoform-binding molecule, e.g., an antibody molecule, or a nucleic acid inhibitor. In another embodiment, the isoform-specific inhibitor is a soluble receptor polypeptide and a fusion form thereof, or a peptide and a functional variant thereof. For example, the isoform-specific inhibitor can be an oncogenic isoform-binding molecule, e.g., an antibody molecule or a nucleic acid inhibitor that specifically interacts with, e.g., binds to, one or more oncogenic isoforms (e.g., oncogenic isoform polypeptides or nucleic acids encoding the same). In another embodiment, the isoform-specific inhibitor is a soluble receptor polypeptide or a fusion form thereof, or a peptide or a functional variant thereof that reduces or inhibits one or more isoform- (e.g., oncogenic isoform-) associated activities. In embodiments, the soluble receptor or fusion reduce or inhibit (e.g., competitively inhibit) an interaction of the isoform (e.g., the oncogenic isoform) polypeptide and its cognate ligand or receptor.

The oncogenic isoforms can arise from, e.g., alternative splicing, frameshifting, translational and/or post-translational events, of various proto-oncogene expression products in a cell, e.g., a hyperproliferative cell (e.g., a cancerous or tumor cell). The isoform-binding molecules described herein bind to such oncogenic isoforms, but do not substantially bind a predominantly non-oncogenic sequence of the proto-oncogene from which the isoform is derived.

The term "isoform" in the context of a protein or polypeptide as used herein refers to polymers of amino acids of any length that can be derived from one or more of alternative splicing, frameshifting, translational and/or post-translational events. Alternative splicing events include processes (during transcription) by which one or more alternative exons (i.e., portion of a gene that codes for a protein) within a given RNA molecule are combined (by RNA Polymerase molecules) to yield different mRNAs from the same gene. Each such mRNA is known as a "gene transcript". Commonly, a single gene can encode several different mRNA transcripts, caused by cell- or tissue-specific combination of different exons. For example, multiple forms of fibroblast growth factor receptor 1-3 (FGFR1-3) are known to be generated by alternative splicing of the mRNAs. A frequent splicing event involving FGFR1 and 2 results in receptors containing three immunoglobulin (ig) domains, commonly referred to the α isoform, or only Immunoglobulin II (IgII) and IgIII, referred to as the β isoform. The α isoform has been identified for FGFR3 and FGFR4. FGF receptors with alternative IgIII domains, referred to herein as "FGFRIIIb" and "FGFR2IIIc," are generated by splicing events of FGFR1-3 involving the C-terminal half of the IgIII domain encoded by two mutually exclusive alternative exons derived from the FGFR2 gene (reviewed in Galzie, Z. et al. (1997) *Biochem. Cell. Biol.* 75:669-685; Burke, D. et al. (1998) *Trends Biochem Sci* 23:59-62). FGFR2-IIIc uses the alternative exon III, which encodes a different sequence than that of isoform FGFR2-IIIb. Other causes/sources of alternative splicing include frameshifting (i.e., different set of triplet codons in the mRNA/transcript is translated by the ribosome) or varying translation start or stop site (on the mRNA during its translation), resulting in a given intron remaining in the mRNA transcript. Different body tissues and some diseases are associated with alternative splicing events, and thus result in different proteins being produced in different tissues; or in diseased tissues.

An "oncogenic isoform" refers to any protein, polypeptide, mRNA, or cDNA that can be derived from one or more of alternative splicing, frameshifting, translational and/or post-translational events, whose presence or abnormal level is associated with cancer or malignant phenotype. For example, it may be found at an abnormal level in cells derived from disease-affected tissues, as compared to a reference value, e.g., a tissue or cells of a non disease control. It may be a protein isoform that is expressed at an abnormally high level, where the altered expression correlates with the occurrence and/or progression of the cancer. An oncogenic isoform may also be the expression product of a gene possessing mutation(s) or genetic variation that is directly responsible or is in linkage disequilibrium with other gene(s) that are responsible for the etiology of cancer. Exemplary oncogenic isoforms include, but are not limited to, FGFR2 (e.g., an oncogenic FGFR2 isoform IIIc), FGFR1 (e.g., an oncogenic FGFR1L), RON receptor tyrosine kinase (e.g., an oncogenic RON receptor tyrosine kinase comprising a deletion of exons 5 and 6), KIT receptor tyrosine kinase (e.g., an oncogenic KIT receptor tyrosine kinase comprising a deletion in exon 11), and PDGF-receptor alpha (e.g., an oncogenic PDGF-receptor alpha comprising a deletion of exons 7 and 8).

Similarly, a "non-oncogenic isoform" or "non-oncogenic protooncogene" refers to a protein, polypeptide, mRNA, or cDNA that is found predominantly in non-cancerous cells or tissues. Such isoforms and protooncogenes may be expressed in malignant conditions, but is not typically associated with the malignant phenotype.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., SEQ ID NO: 2, SEQ ID NO: 4 or SEQ ID NO: 6 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., SEQ ID NO: 1, 3, or 5 are termed substantially identical.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to a nucleic acid (SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25:3389-3402. When utilizing BLAST and Gapped BLAST programs, the default parameters of the respective programs (e.g., XBLAST and NBLAST) can be used. See http://www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein, the term "polypeptide" refers to two or more amino acids linked by a peptide bond between the alpha-carboxyl group of one amino acid and the alpha-amino group of the next amino acid. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

An "oligonucleotide" refers to a single stranded polynucleotide having less than about 100 nucleotides, less than about 75, 50, 25, or 10 nucleotides. An "oligonucleotide," as used herein, refers to an oligomer or polymer of a ribonucleic acid (RNA) or deoxyribonucleic acid (DNA) or mimetics thereof. This term includes oligonucleotides composed of naturally occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Polypeptides of Oncogenic Isoforms, or Epitopes Thereof

The invention provides isolated polypeptides of oncogenic isoforms or epitope thereof, or substantially identical sequences thereto. The term "epitope" or "epitope fragment" refers to the region of an antigen to which an antibody molecule binds preferentially and specifically. A monoclonal antibody binds preferentially to a single specific epitope of a molecule that can be molecularly defined. An epitope of a particular protein or protein isoform may be constituted by a limited number of amino acid residues, e.g. 2-30 residues, that are either in a linear or non-linear organization on the protein or protein isoform. An epitope that is recognized by the antibody may be, e.g., a short peptide of 2-30 amino acids that spans a junction of two domains or two polypeptide fragments of an oncogenic isoform that is not present in the normal isoforms of the protein. An oncogenic isoform may be a translation product of an alternatively spliced RNA variant that either lacks one or more exon(s) or has additional exon(s) relative to the RNA encoding the normal protein. The epitope may comprise, or consist of, residues at positions 15-16, 15-17, 15-18, 15-19, 15-20, 15-21, 15-22, 15-23, 15-24, 15-25, 15-26, 15-27, 15-28, 15-29, or 15-30 of any one of SEQ ID NOs: 10, 12, 14, or 18. In another embodiment, the epitope may comprise, or consist of, residues at positions 14-16, 14-17, 14-18, 14-19, 14-20, 14-21, 14-22, 14-23, 14-24, 14-25, 14-26, 14-27, 14-28, 14-29, or 14-30 of any one of SEQ ID NOs: 10, 12, 14, or 18. In another embodiment, the epitope may comprise, or consist of, residues at positions 13-16, 13-17, 13-18, 13-19, 13-20, 13-21, 13-22, 13-23, 13-24, 13-25, 13-26, 13-27, 13-28, 13-29, or 13-30 of any one of SEQ ID NOs: 10, 12, 14, or 18. In another embodiment, the epitope may comprise, or consist of, residues at positions 12-16, 12-17, 12-18, 12-19, 12-20, 12-21, 12-22, 12-23, 12-24, 12-25, 12-26, 12-27, 12-28, 12-29, or 12-30 of any one of SEQ ID NOs: 10, 12, 14, or 18. In another embodiment, the epitope may comprise, or consist of, residues at positions 11-16, 11-17, 11-18, 11-19, 11-20, 11-21, 11-22, 11-23, 11-24, 11-25, 11-26, 11-27, 11-28, 11-29, or 11-30 of any one of SEQ ID NOs: 10, 12, 14, or 18. In another embodiment, the epitope may comprise, or consist of, residues at positions 10-16, 10-17, 10-18, 10-19, 10-20, 10-21, 10-22, 10-23, 10-24, 10-25, 10-26, 10-27, 10-28, 10-29, or 10-30 of any one of SEQ ID NOs: 10, 12, 14, or 18. In another embodiment, the epitope may comprise, or consist of, residues at positions 9-16, 9-17, 9-18, 9-19, 9-20, 9-21, 9-22, 9-23, 9-24, 9-25, 9-26, 9-27, 9-28, 9-29, or 9-30 of any one of SEQ ID NOs: 10, 12, 14, or 18. In another embodiment, the epitope may comprise, or consist of, residues at positions 8-16, 8-17, 8-18, 8-19, 8-20, 8-21, 8-22, 8-23, 8-24, 8-25, 8-26, 8-27, 8-28, 8-29, or 8-30 of any one of SEQ ID NOs: 10, 12, 14, or 18. In another embodiment, the epitope may comprise, or consist of, residues at positions 7-16, 7-17, 7-18, 7-19, 7-20, 7-21, 7-22, 7-23, 7-24, 7-25, 7-26, 7-27, 7-28, 7-29, or 7-30 of any one of SEQ ID NOs: 10, 12, 14, or 18. In another embodiment, the epitope may comprise, or consist of, residues at positions 6-16, 6-17, 6-18, 6-19, 6-20, 6-21, 6-22, 6-23, 6-24, 6-25, 6-26, 6-27, 6-28, 6-29, or 6-30 of any one of SEQ ID NOs: 10, 12, 14, or 18. In another embodiment, the epitope may comprise, or consist of, residues at positions 5-16, 5-17, 5-18, 5-19, 5-20, 5-21, 5-22, 5-23, 5-24, 5-25, 5-26, 5-27, 5-28, 5-29, or 5-30 of any one of SEQ ID NOs: 10, 12, 14, or 18. In another embodiment, the epitope may comprise, or consist of, residues at positions 4-16, 4-17, 4-18, 4-19, 4-20, 4-21, 4-22, 4-23, 4-24, 4-25, 4-26, 4-27, 4-28, 4-29, or 4-30 of any one of SEQ ID NOs: 10, 12, 14, or 18. In another embodiment, the epitope may comprise, or consist of, residues at positions 3-16, 3-17, 3-18, 3-19, 3-20, 3-21, 3-22, 3-23, 3-24, 3-25, 3-26, 3-27, 3-28, 3-29, or 3-30 of any one of SEQ ID NOs: 10, 12, 14, or 18. In another embodiment, the epitope may comprise, or consist of, residues at positions 2-16, 2-17, 2-18, 2-19, 2-20, 2-21, 2-22, 2-23, 2-24, 2-25, 2-26, 2-27, 2-28, 2-29, or 2-30 of any one of SEQ ID NOs: 10, 12, 14, or 18. In another embodiment, the epitope may comprise, or consist of, residues at positions 1-16, 1-17, 1-18, 1-19, 1-20, 1-21, 1-22, 1-23, 1-24, 1-25, 1-26, 1-27, 1-28, 1-29, or 1-30 of any one of SEQ ID NOs: 10, 12, 14, or 18. The "epitope" may be used to raise antibodies that specifically bind the oncogenic isoform (e.g., do not substantially bind to the non-oncogenic isoform derived from the same proto-oncogene).

In one embodiment, the invention provides isolated polypeptides of human oncogenic isoforms or epitope thereof. In one embodiment, an isoform or epitope thereof is an oncogenic form of a proto-oncogene selected from the group consisting of human FGFR2 (SEQ ID NO: 32), human FGFR1 (SEQ ID NO: 33), human RON Receptor tyrosine kinase (SEQ ID NO: 34), human KIT receptor tyrosine kinase (SEQ ID NO: 35), human PDGF (SEQ ID NO: 36), and human PDGFR-alpha (SEQ ID NO: 37), or a sequence substantially identical thereto.

In one embodiment, the invention provides isolated rat polypeptides of oncogenic isoforms or epitope thereof. In one embodiment, the invention provides isolated mouse polypeptides of human oncogenic isoforms or epitope thereof. In other embodiments, the isolated polypeptides of human oncogenic isoforms or epitope thereof will be derived from other species, including but not limited to, dogs, pigs, guinea pigs and rabbits.

FGFR2

Fibroblast growth factor receptor 2 (FGFR2), also known in the art as bacteria-expressed kinase (BEK), keratinocyte growth factor receptor (KGFR), JWS, CEK3, CFD1, ECT1, TK14, TK25, BFR-1, CD332, K-SAM and FLJ98662. FGFR2 is a member of the fibroblast growth factor receptor family and has high affinity for acidic, basic and/or keratinocyte growth factor. FGFR2 is associated with signal transduction leading to mitogenesis and differentiation. Mutations in FGFR2 have been associated with craniofacial dysostosis 1, Crouzon syndrome, Pfeiffer syndrome, Jackson-Weiss syndrome and Apert syndrome.

The nucleotide acid and protein sequences of human FGFR2 are disclosed, e.g., in Dionne et al., (1990) *EMBO J.* 9:2685-2692 and Miki et al., (1992) *PNAS* 89:246-250). The nucleotide and protein sequences of mouse FGFR2 are disclosed, e.g., in Miki et al., (1991) *Science* 251:72-75 and Mansukhani et al., (1992) *PNAS* 89:3305-3309. The unprocessed precursor of human FGFR2 is about 821 amino acids in length and about 90310 Da in molecular weight. The unprocessed precursor of mouse FGFR2 is about 821 amino acids in length and about 90310 Da in molecular weight.

In one embodiment, the invention provides isolated polypeptides of oncogenic isoforms or epitope thereof encoded by a nucleic acid comprising a segment of nucleotides which arise from an alternative use of Exon III of a nucleic acid encoding a FGFR2. In one embodiment, the alternative use of Exon III results in sequence variation in the region of amino acids from 301-360, when aligned with FGFR2 IIIb. Thus, in one embodiment, the polypeptide consists of, or comprises, a sequence selected from the group of SEQ NOs: 2, 4, 6, and 8. In another embodiment, the polypeptide consists of, or comprises, a sequence encoded by a nucleic acid selected from the group consisting of SEQ NOs: 1, 3, 5, and 7, or sequences substantially identical to the same.

FGFR1

Fibroblast growth factor receptor 1 (FGFR1) is also known in the art as CEK; FLG; FLT2; KAL2; BFGFR; CD331; FGFBR; HBGFR; N-SAM and FLJ99988. FGFR1 is a member of the fibroblast growth factor receptor family and has high affinity for both acidic and basic fibroblast growth factors. FGFR1 is associated with signal transduction leading to mitogenesis and differentiation and is involved in limb induction.

The nucleotide acid and protein sequences of human FGFR1 are disclosed, e.g., in Isacchi et al., *Nucleic Acids Res.* 18:1906-1906 (1990) and Hou et al., *Science* 251:665-668 (1991). The nucleotide and protein sequences of mouse FGFR1 are disclosed, e.g., in Harada et al., *Biochem. Biophys. Res. Commun.* 205:1057-1063 (1994). The unprocessed precursor of human FGFR1 is about 822 amino acids in length and about 90420 Da in molecular weight. The unprocessed precursor of mouse FGFR1 is about 822 amino acids in length and about 90420 Da in molecular weight.

Mutations in FGFR1 have been associated with Pfeiffer syndrome, Jackson-Weiss syndrome, Antley-Bixler syndrome, osteoglophonic dysplasia, and autosomal dominant Kallmann syndrome 2. Chromosomal aberrations involving this gene are associated with stem cell myeloproliferative disorder and stem cell leukemia lymphoma syndrome.

In one embodiment, the invention provides isolated polypeptides of oncogenic isoforms or epitope thereof encoded by a nucleic acid comprising a segment of nucleotides which arise from an alternative deletion of Exons 7 and 8 of a nucleic acid encoding a FGFR1. In one embodiment, the alternative deletion of Exons 7 and 8 results in a deletion of 105 amino acids, when aligned with an FGFR1 proto-oncogene. Thus, in one embodiment, the polypeptide consists of, or comprises, a sequence of SEQ NO: 10, or a sequence substantially identical to the same. In another aspect the polypeptide comprises a sequence encoded by a nucleic acid sequence of SEQ NO: 9, or a sequence substantially identical to the same.

In another embodiment, the epitope consists of, or includes, an amino acid sequence identical the junctional region between Ig-II and Ig-III of FGFR1L (SEQ ID NO: 10) or a fragment thereof, or an amino acid sequence encoded by a nucleotide sequence of SEQ ID NO: 9 or a fragment thereof; or an amino acid or nucleotide sequence substantially identical thereto.

RON Receptor Tyrosine Kinase

Macrophage stimulating 1 receptor (c-met-related tyrosine kinase) (RON) is also known in the art as MST1R, PTK8, CD136 and CDw136. RON is a receptor for macrophage stimulating protein (MSP) and has a tyrosine-protein kinase activity. It is involved in development of epithelial tissue, bone and neuroendocrine derivatives. The nucleotide acid and protein sequences of human RON are disclosed, e.g., in Ronsin C. et al., *Oncogene* 8:1195-1202 (1993); and Collesi C. et al., *Mol. Cell. Biol.* 16:5518-5526 (1996). The nucleotide acid and protein sequences of mouse RON are disclosed e.g., in Iwama A. et al., Blood 83:3160-3169 (1994); Waltz S. E. et al., Oncogene 16:27-42 (1998); and Persons D. A. et al., Nat. Genet. 23:159-165 (1999). The unprocessed precursor of human RON is about 1400 amino acids in length and about 152227 Da in molecular weight. The unprocessed precursor of mouse RON is about 1378 amino acids in length and about 150538 Da in molecular weight.

In one embodiment, the invention provides isolated polypeptides of oncogenic isoforms or epitope fragments thereof encoded by a nucleic acid comprising a segment of nucleotides which arise from an alternative deletion of Exons 5 and 6 of a nucleic acid encoding a RON receptor tyrosine kinase. In one embodiment, the alternative deletion of Exons 5 and 6 results in an in-frame deletion of 109 amino acids in the extracellular domain, when aligned with a RON receptor tyrosine kinase proto-oncogene. In one embodiment, the polypeptide consists of, or comprises, a polypeptide sequence resulting from the fusion and juxtaposition of Exons 4 and 7. Thus, in one embodiment, the polypeptide consists of, or comprises, a sequence of SEQ NO: 12, or a sequence substantially identical to the same. In another embodiment, the polypeptide consists of, or comprises, a sequence encoded by a nucleic acid sequence of SEQ NO: 11, or a sequence substantially identical to the same.

In yet other embodiments, the epitope consists of, or includes, an amino acid sequence identical to the junctional region between exon 4 and exon 7 of isoform RONΔ160 (SEQ ID NO: 12) or a fragment thereof, or an amino acid sequence encoded by a nucleotide sequence of SEQ ID NO: 11 or a fragment thereof; or an amino acid or nucleotide sequence substantially identical thereto.

KIT Receptor Tyrosine Kinase v-kit Hardy-Zuckerman 4 feline sarcoma viral oncogene homolog (KIT) is also known in the art as PBT; SCFR; C-Kit and CD117. KIT encodes the human homolog of the proto-oncogene c-kit. KIT is a type 3 transmembrane receptor for MGF (mast cell growth factor, also known as stem cell factor).

The nucleotide acid and protein sequences of human KIT are disclosed, e.g., in Yarden et al., *EMBO J.* 6:3341-3351 (1987) and Giebel et al., Oncogene 7:2207-2217 (1992). The nucleotide acid and protein sequences of mouse KIT are disclosed e.g., in. Qiu et al., *EMBO J.* 7:1003-1011 (1988) and Rossi et al., *Dev. Biol.* 152:203-207 (1992). The unprocessed precursor of human KIT is about 976 amino acids in length and about 107360 Da in molecular weight. The unprocessed precursor of mouse KIT is about 107250 amino acids in length and about 150538 Da in molecular weight.

Mutations in KIT are associated with gastrointestinal stromal tumors, mast cell disease, acute myelogenous leukemia, and piebaldism.

In one embodiment, the invention provides isolated polypeptides of oncogenic isoforms or epitope fragments thereof encoded by a nucleic acid comprising a segment of nucleotides which arise from an alternative deletion of Exon 11 of a nucleic acid encoding a KIT receptor tyrosine kinase. Thus, in one embodiment, the polypeptide consists of, or comprises, a sequence of SEQ NO: 14, or a sequence substantially identical to the same. In another embodiment, the polypeptide consists of, or comprises, a sequence encoded by a nucleic acid sequence of SEQ NO: 13, or a sequence substantially identical to the same.

In yet another embodiment, the epitope consists of, or includes, an amino acid sequence identical to the junctional region of KIT between exons 10 and 12 of SEQ ID NO: 14 or a fragment thereof, or an amino acid sequence encoded by a nucleotide sequence of SEQ ID NO:13 or a fragment thereof; or an amino acid or nucleotide sequence substantially identical thereto.

PDGF

Platelet-derived growth factor alpha polypeptide (PDGFA) is also known in the art as PDGF1 and PDGF-A. PDGFA encoded a member of the platelet-derived growth factor family. PDGFA is a mitogenic factor for cells of mesenchymal origin and is characterized by a motif of eight cysteines.

The nucleotide acid and protein sequences of human PDGFA are disclosed, e.g., in Bonthron et al., *Proc. Natl. Acad. Sci. U.S.A.* 85:1492-1496 (1988) and Betsholtz et al., *Nature* 320:695-699 (1986). The nucleotide acid and protein sequences of mouse PDGFA are disclosed e.g., in. Rorsman et al., *Growth Factors* 6:303-313 (1992) and Mercola et al., *Dev. Biol.* 138:114-122 (1990). The unprocessed precursor of human PDGFA is about 211 amino acids in length and about 23210 Da in molecular weight. The unprocessed precursor of mouse PDGFA is about 211 amino acids in length and about 23210 Da in molecular weight.

Studies using knockout mice have shown cellular defects in oligodendrocytes, alveolar smooth muscle cells, and Leydig cells in the testis; knockout mice die either as embryos or shortly after birth.

In one embodiment, the invention provides isolated polypeptides of oncogenic isoforms or epitope fragments thereof encoded by a nucleic acid comprising a segment of nucleotides which arise from an alternative in-frame deletion of Exon 6 of a nucleic acid encoding PDGF. Thus, in one embodiment, the polypeptide consists of, or comprises, a sequence of SEQ NO: 16, or sequence substantially identical to the same. In another embodiment, the polypeptide consists of, or comprises, a sequence encoded by a nucleic acid sequence of SEQ NO: 15, or a sequence substantially identical to the same.

In yet another embodiment, the epitope consists of, or includes, an amino acid sequence identical to the junctional region of PDGF between exons 5 and 7 of SEQ ID NO: 16 or a fragment thereof, or an amino acid sequence encoded by a nucleotide sequence of SEQ ID NO: 15 or a fragment thereof; or an amino acid or nucleotide sequence substantially identical thereto.

PDGFR-Alpha

Platelet-derived growth factor receptor, alpha polypeptide (PDGFRA) is also known in the art as CD140A; PDGFR2; MGC74795 and Rhe-PDGFRA. PFGFRA encodes a cell surface tyrosine kinase receptor for members of the platelet-derived growth factor family. These growth factors are mitogens for cells of mesenchymal origin.

The nucleotide acid and protein sequences of human PDGFA are disclosed e.g., in Bonthron et al., *Proc. Natl. Acad. Sci. U.S.A.* 85:1492-1496 (1988) and Betsholtz et al., *Nature* 320:695-699 (1986). The nucleotide acid and protein sequences of mouse PDGFA are disclosed, e.g., in Stiles et al., *Mol. Cell. Biol.* 10:6781-6784 (1990) and Carninci et al., *Science* 309:1559-1563 (2005). The unprocessed precursor of human PDGFA is about 1089 amino acids in length and about 119790 Da in molecular weight. The unprocessed precursor of mouse PDGFA is about 1089 amino acids in length and about 119790 Da in molecular weight.

A fusion of PDGFRA and FIP1L1 (FIP1L1-PDGFRA), due to an interstitial chromosomal deletion, is the cause of some cases of hypereosinophilic syndrome (HES). HES is a rare hematologic disorder characterized by sustained overproduction of eosinophils in the bone marrow, eosinophilia, tissue infiltration and organ damage.

In one embodiment, the invention provides isolated polypeptides of oncogenic isoforms or epitopes thereof encoded by a nucleic acid comprising a segment of nucleotides which arise from an alternative deletion of Exons 7 and 8 (e.g., amino acids 374-456) of a nucleic acid encoding PDGFR-alpha. Thus, in one embodiment, the polypeptide consists of, or comprises, a sequence of SEQ NO: 18, or a sequence substantially identical to the same. In another embodiment, the polypeptide consists of, or comprises, a sequence encoded by a nucleic acid sequence of SEQ NO: 17, or a sequence substantially identical to the same.

In another embodiment, the epitope consists of, or includes, an amino acid sequence identical to the junctional region of PDGFR-alpha between exons 6 and 9 of SEQ ID NO: 18 or a fragment thereof, or an amino acid sequence encoded by a nucleotide sequence of SEQ ID NO: 17 or a fragment thereof; or an amino acid or nucleotide sequence substantially identical thereto.

Alternatively, an isolated polypeptide of an oncogenic isoform or epitope thereof may be encoded by a nucleic acid which is substantially identical to a nucleic acid of an oncogenic isoform or epitope fragment thereof provided herein. Likewise, an isolated polypeptide of an oncogenic isoform or epitope thereof may be substantially identical to an oncogenic isoform or epitope thereof, as provided herein.

Methods of Preparing an Oncogenic Isoform or Epitope Fragment Thereof

The polypeptide oncogenic isoform or epitope fragment thereof can be isolated from natural sources, or can be a product of chemical synthetic procedures, or can be produced by recombinant techniques from a prokaryotic or eukaryotic host.

The invention also provides methods of preparing an oncogenic isoform or epitope fragment thereof, comprising culturing host cells under conditions that permit expression of the oncogenic isoform or epitope fragment thereof; and isolating the oncogenic isoform or epitope fragment thereof, thereby preparing the oncogenic isoform or epitope fragment thereof. In one embodiment, the invention provides a method of preparing a human oncogenic isoform or epitope fragment thereof. Procedures for preparing a polypeptide using the above describe method are well known to those skilled in the art.

Isoform-Specific Inhibitors

The present invention provides, at least in part, isoform-specific inhibitors (e.g., antibody molecules, soluble receptor polypeptides and fusion forms thereof, peptides and functional variants thereof, and nucleic acid inhibitors), which inhibit and/or reduce one or more activities of the isoform, or interact with, or more preferably specifically bind to one or more isoform polypeptides or fragments thereof, or nucleic acids encoding one or more isoform polypeptides or fragments thereof. In one embodiment, the isoform-specific inhibitor is an isoform-binding molecule, e.g., an antibody molecule, or a nucleic acid inhibitor. In another embodiment, the isoform-specific inhibitor is a soluble receptor polypeptide and a fusion form thereof, or a peptide and a functional variant thereof. In some embodiments, the isoform-binding molecules specifically bind to oncogenic isoform polypeptides or fragments thereof, or nucleic acids encoding one or more oncogenic isoform polypeptides or fragments thereof.

Typical isoform-specific inhibitors (e.g., isoform-binding molecules) bind to one or more isoform polypeptides or fragments thereof, or nucleic acids encoding one or more isoform polypeptides or fragments thereof, with high affinity, e.g., with an affinity constant of at least about $10^7$ $M^{-1}$, typically about $10^8$ $M^{-1}$, and more typically, about $10^9$ $M^{-1}$ to $10^{10}$ $M^{-1}$ or stronger; and reduce and/or inhibit one or more activities of the isoforms, e.g., oncogenic isoforms, in a hyperproliferative (e.g., cancerous or malignant) cell and/or tissue. For example, the isoform-specific inhibitor may selectively and specifically reduce or inhibit an oncogenic isoform-associated activity chosen from one or more of: (i) binding of a ligand or co-receptor (e.g., FGF ligand (e.g., FGF8b, FGF2, FGF17 or FGF18)) to FGFR2 isoform IIIc); (ii) receptor dimerization (e.g., FGFR2 isoform IIIc homo-dimerization or FGFR2 isoform IIIc with another receptor or receptor isoform heterodimerization); (iii) isoform signaling, e.g., FGFR2 isoform IIIc signaling; (iv) hyperproliferative (e.g., cancerous or tumor) cell proliferation, growth and/or survival, for example, by induction of apoptosis of the hyperproliferative cell; and/or (v) angiogenesis and/or vascularization of a tumor.

As used herein, the term "specifically binds" refers to a binding interaction that is determinative of the presence of a target (such a specific polypeptide or nucleic acid) in a population of proteins and other biologics. Thus, a binding molecule that "specifically binds" an oncogenic isoform is intended to mean that the compound binds an oncogenic isoform of the invention, but does not bind to a non-oncogenic isoform that is derived from the same proto-oncogene. As the skilled artisan will recognize the isoform-binding molecule may show some degree of cross-reactivity between the oncogenic and non-oncogenic isoforms depending on the conditions used, e.g., target protein concentration, salt and buffer conditions used, among others. In certain embodiments, the term "specifically binds" or "specific binding" refers to a property of the isoform-binding molecule to bind to one or more isoform polypeptides or fragments thereof, or nucleic acids encoding one or more isoform polypeptides or fragments thereof, with high affinity, e.g., with an affinity constant of at least about $10^7$ $M^{-1}$, typically about $10^8$ $M^{-1}$, and more typically, about $10^9$ $M^{-1}$ to $10^{10}$ $M^{-1}$ or stronger, and (2) preferentially bind to the isoform with an affinity that is at least two-fold, 50-fold, 100-fold, 1000-fold, or more greater than its affinity for binding to the non-oncogenic isoform. In certain embodiments, isoform-binding molecule binds preferentially to an oncogenic isoform, but does not substantially bind to (e.g., shows less than 10%, 8%, 5%, 4%, 3%, 2%, 1% cross-reactivity with) to its non-oncogenic counterpart.

Antibody Molecules

In one embodiment, the isoform-binding molecule is an antibody molecule that binds to a mammalian, e.g., human, isoform polypeptide or a fragment thereof (e.g., an Fab, F(ab')$_2$, Fv, a single chain Fv fragment, or a camelid variant). For example, the antibody molecule binds to an isoform polypeptide or fragment expressed and/or associated with a hyperproliferative cell, e.g., a cancerous or tumor cell. For example, the antibody molecule binds specifically to an epitope, e.g., linear or conformational epitope, (e.g., an epitope as described herein) located or expressed primarily on the surface of a hyperproliferative cell, e.g., a cancerous or tumor cell. In embodiments, the epitope recognized by the antibody molecule is expressed or associated with a hyperproliferative disease, e.g., a cancerous or malignant disease. For example, the epitope recognized by the antibody molecule is expressed or associated with an exon sequence predominantly expressed or associated with one or more cancerous or tumor cells or disorders; the epitope may be located at the junctional region between two exons that are predominantly joined together in one or more cancerous or tumor cells or disorders, e.g., as a result of an in-frame exon deletion or the use of an alternatively spliced exon. Exemplary isoform polypeptides or fragments recognized by isoform-binding molecules of the invention include, but are not limited to, oncogenic isoforms of FGFR2, FGFR1, RON receptor tyrosine kinase, KIT receptor tyrosine kinase, PDGF and PDGF-receptor alpha. In one embodiment, the oncogenic isoform to which the antibody molecule binds is a human oncogenic isoform. In another embodiment, the polypeptide isoform to which the antibody molecule binds is a polypeptide of an oncogenic isoform or epitope thereof listed in Table 1.

In one embodiment, the antibody molecule specifically binds a polypeptide comprising the amino acid sequence set forth in SEQ ID NO: 2, 4, 6, 8, 10, 12, 14, 16, or 18, or a substantially identical sequence thereto. In another embodiment, the antibody molecule specifically binds to the polypeptide FGFR2-IIIc isoform of SEQ ID NO: 2, 4, 6, or 8, but does not substantially bind to the polypeptide isoform of human FGFR2-IIIb. In another embodiment, the antibody molecule binds to the human FGFR2 polypeptide of e.g., SEQ ID NO: 19, but does not substantially bind to FGFR2-IIIb (e.g., SEQ ID NO: 21) or other isoforms of FGFR2 (e.g., SEQ ID NOs: 22, 23, 24, 25, 26, 27, 28, 29, 30, 31, 52 and/or 53, respectively).

In another embodiment, the antibody molecule binds specifically to an isoform, e.g., an oncogenic isoform, of FGFR1, e.g., human FGFR1. For example, the antibody molecule binds specifically to isoform FGFR1L having a deletion of about 105 amino acids between exons 7 and 8, corresponding to part of immunoglobulin domain II (Ig-II) and part of Ig-III of FGFR1, thus forming a junctional region between II:III. For example, the antibody molecule binds preferentially to FGFR1L or a fragment thereof, but does not substantially bind to (e.g., shows less than 10%, 8%, 5%, 4%, 3%, 2%, 1% cross-reactivity with) FGFR1 (e.g., non-oncogenic human FGFR1, e.g., FGFR1 isoform 4 (SEQ ID NO: 39), FGFR1 isoform 14 (SEQ ID NO: 40), FGFR1 isoform 16 (SEQ ID NO: 41), FGFR1 isoform 17 (SEQ ID NO: 42), FGFR1 isoform 3 (SEQ ID NO: 43), or FGFR1 isoform 18 (SEQ ID NO: 44). In those embodiments, the antibody molecule binds specifically to at least one epitope found at the junctional region between Ig-II and Ig-III of SEQ ID NO:10 or a fragment thereof, or an amino acid sequence encoded by a nucleotide sequence of SEQ ID NO:9 or a fragment thereof; or an amino acid or nucleotide sequence substantially identical thereto.

In yet other embodiments, the antibody molecule binds to an isoform, e.g., an oncogenic isoform, of RON receptor tyrosine kinase, e.g., human RON receptor tyrosine kinase. For example, the antibody molecule binds specifically to isoform RONΔ160 having an in-frame deletion of about 109 amino acids skipping exons 5 and 6 of the extracellular domain of RON, thus forming a junctional region between exon 4 and exon 7. For example, the antibody molecule binds preferentially to RONΔ160 or a fragment thereof, but does not substantially bind to (e.g., shows less than 10%, 8%, 5%, 4%, 3%, 2%, 1% cross-reactivity with) RON receptor tyrosine kinase (e.g., non-oncogenic human RON receptor tyrosine kinase, e.g., SEQ ID NO: 45). In those embodiments, the antibody molecule binds specifically to at least one epitope found at the junctional region between exon 4 and exon 7 of SEQ ID NO: 12 or a fragment thereof, or an amino acid sequence encoded by a nucleotide sequence of SEQ ID NO: 11 or a fragment thereof; or an amino acid or nucleotide sequence substantially identical thereto.

In yet another embodiment, the antibody molecule binds specifically to an isoform, e.g., an oncogenic isoform, of KIT receptor tyrosine kinase, e.g., human KIT receptor tyrosine kinase. For example, the antibody molecule binds specifically to a KIT isoform having a deletion of exon 11. For example, the antibody molecule binds preferentially to exon 11-deleted KIT isoform (SEQ ID NO: 46) or a fragment thereof, but does not substantially bind to (e.g., shows less than 10%, 8%, 5%, 4%, 3%, 2%, 1% cross-reactivity with) KIT (e.g., non-oncogenic human KIT, e.g., full-length receptor (SEQ ID NO: 47)). In those embodiments, the antibody molecule binds specifically to at least one epitope found at the junctional region between exons 10 and 12 of SEQ ID NO: 14 or a fragment thereof, or an amino acid sequence encoded by a nucleotide sequence of SEQ ID NO:13 or a fragment thereof; or an amino acid or nucleotide sequence substantially identical thereto.

In yet another embodiment, the antibody molecule binds specifically to an isoform, e.g., an oncogenic isoform, of PDGF, e.g., human PDGF. For example, the antibody molecule binds specifically to a PDGF isoform having an in-frame deletion of exon 6. For example, the antibody molecule binds preferentially to exon 6-deleted PDGF isoform or a fragment thereof, but does not substantially bind to (e.g., shows less than 10%, 8%, 5%, 4%, 3%, 2%, 1% cross-reactivity with) PDGF (e.g., non-oncogenic human PDGF, e.g., PDGF isoform 1 (SEQ ID NO: 49)). In those embodiments, the antibody molecule binds specifically to at least one epitope found at the junctional region between exons 5 and 7 of SEQ ID NO: 16 or a fragment thereof, or an amino acid sequence encoded by a nucleotide sequence of SEQ ID NO: 15 or a fragment thereof; or an amino acid or nucleotide sequence substantially identical thereto.

In another embodiment, the antibody molecule binds specifically to an isoform, e.g., an oncogenic isoform, of PDGF receptor alpha, e.g., human PDGF receptor alpha. For example, the antibody molecule binds specifically to a PDGFR-alpha isoform having an in-frame deletion of exons 7 and 8. For example, the antibody molecule binds preferentially to exon 7/8-deleted PDGFR-alpha isoform (SEQ ID NO: 51) or a fragment thereof, but does not substantially bind to (e.g., shows less than 10%, 8%, 5%, 4%, 3%, 2%, 1% cross-reactivity with) PDGFR-alpha (e.g., non-oncogenic human PDGFR-alpha, e.g., PDGFR-alpha isoform 1 (SEQ ID NO: 50) In those embodiments, the antibody molecule binds specifically to at least one epitope found at the junctional region between exons 6 and 9 of SEQ ID NO:18 or a fragment thereof, or an amino acid sequence encoded by a nucleotide sequence of SEQ ID NO:17 or a fragment thereof; or an amino acid or nucleotide sequence substantially identical thereto.

As used herein, the term "antibody molecule" refers to a protein comprising at least one immunoglobulin variable domain sequence. The term antibody molecule includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibodies of the present invention can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

Antibodies of the present invention can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR). The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S, and Kontermann, R., Springer-Verlag, Heidelberg). Generally, unless specifically indicated, the following definitions are used: AbM definition of CDR1 of the heavy chain variable domain and Kabat definitions for the other CDRs. In addition, embodiments of the invention described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the isoform polypeptide, or an epitope thereof. With respect to proteins (or protein mimetics), the antigen-binding site typically includes one or more loops (of at least four amino acids or amino acid mimics) that form an interface that binds to the isoform polypeptide. Typically, the antigen-binding site of an antibody molecule includes at least one or two CDRs, or more typically at least three, four, five or six CDRs.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.*, 32:180-190 (1990)) and also because of potential allergic reactions (see, e.g., LoBuglio et al., *Hybridoma*, 5:5117-5123 (1986)).

The anti-isoform antibody can be a polyclonal or a monoclonal antibody. In other embodiments, the antibody can be recombinantly produced, e.g., produced by phage display or by combinatorial methods.

Phage display and combinatorial methods for generating anti-isoform antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication No. WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-isoform antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368: 856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-isoform antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to an isoform. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are known to those skilled in the art and, for example, may be obtained from a hybridoma producing an antibody against the isoform. The recombinant DNA encoding the humanized antibody, or fragment thereof, can be cloned into an appropriate expression vector.

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In one embodiment, an antibody can be made by immunizing with purified anti-isoform antigen, or a fragment or epitope thereof, e.g., a fragment described herein, membrane associated antigen, tissue, e.g., crude tissue preparations, whole cells, preferably living cells, lysed cells, or cell fractions, e.g., membrane fractions.

The anti-isoform antibody can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target isoform protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference). Similar type of alterations could be described which if applied to the murine, or other species immunoglobulin would reduce or eliminate these functions.

An isoform-specific inhibitor (e.g., an isoform-binding molecule) can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody molecule of the invention may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An anti-isoform antibody molecules may be conjugated to another molecular entity, typically a label or a therapeutic (e.g., a cytotoxic or cytostatic) agent or moiety.

Radioactive isotopes can be used in diagnostic or therapeutic applications. Radioactive isotopes that can be coupled to the anti-PSMA antibodies include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include Taxol®, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585, 499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclinies (e.g., daunorubicin (foimerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, Taxol® and maytansinoids).

The conjugates of the invention can be used for modifying a given biological response. The therapeutic agent is not to be construed as limited to classical chemical therapeutic agents. For example, the therapeutic agent may be a protein or polypeptide possessing a desired biological activity. Such proteins may include, for example, a toxin such as abrin, ricin A, *pseudomonas* exotoxin, diphtheria toxin, or a component thereof (e.g., a component of *pseudomonas* exotoxin is PE38); a protein such as tumor necrosis factor, interferon, nerve growth factor, platelet derived growth factor, tissue plasminogen activator, or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors. Similarly, the therapeutic agent can be a viral particle, e.g., a recombinant viral particle, that is conjugated (e.g., via a chemical linker) or fused (e.g., via a viral coat protein) to an anti-isoform antibody of the invention.

In one aspect, the invention features a method of providing a target binding molecule that specifically binds to an isoform receptor. For example, the target binding molecule is an antibody molecule. The method includes: providing a target protein that comprises at least a portion of non-human protein, the portion being homologous to (at least 70, 75, 80, 85, 87, 90, 92, 94, 95, 96, 97, 98% identical to) a corresponding portion of a human target protein, but differing by at least one amino acid (e.g., at least one, two, three, four, five, six, seven, eight, or nine amino acids); obtaining an antibody molecule that specifically binds to the antigen; and evaluating efficacy of the binding agent in modulating activity of the target protein. The method can further include administering the binding agent (e.g., antibody molecule) or a derivative (e.g., a humanized antibody molecule) to a human subject.

This invention provides an isolated nucleic acid molecule encoding the above antibody molecule, vectors and host cells thereof. The nucleic acid molecule includes but is not limited to RNA, genomic DNA and cDNA.

Soluble Receptors and Fusions Thereof

In other embodiments, the isoform-specific inhibitor is a full length or a fragment of an isoform receptor polypeptide, e.g., an inhibitory ligand-binding domain of an isoform receptor polypeptide. For example, the isoform-specific inhibitor can be a soluble form of an FGFR2 isoform IIIc receptor (e.g., a soluble form of mammalian (e.g., human) FGFR2 isoform IIIc comprising a ligand (e.g., FGF)-binding domain. For example, the isoform-specific inhibitor can include about amino acids 1 to 262 of human FGFR2 isoform IIIc receptor (FIG. 13C; amino acids 1-262 of SEQ ID NO: 55, including the signal sequence); or an amino acid sequence substantially identical thereto. Alternatively, the isoform-specific inhibitor can include an amino acid sequence encoded by the nucleotide sequence from about nucleotides 1 to 786 of human FGFR2 isoform IIIc (FIG. 13B; nucleotides 1-786 of SEQ ID NO: 54); or an amino acid sequence substantially identical thereto.

As used herein, a "soluble form of an FGFR2 isoform IIIc receptor" or a "soluble form of an isoform receptor polypeptide" is a receptor isoform, e.g., an FGFR2 isoform IIIc receptor polypeptide incapable of anchoring itself in a membrane. Such soluble polypeptides include, for example, an isoform receptor polypeptide, e.g., an FGFR2 isoform IIIc receptor polypeptide, as described herein that lack a sufficient portion of their membrane spanning domain to anchor the polypeptide or are modified such that the membrane spanning domain is non-functional. Typically, the soluble isoform receptor polypeptide retains the ability of binding to an isoform ligand, e.g., an FGF ligand. E.g., a soluble fragment of an FGFR2 isoform IIIc receptor polypeptide (e.g., a fragment of an FGFR2 isoform IIIc receptor comprising the extracellular domain of human FGFR2 isoform IIIc receptor, including about amino acids 1 to 262 of human FGFR2 isoform IIIc receptor (FIG. 13C; amino acids 1-262 of SEQ ID NO: 55, including the signal sequence); or an amino acid sequence substantially identical thereto. A soluble FGFR2 isoform IIIc receptor polypeptide can additionally include, e.g., be fused to, a second moiety, e.g., a polypeptide (e.g., an immunoglobulin chain, a GST, Lex-A or MBP polypeptide sequence). For example, a fusion protein can includes at least a fragment of an FGFR2 isoform IIIc receptor polypeptide, which is capable of binding an FGF ligand, fused to a second moiety, e.g., a polypeptide (e.g., an immunoglobulin chain, an Fc fragment, a heavy chain constant regions of the various isotypes, including: IgG1, IgG2, IgG3, IgG4, IgM, IgA1, IgA2, IgD, and IgE).

A soluble form of an isoform receptor polypeptide can be used alone or functionally linked (e.g., by chemical coupling, genetic or polypeptide fusion, non-covalent association or otherwise) to a second moiety, e.g., an immunoglobulin Fc domain, serum albumin, pegylation, a GST, Lex-A or an MBP polypeptide sequence. As used herein, a "fusion protein" refers to a protein containing two or more operably associated, e.g., linked, moieties, e.g., protein moieties. Typically, the moieties are covalently associated. The moieties can be directly associated, or connected via a spacer or linker.

The fusion proteins may additionally include a linker sequence joining the first moiety, e.g., a soluble isoform receptor, to the second moiety. For example, the fusion protein can include a peptide linker, e.g., a peptide linker of about 4 to 20, more preferably, 5 to 10, amino acids in length; the peptide linker is 8 amino acids in length. Each of the amino acids in the peptide linker is selected from the group consisting of Gly, Ser, Asn, Thr and Ala; the peptide linker includes a Gly-Ser element. In other embodiments, the fusion protein includes a peptide linker and the peptide linker includes a sequence having the formula (Ser-Gly-Gly-Gly-Gly)y wherein y is 1, 2, 3, 4, 5, 6, 7, or 8 (SEQ ID NOs: 73-80).

For example, a soluble form of an isoform receptor polypeptide can be fused to a heavy chain constant region of the various isotypes, including: IgG1, IgG2, IgG3, IgG4, IgM, IgA1, IgA2, IgD, and IgE). For example, the fusion protein can include the extracellular domain of a human FGFR2 isoform IIIc receptor (or a sequence homologous thereto), and, e.g., fused to, a human immunoglobulin Fc chain, e.g., human IgG (e.g., human IgG1 or human IgG2, or a mutated form thereof). The Fc sequence can be mutated at one or more amino acids to enhance or reduce effector cell function, Fc receptor binding and/or complement activity. For example, the constant region is mutated at positions 296 (M to Y), 298 (S to T), 300 (T to E), 477 (H to K) and 478 (N to F) of SEQ ID NO: 55 to alter Fc receptor binding. One exemplary fusion protein that includes the amino acid sequence from about amino acids 1 to 262 of human FGFR2 isoform IIIc receptor (FIG. 13C; amino acids 1-262 of SEQ ID NO: 55) fused via an Arg-Ser linker to a human IgG1 Fc is shown in FIG. 13C (SEQ ID NO: 55).

In other embodiments, additional amino acid sequences can be added to the N- or C-terminus of the fusion protein to facilitate expression, detection and/or isolation or purification. For example, the fusion protein may be linked to one or more additional moieties, e.g., GST, His6 tag (His-His-His-His-His-His; SEQ ID NO: 81), FLAG tag. For example, the fusion protein may additionally be linked to a GST fusion protein in which the fusion protein sequences are fused to the C-terminus of the GST (i.e., glutathione S-transferase) sequences. Such fusion proteins can facilitate the purification of the receptor fusion protein.

In another embodiment, the fusion protein is includes a heterologous signal sequence (i.e., a polypeptide sequence that is not present in a polypeptide encoded by a receptor nucleic acid) at its N-terminus. For example, the native receptor signal sequence can be removed and replaced with a signal sequence from another protein. In certain host cells (e.g., mammalian host cells), expression and/or secretion of receptor can be increased through use of a heterologous signal sequence.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *Current Protocols in Molecular Biology*, John Wiley & Sons, 1992). Moreover, many expression vectors are commercially available that encode a fusion moiety (e.g., an Fc region of an immunoglobulin heavy chain). A receptor encoding nucleic acid can be cloned into such an expression vector such that the fusion moiety is linked in-frame to the immunoglobulin protein.

In some embodiments, receptor fusion polypeptides exist as oligomers, such as dimers or trimers.

In other embodiments, the receptor polypeptide moiety is provided as a variant receptor polypeptide having a mutation in the naturally-occurring receptor sequence (wild type) that results in higher affinity (relative to the non-mutated sequence) binding of the receptor polypeptide to a corresponding ligand.

In other embodiments, additional amino acid sequences can be added to the N- or C-terminus of the fusion protein to facilitate expression, steric flexibility, detection and/or isolation or purification. The second polypeptide is preferably soluble. In some embodiments, the second polypeptide enhances the half-life, (e.g., the serum half-life) of the linked polypeptide. In some embodiments, the second polypeptide includes a sequence that facilitates association of the fusion polypeptide with a second polypeptide. In embodiments, the second polypeptide includes at least a region of an immunoglobulin polypeptide. Immunoglobulin fusion polypeptides are known in the art and are described in e.g., U.S. Pat. Nos. 5,516,964; 5,225,538; 5,428,130; 5,514,582; 5,714,147; and 5,455,165. For example, a soluble form of a receptor can be fused to a heavy chain constant region of the various isotypes, including: IgG1, IgG2, IgG3, IgG4, IgM, IgA1, IgA2, IgD, and IgE). Typically, the fusion protein can include the extracellular domain of a human receptor (or a sequence homologous thereto), and, e.g., fused to, a human immunoglobulin Fc chain, e.g., human IgG (e.g., human IgG1 or human IgG2, or a mutated form thereof).

The Fc sequence can be mutated at one or more amino acids to reduce effector cell function, Fc receptor binding and/or complement activity. Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260). Similar type of alterations could be described which if applied to the murine, or other species immunoglobulin would increase or decrease these functions. For example, it is possible to alter the affinity of an Fc region of an antibody (e.g., an IgG, such as a human IgG) for an FcR (e.g., Fc gamma R1), or for C1q binding by replacing the specified residue(s) with a residue(s) having an appropriate functionality on its side chain, or by introducing a charged functional group, such as glutamate or aspartate, or perhaps an aromatic non-polar residue such as phenylalanine, tyrosine, tryptophan or alanine (see e.g., U.S. Pat. No. 5,624,821).

In embodiments, the second polypeptide has less effector function that the effector function of a Fc region of a wild-type immunoglobulin heavy chain. Fc effector function includes for example, Fc receptor binding, complement fixation and T cell depleting activity (see for example, U.S. Pat. No. 6,136,310). Methods for assaying T cell depleting activity, Fc effector function, and antibody stability are known in the art. In one embodiment, the second polypeptide has low or no detectable affinity for the Fc receptor. In an alternative embodiment, the second polypeptide has low or no detectable affinity for complement protein C1q. In other embodiments, the second polypeptide has increased effector cell function, e.g., increased binding to an Fc receptor (e.g., FcγRI, FcγRIIA, FcγRIIB, FcγRIIIA and FcRn receptors) as described in, for example, Shields et al. (*JBC*, 276:6591-6604, 2001) and U.S. Pat. No. 6,737,056.

It will be understood that the antibody molecules and soluble receptor or fusion proteins described herein can be functionally linked (e.g., by chemical coupling, genetic fusion, non-covalent association or otherwise) to one or more other molecular entities, such as an antibody (e.g., a bispecific or a multispecific antibody), toxins, radioisotopes, cytotoxic or cytostatic agents, among others.

Peptides or Functional Variants Thereof

In yet another embodiment, the isoform-specific inhibitor includes a peptide or a functional variant thereof (e.g., a functional analog or derivative thereof).

As used herein, an "analog" of a peptide refers to a compound wherein the amino acid sequence of the compound is the same as that of the peptide except for up to 10, typically up to 8, up to 6, up to 5, up to 4, up to 3, up to 2, or up to 1 amino acid insertions, deletions, and/or substitutions of the amino acid sequence of the peptide. Typically, an analog binds to the same biological receptor as the peptide and thus displays at least some of the biological activity of the peptide. The peptide may be "derivatized" or linked to another functional molecule (e.g., another peptide or protein, e.g., a carrier protein), and/or by the addition of a fluorescent moiety, a radionucleotide, a toxin, an enzyme, polyethylene glycol (PEG), or an affinity ligand such as biotin.

As used herein, the term "carrier protein" is a protein or peptide that improves the production of antibodies to a protein to which it is associated and/or can be used to detect a protein with which it is associated. Many different carrier proteins can be used for coupling with peptides for immunization purposes. The choice of which carrier to use should be based on immunogenicity, solubility, whether adequate conjugation with the carrier can be achieved and screening assays used to identify antibodies to target proteins. The two most commonly used carriers are keyhole limpet hemocyanin (KLH) and bovine serum albumin (BSA). Other examples include secretory alkaline phosphatase (SEAP), horseradish peroxidase, luciferase, beta-galactosidase, IgG Fc (gamma chain), Glutathione-S-Transferase (GST), polyhistidine containing tags and other enzymes like beta-lactamase, other secretary proteins or peptides.

A modified peptide, conjugate or compound of the invention comprises a reactive group covalently attached to the peptide or protein. The reactive group is chosen for its ability to form a stable covalent bond with a serum protein or peptide, for example, by reacting with one or more amino groups, hydroxyl groups, or thiol groups on the serum protein or peptide. Typically, a reactive group reacts with only one amino group, hydroxyl group, or thiol group on the serum protein or peptide. Typically, a reactive group reacts with a specific amino group, hydroxyl group, or thiol group on the serum protein or peptide. A conjugate of the invention comprises a modified peptide, which is covalently attached to a serum protein or peptide via a reaction of the reactive group with an amino group, hydroxyl group, or thiol group on the serum protein or peptide. Thus, a conjugate of the invention comprises a modified peptide, in which a residue of the reactive group has formed a covalent bond to a serum protein or peptide. As used herein, "a residue of a reactive group" or "a reactive group residue" refers to the chemical structure resulting from covalent bond formation between the reactive group and another moiety, e.g., a peptide or protein present in blood. In embodiments of the modified peptides, conjugates or compounds of the invention, the reactive group is a maleimide containing group selected from gamma-maleimide-butrylamide (GMBA), maleimido propionic acid (MPA), N-hydroxysuccinimide (NHS), N-hydroxy-sulfosuccinimide (sulfo-NHS), maleimide-benzoyl-succinimide (MBS) and gamma-maleimido-butyryloxy succinimide ester (GMBS).

The peptides of the invention, including peptide linker groups, may be synthesized by standard methods of solid or solution phase peptide chemistry. A summary of the solid phase techniques may be found in Stewart and Young (1963) *Solid Phase Peptide Synthesis*, W. H. Freeman Co. (San Francisco), and Meienhofer (1973) *Hormonal Proteins and Peptides*, Academic Press (New York). For classical solution synthesis see Schroder and Lupke, *The Peptides, Vol.* 1, Academic Press (New York).

In general, these methods comprise the sequential addition of one or more amino acids or suitably protected amino acids to a growing peptide chain. Normally, either the amino or carboxyl group of the first amino acid is protected by a suitable protecting group. The protected amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth. After all the desired amino acids have been linked in the proper sequence, any remaining protecting groups (and any solid support) are removed sequentially or concurrently to afford the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

In certain embodiments, the peptides of the invention are synthesized with amino- and carboxy-protecting groups for use as pro-drugs. Protecting groups are chemical moieties which block a reactive group on the peptide to prevent undesirable reactions. In one embodiment, a modified peptide of the invention is synthesized with one or more protecting groups that are designed to be cleaved in vivo, thereby exposing the reactive group or groups of the modified peptide to serum proteins after administration of the peptide to a subject.

The term "amino-protecting group" refers to those groups intended to protect the amino-terminal end of an amino acid or peptide or to protect the amino group of an amino acid or peptide against undesirable reactions. Commonly used amino-protecting groups are disclosed in Greene (1981) *Protective Groups in Organic Synthesis* (John Wiley & Sons, New York), which is hereby incorporated by reference. Additionally, protecting groups can be used which are readily cleaved in vivo, for example, by enzymatic hydrolysis, thereby exposing the amino group for reaction with serum proteins in vivo.

The term "carboxy protecting group" refers to a carboxylic acid protecting ester or amide group employed to block or protect the carboxylic acid functionality. Carboxy protecting groups are disclosed in Greene, "Protective Groups in Organic Synthesis" pp. 152-186 (1981), which is hereby incorporated by reference. Additionally, a carboxy protecting group can be used as a pro-drug whereby the carboxy protecting group can be readily cleaved in vivo, for example by enzymatic hydrolysis, thereby exposing the carboxy group for reaction with serum proteins in vivo. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated by reference.

Preferred carboxy-protected peptides of the invention are peptides wherein the protected carboxy group is a lower alkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, and phenylethyl ester or an alkanoyloxyalkyl, cycloalkanoyloxyalkyl, aroyloxyalkyl or an arylalkylcarbonyloxyalkyl ester. Preferred amide carboxy protecting groups are lower alkylaminocarbonyl groups. For example, aspartic acid may be protected at the α-C-terminal by an acid labile group (e.g., t-butyl) and protected at the β-C-terminal by a hydrogenation labile group (e.g., benzyl) then deprotected selectively during synthesis.

In some embodiments, the peptide or functional variant thereof consists of, or includes, an amino acid sequence located at the junctional region between two exons that are predominantly joined together in protein isoforms expressed or associated with one or more cancerous or tumor cells or disorders, e.g., as a result of an in-frame exon deletion or the use of an alternatively spliced exon. In some embodiments, the peptide or functional variant thereof consists of, or includes, an amino acid sequence located at the junctional region between two exons that are predominantly joined together in protein isoforms expressed or associated with one or more cancerous or tumor cells or disorders, e.g., as a result of an in-frame exon deletion or the use of an alternatively spliced exon. In one embodiment, the peptide or functional variant thereof consists of, or includes, an amino acid sequence, up to 60 amino acids or less (e.g., up to 50, 40, 30, 20, 10 or less amino acids), and which is identical to the alternative spliced form of Exon III, e.g., from about amino acids 301 to 360 of FGFR2-IIIc (SEQ ID NO:2); about amino acids 314 to 324 of FGFR2-IIIc (AAGVNTTDKEI, SEQ ID NO:4); about amino acids 328 to 337 of FGFR2-IIIc (YIRNVTFEDA, SEQ ID NO:6); about amino acids 350 to 353 of FGFR2-IIIc (ISFH, SEQ ID NO:8); about amino acids 314-353 of FGFR2 IIIc (AAGVNTTDKEIEVLYIRNVTFED-AGEYTCLAGNSIGISHUSEQ ID NO: 84)); or about amino acids TCLAGNSIGISFH (SEQ ID NO: 86) of FGFR2-IIIc, or an amino acid sequence encoded by a nucleotide sequence of SEQ ID NOs: 1, 3, 5, 7, 83 or 85; or an amino acid or nucleotide sequence substantially identical thereto. In another embodiment, the peptide or functional variant thereof consists of, or includes, an amino acid sequence, up to 60 amino acids or less (e.g., up to 50, 40, 30, 20, 10 or less amino acids), and which is identical the junctional region between Ig-II and Ig-III of FGFR1L (SEQ ID NO:10) or a fragment thereof, or an amino acid sequence encoded by a nucleotide sequence of SEQ ID NO:9 or a fragment thereof; or an amino acid or nucleotide sequence substantially identical thereto. In yet other embodiments, the peptide or functional variant thereof consists of, or includes, an amino acid sequence, up to 60 amino acids or less (e.g., up to 50, 40, 30, 20, 10 or less amino acids), and which is identical to the junctional region between exon 4 and exon 7 of isoform RONΔ160 (SEQ ID NO:12) or a fragment thereof, or an amino acid sequence encoded by a nucleotide sequence of SEQ ID NO:11 or a fragment thereof; or an amino acid or nucleotide sequence substantially identical thereto. In yet another embodiment, the peptide or functional variant thereof consists of, or includes, an amino acid sequence, up to 60 amino acids or less (e.g., up to 50, 40, 30, 20, 10 or less amino acids), and which is identical to the junctional region of KIT between exons 10 and 12 of SEQ ID NO:14 or a fragment thereof, or an amino acid sequence encoded by a nucleotide sequence of SEQ ID NO:13 or a fragment thereof; or an amino acid or nucleotide sequence substantially identical thereto. In yet another embodiment, the peptide or functional variant thereof consists of, or includes, an amino acid sequence, up to 60 amino acids or less (e.g., up to 50, 40, 30, 20, 10 or less amino acids), and which is identical to the junctional region of PDGF between exons 5 and 7 of SEQ ID NO:16 or a fragment thereof, or an amino acid sequence encoded by a nucleotide sequence of SEQ ID NO:15 or a fragment thereof; or an amino acid or nucleotide sequence substantially identical thereto. In another embodiment, the peptide or functional variant thereof consists of, or includes, an amino acid sequence, up to 60 amino acids or less (e.g., up to 50, 40, 30, 20, 10 or less amino acids), and which is identical to the junctional region of PDGFR-alpha between exons 6 and 9 of SEQ ID NO:18 or a fragment thereof, or an amino acid sequence encoded by a nucleotide sequence of SEQ ID NO:17 or a fragment thereof; or an amino acid or nucleotide sequence substantially identical thereto.

The peptides or a functional variant thereof can be made recombinantly or synthetically, e.g., using solid phase synthesis. The isoform-specific inhibitor may include at least one, or alternatively, two or more peptide or variants thereof as described herein. For example, any combination of two or more peptide or peptide variants can be arranged, optionally, via a linker sequence. The peptides can be functionally linked (e.g., by chemical coupling, genetic fusion, non-covalent association or otherwise) to one or more other molecular entities, e.g., carriers (e.g., an immunoglobulin Fc domain, serum albumin, pegylation, a GST, Lex-A or an MBP polypeptide sequence) to enhance the peptide stability in vivo. Alternatively, the peptides can be modified by, e.g., addition of chemical protecting groups, to enhance the peptide stability in vivo.

Pegylation

One widely used techniques for increasing the half-life and/or the reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibody molecules; reference is made to for example Chapman, *Nat. Biotechnol.*, 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., *Protein Engineering*, 16, 10, 761-770 (2003). For example, for this purpose, PEG may be attached to a cysteine residue that naturally occurs in an isoform-specific inhibitor, an inhibitor may be modified so as to suitably introduce one or more cysteine residues for attachment of PEG, or an amino acid sequence comprising one or more cysteine residues for attachment of PEG may be fused to the N- and/or C-terminus of an inhibitor of the invention, all using techniques of protein engineering known per se to the skilled person.

Preferably, for the isoform-specific inhibitor, a PEG is used with a molecular weight of more than 5000, such as more than 10,000 and less than 200,000, such as less than 100,000; for example in the range of 20,000-80,000.

With regard to pegylation, its should be noted that generally, the invention also encompasses any SDAB molecule that has been pegylated at one or more amino acid positions, preferably in such a way that said pegylation either (1) increases the half-life in vivo; (2) reduces immunogenicity; (3) provides one or more further beneficial properties known per se for pegylation; (4) does not essentially affect the affinity of the SDAB molecule (e.g. does not reduce said affinity by more than 90%, preferably not by more than 50%, and by no more than 10%, as determined by a suitable assay, such as those described in the Examples below); and/or (4) does not affect any of the other desired properties of the isoform-specific inhibitor. Suitable PEG-groups and methods for attaching them, either specifically or non-specifically, will be clear to the skilled person.

Suitable kits and reagents for such pegylation can for example be obtained from Nektar (CA, USA).

Another, usually less preferred modification comprises N-linked or O-linked glycosylation, usually as part of co-translational and/or post-translational modification, depending on the host cell used for expressing the isoform-specific inhibitor.

Nucleic Acid Binding Molecules

In another embodiment, the isoform-specific inhibitor (e.g., the isoform-binding molecule) inhibits the expression of nucleic acid encoding the isoform, e.g., the oncogenic isoform (e.g., an oncogenic isoform as described herein). Examples of such isoform-binding molecules include nucleic acid molecules, for example, antisense molecules, ribozymes, RNAi, triple helix molecules that hybridize to a nucleic acid encoding the isoform, e.g., the oncogenic isoform, or a transcription regulatory region, and blocks or reduces mRNA expression of the isoform, e.g., the oncogenic isoform. In one embodiment, the nucleic acid binding molecule capable of inhibiting the expression of an oncogenic isoform is an antisense oligonucleotide capable of specifically hybridizing to the oncogenic isoform.

It is understood in the art that the sequence of an antisense compound need not be 100% complementary to that of its target nucleic acid to specifically hybridize to that sequence. An antisense compound specifically hybridizes to a target DNA or RNA sequence when binding of the compound to the target DNA or RNA sequence interferes with the normal function of the target DNA or RNA. This interference should cause a loss of utility, and there should be a sufficient degree of complementarity to avoid non-specific binding of the antisense compound to non-target sequences under conditions in which specific binding is desired, i.e., under physiological conditions in the case of in vivo assays or therapeutic treatment, and in case of in vitro assays, under conditions in which the assays are performed.

The sequence of an antisense oligonucleotide capable of specifically hybridizing to an oncogenic isoform can be identified through routine experimentation. In one embodiment the antisense oligonucleotide is capable of specifically hybridizing to a nucleic acid sequence provided herein, such as, e.g., a sequence encoding a polypeptide selected from the group consisting SEQ ID NOs: 2, 4, 6, 8, 10, 12, 14, 16, and 18. In another embodiment, the antisense oligonucleotide is capable of specifically hybridizing to a nucleic acid comprising the sequence of SEQ ID NO: 1, 3, 5, 7, 9, 11, 13, 15, or 17.

In another embodiment, the compound capable of inhibiting the expression of an oncogenic isoform is an RNAi construct. In one embodiment the RNAi construct is capable of specifically hybridizing to a nucleic acid sequence provided herein, such as, e.g., a sequence encoding a polypeptide selected from the group consisting SEQ ID NOs: 2, 4, 6, 8, 10, 12, 14, 16, and 18 or a substantially identical sequence thereof.

The antisense oligonucleotides and RNAi constructs can be used to specifically inhibit the expression of the oncogenic polypeptide isoforms without inhibiting the non-oncogenic polypeptide isoforms derived from the same proto-oncogene. Using this technology, the specific function of each oncogenic polypeptide isoform can be studied. Further, antisense oligonucleotides and RNAi constructs may be used for disease treatment.

Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability. See, for example, Antisense Technology in Methods in Enzymology, Vols. 313-314, ed. by Phillips, Abelson and Simon, Academic Press, 1999.

The oligonucleotides can be DNA or RNA, or chimeric mixtures or derivatives or modified versions thereof, single-stranded or double-stranded. The oligonucleotide can be modified at the base moiety, sugar moiety, or phosphate backbone, for example, to improve its stability, hybridization, etc. The oligonucleotide may include other appended groups such as peptides (e.g., for targeting host cell receptors), or agents facilitating transport across the cell membrane (see, e.g., Letsinger et al., *Proc. Natl. Acad. Sci. U.S.A.* 86:6553-56 (1989); Lemaitre et al., *Proc. Natl. Acad. Sci. U.S.A.* 84:648-52 (1987); International Patent Publication No. WO88/09810) or the blood-brain barrier (see, e.g., International Patent Publication No. WO89/10134), hybridization-triggered cleavage agents (see, e.g., Krol et al., *BioTechniques* 6:958-76 (1988)) or intercalating agents. (see, e.g., Zon, *Pharm. Res.* 5:539-49 (1988)). To this end, the oligonucleotide may be conjugated to another molecule. The antisense oligonucleotide can also contain a neutral peptide-like backbone. Such molecules are termed peptide nucleic acid (PNA)-oligomers and are described, e.g., in Perry-O'Keefe et al., *Proc. Natl. Acad. Sci. U.S.A.* 93:14670 (1996) and in Eglom et al., *Nature* 365:566 (1993).

Oligonucleotides of the invention may be synthesized by standard methods known in the art, e.g., by use of an automated DNA synthesizer (such as are commercially available from Biosearch Technologies, Inc. (Novato, Calif.), Applied Biosystems (Foster City, Calif.), and others). As examples, phosphorothioate oligonucleotides may be synthesized by the method of Stein et al. (*Nucl. Acids Res.* 16:3209 (1988)), and methylphosphonate oligonucleotides can be prepared by use of controlled pore glass polymer supports (Sarin et al., *Proc. Natl. Acad. Sci. U.S.A.* 85:7448-51 (1988)).

The selection of an appropriate oligonucleotide can be readily performed by one of skill in the art, based upon the present description. Given the nucleic acid encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across proteins may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific, or substantially specific, for a particular protein.

A number of methods have been developed for delivering antisense DNA or RNA to cells, e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically to a subject. See, for example, Antisense Technology in Methods in Enzymology, Vols. 313-314, ed. by Phillips, Abelson and Simon, Academic Press, 1999.

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by any particular theory, RNAi appears to involve mRNA degradation; however, the biochemical mechanisms remain an active area of research.

As used herein, the term "dsRNA" refers to siRNA molecules, or other RNA molecules including a double stranded feature and able to be processed to siRNA in cells, such as hairpin RNA moieties.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts, which can produce siRNAs in vivo.

"RNAi expression vector" (also referred to herein as a "dsRNA-encoding plasmid") refers to a replicable nucleic acid constructs used to express (transcribe) RNA, which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Methods of chemically modifying RNA molecules can be adapted for modifying RNAi constructs (see, e.g., Heidenreich et al., *Nucleic Acids Res.* 25:776-80 (1997); Wilson et al., *J. Mol. Recog.* 7:89-98 (1994); Chen et al., *Nucleic Acids Res.* 23:2661-68 (1995); Hirschbein et al., *Antisense Nucleic Acid Drug Dev.* 7:55-61 (1997)). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

The siRNA molecules can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen et al., *Proc. Natl. Acad. Sci. U.S.A.*, 98:9742-47 (2001); Elbashir et al., *EMBO J.*, 20:6877-88 (2001)). These double-stranded siRNA structures can then be directly introduced to cells, either by passive uptake or a delivery system of choice, such as described below.

The invention also provides methods of inhibiting the expression of an oncogenic isoform provided herein in a cell comprising contacting the cell with a compound capable of inhibiting the expression of the oncogenic isoform. Inhibition of expression of an oncogenic isoform may be useful for the prevention and/or treatment of cancer. Inhibiting expression of an FGFR2-IIIc oncogenic isoform may be used to prevent and/or treat hormone-refractory prostate cancer, breast cancer, bladder cancer, thyroid cancer, or other form of cancer. Inhibiting expression of FGFR1L may be used to prevent and/or treat pancreatic adenocarcinoma, prostate cancer, or other form of cancer. Inhibiting expression of a RON receptor tyrosine kinase A160 isoform may be used to prevent and/or treat metastatic colorectal cancer, breast cancer, ovarian cancer, lung cancer, bladder cancer, or other form of cancer. Inhibiting expression of a KIT receptor tyrosine kinase oncogenic isoform may be used to prevent and/or treat gastrointestinal stromal tumors (GISTs) or other form of cancer. Inhibiting expression of a PDGFR-alpha isoform may be used to prevent and/or treat brain cancer, glioblastoma, prostate cancer, bone metastasis, GIST, or other form of cancer.

In one embodiment the method is carried out in vitro. In another embodiment the method will be carried out in vivo. These methods could be used in research, diagnosis and treatment of a cancer associated with expression of the oncogenic isoform. In research, these methods could be used, for example, to elucidate the mechanism of action of an oncogenic isoform of the invention.

Pharmaceutical Compositions and Kits

In another aspect, the present invention provides compositions, e.g., pharmaceutically acceptable compositions, which include an isoform-specific inhibitor described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The isoform-specific inhibitor of the present invention can be administered by a variety of methods known in the art, although for many therapeutic applications, the preferred route/mode of administration is intravenous injection or infusion. For example, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an isoform-specific inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can also be administered with medical devices known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. The isoform-specific inhibitor can be administered by intravenous infusion at a rate of less than 10 mg/min, preferably less than or equal to 5 mg/min to reach a dose of about 1 to 100 mg/m$^2$, preferably about 5 to 50 mg/m$^2$, about 7 to 25 mg/m$^2$, and more preferably, about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the modified antibody or antibody fragment is outweighed by the therapeutically beneficial effects. A "therapeutically effective dosage" preferably inhibits a measurable parameter, e.g., tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention is a kit comprising an isoform-specific inhibitor. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject. Instructions for use can include instructions for diagnostic applications of the isoform-binding molecule, in vitro, e.g., in a sample, e.g., a biopsy or cells from a patient having a cancer or prostatic disorder, or in vivo. The instructions can include instructions for therapeutic application including suggested dosages and/or modes of administration, e.g., in a patient with a cancer or prostatic disorder. Other instructions can include instructions on coupling of the antibody to a chelator, a label or a therapeutic agent, or for purification of a conjugated antibody, e.g., from unreacted conjugation components. As discussed above, the kit can include a label, e.g., any of the labels described herein. As discussed above, the kit can include a therapeutic agent, e.g., a therapeutic agent described herein. The kit can include a reagent useful for chelating or otherwise coupling a label or therapeutic agent to the antibody, e.g., a reagent discussed herein. For example, a macrocyclic chelating agent, preferably 1,4,7,10-tetraazacyclododecane-N,N', N",N"',4-tetraacetic acid (DOTA), can be included. The DOTA can be supplied as a separate component or the DOTA (or other chelator or conjugating agent) can be supplied already coupled to the antibody. Additional coupling agents, e.g., an agent such as N-hydroxysuccinimide (NHS), can be supplied for coupling the chelator, e.g., DOTA, to the antibody. In some applications the antibody will be reacted with other components; e.g., a chelator or a label or therapeutic agent, e.g., a radioisotope, e.g., yttrium or lutetium. In such cases the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional isoform-specific inhibitor, formulated as appropriate, in one or more separate pharmaceutical preparations.

The kit can further contain a radioprotectant. The radiolytic nature of isotopes, e.g., $^{90}$Yttrium ($^{90}$Y) is known. In order to overcome this radiolysis, radioprotectants may be included, e.g., in the reaction buffer, as long as such radioprotectants are benign, meaning that they do not inhibit or otherwise adversely affect the labeling reaction, e.g., of an isotope, such as of $^{90}$Y, to the antibody.

The formulation buffer of the present invention may include a radioprotectant such as human serum albumin (HSA) or ascorbate, which minimize radiolysis due to yttrium or other strong radionuclides. Other radioprotectants are known in the art and can also be used in the formulation buffer of the present invention, i.e., free radical scavengers (phenol, sulfites, glutathione, cysteine, gentisic acid, nicotinic acid, ascorbyl palmitate, HOP(:O)H$_2$I glycerol, sodium formaldehyde sulfoxylate, Na$_2$S$_2$0, Na$_2$S$_2$0$_3$, and S0$_2$, etc.).

A preferred kit is one useful for radiolabeling a chelator-conjugated protein or peptide with a therapeutic radioisotope for administration to a patient. The kit includes (i) a vial containing chelator-conjugated antibody, (ii) a vial containing formulation buffer for stabilizing and administering the radiolabeled antibody to a patient, and (iii) instructions for performing the radiolabeling procedure. The kit provides for exposing a chelator-conjugated antibody to the radioisotope or a salt thereof for a sufficient amount of time under amiable conditions, e.g., as recommended in the instructions. A radiolabeled antibody having sufficient purity, specific activity and binding specificity is produced. The radiolabeled antibody may be diluted to an appropriate concentration, e.g., in formulation buffer, and administered directly to the patient with or without further purification. The chelator-conjugated antibody may be supplied in lyophilized form.

Uses of the Invention

The isoform-specific inhibitors of the invention have in vitro and in vivo diagnostic, as well as therapeutic and prophylactic utilities. For example, these binding molecules can be administered to cells in culture, e.g. in vitro or ex vivo, or in a subject, e.g., in vivo, to treat, prevent, and/or diagnose a variety of disorders, such as cancers (prostatic and non-prostatic cancers). As used herein, the term "subject" is intended to include human and non-human animals. Preferred human animals include a human patient having a disorder characterized by abnormal functioning of an isoform-expressing cell, e.g., a cancer cell or a prostatic cell. The term "non-human animals" of the invention includes all vertebrates, e.g., mammals and non-mammals, such as non-human primates, sheep, dog, cow, chickens, amphibians, reptiles, etc.

In one embodiment, the subject is a human subject. Alternatively, the subject can be a mammal expressing an isoform-like antigen with which an isoform-specific inhibitor of the invention cross-reacts. An isoform-specific inhibitor of the invention can be administered to a human subject for therapeutic purposes (discussed further below). Moreover, an isoform-specific inhibitor can be administered to a non-human mammal expressing the isoform-like antigen with which the modified antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

Therapeutic Uses

In one embodiment, the invention provides a method of treating, e.g., ablating or killing, a hyperproliferative cell, e.g., a prostatic cell (e.g., a cancerous prostatic), or a malignant, non-prostatic cell, e.g., cell found in a non-prostatic solid tumor, a soft tissue tumor, or a metastatic lesion (e.g., a cell found in renal, urothelial (e.g., bladder), testicular, colon, rectal, lung (e.g., non-small cell lung carcinoma), breast, liver, neural (e.g., neuroendocrine), glial (e.g., glioblastoma), pancreatic (e.g., pancreatic duct) cancer and/or metastasis, melanoma (e.g., malignant melanoma), or soft tissue sarcoma). Methods of the invention include the steps of contacting the hyperproliferative cell, with an isoform-specific inhibitor described herein, in an amount sufficient to treat, e.g., reduce the activity, ablate or kill, the hyperproliferative cell.

The subject method can be used on cells in culture, e.g. in vitro or ex vivo. For example, cancerous or metastatic cells (e.g., prostatic, renal, an urothelial, colon, rectal, lung, breast or liver, cancerous or metastatic cells) can be cultured in vitro in culture medium and the contacting step can be effected by adding the isoform-specific inhibitor, to the culture medium. The method can be performed on cells (e.g., cancerous or metastatic cells) present in a subject, as part of an in vivo (e.g., therapeutic or prophylactic) protocol. For in vivo embodiments, the contacting step is effected in a subject and includes administering the isoform-specific inhibitor to the subject under conditions effective to permit inhibiting and/or reducing one or more activities of the isoform, or binding of the isoform-binding molecule to the cell, and thereby treating, e.g., the killing or ablating of the cell.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting prostate, lung, breast, lymphoid, gastrointestinal (e.g., colon), and genitourinary tract (e.g., renal, urothelial cells), pharynx. Adenocarcinomas include malignancies such as most colon cancers, rectal cancer, renal-cell carcinoma, liver cancer, non-small cell carcinoma of the lung, cancer of the small intestine and cancer of the esophagus. Metastatic lesions of the aforementioned cancers can also be treated or prevented using the methods and compositions of the invention.

The subject method can be useful in treating malignancies of the various organ systems, such as those affecting lung, breast, lymphoid, gastrointestinal (e.g., colon), bladder, genitourinary tract (e.g., prostate), pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

Methods of administering the isoform-specific inhibitors of the invention are described above. Suitable dosages of the molecules used will depend on the age and weight of the subject and the particular drug used. The modified antibody molecules can be used as competitive agents for ligand binding to inhibit, reduce an undesirable interaction.

The isoform-specific inhibitors of the invention can be used by themselves or conjugated to a second agent, e.g., a cytotoxic drug, radioisotope, or a protein, e.g., a protein toxin or a viral protein. This method includes: administering the isoform-specific inhibitors, alone or conjugated to a cytotoxic drug, to a subject requiring such treatment.

The isoform-specific inhibitors of the invention may be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof. The therapeutic agent can be an intracellularly active drug or other agent, such as short-range radiation emitters, including, for example, short-range, high-energy α-emitters, as described herein. In some embodiments, the isoform-specific inhibitors of the invention can be coupled to a molecule of plant or bacterial origin (or derivative thereof), e.g., a maytansinoid.

Maytansine is a cytotoxic agent that effects cell killing by preventing the formation of microtubules and depolymerization of extant microtubules. It is 100- to 1000-fold more cytotoxic than anticancer agents such as doxorubicin, methotrexate, and vinca alkyloid, which are currently in clinical use. Alternatively, the isoform-binding molecule can be coupled to a taxane, a calicheamicin, a proteosome inhibitor, or a topoisomerase inhibitor. R1R)-3-methyl-1-[[(2S)-1-oxo-3-phenyl-2-[(3-mercaptoacetyl)amino]propyl]amino/butyl] Boronic acid is a suitable proteosome inhibitor. N,N'-bis[2-(9-methylphenazine-1-carboxamido)ethyl]-1,2-ethanediamine is a suitable topoisomerase inhibitor.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. In one embodiment, the isoform-binding molecule is conjugated to maytansinoids, e.g., maytansinol (see U.S. Pat. No. 5,208,020), CC-1065 (see U.S. Pat. Nos. 5,475,092, 5,585,499, 5,846,545). Procedures for preparing enzymatically active polypeptides of the immunotoxins are described in WO84/03508 and WO85/03508, which are hereby incorporated by reference. Examples of cytotoxic moieties that can be conjugated to the antibodies include adriamycin, chlorambucil, daunomycin, methotrexate, neocarzinostatin, and platinum.

To kill or ablate cancerous prostate epithelial cells, a first isoform-binding molecule can be conjugated with a prodrug which is activated only when in close proximity with a prodrug activator. The prodrug activator is conjugated with a second isoform-binding molecule according to the present invention, preferably one that binds to a non-competing site on the prostate specific membrane antigen molecule. Whether two modified antibodies bind to competing or non-competing binding sites can be determined by conventional competitive binding assays. Drug-prodrug pairs suitable for use in the practice of the present invention are described in Blakely et al., "ZD2767, an Improved System for Antibody-directed Enzyme Prodrug Therapy That Results in Tumor Regressions in Colorectal Tumor Xenografts," (1996) *Cancer Research*, 56:3287-3292, which is hereby incorporated by reference.

Alternatively, the isoform-binding molecules of the invention can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303-316 (Academic Press 1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y. Radiotherapy is expected to be particularly effective, because prostate epithelial cells and vascular endothelial cells within cancers are relatively radiosensitive. Moreover, Lu$^{117}$ may also be used as both an imaging and cytotoxic agent.

Radioimmunotherapy (RIT) using antibodies labeled with $^{131}$I, $^{90}$Y and $^{117}$Lu is under intense clinical investigation. There are significant differences in the physical characteristics of these three nuclides and as a result, the choice of radionuclide can be important in order to deliver maximum radiation dose to the tumor. The higher beta energy particles of $^{90}$Y may be good for bulky tumors, but it may not be necessary for small tumors and especially bone metastases, (e.g. those common to prostate cancer). The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the tumor residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al., (1995) *Clin Cancer Res.* 1:1447-1454; Meredith R F, et al. (1996) *J Nucl Med* 37:1491-1496; Alvarez R D, et al., (1997) *Gynecologic Oncology* 65: 94-101).

The isoform-specific inhibitors of the invention can also be conjugated or fused to viral surface proteins present on viral particles. For example, an isoform-binding molecule of the invention could be fused (e.g., to form a fusion protein) to a viral surface protein. Alternatively, a whole isoform-specific inhibitor could be chemically conjugated (e.g., via a chemical linker) to a viral surface protein. Preferably, the virus is one that fuses with endocytic membranes, e.g., an influenza virus, such that the virus is internalized along with the isoform-specific inhibitor and thereby infects isoform-expressing cells. The virus can be genetically engineered as a cellular toxin. For example, the virus could express or induce the expression of genes that are toxic to cells, e.g., cell death promoting genes. Preferably, such viruses would be incapable of viral replication.

The isoform-specific inhibitors of the invention can be used directly in vivo to eliminate antigen-expressing cells via natural complement or antibody-dependent cellular cytotoxicity (ADCC). Isoform-specific inhibitors of the invention, which have complement binding sites, such as portions from IgG1, -2, or -3 or IgM which bind complement can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with modified antibodies or fragments thereof of the invention can be improved by binding of complement proteins. In another embodiment, target cells coated with the isoform-specific inhibitors of the invention can also be lysed by complement.

Also encompassed by the present invention is a method of killing or ablating cells which involves using the isoform-specific inhibitors of the invention for preventing an isoform-related disorder. For example, these materials can be used to prevent or delay development or progression of prostate or other cancers.

Use of the therapeutic methods of the present invention to treat prostate and other cancers has a number of benefits. Since isoform-specific inhibitors according to the present invention only target cancerous cells, other tissue is spared. As a result, treatment with such isoform-specific inhibitors is safer, particularly for elderly patients. Treatment according to the present invention is expected to be particularly effective, because it directs high levels of isoform-specific inhibitors to the bone marrow and lymph nodes where prostate cancer metastases and metastases of many other cancers predominate. Moreover, the methods of the present invention are particularly well-suited for treating prostate cancer, because tumor sites for prostate cancer tend to be small in size and, therefore, easily destroyed by cytotoxic agents. Treatment in accordance with the present invention can be effectively monitored with clinical parameters, such as, in the case of prostate cancer, one or more markers chosen from: serum PSA, PSMA, PSCA, AR, chromogranin, synaptophysin, MIB-1, and/or AMACR), and/or pathological features of a patient's cancer, including stage, Gleason score, extracapsular, seminal, vesicle or perineural invasion, positive margins, involved lymph nodes, disease related pain, etc. Alternatively, these parameters can be used to indicate when such treatment should be employed.

Also provided herein are DNA vaccines comprising a nucleotide sequence encoding an epitope of an oncogenic polypeptide isoform, which may be used for the prevention or treatment of cancer. The epitope may be a short peptide of 10-15 amino acid residues from a linear or non-linear sequence of an oncogenic polypeptide isoform. The epitope preferably spans a junction site between two exons, which junction is unique to the particular polypeptide isoform that is associated with cancer and not present in the protein isoform that is found in normal subjects or in normal tissues of diseases subjects. In certain embodiments, DNA vaccines will encode two or more epitopes from a single protein isoform or from multiple protein isoforms and may be used in such combination, e.g., for certain disease indications. DNA vaccines may also encode an epitope specific sequence, e.g., encoding 10-15 amino acids, fused in frame to a carrier protein such as serum albumin, SEAP or other secreted peptide or protein. DNA vaccines may be used for preventing or treated diseases as further described herein. Exemplary DNA vaccines comprise nucleotide sequences encoding peptides of sequences described herein, or identified as described herein.

To test the efficacy of a DNA vaccine, the vaccine may be given to an experimental animal model. Animal models are well known in the art for numerous diseases, for example, for human tumors. In an illustrative embodiment, a vaccinated animal will be challenged with inoculated human tumors either before or after vaccination with a DNA vaccine. A protective or positive effect of the vaccine should be reflected by reduced tumor burden in the experimental animals. Without wanting to be limited to a particular mechanism of action, a tumor-specific vaccine may stimulate either one or both body's immune arms, i.e. cellular immunity and humoral immunity.

Combination Therapy

The isoform-specific inhibitors of the invention may be used in combination with other therapies. For example, the combination therapy can include a composition of the present invention co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the isoform-specific inhibitors are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Isoform-specific inhibitors of the invention can be administered in combination with one or more of the existing modalities for treating prostate cancers, including, but not limited to: surgery (e.g., radical prostatectomy); radiation therapy (e.g., external-beam therapy which involves three dimensional, conformal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy); hormonal therapy, which can be administered before or following radical prostatectomy or radiation (e.g., treatments which reduce serum testosterone concentrations, or inhibit testosterone activity, e.g., administering a leuteinizing hormone-releasing hormone (LHRH) analog or agonist (e.g., Lupron, Zoladex, leuprolide, buserelin, or goserelin) or antagonists (e.g., Abarelix). Non-steroidal anti-androgens, e.g., flutamide, bicalutimade, or nilutamide, can also be used in hormonal therapy, as well as steroidal anti-androgens (e.g., cyproterone acetate or megastrol acetate), estrogens (e.g., diethylstilbestrol), PROSCAR®, secondary or tertiary hormonal manipulations (e.g., involving corticosteroids (e.g., hydrocortisone, prednisone, or dexamethasone), ketoconazole, and/or aminogluthethimide), inhibitors of 5a-reductase (e.g., finisteride), herbal preparations (e.g., PC-SPES), hypophysectomy, and adrenalectomy. Furthermore, hormonal therapy can be performed intermittently or using combinations of any of the above treatments, e.g., combined use of leuprolide and flutamide.

In other embodiments, the isoform-specific inhibitors of the invention are administered in combination with an immunomodulatory agent, e.g., IL-1, 2, 4, 6, or 12, or interferon alpha or gamma. For example, the combination of antibodies having a human constant regions and IL-2 potentially is expected to enhance the efficacy of the monoclonal antibody. IL-2 will function to augment the reticuloendothelial system to recognize antigen-antibody complexes by its effects on NK cells and macrophages. Thus, by stimulating NK cells to release IFN, GM-CSF, and TNF, these cytokines will increase the cell surface density of Fc receptors, as well as the phagocytic capacities of these cells. Therefore, the effector arm of both the humoral and cellular arms will be artificially enhanced. The net effect will be to improve the efficiency of monoclonal antibody therapy, so that a maximal response may be obtained. A small number of clinical trials have combined IL-2 with a monoclonal antibody (Albertini et al. (1997) *Clin Cancer Res* 3: 1277-1288; Frost et al. (1997) *Cancer* 80:317-333; Kossman et al. (1999) *Clin Cancer Res*

5:2748-2755). IL-2 can be administered by either bolus or continuous infusion. Accordingly, the antibodies of the invention can be administered in combination with IL-2 to maximize their therapeutic potential.

Diagnostic Uses

In one aspect, the present invention provides a diagnostic method for detecting the presence of an isoform, e.g., an isoform protein in vitro (e.g., in a biological sample, such as a tissue biopsy, e.g., from a cancerous tissue) or in vivo (e.g., in vivo imaging in a subject). The method includes: (i) contacting the sample with an isoform-binding molecule described herein (e.g., an anti-FGFR2-IIIc antibody molecule described herein), or administering to the subject, the isoform-binding molecule; (optionally) (ii) contacting a reference sample, e.g., a control sample (e.g., a control biological sample, such as plasma, tissue, biopsy) or a control subject)); and (iii) detecting formation of a complex between the isoform-binding molecule, and the sample or subject, or the control sample or subject, wherein a change, e.g., a statistically significant change, in the formation of the complex in the sample or subject relative to the control sample or subject is indicative of the presence of isoform in the sample. The isoform-binding molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting polypeptides includes, but is not limited to, cells, cell lysates, proteins or membrane extracts of cells, body fluids, or tissue samples.

Complex formation between the isoform-binding molecule and the isoform can be detected by measuring or visualizing either the binding molecule bound to the isoform antigen or unbound binding molecule. Conventional detection assays can be used, e.g., an enzyme-linked immunosorbent assays (ELISA), a radioimmunoassay (RIA) or tissue immunohistochemistry. Alternative to labeling the isoform-binding molecule, the presence of the isoform can be assayed in a sample by a competition immunoassay utilizing standards labeled with a detectable substance and an unlabeled isoform-binding molecule. In this assay, the biological sample, the labeled standards and the binding molecule are combined and the amount of labeled standard bound to the unlabeled binding molecule is determined. The amount of isoform in the sample is inversely proportional to the amount of labeled standard bound to the binding molecule.

In still another embodiment, the invention provides a method for detecting the presence of isoform-expressing cancerous tissues in vivo. The method includes (i) administering to a subject (e.g., a patient having a cancer) an isoform-binding molecule conjugated to a detectable marker; (ii) exposing the subject to a means for detecting said detectable marker to the isoform-expressing tissues or cells. In one embodiment, the binding molecule capable of specifically binding the polypeptide oncogenic isoform is an antibody molecule described above. In another embodiment, the binding molecule is an anti-FGFR2-IIIc antibody molecule described herein. In one embodiment, the antibody specifically binds a polypeptide comprising an amino acid sequence set forth in SEQ ID NO: 2, 4, 6, 8, 10, 12, 14, 16, or 18 or a substantially identical sequence thereof.

Determining whether a subject is expressing an oncogenic isoform may be useful to diagnose cancer. Determining whether a subject is expressing an FGFR2-IIIc oncogenic isoform may be used to diagnose hormone-refractory prostate cancer, breast cancer, bladder cancer, thyroid cancer, or other form of cancer. Determining whether a subject is expressing FGFR1L may be used to diagnose pancreatic adenocarcinoma, prostate cancer, or other form of cancer. Determining whether a subject is expressing a RON receptor tyrosine kinase A160 isoform may be used to diagnose metastatic colorectal cancer, breast cancer, ovarian cancer, lung cancer, bladder cancer, or other form of cancer. Determining whether a subject is expressing a KIT receptor tyrosine kinase oncogenic isoform may be used to diagnose gastrointestinal stromal tumors (GISTs) or other form of cancer. Determining whether a subject is expressing a PDGFR-alpha isoform cancer may be used to diagnose brain cancer, glioblastoma, prostate cancer, bone metastasis, GIST, or other form of cancer.

When no compound is determined to have bound at a significant level an oncogenic polypeptide isoform, a negative diagnosis is made. When the compound is determined to have bound at a significant level an oncogenic polypeptide isoform, a positive diagnosis is made.

Examples of labels useful for diagnostic imaging in accordance with the present invention are radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. These isotopes and transrectal detector probes, when used in combination, are especially useful in detecting prostatic fossa recurrences and pelvic nodal disease. The modified antibody can be labeled with such reagents using techniques known in the art. For example, see Wensel and Meares (1983) *Radioimmunoimaging and Radioimmunotherapy*, Elsevier, N.Y., which is hereby incorporated by reference, for techniques relating to the radiolabeling of antibodies. See also, D. Colcher et al., (1986) *Meth. Enzymol.* 121: 802-816, which is hereby incorporated by reference.

In the case of a radiolabeled modified antibody, the modified antibody is administered to the patient, is localized to the tumor bearing the antigen with which the modified antibody reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65785 (Academic Press 1985), which is hereby incorporated by reference. Alternatively, a positron emission transaxial tomography scanner, such as designated Pet VI located at Brookhaven National Laboratory, can be used where the radiolabel emits positrons (e. g., $^{11}$C, $^{18}$F, $^{15}$O, and $^{13}$N).

Fluorophore and chromophore labeled modified antibodies can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescent compounds and chromophores are described by Stryer (1968) *Science,* 162:526 and Brand, L. et al., (1972) *Annual Review of Biochemistry,* 41:843-868, which are hereby incorporated by reference. The isoform-binding molecule can be labeled with fluorescent chromophore groups by conventional procedures such as those disclosed in U.S. Pat. Nos. 3,940,475, 4,289,747, and 4,376,110, which are hereby incorporated by reference.

One group of fluorescers having a number of the desirable properties described above is the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-O— carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

In other embodiments, the invention provide methods for determining the dose, e.g., radiation dose, that different tissues are exposed to when a subject, e.g., a human subject, is administered an isoform-binding molecule that is conjugated to a radioactive isotope. The method includes: (i) administering an isoform-binding molecule as described herein, e.g., an isoform-binding molecule, that is labeled with a radioactive isotope to a subject; (ii) measuring the amount of radioactive isotope located in different tissues, e.g., prostate, liver, kidney, or blood, at various time points until some or all of the radioactive isotope has been eliminated from the body of the subject; and (iii) calculating the total dose of radiation received by each tissue analyzed. The measurements can be taken at scheduled time points, e.g., day 1, 2, 3, 5, 7, and 12, following administration (at day 0) of the radioactively labeled isoform-binding molecule to the subject. The concentration of radioisotope present in a given tissue, integrated over time, and multiplied by the specific activity of the radioisotope can be used to calculate the dose that a given tissue receives. Pharmacological information generated using isoform-binding molecules labeled with one radioactive isotope, e.g., a gamma-emitter, e.g., $^{111}$In, can be used to calculate in the expected dose that the same tissue would receive from a different radioactive isotope which cannot be easily measured, e.g., a beta-emitter, e.g., $^{90}$Y.

Pharmacogenomics

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, gene expression, and protein biomarker expression analysis to drugs in clinical development and on the market. See, for example, Eichelbaum, M. et al., (1996) *Clin. Exp. Pharmaco. Physiol.* 23:983-985 and Linder, M. W. et al. (1997) *Clin. Chem.* 43:254-266. Differences in metabolism of therapeutics can lead to severe toxicity or therapeutic failure by altering the relation between dose and blood concentration of the pharmacologically active drug. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. More specifically, the term refers the study of how a patient's genes determine his or her response to a drug (e.g., a patient's "drug response phenotype," or "drug response genotype.") Thus, another aspect of the invention provides methods for tailoring an individual's prophylactic or therapeutic treatment according to that individual's drug response genotype.

Information generated from pharmacogenomic research can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a composition consisting of one or more isoform-specific inhibitors, or derivatized form(s) thereof, to a patient, as a means of treating a disorder, e.g., a cancer as described herein.

In one embodiment, a physician or clinician may consider applying knowledge obtained in relevant pharmacogenomics studies when determining whether to administer a pharmaceutical composition, e.g., a composition consisting of one or more isoform-specific inhibitors, derivatized form(s) thereof, and optionally a second agent, to a subject. In another embodiment, a physician or clinician may consider applying such knowledge when determining the dosage, e.g., amount per treatment or frequency-of treatments, of a pharmaceutical composition, e.g., a pharmaceutical composition as described herein, administered to a patient.

In yet another embodiment, a physician or clinician may determine the genotypes, at one or more genetic loci, of a group of subjects participating in a clinical trial, wherein the subjects display a disorder, e.g., a cancer or prostatic disorder as described herein, and the clinical trial is designed to test the efficacy of a pharmaceutical composition, e.g., a composition consisting of one or more isoform-specific inhibitors, and optionally a second agent, and wherein the physician or clinician attempts to correlate the genotypes of the subjects with their response to the pharmaceutical composition.

Methods of Detecting Nucleic Acids Encoding Oncogenic Isoforms Using RT-PCR or PCR The invention also provides methods of detecting a nucleic acid which encodes an oncogenic isoform provided herein, comprising: (a) obtaining cDNA from mRNA obtained from a suitable sample; (b) amplifying the cDNA corresponding to the proto-oncogene, oncogenic isoform, or an epitope fragment thereof; (c) comparing the amplified cDNA to the DNA of a nucleic acid known to encode proto-oncogene, oncogenic isoform, or epitope fragment thereof, wherein the presence of the oncogenic isoform in the amplified cDNA indicates the detection of a nucleic acid encoding the oncogenic isoform.

The invention also provides methods for detecting a nucleic acid which encodes an oncogenic isoform provided herein, comprising: (a) contacting a suitable sample with a compound capable of specifically binding a nucleic acid encoding oncogenic isoform provided herein; and (b) determining whether any compound is bound to the nucleic acid, where the presence of compound bound to the nucleic acid in the sample indicates the detection of a nucleic acid encoding the oncogenic isoform.

The term "sample," as it refers to samples used for detecting nucleic acids includes, but is not limited to, cells, cell lysates, nucleic acids extracts of cells, tissue samples, or body fluids. Body fluids include, but are not limited to, blood, serum and saliva. In one embodiment, the suitable sample is obtained from a subject.

Methods of obtaining mRNA from a suitable sample are well known in the art. Further, methods of making cDNA from mRNA, such as reverse transcription, are also well known in the art.

As used herein, "amplifying" means increasing the numbers of copies of a specific DNA fragment. In one embodiment, the amplifying of the cDNA is carried out using PCR (polymerase chain reaction).

In one embodiment, the amplifying of the cDNA is accomplished using primers flanking the entire reading frame of a proto-oncogene encoding an oncoogenic isoform polypeptide. In another embodiment, the amplifying of the cDNA is accomplished out using primers flanking a portion, e.g. an exon, of a nucleic acid encoding the polypeptide oncogenic isoform. In yet another embodiment, one or more of the primers hybridize to sequences of the oncogenic isoform which are present in the nucleic acid encoding the oncogenic isoform, but absent in the nucleic acid encoding a non-oncogenic isoform, or vice versa. In yet another embodiment, a primer may hybridize to a sequence selected from the group consisting of SEQ ID NOs: 1, 3, 5, 7, 9, 11, 13, 15, or 17. In certain embodiments, a primer may be 18-22 nucleotides in length.

In one embodiment, comparing the amplified cDNA to the cDNA of a nucleic acid known to encode the proto-oncogene, oncogenic isoform, or epitope fragment thereof is accomplished by comparing the sequence of the amplified cDNA to the known sequence corresponding to the proto-oncogene, oncogenic isoform, or epitope fragment thereof. The presence or absence of sequence in the amplified sequence will indicate that the oncogenic isoform is present or absent.

In another embodiment, comparing the amplified cDNA to the cDNA of a nucleic acid known to encode the proto-oncogene, oncogenic isoform, or epitope fragment thereof is accomplished by comparing the size of the amplified cDNA to the size of the DNA of a gene known to correspond to the proto-oncogene, oncogenic isoform, or epitope fragment thereof. A difference in size will indicate that the amplified DNA encodes an oncogenic isoform.

The invention also provides methods of determining whether a subject is expressing an oncogenic isoform comprising: (a) obtaining cDNA from mRNA obtained from a suitable sample from the subject; (b) amplifying the cDNA corresponding to the proto-oncogene, oncogenic isoform, or an epitope fragment thereof; and (c) comparing the amplified cDNA to the cDNA of a nucleic acid known to encode the proto-oncogene, oncogenic isoform, or an epitope fragment thereof, wherein the presence of the oncogenic isoform in the amplified cDNA indicates that the subject is expressing the oncogenic isoform.

A "suitable sample" in connection with the above method of determining whether a subject is expressing an oncogenic isoform refers to any sample from the subject that could contain the oncogenic isoform. Examples include, but are not limited to, body fluids and tissue samples. Examples of body fluids include, but are not limited to, blood, serum, urine and saliva.

Amplifying, comparing, and determining the presence of the cDNA may be accomplished as stated above.

Nucleic Acids

The invention also features nucleic acids comprising nucleotide sequences that encode heavy and light chain variable regions and CDRs of the anti-FGFR2-IIIc antibody molecules, as described herein. For example, the invention features a first and second nucleic acid encoding heavy and light chain variable regions, respectively, of an anti-FGFR2-IIIc antibody molecule chosen from one or more of, e.g., Atto-MuMab-01, Atto-MuMab-02, Atto-MuMab-03, Atto-HuMab-01, Atto-MuMab-06, or Atto-MuMab-08, as described herein. The nucleic acid can comprise a nucleotide sequence as set forth in FIG. 29A, 29C, 29E, 30A, 30C, 30E, 34A (SEQ ID NO: 87 for VH), 34B (SEQ ID NO: 89 for VL), or 37B, or a sequence substantially identical thereto (e.g., a sequence at least about 85%, 90%, 95%, 99% or more identical thereto, or which differs by no more than 3, 6, 15, 30, or 45 nucleotides from the sequences shown in FIG. 29A, 29C, 29E, 30A, 30C, 30E, 34A (SEQ ID NO: 87 for VH), 34B (SEQ ID NO: 89 for VL), or 37B.

In certain embodiments, the nucleic acid can comprise a nucleotide sequence encoding at least one, two, or three CDRs from a heavy chain variable region having an amino acid sequence as set forth in FIG. 35 (SEQ ID NOs: 92, 94 and 96 for VH CDRs 1-3, respectively), 28, 29F (SEQ ID NOs: 147-149 for VH CDRs 1-3, respectively), 30F (SEQ ID NOs: 147, 158 and 159 for VH CDRs 1-3, respectively), 38, 39 (SEQ ID NOs: 147-149 for VH CDRs 1-3, respectively), or 40, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs from a light chain variable region having an amino acid sequence as set forth in FIG. 35 (SEQ ID NOs: 98, 100 and 102 for VL CDRs 1-3, respectively), 28, 29D (SEQ ID NOs: 155, 156 and 146 for VL CDRs 1-3, respectively), 30D (SEQ ID NOs: 155-157 for VL CDRs 1-3, respectively), 38, 39 (SEQ ID NOs: 144-146 for VL CDRs 1-3, respectively), or 40, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs from heavy and light chain variable regions having an amino acid sequence as set forth in FIG. 35 (SEQ ID NOs: 92, 94 and 96 for VH CDRs 1-3, and SEQ ID NOs: 98, 100 and 102 for VL CDRs 1-3, respectively), 28, 29D (SEQ ID NOs: 155, 156 and 146 for VL CDRs 1-3, respectively), 29F (SEQ ID NOs: 147-149 for VH CDRs 1-3, respectively), 30D (SEQ ID NOs: 155-157 for VL CDRs 1-3, respectively), 30F (SEQ ID NOs: 147, 158 and 159 for VH CDRs 1-3, respectively), 38, 39 (SEQ ID NOs: 144-146 for VH CDRs 1-3, and SEQ ID NOs: 147-149 for VL CDRs 1-3, respectively), or 40, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs from a heavy chain variable region having the nucleotide sequence as set forth in FIG. 34A (SEQ ID NOs: 91, 93 and 95 for VH CDRs 1-3, respectively), 29E (SEQ ID NOs: 187-189 for VH CDRs 1-3, respectively), 30E (SEQ ID NOs: 181-183 for VH CDRs 1-3, respectively), or 37B (SEQ ID NOs: 175-177 for VH CDRs 1-3, respectively), a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs from a light chain variable region having the nucleotide sequence as set forth in FIG. 34B (SEQ ID NOs: 97, 99 and 101 for VL CDRs 1-3, respectively), 29C (SEQ ID NOs: 184-186 for VL CDRs 1-3, respectively), 30C (SEQ ID NOs: 178-180 for VL CDRs 1-3, respectively), or 37B (SEQ ID NOs: 172-174 for VL CDRs 1-3, respectively), or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs from heavy and light chain variable regions having the nucleotide sequence as set forth in FIG. 34A (SEQ ID NOs: 91, 93 and 95 for VH CDRs 1-3, respectively), 34B (SEQ ID NOs: 97, 99 and 101 for VL CDRs 1-3, respectively), 29C (SEQ ID NOs: 184-186 for VL CDRs 1-3, respectively), 29E (SEQ ID NOs: 187-189 for VH CDRs 1-3, respectively), 30C (SEQ ID NOs: 178-180 for VL CDRs 1-3, respectively), 30E (SEQ ID NOs: 181-183 for VH CDRs 1-3, respectively), or 37B (SEQ ID NOs: 175-177 for VH CDRs 1-3, and SEQ ID NOs: 172-174 for VL CDRs 1-3, respectively), or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail hereinbelow.

In one embodiment the invention provides isolated nucleic acids encoding the oncogenic polypeptide isoforms provided herein, or a substantially identical sequence thereof.

In one embodiment, the invention also provides isolated nucleic acids encoding the polypeptides of oncogenic isoforms or epitope fragments thereof. In one embodiment, the invention provides isolated nucleic acids encoding polypeptides of human oncogenic isoforms or epitope fragments thereof. In one embodiment, the isolated nucleic acid encodes an isoform or epitope fragment thereof of an oncogenic form of a proto-oncogene is selected from the group consisting of FGFR2, FGFR1, RON Receptor tyrosine kinase, KIT receptor tyrosine kinase, PDGF, and PDGFR-alpha.

In one embodiment, the invention provides isolated nucleic acids encoding rat polypeptides of oncogenic isoforms or epitope fragments thereof. In one embodiment, the invention provides isolated nucleic acids encoding mouse polypeptides of human oncogenic isoforms or epitope fragments thereof. In other embodiments the isolated nucleic acids encoding polypeptides of human oncogenic isoforms or epitope fragments thereof will be derived from other species, including but not limited to, dogs, pigs, guinea pigs and rabbits.

FGFR2

In one embodiment the invention provides an isolated nucleic acid encoding an oncogenic polypeptide isoform or epitope fragment thereof comprising a segment of nucleotides which arise from an alternative use of Exon III of a nucleic acid encoding a FGFR2. In one embodiment, the alternative use of Exon III results in sequence variation in the region of amino acids from 301-360, when aligned with FGFR2 IIIb. Thus, in one aspect the nucleic acid encodes a polypeptide comprising a sequence selected from the group of SEQ NOs: 2, 4, 6, and 8. In another aspect the nucleic acid comprises a sequence selected from the group consisting of SEQ NOs: 1, 3, 5, and 7.

FGFR1

In another embodiment, the invention provides an isolated nucleic acid encoding an oncogenic polypeptide isoform or epitope fragment thereof comprising a segment of nucleotides which arise from an alternative deletion of Exons 7 and 8 of FGFR1. In one embodiment, the alternative deletion of Exons 7 and 8 results in a deletion of 105 amino acids, when aligned with an FGFR1 proto-oncogene. Thus, in one aspect the isolated nucleic acid encodes a polypeptide comprising a sequence of SEQ NO: 10. In another aspect, the nucleic acid comprises the sequence of SEQ NO: 9.

RON Receptor Tyrosine Kinase

In another embodiment, the invention provides an isolated nucleic acid encoding polypeptides of oncogenic isoforms or epitope fragments thereof comprising a segment of nucleotides which arise from an alternative deletion of Exons 5 and 6 of RON receptor tyrosine kinase. In one embodiment, the alternative deletion of Exons 5 and 6 results in an in-frame deletion of 109 amino acids in the extracellular domain, when aligned with a RON receptor tyrosine kinase proto-oncogene. In one aspect, the isolated nucleic acid comprises a juxtaposition of Exons 4 and 7. Thus, in one aspect the isolated nucleic acid encodes a polypeptide comprising the sequence of SEQ NO: 12. In another aspect the isolated nucleic acid comprises the sequence of SEQ NO: 11.

KIT Receptor Tyrosine Kinase

In another embodiment, the invention provides an isolated nucleic acid encoding a polypeptide of an oncogenic isoform or epitope fragment thereof comprising a segment of nucleotides which arise from an alternative deletion of Exon 11 of a nucleic acid encoding KIT receptor tyrosine kinase. Thus, in one aspect the isolated nucleic acid encodes a polypeptide comprising the sequence of SEQ NO: 14. In another aspect the nucleic acid comprises the sequence of SEQ NO: 13.

PDGF

In another embodiment, the invention provides an isolated nucleic acid encoding a polypeptide of an oncogenic isoform or epitope fragment thereof comprising a segment of nucleotides which arise from an alternative in-frame deletion of Exon 6 of PDGF. Thus, in one aspect the isolated nucleic acid encodes a polypeptide comprising the sequence of SEQ NO: 16. In another aspect the isolated nucleic acid comprises the sequence of SEQ NO: 15.

PDGFR-Alpha

In another embodiment, the invention provides an isolated nucleic acid encoding a polypeptide of an oncogenic isoform or epitope fragment thereof comprising a segment of nucleotides which arise from an alternative deletion of Exons 7 and 8 (e.g., amino acids 374-456) of PDGFR-alpha. Thus, in one aspect the isolated nucleic acid encodes a polypeptide comprising the sequence of SEQ NO: 18. In another aspect the nucleic acid comprises the sequence of SEQ NO: 17.

Alternatively, an isolated nucleic acid encoding a polypeptide of an oncogenic isoform or epitope fragment thereof may be encoded by a nucleic acid which is substantially identical to a nucleic acid of an oncogenic isoform or epitope fragment thereof provided herein. Likewise, an isolated nucleic acid may encode a polypeptide of an oncogenic isoform or epitope fragment thereof which is substantially identical to an oncogenic isoform or epitope fragment thereof, as provided herein.

A sequence (polypeptide or nucleic acid) that "substantially corresponds" to another sequence may be a sequence that allows single amino acid or nucleotide substitutions, deletions and/or insertions. In one embodiment, sequences that substantially correspond have 80% sequence identity. In another embodiment, sequences that substantially correspond have 85% sequence identity. In another embodiment, sequences that substantially correspond have 90% sequence identity. In another embodiment, sequences that substantially correspond have 95% sequence identity. In another embodiment, sequences that substantially correspond have 97% sequence identity. In another embodiment, sequences that substantially correspond have 99% sequence identity.

In another embodiment, the nucleic acid encodes an oncogenic isoform or epitope fragment thereof comprising the amino acid sequence set forth in SEQ ID NOs: 2, 4, 6, 8, 10, 12, 14, 16, 18, 19, or 20, but with a conservative amino acid substitution. In another embodiment, the nucleic acid encodes an oncogenic isoform or epitope fragment thereof comprising 1, 2, 3, 4, 5, 6, 7, 8, 9 or 10 conservative amino acid substitutions with respect to SEQ ID NOs: 2, 4, 6, 8, 10, 12, 14, 16, 18, 19, or 20. In another embodiment, the nucleic acid encodes an oncogenic polypeptide insert variant comprising 11, 12, 13, 14, 15, 16, 17, 18, 19, or 20 conservative amino acid substitutions with respect to SEQ ID NOs: 2, 4, 6, 8, 10, 12, 14, 16, 18, 19, or 20.

The invention also provides an isolated nucleic acid that specifically binds to a nucleic acid provided herein or a nucleic acid capable of hybridizing under high stringency conditions to a nucleic acid described herein, or a substantially identical sequence thereof.

The invention provides an isolated nucleic acid capable of hybridizing under high stringency conditions to a nucleic acid encoding an oncogenic isoform or epitope fragment thereof comprising SEQ ID NO: 2, 4, 6, 8, 10, 12, 14, 16, 18, 19, or 20 or a substantially identical sequence thereof. The invention provides an isolated nucleic acid capable of hybridizing under high stringency conditions to a nucleic acid comprising the sequence of SEQ ID NO: 1, 3, 5, 7, 9, 11, 13, 15, or 17, or a fragment thereof.

This invention also provides isolated nucleic acids encoding an oncogenic isoform or epitope fragment thereof, wherein the nucleic acid is at least 80% identical to a nucleic acid encoding an oncogenic isoform or epitope fragment thereof, wherein the nucleic acid encoding the oncogenic isoform or epitope fragment thereof comprises a segment of nucleotides at a position which corresponds to the alternative slice junction which when used renders the polypeptide oncogenic. In increasingly more preferred embodiments, rather than 80%, the percent identity is 85%, 90%, 95%, 97%, or 99%.

The nucleic acids described herein can be labeled with a detectable marker. Detectable markers include, but are not limited to: a radioactive marker, a colorimetric marker, a luminescent marker, an enzyme marker and a fluorescent marker. Radioactive markers include, but are not limited to: $^{3}$H, $^{14}$C, $^{32}$P, $^{33}$P, $^{35}$S, $^{36}$Cl, $^{51}$Cr, $^{57}$Co, $^{59}$Fe, $^{90}$Y, $^{125}$I, $^{131}$I, and $^{186}$Re. Fluorescent markers include, but are not limited to, fluorescein, rhodamine and auramine. Colorimetric markers include, but are not limited to, biotin and digoxigenin. Any suitable method for attaching markers to nucleic acids may be used with the nucleotides of the invention, and many such methods are well known in the art.

Further, the invention provides nucleic acids complementary to the nucleic acids disclosed herein. By a nucleic acid sequence "homologous to" or "complementary to", it is meant a nucleic acid that selectively hybridizes, duplexes or binds to a target nucleic acid sequence. For example, adenine is complementary to thymine as they can form two hydrogen bonds. Similarly, guanine and cytosine are complementary since they can form three hydrogen bonds. A nucleic acid sequence, which is homologous to a target sequence, can include sequences, which are shorter or longer than the target sequence as long as they meet the functional test set forth.

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid encoding the polypeptide to which the relevant sequence listing relates.

Vectors

The invention also provides vectors comprising nucleotides encoding a polypeptide of an oncogenic isoform or epitope thereof provided herein. In one embodiment, the vectors comprise nucleotides encoding a polypeptide of an oncogenic isoform or epitope fragment thereof provided herein. In one embodiment, the vectors comprise the nucleotide sequences described herein. The vectors include, but are not limited to, a virus, plasmid, cosmid, lambda phage or a yeast artificial chromosome (YAC).

In accordance with the invention, numerous vector systems may be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity. Expression of the gene encoding a polypeptide of an oncogenic isoform or epitope fragment thereof results in production of the polypeptide of an oncogenic isoform or epitope fragment thereof.

Methods and conditions for culturing the resulting transfected cells and for recovering the polypeptide of an oncogenic isoform or epitope fragment thereof so produced are well known to those skilled in the art, and may be varied or optimized depending upon the specific expression vector and mammalian host cell employed, based upon the present description.

Cells

The invention also provides host cells comprising a nucleic acid encoding a polypeptide of an oncogenic isoform or epitope fragment thereof as described herein.

In one embodiment, the host cells are genetically engineered to comprise nucleic acids encoding a polypeptide of an oncogenic isoform or epitope fragment thereof.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

The Examples that follow are set forth to aid in the understanding of the inventions but are not intended to, and should not be construed to, limit its scope in any way.

EXAMPLES

Example 1

Isoform Specific Epitopes

Example 1.1

FGFR2: Isoform FGFR2-IIIc (SEQ ID NO: 19)

This isoform of Fibroblast Growth Factor Receptor 2 (FGFR2) is predominantly expressed in hormone-refractory prostate cancer. Alternative usage of exon III results in different sequence in the Ig-like loop III of the extracellular domain, which is critical for ligand binding. Isoform IIIb is expressed in normal prostate epithelial cells. Malignant prostate cancer cells switch to IIIc isoform, which has high binding affinity to growth factors with high transforming activities, e.g., FGF8b isoform.

FGFR2-IIIc uses the alternative exon III, which encodes difference sequence than that in isoform FGFR2-IIIb. FGFR2-IIIc isoform contains non-homologous sequence with IIIb isoform in the region of the carboxyl terminal half of the Ig-loop III region, from amino acid position 314 to 353. The isoform structure of FGFR2 is shown in FIG. 1.

Sequence alignment of IIIc and IIIb isoforms shows the differences in carboxyl terminal half of the Ig loop III region (FIG. 2).

Amino acid (SEQ ID NO: 19) and nucleotide (SEQ ID NO: 20) sequences of FGFR2-IIIc are shown in FIGS. 3A and 3B respectively.

Nucleotide (SEQ ID NO: 1) and amino acid (SEQ ID NO: 2) sequences of FGFR2Exon-IIIc are shown in FIGS. 4A and 2, respectively. Nucleotide (SEQ ID NO: 64) and amino acid (SEQ ID NO: 65) sequences of FGFR2Exon-IIIb are shown in FIGS. 4B and 2, respectively.

Short peptide sequences were also used as epitopes for generation of monoclonal antibodies. Amino acid (SEQ ID NO: 4) and nucleotide (SEQ ID NO: 3) sequences of IIIc-314, are shown in FIG. 5A. Amino acid (SEQ ID NO: 6) and nucleotide (SEQ ID NO: 5) sequences of IIIc-328 are shown in FIG. 5B. Amino acid (SEQ ID NO: 8) and nucleotide (SEQ ID NO: 7) sequences of IIIc-350 are shown in FIG. 5C. Amino acid (SEQ ID NO: 56) and nucleotide (SEQ ID NO: 60) sequences of IIIb (Loop3-C') fragment: amino acids 314-351, are shown in FIG. 6A. Amino acid (SEQ ID NO: 57) and nucleotide (SEQ ID NO: 61) sequences of IIIb epitope: amino acids 314-328 are shown in FIG. 6B. Amino acid (SEQ ID NO: 58) and nucleotide (SEQ ID NO: 62) sequences of IIIb epitope: amino acids 340-351 are shown in FIG. 6C.

Example 1.2

FGFR1: Isoform FGFR1L (Deletion of Exon 7 & 8; 105 Amino Acids; Part of Ig-II and Part of Ig-III)

Figures 7, 8:
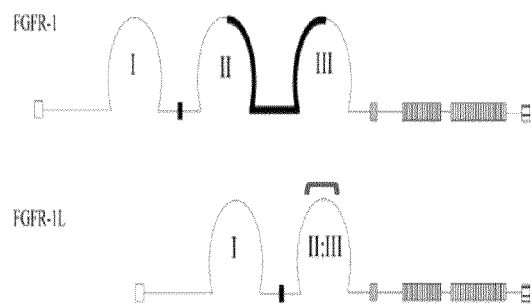
FIG. 7 depicts the isoform structure of FGFR1.
FIG. 8 depicts the nucleotide (SEQ ID NO: 9) and amino acid (SEQ ID NO: 10) sequences of FGFR1L epitope sequence at the junction.

The isoform structure of Fibroblast Growth Factor Receptor 1 (FGFR1) is shown in FIG. 7. The amino acid (SEQ ID NO: 10) and nucleotide (SEQ ID NO: 9) sequences for the epitope at the junction are shown in FIG. 8.

Example 1.3

RON Receptor Tyrosine Kinase: Isoform RONΔ160

This isoform of Macrophage stimulating 1 receptor (RON) is constitutively active. Skipping of exons 5 and 6 results in an in-frame deletion of 109 amino acids in the extracellular domain.

The epitope is at the junction between exon 4 and exon 7. The nucleotide (SEQ ID NO: 11) and amino acid (SEQ ID NO: 12) sequences of this epitope are shown in FIG. 9.

Example 1.4

KIT Receptor Tyrosine Kinase (Deletion in Exon 11)

Most gastrointestinal stromal tumors, GISTs, harbor oncogenic mutations in the v-kit Hardy-Zuckerman 4 feline sarcoma viral oncogene homolog (KIT) gene, and the majority of these mutations affect the juxtamembrane domain of the kinase encoded by exon 11.

The nucleotide (SEQ ID NO: 13) and amino acid (SEQ ID NO: 14) sequences for this epitope are shown in FIG. 10.

Example 1.5

PDGF: Isoform 2 (in-Framed Deletion of Exon 6)

Platelet-Derived Growth Factor (PDGF) isoform 2 has in-frame deletion of exon 6. The nucleotide (SEQ ID NO: 15) and amino acid (SEQ ID NO: 16) sequences for this epitope are shown in FIG. 11.

Example 1.6

PDGFR-Alpha: Delta—Exon 7 and 8 (Amino Acids 374 to 456)

Platelet-Derived Growth Factor Receptor alpha (PDGFR-alpha) has deletion in exons 7 and 8. The nucleotide (SEQ ID NO: 17) and amino acid (SEQ ID NO: 18) sequences for this epitope are shown in FIG. 12.

TABLE 1

Sequences used for designing epitopes for isoform-specific antibodies:

| SEQ ID | Protein Isoform | Epitope | Sequence for Epitope Design |
|---|---|---|---|
| 1 | FGFR2-IIIc | Exon-IIIc | 5'tacgggcccgacgggctgccctacctcaaggttctcaaggccgccgg tgttaacaccacggacaaagagattgaggttctctatattcggaatgta acttttgaggacgctggggaatatacgtgcttggcgggtaattctattg ggatatcctttcactctgcatggttgacagttctg 3' |
| 2 | FGFR2-IIIc | Exon-IIIc (a.a 301-360) | YGPDGLPYLKVLKAAGVNTTDKEIEVLYIR NVTFEDAGEYTCLAGNSIGISFHSAWLTVL |
| 3 | FGFR2-IIIc | IIIc-314 | 5' gcc gcc ggt gtt aac acc acg gac aaa gag att 3' |
| 4 | FGFR2-IIIc | IIIc-314 | AAGVNTTDKEI |
| 5 | FGFR2-IIIc | IIIc-328 | 5' tat att cgg aat gta act ttt gag gac gct 3' |
| 6 | FGFR2-IIIc | IIIc-328 | YIRNVTFEDA |
| 7 | FGFR2-IIIc | IIIc-350 | 5' ata tcc ttt cac 3' |
| 8 | FGFR2-IIIc | IIIc-350 | ISFH |
| 9 | FGFR1L | Ig-II/III | 5' AAT GGC AAA GAA TTC AAA CCT GAC CAC AGA ATT GGA GGC TAC AAG //ACT GCT GGA GTT AAT ACC ACC GAC AAA GAG ATG GAG GTG CTT CAC 3' |
| 10 | FGFR1L | Ig-II/III | NGKEFKPDHRIGGYK//TAGVNTTDKEMEVLH |
| 11 | RON receptor, RONΔ160 | Exon4/7 | 5' Cct ggc tcc tgg caa cag gac cac tgc cca cct aag ctt act gag Gag cca gtg ctg ata gca gtg caa ccc ctc ttt ggc cca cgg gca 3' |
| 12 | RON receptor, RONΔ160 | Exon4/7 | PGSWQQDHCPPKLTEEPVLIAVQPLFGPRA |
| 13 | KIT receptor | Delta-Exon11 | 5' Atg atg tga att att gtg Atg att ctg acc tac aaa tat tta cag gtt gtt gag gag ata aat gga aac aat tat gtt tac ata gac cca 3' |
| 14 | KIT receptor | Delta-Exon11 | MMCIIVMILTYKYLQVVEEINGNNYVYIDP |
| 15 | PDGF isoform-2 | Delta-exon6 | 5' tgc gcg acc aca agc ctg aat ccg gat tat cgg gaa gag gac acg gat gtg agg 3' |
| 16 | PDGF isoform-2 | Delta-exon6 | C A T T S L N P D Y R E E D T D V R |
| 17 | PDGFR-a | Delta-exon7&8 | 5' ctcactgagatcaccactgatgtggaaaagattcaggaaataagg//aataatgaa acttcctggactattttggccaacaatgtctcaaac 3' |
| 18 | PDGFR-a | Delta-exon7&8 | LTEITTDVEKIQEIR//NNETSWTILANNVSN |

Shaded area = nucleotide seq
Clear area = amino acid seq

Example 2

Generation of FGFR2 Isoform Specific Antibody

Antibodies to FGFR2 (non-specific to the isoforms) are commercially available. However, these antibodies do not significantly distinguish between different isoforms. For the purpose of studying the isoform protein distribution and function in tumor and normal tissues, antibodies recognizing isoform-specific sequences for FGFR2-IIIc and IIIb (FIG. 1) were designed. Monoclonal antibodies were generated by common hybridoma technology. Briefly, coding sequences were either PCR amplified or chemically synthesized based on gene sequences of SEQ ID NOs: 19 and 63, respectively. The DNA fragments were subsequently cloned into a commercially available mammalian expression vector. The expression vectors were used for genetic immunization of 5 mice for each antigen. Immunized mice that had serum titer greater than 40.000-fold by ELISA test were used for fusion with myeloma SP 2/0 cells for generation of hybridoma clones.

Monoclonal antibodies were screened by ELISA and Western blots for affinity and specificity. Multiple monoclonal antibody clones for each isoform were further characterized by binding specificity, affinity and $IC_{50}$ (concentration at 50% inhibition) against target receptors. Receptors were prepared either as full-length membrane bound receptor (for cell-based assays) or as soluble form of the extracellular domain fused to human IgG Fc (for ELISA based tests). Positive monoclonal antibody clones to FGFR2IIIc were chosen for further development based on the following criteria (i) no detectable cross-reactivity with FGFR2 IIIb isoform, (ii) nanomolar affinity to its receptor based on $EC_{50}$ value, (iii) staining profile in prostate tumor, other tumors and normal tissue controls. Anti-FGFR2 IIIb monoclonal antibody clones were chosen by similar criteria and used as a control for in vitro studies and for IHC staining of normal and tumor tissues.

These monoclonal antibodies can be humanized by using routine procedures. For example, humanized anti-FGFR2 isoform specific antibodies can be generated by replacing sequences of the Fv variable region which are not directly involved in antigen binding with equivalent sequences from human Fv variable regions, as described by, e.g., Morrison, S. L., 1985, *Science* 229:1202-1207, by Oi et al., 1986, *BioTechniques* 4:214, and by Queen et al., U.S. Pat. No. 5,585,089, U.S. Pat. No. 5,693,761 and U.S. Pat. No. 5,693,762, the contents of all of which are hereby incorporated by reference. Humanized anti-FGFR2 isoform specific antibodies can also be produced by CDR-grafting or CDR substitution, wherein one, two, or all CDRs of an immunoglobulin chain are replaced, as described in, e.g., U.S. Pat. No. 5,225,539; Jones et al., 1986 *Nature* 321:552-525; Verhoeyan et al., 1988 *Science* 239:1534; Beidler et al., 1988 *J. Immunol.* 141:4053-4060; Winter U.S. Pat. No. 5,225,539, the contents of all of which are hereby expressly incorporated by reference.

The anti-FGFR2 isoform specific antibodies can also be produced by phage display technology. Phage display techniques for generating anti-FGFR2 isoform specific antibodies are known in the art (as described in, e.g., Ladner et al. U.S. Pat. No. 5,223,409; Kang et al., International Publication No. WO 92/18619; Dower et al. International Publication No. WO 91/17271; Winter et al., International Publication WO 92/20791; Markland et al., International Publication No. WO 92/15679; Breitling et al., International Publication WO 93/01288; McCafferty et al., International Publication No. WO 92/01047; Garrard et al., International Publication No. WO 92/09690; Ladner et al., International Publication No. WO 90/02809; Fuchs et al., (1991) *Bio/Technology* 9:1370-1372; Hay et al., (1992) *Hum Antibod Hybridomas* 3:81-85; Huse et al., (1989) *Science* 246:1275-1281; Griffths et al., (1993) *EMBO J.* 12:725-734; Hawkins et al. (1992) *J Mol Biol* 226:889-896; Clackson et al. (1991) *Nature* 352:624-628; Gram et al., (1992) *PNAS* 89:3576-3580; Garrad et al., (1991) *Bio/Technology* 9:1373-1377; Hoogenboom et al., (1991) *Nuc Acid Res* 19:4133-4137; and Barbas et al., (1991) *PNAS* 88:7978-7982, the contents of all of which are incorporated by reference herein).

Example 3

Generation of Soluble FGFR2 IIIc—Fc Receptor

A DNA sequence encoding the extracellular domain of the human FGFR2 beta (IIIc) protein (nucleotides 1-786 of SEQ ID NO: 54) was fused to the carboxy-terminal Fc region of human IgG1. The two gene fragments were jointed by a 6 nucleotide linker from a restriction enzyme (Bgl-II), which created two amino acid residues, Arginine and Serine. The total sequence encodes a polypeptide of 491 amino acids. The signal sequence is 21 amino acids; therefore the mature protein of this chimera is 470 amino acids in length. The calculated molecular weight is 52.81 kilodaltons (kDa).

The structure of this fusion protein is illustrated in FIG. 13A.

The nucleotide (SEQ ID NO: 54) and amino acid (SEQ ID NO: 55) sequences of the soluble FGFR2 IIIc-Fc fusion protein are shown in FIGS. 13B and 13C, respectively.

The fusion protein was expressed by generation of stable cell lines in CHO host cells. The recombinant protein is soluble and secreted in the culture media. By analysis on SDS-PAGE under reduced conditions, the recombinant protein migrates as an approximately 95 kDa protein, presumably as a result of glycosylation (FIG. 13D). In FIG. 13D, lane 7 shows the molecular weight standards. Thirteen clonal cell lines were analyzed on the blot (lanes 1-6, 8-14). The conditioned media (20 microliter per lane) from each clone was run on the SDS-PAGE gel, subsequently transferred onto Western blot. The blot was stained with a secondary antibody, goat-anti-human IgG conjugated with alkaline phosphatase. Lane 3, 10, 11 and 14 show positive expression of the Fc fusion protein of FGFR2 beta-ECD from stable clone number 1D2, 1F5, 1F7 and 1F10.

Figure 13E:
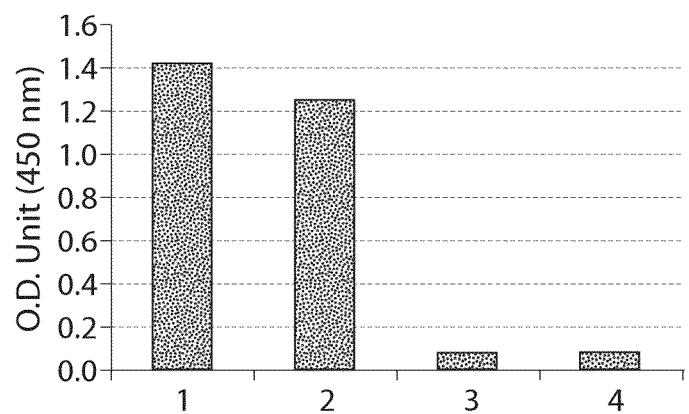
FIG. 13E is a bar graph depicting soluble receptor binding of FGFR2 beta-ECD to the FGF8b ligand.

Clone 1D2 was used as a cell line for production of cell conditioned media for protein purification. The supernatant of cell conditioned medium was collected after 72 hours of cell culture. Fusion protein of FGFR2 beta-ECD was purified by affinity chromatography using Protein-G Sepharose fast Flow (GE Healthcare, Life Sciences—Products) according to manufacturer's protocol. The functional activity of the purified soluble receptor was demonstrated by ligand binding assay as shown in FIG. 13E. The ligand protein FGF8b was coated on ELISA plates at 2 microgram per milliliter, at 4 C over night. Coated plates were washed in PSB containing 0.05% Tween-20 (PBST), subsequently blocked in 2% BSA in PBST buffer at room temperature for 2 hours. Subsequently, preparations of purified fusion protein FGFR2 beta-ECD, at concentration of 4 microgram per milliliter, was allowed to bind to the FGF8b coated on the plates. The binding was detected by adding a secondary antibody, goat anti-human IgG Fc conjugated with horseradish peroxidase (HRP) and by using a chromogenic substrate 3,3',5,5'-tetramethylbenzidine (TMB). The signal was measured in an ELISA plate reader at absorbance wavelength 450 nm.

In FIG. 13E, two different preparations of Protein-G purified soluble fusion receptor FGFR2c beta-EDC (prep-A, and prep-B) were added to the plate, 100 microliter per well at 4 microgram/ml. After incubation at room temperature for 60 minutes, the binding was measured with a goat anti-human IgG Fc-HRP and TMB substrate. The signal was measured at 450 nm on a plate reader. Results showed that both preparations of purified soluble receptor exhibited similar binding activity to its ligand FGF8b in the ELISA binding assay.

The assay method described in FIG. 13E was used for testing antibody anti-FGFR2IIIc inhibitory activity for blocking ligand binding to the isoform receptor FGFR2IIIc. FGF8b is a specific growth factor ligand for isoform IIIc of receptor FGFR2, it does not detectably bind to IIIb isoform of the same receptor (data not shown; Zhang et al., (2006) *J Biol. Chem.* 281, 15694-15700).

Figure 13F:
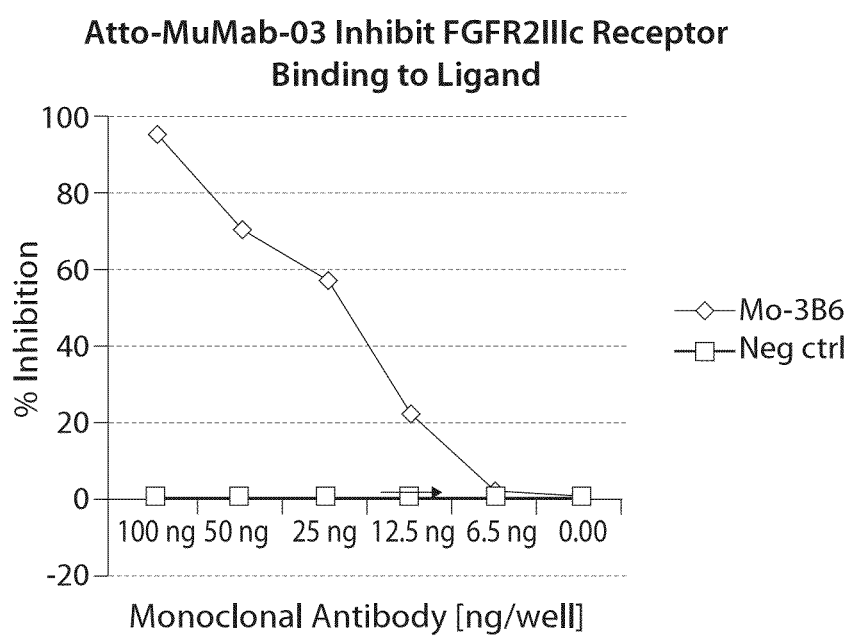
FIG. 13F is a linear graph depicting inhibition of binding of the FGFR2IIIc to the FGF8b ligand in the presense of murine antibody Atto-MuMab-03.

To demonstrate that the mouse monoclonal antibody Mo-3B6 (also referred to herein as "Atto-MuMab-03") can block ligand binding of the receptor FGFR2IIIc, a ligand binding assay as described above in FIG. 13E was performed in the presence or absence of the monoclonal antibody Atto-MuMab-03. Atto-MuMab-03 was pre-incubated with FGFR2IIIc-ECD-Fc before adding to the ligand (FGF8b) coated plates. The binding of FGFR2IIIc to the ligand in the presence or absence of different concentrations of Atto-MuMab-03 was measured via a secondary antibody conjugated with HRP (goat anti-human IgG Fc-HRP). Shown in FIG. 13F, antibody Atto-MuMab-03 exhibited specific and concentration-dependent inhibition to receptor FGFR2IIIc in ligand binding activity. The negative control mouse antibody, an irrelevant monoclonal clone, called 5D3, showed no significant blocking effect to receptor FGFG2IIIc binding to the ligand.

Example 4

Generation of FGFR2 IIIc Peptide

Isoform-specific peptides of FGFR2 IIIc can be generated by standard recombinant or solid phase synthesis.

For example, peptides having the amino acid sequences shown in Table 1 and FIGS. 6A-6C can be generated by cloning the corresponding nucleotide sequences into an expression vector as described in Example 2.

Alternatively, peptides can be synthesized by standard methods of solid or solution phase peptide chemistry. A summary of the solid phase techniques can be found in Stewart and Young (1963) Solid Phase Peptide Synthesis, W. H. Freeman Co. (San Francisco), and Meienhofer (1973) Hormonal Proteins and Peptides, Academic Press (New York). For classical solution synthesis see Schroder and Lupke, The Peptides, Vol. 1, Academic Press (New York). In general, one or more amino acids or suitably protected amino acids can be sequentially added to a growing peptide chain. The protected amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth. After all the desired amino acids have been linked in the proper sequence, any remaining protecting groups (and any solid support) are removed sequentially or concurrently to afford the final peptide. More than one amino acid can be added at a time to a growing chain, for example, by coupling (under conditions which do not racemize chiral centers) a protected tripeptide with a properly protected dipeptide to form, after deprotection, a pentapeptide.

Example 5

Testing of Antibody Molecules for Targeting of Fibroblast Growth Factor Receptor-2 (FGFR2) Isoform IIIc in Prostate Cancer This example evaluates the therapeutic feasibility of an antibody drug against FGFR2 IIIc (anti-FGFR2-IIIc antibody) in prostate cancer models. The molecular target of the antibody, FGFR2 isoform Inc, has been associated with androgen-independent tumor growth and metastasis. This approach is based on the high expression level of this receptor on hormone-refractory prostate cancer (HRPC) and its key role in enhancing the invasive behavior of tumor cells (epithelial-to-mesenchymal transition, EMT). This isoform-specific antibody drug is designed with the intention of targeting the "bad isoform" of FGFR2 receptor on tumor, but spare the "good isoform" FGFR2-IIIb on normal prostate epithelium that functions to suppress tumor growth.

Cell Lines

The androgen-independent human prostate cancer cells DU145 (ATCC) and DU9479 (Duke University) used in this study are both well-characterized cell lines displaying metastatic properties and androgen-independent growth. DU145 was derived from carcinoma of prostate cancer metastasized to the brain (Stone et al. (1978) *Int. J. Cancer* 21: 274-281). This cell line expresses predominantly FGFR2-IIIc (Carstens et al., (1997) *Oncogene* 15, 3059-3065). It has been frequently used in animal model studies for tumor growth and angiogenesis (Garrison et al., (2007) *Cancer Res.* 67:11344-11352; Russel and Voeks (2003) *Methods in Molecular Medicine™: "Prostate Cancer: Methods and Protocols" Animal Models of Prostate Cancer.* Page 89-112). Other human prostate tumor lines, e.g. PC-3 (hormone-independent) or LNCaP (hormone dependent, express IIIb) are used for some work as comparisons or negative controls. DU9479 is another androgen insensitive line, and consists of entirely FGFR2IIIc isoform (Carstens et al., (1997) *Oncogene* 15, 3059-3065).

For in vitro cell based assays, DU145 is suitable for most of the experiments, including proliferation and receptor activation assays. For the ligand binding assay, Transfected cells that express the recombinant FGFR2IIIc target can be used.

Monoclonal antibodies anti-FGFR2-IIIc and IIIb were generated and characterized (referenced herein as "Ab-1" or "Atto-MuMab-01" and "Ab-2" or "Atto-MuMab-02," respectively). Other biochemical reagents (FGFs) and immunochemical reagents (e.g., antibodies to phosphotyrosine, signaling molecules of Grb2, ERK1/2, STAT1 and SHP2) can be purchased from various commercial vendors.

The antibody molecules can be tested in vitro and in vivo using hormone-independent tumor lines, DU145 and DU9479. The following experiments can be conducted:
1) Testing Ab-1 In Vitro Activity and Cellular Mechanism
   a. Inhibition of receptor activation and signaling
   b. Blocking ligand binding or receptor dimerization
   c. Effects on cell proliferation and apoptosis
2) Testing Ab-1 In Vivo Efficacy in Human Prostate Cancer Xenografts
   d. Effect on inhibiting tumor growth, tumor angiogenesis Monoclonal antibody Atto-MuMab-01 was developed with a dual functionality in the design. The mode-of-action for this antibody can include both inhibitor function, i.e. blocking receptor's activation, and immunological function, i.e. inducing cytotoxic T-cell activity. Atto-MuMab-01 binds to the isoform-specific domain of Ig-like loop-3 on the FGFR2IIIc receptor. This domain is involved in ligand binding specificity as previously demonstrated by crystal structure analysis (Shaun et al., (2006) *Genes & Dev.* 20: 185-198). It is expected that antibody Atto-MuMab-01 can block ligand binding, therefore, inhibiting receptor activation. Secondly, the antibody can activate the body's cellular immunity. This antibody is a human IgG1 isotype and can elicit strong immune responses of antibody-dependent cellular cytotoxicity (ADCC) and/or complement-mediated cell lysis. Atto-MuMab-01 is engineered at amino acid position 333 from glutamine to alanine in the Fc region to further enhance the ADCC activity of the antibody. Therefore, when the antibody binds to FGFR2IIIc positive tumor cells, it can recruit cytotoxic T-cells via ADCC to mount potent tumor killing activities.

Thus, Atto-MuMab-01 can have robust anti-tumor activity, and at the same time, can have an attractive safety feature. Because it binds strictly to the IIIc-positive tumor, it can selectively kill tumor cells without causing serious side-effects to normal epithelial tissues (which express IIIb isoform).

Example 5.1

Validation Studies for Expression of FGFR2IIIc

Validation studies for expression of FGFR2IIIc in a broad range of cancer cell lines, including prostate, bladder, lung (NSCLC) and thyroid, were performed. FGFR2IIIc expression was also investigated by tissue-distribution profiling (IHC staining). The following studies were conducted.
   Demonstrate specific binding to prostate tumor cells, not by matched normal prostate (Tissue Arrays compliant with FDA, from US Biomax, Rockville, Md. 20849; Multi-Tumor Microarrays from Invitrogen)
   IHC staining for 30 organ tissue arrays to demonstrate no cross reactivity to healthy tissue (Tissue Arrays from US Biomax, Rockville, Md. 20849)

Example 5.2

Construction of FGF8-SEAP

This construct was made to facilitate a sensitive, non-labeling ligand-binding assay. The coding sequence of FGF8b was PCR cloned from cDNA template (SEQ ID NO: 66) and inserted behind the secreted alkaline phosphatase gene in a commercially available expression vector. A flexible linker of 10-amino acid GGGGSGGGGS (SEQ ID NO: 59) was added between the two fragments, and a His-tag was added to the C-terminal of the fusion protein to facilitate protein purification. The resulting fusion protein, FGF8-SEAP can be easily prepared as secreted form in cell supernatant and used directly for most of the assays. To quantify the enzymatic activity, purified SEAP (commercially available) was used as a standard, and chemiluminescent substrate was used for measuring the light signal. SEAP activity directly correlates with the quantity of the ligand FGF8b.

Example 5.3

In Vitro Studies for Cellular Mechanisms

Established anti-cancer antibody drugs, such as Herceptin (anti-Her2 receptor for breast cancer) and Erbitux (anti-EGFR receptor for head and neck cancer) exhibit their anti-tumor activities via diverse mechanisms. These mechanisms include blocking receptor signaling, interfering with ligand-receptor binding, triggering apoptosis, and inducing cytotoxic effects via ADCC or complement-mediated lysis (Baselga et al., (2001) *Semin Oncol.* 5 Suppl 16:4-11; Trauth et al. (1989) *Science* 245:301; Yang et al. (1999) *Cancer Res.* 59:1236). In this case, several in vitro experiments can be used to investigate the anti-tumor activity of Ab-1 to prostate cancer cells, with the intention to provide information for understanding drug's cellular mechanism in prostate cancer cells.

To provide evidence for understanding the cellular mechanism of antibody's action on tumor cells, three aspects of the cellular function can be examined.

a. Effect of Antibody Ab-1 in Blocking FGF Signaling

Receptor Activation Assay—Dose Dependent Inhibition: The neutralizing activity of antibody on FGFR2 receptor activation in DU145 cells can be examined. DU145 is known to express FGFR1, FGFR2IIIc (predominantly) and FGFR4 (Coombes et al., (2000) Book "Endocrine Oncology", Chapter 12, 237-253; Carstens et al., (1997) *Oncogene* 15, 3059-3065). FGFR2IIIc binds and responds to FGF8 and FGF2, whereas isoform IIIb receptor does not respond to those two growth factors (Zhang et al., (2006) *J Biol. Chem.* 281: 15694-15700). Receptor activation can be analyzed as increased phosphorylation by Western blot analysis on cell lysate. In some cases, it is necessary to "pull down" the receptors from total cell lysate by immunoprecipitation with the anti-receptor FGFR2IIIc. The resulting immunoprecipitates are analyzed on SDS-gel, followed by Western blotting using an anti-phosphotyrosine antibody.

To obtain a dose dependent inhibition curve for $IC_{50}$ value, DU145 cells are incubated with or without increasing concentrations of antibody before challenging with FGF8. The range of antibody concentration can be empirically determined, which is dictated by antibody affinity and receptor expression level on the particular cells. Antibody's inhibition curve can be established via quantification of phosphorylated receptors (e.g., densitometry scan), thus an $IC_{50}$ value for antibody inhibition of receptor activation can be deduced through these analyses.

In addition, downstream signaling events can be examined by analyzing the signaling molecules or effectors of FGFR2, e.g. Grb2, ERK1/2, p38 or STAT1. These additional readouts can be used to confirm the data. Together with receptor activation, phosphorylation analyses, these results provide information for the potential potency of the drug.

These data can demonstrate whether antibody Ab-1 has neutralizing activity. Mechanistically, the antibody could compete with ligand binding to the receptor, or it could block receptor dimerization. Both can give the same readout as inhibition of receptor activation and signaling. The following experiments are designed to answer those questions.

b. Effect of Blocking Ligand Binding or Receptor Dimerization

Previously reported FGFR2 crystal structure analysis (Olsen et al., (2006) *Genes & Dev.* 20: 185-198) indicated that the C'-terminal half of the loop-3, which is encoded by the alternative exon 8, is involved in ligand binding specificity of the receptor. Loop-3 in IIIc isoform binds to FGF8, whereas loop-3 of IIIb binds to FGF7. However, it has also been reported that loop-2 of the receptor may also contribute to ligand binding. Therefore, it is necessary to obtain direct evidence through the experiments to demonstrate whether Ab-1, by binding to its epitope in C'-terminal half of the loop-3, can completely block ligand FGF8 binding to its receptor FGFR2IIIc. The assay for antibody inhibition of ligand binding can be performed as below.

Separately, another effect—whether antibody binding to receptor can interfere with receptor dimerization, a prerequisite step for receptor activation and signaling, can be tested. Together, these molecular interaction analyses can provide a detailed understanding of the molecular mechanism of antibody's mode-of-action.

Ligand Binding Assay:

To assess antibody inhibition on ligand binding, transfected HEK293 cells expressing the receptor FGFR2-IIIc can be used in a 96-well plate assay. Non-radioactive and sensitive luminescence assays to measure ligand binding to its receptor were developed. This assay format involves using a recombinant FGF8 infused with secreted alkaline phosphatase, FGF8-SEAP (as described above). This assay format allows instant enzymatic readout for ligand-receptor binding event via a robust luminescent signal. FGF8-SEAP can be used in the 20 µM to 5 nM concentration range according to previously reported ligand binding conditions (Zhang et al., (2006) *J Biol. Chem.* 281: 15694-15700). Heparin is added at a concentration of 10 µg/ml to facilitate FGF8 binding to the receptor. The receptor bound ligand can be directly quantified by adding chemiluminescence substrate of SEAP (CDP-Star® from Applied Biosystems, or PhosphaGLO™ from KPL), and measured in a microplate reader (Luminoskan, Thermo Scientific).

The $IC_{50}$ value can be obtained from a competition experiment, in which antibody Ab-1 is pre-incubated with cells at a concentration range from 1 µM to 100 nM. Subsequently, ligand SEAP-FGF8 is added to the cell culture. Dose dependent reduction of SEAP signal means that antibody competes with ligand binding site on the receptor.

Statistics

Binding curves can be analyzed by fitting sigmoid curves with variable slope using nonlinear regression. Group data are reported as mean+/−SD or SEM.

Receptor Dimerization Assay:

It is known that FGFs bind to their receptors to induce receptor dimerization. This can be demonstrated using chemical cross-linking reagent, such as cross-linker SDP (succinimidylpropionate). Monomer and dimer receptors are distinguished based on apparent molecular weights on a non-reducing SDS-gel, followed by Western blotting. Receptor from un-treated cells should exist as a monomer (92 Kda). FGF8 treated cells should display predominantly dimmers (~180 Kda).

To examine whether antibody Ab-1 can block receptor dimerization, transfected cells expressing FGFR2IIIc (in 6-well culture plate) are pre-incubated with antibody at 0, $EC_{50}$, and saturation concentrations. An irrelevant antibody can be used as a negative control. After antibody pre-incubation, FGF8 is added to the cells to induce receptor dimerization. Chemical cross-linker DSP is then added to the cells for an additional incubation of 10 to 15 minutes at room temperature. Finally, cell lysate is prepared and analyzed on Western blot with an anti-receptor antibody. The blot reveals primarily receptor monomers in un-stimulated cells, and increased dimers in FGF8 stimulated cells (in the absence of Ab-1 treatment). Pre-incubation with negative control antibody does not reduce the amount of dimer in FGF8 stimulated sample. Ab-1 treated cells are compared with cells treat with negative control antibody for any reduction of dimers after FGF8 induction. This data provide evidence for whether Ab-1 antibody can block receptor dimer formation.

c. Effect of Ab-1 in Cell Proliferation and Apoptosis:

The anti-proliferative effect of antibody Ab-1 can be evaluated. In addition, the pro-apoptosis effect of antibody Ab-1 on tumor cells can also be analyzed.

Proliferation Assay:

Several cell lines from prostate cancer, including PC-3, DU145 and LNCaP, can be analyzed in 96-well plates using MTT assay as previously described (Mosmann et al., (1983) *J. Immunol. Methods*, 65:55-63). MTT provides a measure of mitochondrial dehydrogenase activity within the cell therefore offers an indication of cellular proliferation status.

Cells at exponential growth can be seeded at 2000-3000 cell density in the wells of 96-well plates. AB-1 at nM range is added to the wells with culture medium and incubated for 48 hours. MTT (1 mg/ml) is added to the cells for incubation of 2 hours at 37 C. Cells are lysed, and absorbance of the dye measured in micro-plate reader at 600 nm.

Assessment of Apoptosis:

The effect of antibody Ab-1 on induction of apoptosis in tumor cells can be examined using the lipophilic dye MC540 in combination of DNA-staining dye Hoechest 33342 as previously described procedures (Reid et al., (1996) *J Immunol Methods*, 192:43-54). MC540 detects early stage of apoptosis (i.e. conformational changes in the plasma membrane). Tumor cells are treated with antibody similarly as described above for proliferation assay. The membrane change is measured by incorporation of the dye MC540. To further assess biochemical alteration in apoptotic cells, Applicants examine the expression of the active form of caspase-7 by Western blotting. Anti-caspase-7 can be purchased from Cell Signaling Technology.

Example 5.4

In Vivo Study for Ab-1 Effect on Human Tumor Xenografts

In vivo efficacy for Ab-1 in hormone-independent tumor can be examined in nude mice with DU145 implants. Endpoints include tumor volume, weight, tumor vasculature and metastasis index. Additional readouts, e.g. survival time, immunological responses, and toxicology can also be analyzed.

d. Effect on Blocking Tumor Growth and/or Tumor Angiogenesis in Xenografts

Mice participating in experiments are checked every 2 days for signs of toxicity and discomfort including weight, level of activity, skin abnormalities, diarrhea, and general appearance.

A well-established subcutaneous (s.c.) tumor xenograft model using DU145 prostate cancer cells (Coombes et al., Book "Endocrine Oncology", Edited by Stephen P. Ethier. Chapter 12, 237-253) can be adapted. Briefly, $5\times10^6$ tumor cells are inoculated into 6-week-old nude mice and allowed tumor to grow to 1 $cm^3$ (3-4 weeks for DU145). Tumor fragments of 100 $mm^3$ volume are implanted into mice. Tumor growth is monitored every 3-days by external measurements with a caliper. Tumor-bearing mice are divided into 3 groups of 10 mice. Group-1 can be treated with Taxol® as positive control group. Group-2 can be treated with antibody Ab-1 at 10 mg/kg, 2 times a week, i.p. injection for 5 weeks. Group-3 can be treated with vehicle as a negative control group. Tumor growth is monitored by external measurement. Heparinized blood samples are drawn from the retro-orbital plexus for determination of plasma Ab-1 concentrations.

At the end of the experiments, tumors are excised, weighed, and fixed in formalin. The following endpoint data are collected:

1. Tumor wet weight (grams)
2. Metastasis in secondary sites—lymph node, lung, pancreas, spleen, kidney, adrenal, diaphragm, bone and brain
3. Immunohistochemical staining analysis on fixed specimens for target FGFR2IIIc expression on tumor, FGFR2IIIc activation/phosphorylation, and accumulation of Ab-1 on tumors (using anti-human antibody staining by IHC method)
4. Vascularity evaluation using anti-CD31 staining (Dako). Positive endothelial cells will be counted in five different fields Statistical Analysis Tumor volume is calculated as $V=(L^2/l)/2$, where L and l represent the larger and the smaller tumor diameter. Endpoint measurement for tumor is wet weight in grams. Statistical comparisons are performed using ANOVA for analysis of significance between different values. Regression analysis for caliper volume and wet weight are performed. Group data are reported as mean+/−SD or SEM. P values<0.005 were considered significant.

Example 5.5

Alternative Strategies a. Xenograft Studies:

For metastatic HRPC, complex mechanisms and multiple steps are involved in disease progression. Critical steps of the disease mechanisms involving FGFR2IIIc can be explored using Ab-1, and Ab-1's anti-tumor activity can be demonstrated in a well-established xenograft model. This study can be used to ascertain the activity of the monoclonal antibody in a tumor model. Additional studies may require using different tumor inoculation methods such as orthotopic inoculation or intracardiac injection, in order to dissect the major stages of tumor metastasis.

Besides DU145 xenograph, other CaP tumor lines, which have high expression of the targeted receptor, can also be used.

Alternatively, Dunning rat prostate cancer model and the AT-3 hormone-independent cell line can be used. This model system has been used extensively for studying the FGFR2 isoform function/regulation and is considered relevant to human HRPC (Sebastian et al., (2006) *PNAS* 103:14116-14121; Muh et al., (2002) *JBC* 277:50143-50154; Carstens et al., (2000) *MCB*, 20:7388-7400). This approach can be evaluated to confirm that monoclonal antibodies, Ab-1 and Ab-2 (anti-FGFR2IIIc and anti-FGFR2 IIIb, respectively) cross-react with rat receptors. The amino acid sequences in the alternatively spliced regions of both IIIc (Human: amino acids 301-353 of SEQ ID NO: 2; Rat: SEQ ID NO: 67) and IIIb (Human: amino acids 301-351 of SEQ ID NO: 65; Rat: SEQ ID NO: 68) are completely conserved between human and rat (FIG. 14).

b. In Vitro Study

Besides DU145 cells, transfected cells with low endogenous FGFR2IIIc expression can be used in the in vitro study.

Example 5.6

Other Experiments

Figure 15:
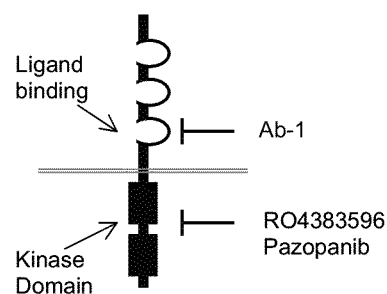
FIG. 15 depicts the dual targeting strategy for FGFR2 receptor. Antibody Ab-1 targets the extracellular ligand binding site of the receptor; and TKI (e.g., R04383596 or Pazopanib) targets the intracellular tyrosine kinase domain.

Other experiments include testing the immunological effects of the Ab-1 from ex vivo studies and measure T-cell mediated cytotoxicity in monoclonal antibody treated tumor cells. In addition, dual targeted strategy using antibody and FGFR selective tyrosine kinase inhibitors (TKIs) in combination, e.g. R04383596 or Pazopanib (as illustrated in FIG. 15), can be analyzed. Particularly, Ab-1 effects on TKI drug resistant tumor cells are investigated. This dual targeted strategy has shown in EGFR-targeted cancers enhanced anti-tumor activity (Huang et al., (2004) *Cancer Res*. 64: 5355-5362).

Example 6

FGFR2-IIIc as a Potential Biomarker for Circulating Tumor Cells in Prostate Cancer This example examines the presence of FGFR2 IIIc receptors on cell lines resembling hormone refractory prostate cancer in peripheral blood cells from patients via testing positive for CTC by the conventional, approved histopathology methods. Additional verification of the tumor nature of cells positive for FGFR2 IIIc expression can be done by PCR methods using isoform specific primer sets. The outcome of this study is to recognize a subgroup of patients, whose tumor and metastasis is dependent on the expression of FGFR2 isoform IIIc, and an additional enhancement of the specificity of the existing and approved CTC test using Ep-CAM.

Specifically, this example evaluates the feasibility to detect and enrich CTCs (or epithelial-to-mesenchymal (ETM) transformed prostate tumor cells) expressing the oncogenic receptor FGFR2 isoform IIIc (FGFR2 IIIc) with an isoform specific antibody. The initial focus is the identification and detection of circulating cells bearing FGFR2 IIIc from peripheral blood from patients with known metastatic diseases. Once the positive detection and specificity data are established, the technical optimization can be pursued on sensitivity of the detection in a healthy control group, patients with benign prostate hyperplasia, and prostate cancer patients. The following are the specific aims for this example:

1) Investigate the presence of FGFR2 IIIc positive CTCs from peripheral blood and confirm these cells as cancer cells.
2) Enrich and isolate FGFR2 IIIc positive CTCs by immunomagnetic purification.
3) Confirm the existence of CTC-bearing FGFR2-IIIc receptor by RT-PCR analysis using exon-specific PCR primers.

This example is a feasibility study for the utility of FGFR2 IIIc as a valid biomarker for identification of prostate cancer CTCs for diagnosing metastatic disease and malignancy in asymptomatic prostate cancer patients. Further study focuses on:

a. Optimize the detection method by quantitative recovery of spiked-in prostate tumor cells (FGFR2-IIIc positive, such as DU145, PC3) in peripheral blood samples.
b. Enumerate FGFR2IIIc positive cells in peripheral blood from patients before and after prostatectomy, before and after TURP (transurethral prostate resection) for benign prostate.
c. Collect large data sets from asymptomatic and symptomatic hormone-refractory prostate cancer patients to determine the diagnostic and prognostic value of the test.

Example 6.1

Significance of the Test for Detection of Circulating Tumor Cells

Metastatic tumor cells spread through the blood or lymph as "circulating tumor cells" (CTCs), and bone marrow as "disseminated tumor cells" (DTCs). CTCs and DTCs represent unique diagnostic and therapeutic targets. Circulating tumor cells are extremely rare in patients with nonmalignant diseases but are present in various metastatic carcinomas with a wide range of frequencies (Allard et al. (2004) *Clin Cancer Res*. 10:6897-6904). Some clinical studies indicate the assessment of CTCs can assist physicians in monitoring and predicting cancer progression and in evaluating response to therapy in patients with metastatic cancer (Berrepoot et al., (2004) *Ann Oncol*. 15:139-145; Aquino et al., (2002) *J. Chemother*. 14:412-416; Katoh et al., (2004) *Anticancer Res*. 24:1421-1425). Recent studies on relationship between post-treatment CTC count and overall survival (OS) in castration-resistant prostate cancer (CRPC) indicated that CTC counts predicted OS better than PSA decrement algorithms at all time points (de Bono et al., (2008) *Clin Cancer Res*. 4(19): 6302-9).

Current CTC detection methods based on epithelial markers, e.g. Ep-CAM may miss FGFR2-IIIc positive circulating tumor cells, because FGFR2 IIIc expression on prostate cancer cells is associated with loss of epithelial markers and gain of mesenchymal markers (Moffa and Ethier (2007) *J Cell Physiol*. 210(3):720-31).

Several frequently used methodologies for detecting CTCs used either alone or in combination can be categorized as—
i) Molecular biological: e.g. RT-PCR (reverse-transcription PCR)
ii) Immunochemical: e.g. antibody-coupled magnetic beads; immunofluorescent microscopy; flow cytometry (FACS) analysis RT-PCR offers a highly sensitive method to detect genes. However, PCR detects living cells, dead cells, and free DNA, resulting in potential false-positives. The specificity of the amplified target genes is a limiting factor for its diagnostic or prognostic value.

Tumor cells bearing an oncogenic receptor FGFR2 IIIc isoform found on androgen-independent tumors are believed to be responsible for invasive tumor growth and metastasis by intra-organ spread and by dissemination via blood stream, respectively. The identification of prostate-derived circulating tumor cells (CTCs) by a FGFR2 IIIc specific antibody is an alternative step in the diagnosis and staging of prostate cancer. The continued presence of these cells in the circulation after prostatectomy may indicate the development of metastatic disease. Therefore, CTC detection shown in this example can provide additional sensitivity and specificity for diagnosing metastasis in HPCR patients.

Example 6.2

CTC Enumeration for Overall Survival Prediction in Prostate Cancer

It has been known that CTC enumeration at baseline and over time by immunomagnetic capture more reliably predicts unfavorable outcome measured as overall survival than PSA levels and changes (de Bono et al., (2008) Clin Cancer Res. 14(19):6302-9; Danila et al., (2007) Clin Cancer Res. 13(23): 7053-8). The detection of FGFR2 IIIc as a potential biomarker for CTCs in prostate cancer adds an additional level of understanding to the molecular mechanisms of prostate cancer and metastatic disease. In addition, this assay can provide a specific test for currently unrecognized HRPC subpopulation.

Example 6.3

Immunomagnetic Purification of DU145 Tumor Cells Spiked in Normal Blood

To purify DU145 tumor cells spiked in normal blood, the following protocol can be used.
a. Prepare immunomagnetic beads: monoclonal antibody against FGFR2 IIIc (in 0.1 mg/ml in PBS containing 1% BSA) is immobilized onto magnetic beads pre-coupled with goat anti-mouse Fc (from Becton Dickinson) by an overnight incubation at 4° C.
b. Tumor cell spiking experiment: PC12 (FGFR2 IIIc negative), DU145 (FGFR2-IIIc positive) tumor cells are preload with fluorescent dye calcein AM for viable cells (from Molecular Probes, Eugene, Oreg.) by a 5-minute incubation at 37° C. Labeled cells are spiked in 7.5 ml normal blood cells at the following ratios: 1000 cells, 500 cells, 100 cells, 50 cells, 10 cells. These labeled cells are exposed to immunomagnetic beads, recovered fluorescent cells can be counted under a fluorescent microscope using a 20× magnification or by flow cytometry FACS analysis. A constant recovery rate is the demonstration of good efficiency of immunomagnetic selection of FGFR2-IIIc positive cells.

Example 6.4

Detection and Enrichment of CTCs from Patients with Prostate Cancer

This follows published procedure and the instrumentation by Veridex (de Bono et al., (2008) Clin Cancer Res. 14(19): 6302-9). Blood samples from patients can be used to detect CTCs bearing FGFR2-IIIc by previously reported procedure (Berrepoot et al., (2004) Ann Oncol. 15:139-145; Aquino et al., (2002) J. Chemother. 14:412-416; Katoh et al. (2004) Anticancer Res. 24:1421-1425; Allard et al. (2004) Clin Cancer Res. 10:6897-6904; de Bono et al., (2008) Clin Cancer Res. 14(19):6302-9). Essentially, blood samples are drawn into 10-ml EDTA Vacutainer tubes (Becton Dickinson) to which a cell preservative was added (Berrepoot et al., (2004) Ann Oncol. 15:139-145; Aquino et al., (2002) J. Chemother. 14:412-416; Katoh et al. (2004) Anticancer Res. 24:1421-1425; Allard et al. (2004) Clin Cancer Res. 10:6897-6904; de Bono et al., (2008) Clin Cancer Res. 14(19):6302-9). Samples are maintained at room temperature and processed within 72 hours after collection. Cells are allowed to incubate with anti-FGFR2-IIIc loaded magnetic beads. Fluorescent nucleic acid dye DAPI (4,2-diamidino-2-phenylindole dihydrochloride) is used to stain nucleated cells. The identification and enumeration of FGFR2-IIIc positive CTCs can be performed with the use of the CellSpotter Analyzer, a semi-automated fluorescence-based microscopy system that permits computer-generated reconstruction of cellular images. Circulating tumor cells are counted as nucleated cells expressing FGFR2-IIIc. To confirm the epithelial cell nature of the isolated CTCs, cells can be double stained with an epithelial cell marker cytokeratin19, labeled with another fluorescent dye phycoerytherin (PE).

Example 6.5

RT-PCR of FGFR2-IIIc isoform

Figure 16:
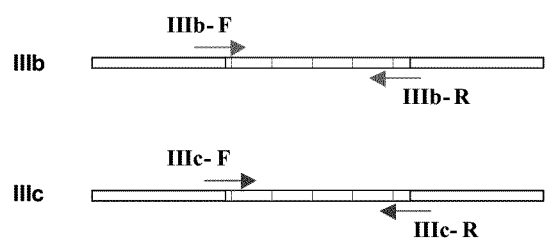
FIG. 16 depicts the isoform specific primers for PCR analysis of FGFR2 IIIc and IIIb.

To demonstrate the specificity of the immunomagnetic selection for FGFR2 IIIc positive CTCs, RT-PCR experiment can be performed to confirm the isoform FGFR2-IIIc expression in isolated cells. RNA can be isolated using RNeasy Mini Kit, including RNase-Free DNase Set (Qiagen, Hilden, Germany). For reverse transcription, RNA is diluted in 15 μl of RNase-free water, incubated for 5 min at 65° C., and placed on ice. A 7.5 μl mixture containing 2 μl of oligo-p(dT)15 primer (0.8 μg/μl), 2 μl of deoxynucleoside triphosphate (5 mM), 0.5 μl of RNAsin (40 units/μl), 1 μl of Omniscript Reverse Transcriptase (4.5 units/μl), and 2 μl of reverse transcriptase buffer (×10) are prepared and added to the diluted RNA. After incubation at 37° C. for 1 h, Omniscript Reverse Transcriptase is inactivated for 5 min at 95° C., and cDNA can be stored at −20° C. PCR amplification is performed using IIIc exon specific primers (IIIc-F: aggttctcaaggccgccggtgt (SEQ ID NO: 71) and IIIc-R: caaccatgcagagtgaaagga (SEQ ID NO: 72). IIIb exon specific primers (IIIb-F: ggttctcaag-cactcgggga (SEQ ID NO: 69) and IIIb-R: gccaggcagactggt-tggcc (SEQ ID NO: 70)) are used as reference. The design of isoform-specific primers for PCR analysis is shown in FIG. 16. Tumor cells, PC-3 (IIIb positive) and DU145 (IIIc positive) can be used as positive controls for the PCR experiments. The PCR product should be appear as a 140 base-pair band on agarose gel.

Example 6.6

Other Experiments

Other experiments include optimizing the test protocol and validate/enhance the clinical relevance of enumeration of CTCs in HRPC patient's clinical outcomes. Biostatistical methods are used for data analysis and interrogation.

Example 7

FGFR2 III-c as a Biomarker for Detection of Hormone-Refractory Prostate Cancer

This example describes the establishment of an immuno-histochemical staining (IHC) test for the detection of invasive, hormone-resistant prostate cancer. As disclosed, FGFR2 isoform IIIc, is associated with androgen-independent tumor growth and metastasis, and it is expressed on the surface of cancerous prostate tissue.

Several biomarkers have been developed as immunohistochemical (IHC) staining tests for prostate cancer. These include prostate-specific antigen (PSA), prostate-specific membrane antigen (PSMA), prostate stem cell antigen (PSCA), androgen receptor (AR), chromogranin, synaptophysin, MIB-1, and α-methylacyl-CoA racemase (AMACR). These markers are not specific for metastatic status or metastatic potential. An examination of FGFR2 isoform IIIc and IIIb expression in the biopsies and surgical specimens should provide additional information for patient with hormone refractory disease and a potential for metastasis.

Prostate cancer cell lines DU145 and LNCaP, were originally obtained from the American Type Culture Collection (ATCC). These cell cultures are maintained using standard protocols.

Prostate cancer with matched normal prostate tissue Arrays, and human tissue arrays can be obtained from US Biomax (Rockville, Md. 20849); Multi-Tumor Microarrays will be obtained from Invitrogen (CA). These tissues should be in compliant with FDA and regulatory requirements. Patients' clinical data, e.g. Gleason score and pathological stage of disease are available. Patient's private information is protected.

IHC tests can be used for surgical samples from radical prostatectomy, or needle biopsies (NBX) and transurethral resections of the prostate (TURP).

Objectives of this example include (i) establishing the IHC test protocol by using tumor cell lines fixed in paraffin as cell pellets; (ii) evaluating the utility of this IHC diagnostic test using tissue specimens from patients with prostate cancer and patients with benign prostate hypertrophy.

The following experiments can be conducted:
i. Investigate the differential expression of the two functionally distinct isoform receptors of FGFR2 in prostate tumor cell lines, DU145 (IIIc positive) and LNCaP (IIIb positive). Demonstrate the specificities and sensitivity of mAbs to each isoform for IHC application. Establish the IHC protocol.
ii. Stain 30-organ tissue arrays to survey the distinct tissue distribution of IIIb and IIIc using Tissue Arrays from US Biomax (Rockville, Md. 20849)
iii. Examine about 20 cases of each, prostate carcinomas, benign prostate hyperplasias (BPHs), to distinguish between neoplastic and noncancerous tissues (Tumor arrays from Invitrogen, CA)
iv. Analyze IHC staining and define the grading and staining patterns; e.g. positive, negative scoring, and FGFR2-IIIc expression patterns in tumor tissues/cells (work with a pathologist expert)
v. Explore the clinical relevance of biomarker expression with disease severity and evaluate the benefit of using targeted antibody drug for blocking metastatic disease.

This biomarker can also be used in combination with other IHC tissue markers in a multi-biomarker analysis.

Example 7.1

IHC Staining Protocol

A general staining protocol for mAbs against FGFR2 receptor is described below. Experimental conditions can be optimized for each mAbs of anti-FGFR IIIc or IIIb.

Immunohistochemistry with Paraffin-Embedded Tissue Sections

Antibodies: Monoclonal anti-FGFR2 IIIc and anti-FGFR2 IIIb antibodies are generated as described above. A monoclonal anti-Cytokeratin (Pan) Clone AE1/AE3 antibody is from Zymed (San Francisco, Calif.) and a polyclonal anti-PSA antibody is from Dako Cytomation. Secondary antibody coupled with peroxidase, ChemMate™, DAKO Envision™ Detection Kit are from Dako Cytomation (Denmark).

Diaminobenzidine (DAB) can be used as chromogen followed by Meyer's hematoxylin counterstaining.

I. Preparation of Slides

Cell pellets are created from DU145 and LNCaP cells, fixed in 10% formalin overnight, and then processed in the regular manner for pathology specimens to produce paraffin embedded cell blocks. Tissue slides are already prepared from paraffin-blocks by commercial vendors.

II. Deparaffinization

1, Label all slides clearly with a pencil, noting antibody and dilution.
2. Deparaffinize and rehydrate as follows: Three times for 5 minutes in xylene; two times for 5 minutes in 100% ethanol; two times for 5 minutes in 95% ethanol; and once for 5 minutes in 80% ethanol,
3, Place all sections in endogenous blocking solution (methanol+2% hydrogen peroxide) for 20 minutes at room temperature.
4. Rinse sections twice for 5 minutes each in deionized water.
5. Rinse sections twice for 5 minutes in phosphate buffered saline (PBS), pH7.4.

III. Blocking and Staining

1, Block all sections with PBS/1% bovine serum albumin (PBA) for 1 hour at room temperature.
2. Incubate sections in rabbit serum diluted in PBA (2%) for 30 minutes at room temperature to reduce non-specific binding of antibody. Perform the incubation in a sealed humidity chamber to prevent air-drying of the tissue sections.
3. Gently shake off excess antibody and cover sections with mAb diluted in PBA. Replace the lid of the humidity chamber and incubate either at room temperature for 1 hour or overnight at 4° C.
4, Rinse sections twice for 5 minutes in PBS, shaking gently,
5. Gently remove excess PBS and cover sections with diluted HRP conjugated rabbit anti-mouse antibody in PBA for 30 minutes to 1 hour at room temperature in the humidity chamber.
6. Rinse sections twice for 5 minutes in PBS, shaking gently.

Scoring IHC Staining:

Stained slides can be evaluated by experienced urological pathologists (consultants). A scoring method will be developed based on a varying degree of staining intensity and percentage of cells staining. The evaluation will be done in a blinded fashion.

Statistical Analysis:

Univariate associations between FGFR2 expression and Gleason score, clinical stage and progression to androgen-independence can be calculated using Fisher's Exact Test. For all analyses, $p<0.05$ was considered statistically significant.

Example 7.3

Other Experiments

Other experiments include the utility of this assay in the selection and characterization of patients in the clinical development of AB-1 as a therapeutic agent in prostate cancer. Retrospective analysis of larger data sets from patients and correlation analyses on biomarker expression profile with disease severity and clinico-pathological parameters are also conducted.

Example 8

Generation of FGFR2 IIIc Specific Monoclonal Antibodies

Balb/c mice were immunized either with the DNA construct encoding a 40-amino acid FGFR2 IIIc fragment (SEQ ID NO: 84; amino acid residues 314-353 of FGFR2 IIIc) or with a synthetic FGFR2 IIIc-specific peptide (TCLAGNSIGISFH (SEQ ID NO: 86)), purified and conjugated to KLH.

In the first approach, a 40-amino acid fragment (amino acid residues 313-352 of FGFR2 IIIc; AAGVNTTDKEIEVL YIRNVTFEDAGEYTCLAGNSIGISFH(SEQ ID NO: 84)) fused at its carboxyl-terminus to mouse IgG1 Fc was used as the immunogen. Capital and underlined letters indicate unique residues in isoform FGFR2 IIIc that are non-homologous with isoform FGFR2 IIIb. Nucleotide sequence encoding the 40-amino acid FGFR2 IIIc fragment (SEQ ID NO: 84; amino acid residues 313-352) was inserted into a modified vector pVAC from Invivogen, San Diego Calif. that results in membrane-bound surface expression of the 40-amino acid fragment of the extracellular (EC) domain of FGFR2-IIIc The modified pVAC-40-amino acid vector was used for DNA immunization. It was expressed as a membrane-anchored protein. mFc-40 amino acid was used as a protein antigen. It was purified as a secreted protein from conditioned media from transfected CHO cells.

The following PCR primers were designed for cloning the coding region of the nucleotide sequence from position 1242 to 1361 (nt) of FGFR2 IIIc:

Sense Primer (including BamH I site): ATAGGATCCT-TGCCGCCGGTGTTAAC (SEQ ID NO: 103)

Antisense Primer (including EcoR I site): GCGGAAT-TCGTGAAAGGATATCCC (SEQ ID NO: 104)

To generate FGFR2 IIIc (40 aa)-mFc, a nucleotide sequence encoding the 40-amino acid fragment of FGFR2 IIIc extracellular (EC) domain (amino acid residues 314-353) was fused in-frame with mouse IgG1-Fc. The following PCR primers were designed to PCR the 120 bp fragment encoding the 40-amino acid. Each oligo primer sequence contains a restriction enzyme site and a 3-base overhang.

```
PCR primers:
Sense Primer (including BamH I site):
                                (SEQ ID NO: 105)
ATAGGATCCTT GCCGCCGGTGTTAAC
```

```
Antisense Primer (including EcoR I site):
                                (SEQ ID NO: 106)
GCGGAATTC GTGAAAGGATATCCC
```

In the second approach, epitope peptide from amino acid residues 337-352 (TCLAGNSIGISFH; SEQ ID NO: 86)) of FGFR2 IIIc, conjugated with KLH, was used as the immunogen. Capital and underlined letters indicate unique residues in isoform FGFR2 IIIc that are non-homologous with isoform FGFR2 IIIb.

Immunized mice with high titers in their antisera were used for isolation of splenocytes. Splenocytes were fused with the myeloma cell line SP20/Ag-14 (ATCC number CRL-1581) for the production of hybridoma cells according to the established protocols (Georges Kohler and Cesar Milstein 1975). SP20/Ag-14 cells were maintained in Dulbecco's Modified Eagle's Medium, and 10% fetal bovine serum. Positive hybridoma populations in the culture were first screened for positive binding to the FGFR2 IIIc-epitope peptide (TCLA-GNSIGISFH (SEQ ID NO: 86)) conjugated to a carrier protein BSA in a standard ELISA. Positive clones were further tested for binding to recombinant receptor protein FGFR2 IIIc-Fc as described below in Example 9.

In the ELISA, antisera were diluted from 1:1000 to 1:27000 as shown in Table 2. The binding to antigen coated on plate was detected by using a goat-anti-mouse IgG conjugated with HRP. Table 2 shows the detected signal of O.D. values.

TABLE 2

ELISA test for antiserum titer from epitope peptide immunized mice

| Mouse # | Antigen for ELISA | 1:1000 | 1:3000 | 1:9000 | 1:18000 | 1:27000 | Pre-immune 1:1000 |
|---|---|---|---|---|---|---|---|
| 1 | BSA-peptide | 1.828 | 1.295 | 0.815 | 0.624 | 0.261 | 0.181 |
| 2 | BSA-peptide | 1.909 | 1.241 | 0.806 | 0.52 | 0.325 | 0.121 |
| 3 | BSA-peptide | 1.928 | 1.320 | 0.808 | 0.337 | 0.223 | 0.078 |
| 4 | BSA-peptide | 1.568 | 0.964 | 0.476 | 0.136 | 0.078 | 0.079 |
| 1 | FGFR2 IIIc-Fc | 1.929 | 0.847 | 0.495 | 0.260 | 0.183 | 0.128 |
| 2 | FGFR2 IIIc-Fc | 1.941 | 0.940 | 0.38 | 0.172 | 0.104 | 0.105 |
| 3 | FGFR2 IIIc-Fc | 1.807 | 0.904 | 0.35 | 0.219 | 0.142 | 0.084 |
| 4 | FGFR2 IIIc-Fc | 1.858 | 1.028 | 0.396 | 0.134 | 0.088 | 0.086 |

Single hybridoma clones were obtained by limited dilution in 96-well culture plates. A single clone was observed by visual inspection under the microscope. This process was repeated for a second round until single clones were obtained.

The isotypes of individual monoclonal antibodies were determined using a mouse antibody isotyping kit according to manufactures instructions (Sigma-Aldrich, Catalog number ISO-2).

Synthetic peptides and conjugation to KLH or BSA were obtained from GenScript Corporation, Piscataway, N.J. PCR primers and sequencing primers were obtained from Sigma-Genosys, Sigma-Aldrich, St Louis, Mo. Secondary antibodies conjugated to either horseradish peroxidase (HRP) or alkaline phosphatase (AP) were purchased from Santa Cruz Biotechnology Inc., Santa Cruz, Calif., or Sigma-Aldrich, St Louis, Mo.

Conclusion:

Mice immunized with epitope-specific peptide generated immune response to the isoform receptor with high titer (at 18,000-fold of dilution) and antibodies generated from an epitope peptide antigen recognized native receptor FGFR2 IIIc.

Example 9

Screening for Monoclonal Antibodies that Selectively Bind to FGFR2 IIIc

Hybridoma screening assays were carried out to select mAbs that bound to FGFR2 IIIc with selectivity, and to eliminate clones that cross-react with isoform FGFR2 IIIb. The primary screening was carried out by ELISA analysis using FGFR2 IIIc-Fc to select hybridomas that could bind to the FGFR2 IIIc isoform. In a secondary ELISA screen, FGFR2 IIIb-Fc was used to identify and eliminate antibodies cross-reacting with the IIIb isoform. Human IgG1 was used as a negative control to eliminate any antibodies cross-reacting with the Fc portion of human IgG.

The ELISA protocol is described as follows. Polystyrene microplates (Maxisorb/NUNC, Roskilde, Denmark) were coated with protein antigens at 2 µg/ml in 0.05 M bicarbonate buffer (pH 9.6) overnight at 4° C. After washing with phosphate-buffered saline containing 0.05% Tween 20, plates were blocked with 1% bovine serum albumin at room temperature for 2 h. Hybridoma secreted conditioned media were added 100 µl per well, and incubated for 1 h at 37° C. Following washing the wells, bound antibodies were detected by using horseradish peroxidase-conjugated goat anti-mouse antibody (Santa Cruz Biotechnology, USA).

In another ELISA based binding assay, monoclonal antibodies were captured on ELISA plates, which were pre-coated with goat anti-mouse IgG at 5 µg/ml. Following washing and blocking steps, FGFR2 IIIc (128 amino acids)-AP and a unrelated control protein in the same fusion with alkaline phosphatase (human PRL3-AP) were added to the plates and incubated for 1 hour at 37° C. Following washing the wells, bound antigens were detected by adding substrate for alkaline phosphatase, pNPP (Sigma-Aldrich).

FGFR2 IIIc (128 amino acids)-AP was generated by in-frame fusion of alkaline phosphatase to the carboxyl-terminal domain of a 128 amino acid FGFR2 IIIc fragment (SEQ ID NO: 107; amino acid residues 250-377 of FGFR2 IIIc) and was expressed from DNA construct pATTO-FGFR2 IIIc (128 aa)-AP. The template cDNA clone was ordered from Open Biosystems (BC039243; Protein ID: AAH39243).

The amino acid sequence for the cloned fragment containing the coding sequence of the third Ig-like loop of FGFR2 IIIc is as follows: (the 2 resides "R" and "T" were created by cloning site on the vector):

```
                                          (SEQ ID NO: 82)
RTERSPHRPI LQAGLPANAS TVVGGDVEFV CKVYSDAQPH

IQWIKHVEKN GSKYGPDGLP YLKVLKAAGV NTTDKEIEVL

YIRNVTFEDA GEYTCLAGNS IGISFHSAWL TVLPAPGREK

EITASPDYLE
```

The following PCR primers were designed for cloning the nucleotide sequence encoding the 128-amino acid FGFR2 IIIc fragment:

```
Sense Primer:
                       (SEQ ID NO: 108)
GAGCGATCGCCTCACCGGCC

Antisense Primer:
                       (SEQ ID NO: 109)
CTCCAGGTAGTCTGGGGAAGCT
```

In yet another ELISA-based binding assay, FGFR2IIIc-Fc' and FGFR2IIIb-Fc' (purchased from R&D Systems, Inc. Minneapolis, Minn.; Catalog numbers: 665-FR and 684-FR) were used for coating ELISA plates at 2 mg/ml (4° C. incubation over night). Monoclonal antibodies in the hybridoma-conditioned media (100 ml) were allowed to bind to coated proteins by incubation at room temperature for 1 hour. Binding was detected using HRP conjugated secondary antibody (goat anti-mouse-HRP), followed by adding substrate tetramethylbenzidine (TMB). O.D. values at 450 nm were measured. Among 25 clones that were screened, four clones were selected based on selective binding to the FGFR2 IIIc isoform. Clones-4, 9, 16 and 21 exhibited strong selective binding to FGFR2 IIIc, with either background level of binding, or very weak binding to the FGFR2 IIIb isoform. Monoclonal antibodies from hybridoma clone-9 and −21 have been tested for isotypes, and both antibodies are murine IgG2b. These two monoclonal antibodies have been designated as Atto-MuMab-01 and Atto-MuMab-02, respectively.

Example 10

Western Blot Analysis of Antibody Binding to FGFR2 IIIc

Western blot analysis was performed to detect specific antibody binding to soluble forms of FGFR2 fusion proteins (Fc-fusion proteins), FGFR2 IIIc-Fc or FGFR2 IIIb-Fc either as purified protein or as CHO cell secreted protein in the conditioned media. Proteins were subjected to electrophoresis on an 8% SDS-PAGE gel, and blotted onto a nitrocellulose membrane (Amersham Pharmacia Biotech, Uppsala, Sweden). Nonspecific binding was blocked with 5% nonfat milk in phosphate-buffered saline overnight at 4° C. The nitrocellulose membrane was incubated with mAb Atto-MuMab-01 for 1 hour at room temperature, followed by horseradish peroxidase-conjugated goat anti-mouse IgG for 1 hour at room temperature. After several washes, it was processed by adding the colorimetric substrate DAB (DAKO, Carpinteria, Calif., USA)

Positive controls of Fc-fusion proteins of FGFR2 IIIc' and FGFR2 IIIb' (IIIb' and IIIc') were purchased from R&D Systems, Inc. Minneapolis, Minn.; Catalog numbers: 665-FR and 684-FR). Fc-fusion protein of FGFR2 IIIb (IIIb) and FGFR2 IIIc (IIIc) were prepared as secreted protein from transfected CHO cells. FGFR2 IIIc-Fc was generated by in-frame fusion of human IgG1-Fc (227 amino acids) to the carboxyl terminus of the extracellular (EC) domain of FGFR2 IIIc (amino acid residues 1-262 of FGFR2 IIIc) as described in Example 3. The following PCR primers were designed for cloning the coding region of the nucleotide sequence from position 64 to 786 (nt) of FGFR2 IIIc:

```
Sense Primer (including EcoR I site):
                             (SEQ ID NO: 112)
AGAGAATTCGCGGCCCTCCTTCAGTTTAGT Antisense Primer (including Bgl II site):
                             (SEQ ID NO: 113)
GTGAGATCTCTCCAGGTAGTCTGGGGAAGCT
```

FGFR2 IIIb-Fc was generated by in-frame fusion of human IgG1-Fc (SEQ ID NO: 110; 227 amino acids) to the carboxyl-terminus of the extracellular (EC) domain of FGFR2 IIIb SEQ ID NO: 114; amino acid residues 32-289 of FGFR2 IIIb (SEQ ID NO: 192)). The following PCR primers were designed for cloning of the coding region of the nucleotide sequence from position 94 to 867 (nt) of SEQ ID NO: 193:

```
Sense Primer (including EcoR I site):
                                  (SEQ ID NO: 115)
AGAGAATTCGCGGCCCTCCTTCAGTTTAGT Antisense Primer (including Bgl II site):
                                  (SEQ ID NO: 116)
GTGAGATCTCTCCAGGTAGTCTGGGGAAGC
```

The DNA template for PCR amplification of FGFR2 IIIb was purchased from Open Biosystems, Thermo Scientific, Huntsville Ala. (Catalog number IHS1380-8840381).

Example 11

Anti-FGFR2IIIc Antibody Binds to Endogenous Protein in Tumor Cells

This Example shows binding to anti-FGFR2IIIC antibodies of the invention to tumor cells, such as DU145 and Hep G2. Cell lysates were analyzed by immunoprecipitation (IP) followed by Western blotting.

DU 145, a human prostate cancer cell line, was obtained from ATCC (ATCC number HTB-81). It was originally derived from a human prostate adenocarcinoma metastatic to the brain. This cell line was propagated in Eagle's Minimum Essential Medium, and 10% fetal bovine serum.

HepG2, a liver cancer cell line, was analyzed by immunoprecipitation (IP) followed by Western blotting.

For immunoprecipitation, cell lysate was prepared from a fresh culture of DU 145 cells or HepG2 cells as follows. Cells were harvested, centrifuged to pellet the cells and resuspended in lysis buffer containing 50 mM Tris (pH 7.5), 150 mM NaCl, 1% Triton-X100, 10 mM DTT, and protease inhibitor cocktails (PMSF, aprotinin, leupeptin, pepstatin). Cells were incubated in lysis buffer on ice for 15-minutes and then centrifuged at 10,000 g for 10 minutes at 4° C. The lysate supernatant was used for immunoprecipitation by incubation with Atto-Mu mAb-01 or Atto-Mu mAb-B7 (also referred to herein as "Atto-mu Mab-03") over night at 4° C. Protein-A Sepharose was used to purify the immune complexes, which were then separated by SDS PAGE and analyzed by Western blot as described below.

For Western blot, samples were analyzed by SDS-PAGE on 8% polyacrylamide gels, and subsequently electroblotted onto a nitrocellulose membrane (Amersham Pharmacia Biotech, Uppsala, Sweden). Nonspecific binding was blocked with 5% nonfat milk in phosphate-buffered saline overnight at 4° C. Then the nitrocellulose membrane was incubated with Atto-Mu mAb-01 or Atto-mu Mab-03 for 1 hour at room temperature, followed with incubation with horseradish peroxidase-conjugated goat anti-mouse IgG for 1 hour at room temperature. After washing, the blot was processed for enhanced chemiluminescence (ECL) according to the kit instructions (Amersham Pharmacia Biotech). The result was documented on an X-ray film.

Figures 31, 32:
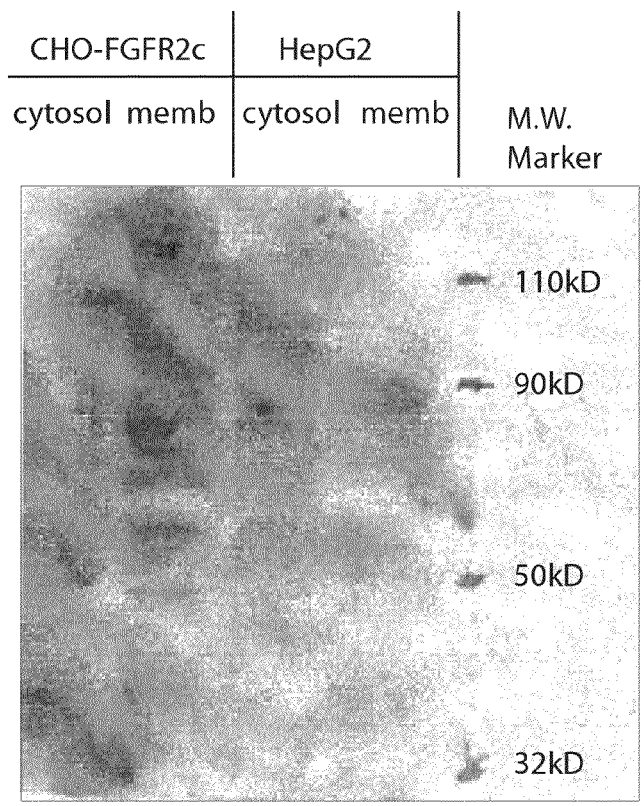
FIG. 31 is a table depicting the phage clone recovery yield in library screening.
FIG. 32 is photograph of a Western blot depicting binding of the monoclonal antibody Atto-MuMab-03 to endogenous FGFR2IIIc in tumor cells.

FIG. 32 depicts a Western blot showing the binding of mAb ATTO-mu Mab-03 to the endogenous FGFR2IIIc in the liver carcinoma cell line, HepG2. Lane 1 and 2: cytosol and membrane fractions from a positive control stable CHO expressing FGFR2IIIc receptor. Lane 3 and 4: cytotosol and membrane fraction of HepG2. As shown in FIG. 32, a band of apparent molecular weight of 85 KDa was recognized by ATTO-Mu mAb-B7. Thus, monoclonal antibody ATTO-Mu mAb-B7 binds endogenous FGFR2IIIc in tumor cells.

Figure 33:
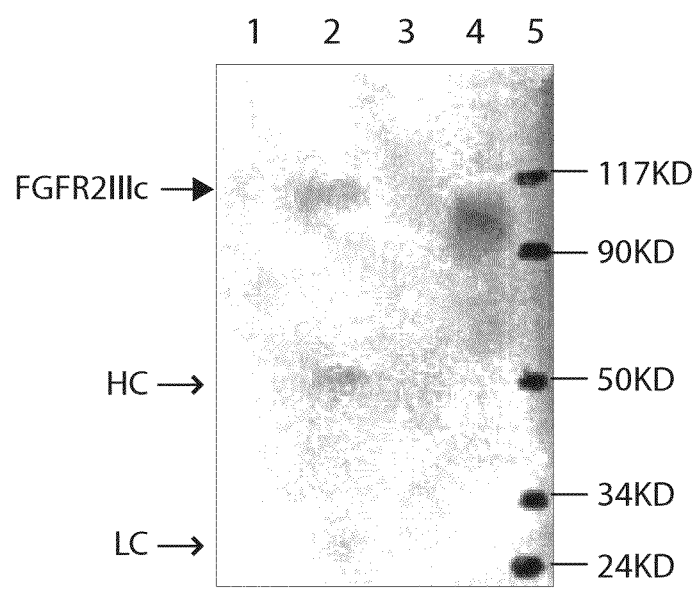
FIG. 33 depicts a Western blot showing the binding of mAb Atto-MuMab-01 to the endogenous FGFR2 IIIc protein in the prostate cancer cell line, DU145. Lane 1: DU145 cell lysate from 50,000 cells; Lane 2: mAb IP from lysate of 500,000 DU145 cells; Lane 3: blank; Lane 4: Positive control of FGFR2IIIc-Fc (100 ng).

As shown in FIG. 33, a band of apparent molecular weight of 110 KDa was recognized by mAb Atto-Mu mAb-01. The 50 KDa and 25 KDa bands are IgG heavy chain and light chain respectively, derived from mAb used in the IP.

Example 12

Mouse Monoclonal Antibody Clones Selectively Bind to IIIc Isoform of FGFR2

Figures 24A, 24B:
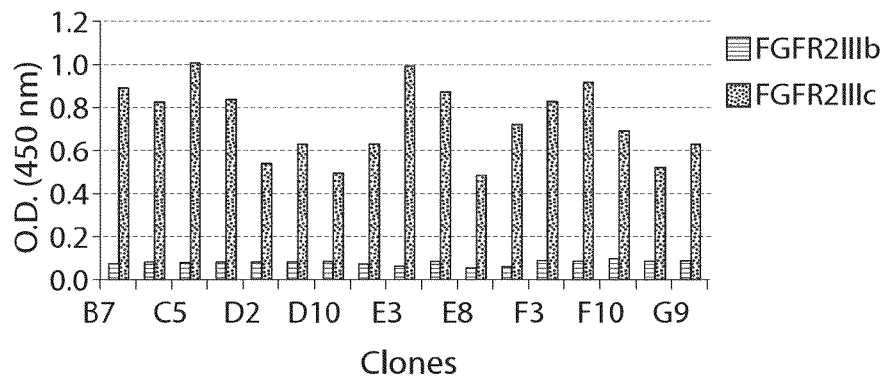
FIG. 24A is a bar graph depicting selective binding of monoclonal antibody clones B7, C5, D2, D10, E3, E8, F3, F10 and G9 to FGFR2IIIc-Fc compared to binding to FGFR2 IIIb. Clone B7 has been designated herein as "Atto-MuMab-03."
FIG. 24B is a table depicting the OD values and standard deviation of binding of the indicated monoclonal antibody clones to FGFR2IIIc-Fc (including Atto-MuMab-03) compared to binding to FGFR2 IIIb.

Immunized mice with serum titer above 16,000 were used for fusion with myeloma cells SP2/0 for production of hybridoma cells. After growth in HAT selection medium for 7 to 10 days, hybridoma cells were screened by ELISA using antigen-coated plates, e.g. 128aa-mFc or 40aa-mFc. Positive binders were further tested for isoform-selectivity against IIIc or IIIb soluble receptor protein, FGFR2IIIc beta-ECD and FGFR2IIIb beta-ECD. Binding of the monoclonal antibodies to the soluble receptor coated on the plates were measured by using goat anti-mouse IgG Fc-HRP. FIG. 24A is a bar graph depicting strong binding signal of the specified clones to FGFR2IIIc, whereas low or no binding activity was detected with these clones to the FGFR2IIIb isoform. In the graph, background signal was not subtracted (FIG. 24B). Clone B7 has been designated herein as "Atto-Mu-Mab03."

Example 13

Isolation of Human Antibody scFv by Screening Phage Display Library

Human phage display libraries containing approximately 1 to $10 \times 10^{10}$ phage antibodies were prepared as previously described in Sblattero D. et al. (2000) Nature Biotechnology 18, 74-80. To screen the library for isoform specific antibodies, fusion proteins with fragments of FGFR2IIIc epitope inserts (described in Example 1.1) were used as baits in the bio-panning procedures. The fusion proteins were constructed in mouse IgG Fc fusion backbone, e.g. the FGFR2IIIc isoform loop-3 region containing 128-amino acid (amino acid 235-353) 120-amino acid (mFc), or 40-amino acid (aminoa acid 314-353) 40aa-mFc.

Phage antibody selection was performed by using fusion proteins coupled to immunotubes (Nunc, Rochester, N.Y.) at 4 microgram/ml overnight, blocked in 2% nonfat milk-phosphate buffered saline (MPBS) and incubated with the phage antibody library (also blocked in MPBS) for 1-2 h. Washing after the first cycle involved five PBS and five PBS-0.1% Tween-20 washes. Phage were eluted by the addition of 1 ml DHSaF at OD550 0.5. Following elution, bacteria were amplified and phage prepared for further cycles of selection. Subsequent washes were more stringent, and phage antibodies were tested for reactivity by ELISA after the forth cycle. FIG. 31 showed a summary table for each round of enrichment for phage that bound to the target protein.

Figures 25A, 25B:
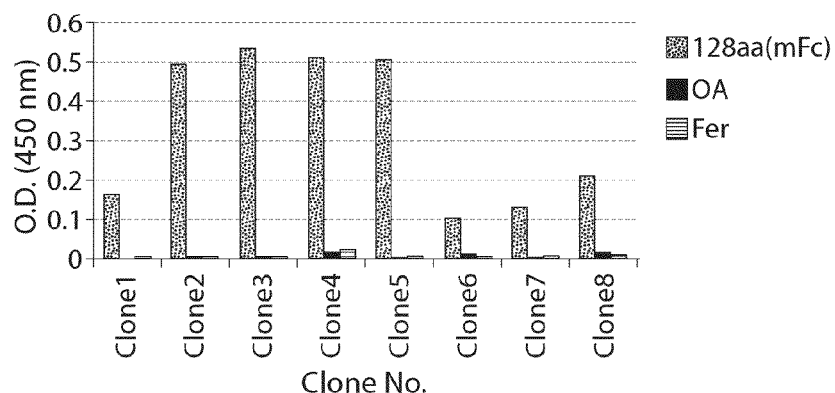
FIG. 25A is a bar graph depicting the selective binding of a panel of human antibody scFv clones 1-8 to the loop-3 region of FGFR2IIIc isoform containing 128-amino acid (amino acid 235-353) (mFc), compared to binding to irrelevant human ovalbumin (OA) and human ferritin (Fer) controls.
FIG. 25B is a table depicting the OD values and standard deviation of binding of the indicated panel of human antibody scFv clones to the 128 amino acid-fragment of FGFR2IIIc (mFc), compared to binding to irrelevant OA and Fer controls.

To test the antibody binding specificity, phage ELISA was used to identify positive clones that can bind to the target protein, e.g., 128aa (mFc). Negative control proteins for non-specific binding were checked by using two irrelevant proteins, human ovalbumin (OA) and human ferritin (Fer). Briefly, individual phage clones were picked after four rounds of bio-panning and screening, and tested in a phage-ELISA. FIG. 25A is a bar graph depicting a representative result from testing eight clones in a binding assay to FGFR2IIIc-128aa coated ELISA plates. Negative control proteins used human ovalbumin (OA) and Feritin (Fer) coated on the plates. These clones showed positive binding to FGFR2IIIc-128aa antigen protein, and no detectable binding to irrelevant control proteins of human ovalbumin (OA) and human ferritin (Fer).

Figures 27A, 27B:
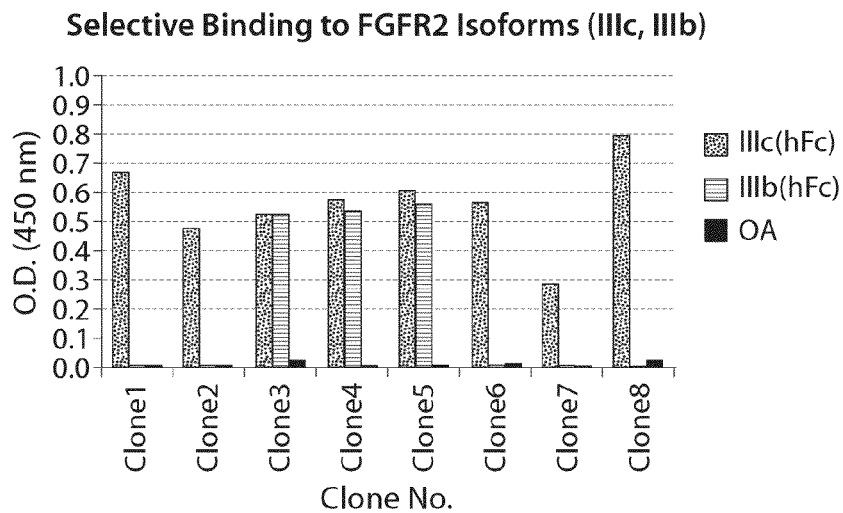
FIG. 27A is a bar graph depicting the binding selectivity of the indicated human antibody scFv clones to FGFR2 isoform IIIc versus FGFR2IIIb.
FIG. 27B is a table depicting the OD values and standard deviation of the indicated human scFv clones to isoform IIIc versus FGFR2IIIb.

Phage ELISA assays were also performed on individual phage clones for binding specificity to the targeted isoform receptor FGFR2IIIc. The binding assay was performed using ELISA format. Soluble receptor FGFR2IIIc beta-ECD was used at 2 microgram/ml for coating the ELISA plate. The counter isoform receptor fusion protein FGFR2IIIb beta-ECD was used at the same concentration for cross-reactivity test. Ovalbumin (OA) was used as a negative control. FIGS. 27A-27B show the results of binding of soluble scFv antibodies to FGFR2IIIc versus FGFR2IIIb. ELISA plates were coated with FGFR2IIIc-hFc (2 microgram per milliliter), or FGFR2IIIb-hFc (2 microgram per mililiter). Soluble antibodies prepared from scFv clones were allowed to bind to isoform receptors coated on the plates. Ovalbumin (OA) was used as a negative control. Out of 30 induced clones, 8 clones exhibited activity by ELISA binding assay against antigen FGFR2IIIc (128aa-mFc). These clones were tested for selectivity towards isoform FGFR2IIIc. Shown in FIG. 27A, five out of eight clones showed selective binding to isoform IIIc. Three out of eight clones bind both isoform IIIc and IIIb.

Figure 26:
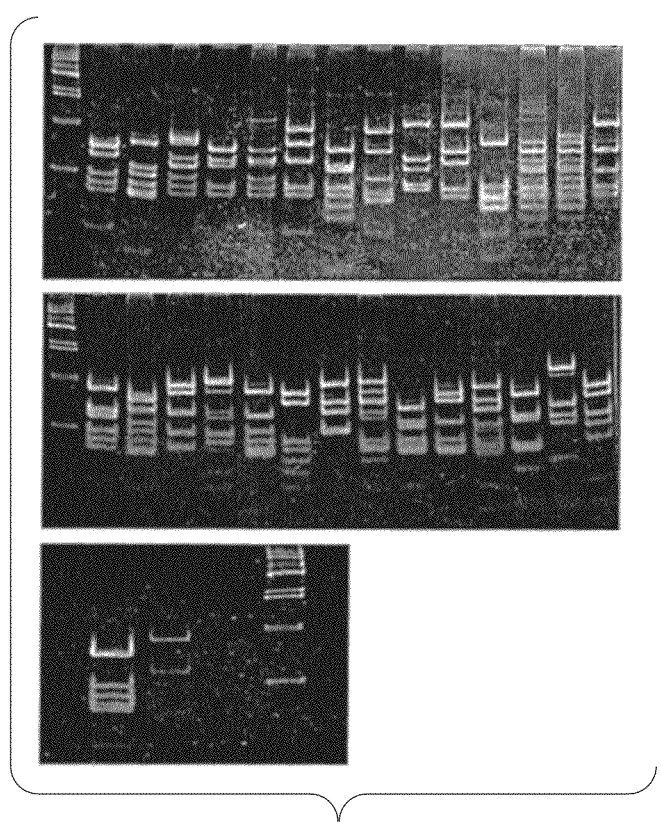
FIG. 26 is a photograph of DNA fingerprints of thirty different human antibody scFv clones against FGFR2IIIc.

To determine that the phage antibody clones are distinct clones with different coding sequences, clones were analyzed by DNA finger printing. From one round of library screening, 101 clones are analyzed by their patterns of DNA finger prints. PCR amplification of the CDR region was performed for these clones. CL-6B micro-columns were used to separate the PCR products. DNA products were digested with restriction enzyme Mva1. DNA fragments shown in FIG. 26 identified 30 individual clones with distinct DNA fingerprint patterns.

Sequencing analysis was carried out for these positive clones. The identity of the different V genes was analyzed by submitting the sequence to V BASE19, and by using online informatics tools. FIG. 28 depicts an amino acid sequence alignment of human scFv Clone-6 and Clone-8. The locations of the complementarity determining regions (CDRs) of the light and heavy chain variable regions are underlined and labeled as VL-CDR-1, -2, and -3, and VH-CDR-1, -2, and -3, respectively. The linker sequence is shaded. Clone-6 and Clone-8 are also referred to herein as "Atto-HuMab-06" and "Atto-HuMab-08," respectively. The data indicated that they are distinct antibody clones with divergent coding sequences in the CDR domains.

FIGS. 29A-29B depict the nucleotide and amino acid sequence, respectively, for the full length coding region of the light chain variable domain and the heavy chain variable domain of human scFv Clone 8 (Atto-HuMab-08). The linker sequence is shaded.

FIGS. 29C-29D depict the nucleotide and amino acid sequence, respectively, of the light chain variable domain of the human scFv Clone 8 (Atto-HuMab-08). The CDR sequences are underlined.

FIGS. 29E-29F depict the nucleotide and amino acid sequence, respectively, of the heavy chain variable domain of the human scFv Clone 8 (Atto-HuMab-08). The CDR sequences are underlined.

FIGS. 30A-30B depict the nucleotide and amino acid sequence, respectively, for the full length coding region of the light chain variable domain and the heavy chain variable domain of human scFv Clone 6 (Atto-HuMab-06). The linker sequence is shaded.

FIGS. 30C-30D depict the nucleotide and amino acid sequence, respectively, of the light chain variable domain of the human scFv Clone 6 (Atto-HuMab-06). The CDR sequences are underlined.

FIGS. 30E-30F depict the nucleotide and amino acid sequence, respectively, of the heavy chain variable domain of the human scFv Clone 6 (Atto-HuMab-06). The CDR sequences are underlined.

Soluble scFv antibody expression was performed for preparation of soluble antibodies in the *E. coli* system. Soluble expression was detected for 30 independent clones identified by gene finger-print were prepared by infecting HB2151 strain with helper phage M13. Secreted soluble antibodies of scFv were produced after 0.5 mM IPTG induction. Antibodies were purified by chromatography using Nickel columns. These purified antibody samples were used for binding studies in tumor cells and tumor specimens by immunochemical, immunofluorescence, and immunohistochemical techniques. The blocking activities of these scFv antibodies can be performed by proliferation assays, ligand binding assays and cell-based receptor activation assays. The in vivo activity of the antibodies in blocking tumor growth, invasion and survival rate can be conducted in tumor xenograft models in mice.

Example 14

Cloning of the Heavy and Light Chain Variable Domains for Antibodies Atto-MuMab-01 and Atto-MuMab-02

Hybridoma cells ($10^5$ cells) were used for RNA isolation using MagMAX™-96 Total RNA Isolation Kit (Ambion). First strand cDNA was synthesized using Superscript™ III Reverse Transcriptase (Invitrogen). The following primers were used for cDNA synthesis:

```
                                          (SEQ ID NO: 117)
Cγ2b: CGACTAGTCGACCAGGGATCCAGAGTTCCAAG (SEQ ID NO: 118)
MKVL: GCGCCGTCTAGAATTAACACTCATTCCTGTTGAA
```

CDR coding sequences for heavy chain (VH) and light Chain (VL) were amplified by PCR method using the primers as follows:

```
    PCR primers for VH:
                                          (SEQ ID NO: 119)
    VHB1: SAGGTCCAGCTGCAGCAGYYTGG (SEQ ID NO: 120)
    VHB2: GAGGTTCAGCTGCAGCAGTCTGK (SEQ ID NO: 121)
    VHF1: GAGGAAACGGTGACCGTGGT (SEQ ID NO: 122)
    VHF2: GAGGAGACTGTGAGAGTGGT (SEQ ID NO: 123)
    VHF3: GCAGAGACAGTGACCAGAGT (SEQ ID NO: 124)
    VHF4: GAGGAGACGGTGACTGAGGT PCR primers for VL:
                                          (SEQ ID NO: 125)
    VLB1: GATGYTKTKVTGACCCAAACTCC (SEQ ID NO: 126)
    VLB2: GATATCCAGATGACACAGACTAC (SEQ ID NO: 127)
    VLB3: RACATTGTGCTGACMCAATCTCC
```

-continued

```
VLB4:  SAAAWTGTKCTCWCCCAGTCTCC          (SEQ ID NO: 128)

VLB5:  GAMATCMWGATGACCCARTCTCC          (SEQ ID NO: 129)

VLB6:  RRCATTGTGATGACCCAGWCTCM          (SEQ ID NO: 130)

VLB7:  GATATTGTGATRACBCAGGYTGM          (SEQ ID NO: 131)

VLB8:  RAMATTDTGWTGWCACAGTCTAY          (SEQ ID NO: 132)

VLB9:  GACATCCAGATGACWCARTCTYC          (SEQ ID NO: 133)

VLB10: GACATCCAGATGAMMCAGTCTCC          (SEQ ID NO: 134)

VLB11: GAYATYSTGMTRACRCAGTCTCC          (SEQ ID NO: 135)

VLB12: GACATTGTGATGACTCAGTCTCC          (SEQ ID NO: 136)

VLB13: GAAACAACTGTGACCCAGTCTCC          (SEQ ID NO: 137)

VLF1:  ACGTTTGATTTCCAGCTTGG             (SEQ ID NO: 138)

VLF2:  ACGTTTTATTTCCAGCTTGG             (SEQ ID NO: 139)

VLF3:  ACGTTTTATTTCCAACTTTG             (SEQ ID NO: 140)

VLF4:  ACGTTTCAGCTCCAGCTTGG             (SEQ ID NO: 141)
```

The PCR program was as follows: 5 minute denaturation at 94° C., followed by 7 cycles of 1 minute at 94° C., 30 s at 63° C., 50 seconds at 58° C., 1 minute at 72° C., and 23 cycles of 1 minute at 94° C., 30 seconds at 63° C., 1 minute at 72° C., finally 5 minute at 72° C.

PCR amplified DNA fragments were cloned into pUCm-T vector (Biomatik USA, L LC, Wilmington, Del., USA).

The nucleotide sequences of Atto-MuMab-02 heavy (SEQ ID NO: 87) and light (SEQ ID NO: 89) chain variable regions are shown in FIGS. 34A and 34B, respectively. The amino acid sequences of Atto-MuMab-02 heavy (SEQ ID NO: 88) and light (SEQ ID NO: 90) chain variable regions are shown in FIG. 35. As shown in FIGS. 36A and 36B, amino acid sequence alignment of Atto-MuMab-02 immunoglobulin heavy (SEQ ID NO: 88) or light (SEQ ID NO: 90) chain variable region with mouse immunoglobulin gene database reveals 91% homology between the Atto-MuMab-02 heavy chain variable region (SEQ ID NO: 88) and mouse immunoglobulin mu chain variable region (SEQ ID NO: 142; GeneBank: AAA88255.1) and 92% homology between the light chain variable region (SEQ ID NO: 90) and anti-human melanoma immunoglobulin light chain variable region (SEQ ID NO: 143; GenBank: AAO49727.1), respectively, indicating both the heavy and light chain sequences from Atto-MuMab-02 are novel sequences.

Example 15

Cloning and Analysis of Human Antibody ATTO-HuMAb-01 That Selectively Binds to IIIc Isoform of FGFR2

Human antibody ATTO-HuMAb-01 that selectively binds to the IIIc isoform of FGFR2 is derived from the original human scFv clone 1 (scFv-1). For example, several single-chain human antibody clones were described in Example 13, such as scFv-1, scFv-2, scFv-6, and scFv-8. In particular, scFv-1 was described, e.g., in FIGS. 25A-25B, 26, and 27A-27B. Analysis of sequence alignments among the scFv antibody clones as described in this Example showed high homologies in the light chain and heavy chain VL-CDR or VH-CDR regions. Further studies showed that scFv-1 had similar or better binding properties (e.g., binding to the target receptor as soluble molecule, and to the target receptor expressed on the cell surface) and more stable expression and structural features, than scFv-2, scFv-6, and scFv-8.

As shown in this Example, scFv-1 clone has been constructed and tested in the following antibody forms: phage-displayed scFv fragment, designated herein as "scFv-1 (phage)"; E. coli expressed secreted form, as purified scFv soluble antibody, designated herein as "scFv-1 (sol)"; double-chain construct as human IgG1 Fc-fusion, designated herein as "dcFv-01"; and whole human IgG molecule (in a framework of a conventional IgG1 structure with full-length heavy chain and light chains), designeated herein as "ATTO-HuMAB-01."

Example 15.1

Analysis of Sequence Alignments Among scFv Antibody Clones

FIGS. 37A-37B depicts the amino acid and nucleotide sequences, respectively, for the full length coding region of the light chain variable domain and the heavy chain variable domain of human scFv-1. The linker sequence is shaded. The complementarity determining region (CDR) sequences are underlined.

An amino acid sequence alignment of human scFv-1 and scFv-6 is shown in FIG. 38. The locations of the CDRs of the light and heavy chain variable regions are underlined and labeled as VL-CDR-1, -2, and -3, and VH-CDR-1, -2, and -3, respectively. The result of sequence alignment revealed 217/252 (86%) Identities, 232/252 (92%) Positives, and 1/252 (0%) Gaps (Score=434 bits (1117), Expect=8e-127, Method: Compositional matrix adjust) between scFv-1 and scFv-6.

An amino acid sequence alignment of human scFv-1 and scFv-8 is shown in FIG. 39. The locations of the complementarity determining regions (CDRs) of the light and heavy chain variable regions are underlined and labeled as VL-CDR-1, -2, and -3, and VH-CDR-1, -2, and -3, respectively. The result of sequence alignment revealed 240/252 (95%) Identities, 247/252 (98%) Positives, and 0/252 (0%) Gaps (Score=491 bits (1264), Expect=6e-144, Method: Compositional matrix adjust) between scFv-1 and scFv-8.

CDR region comparison among scFv antibody clones (scFv-1, scFv-6, and scFv-8) is shown in FIG. 40. As shown in FIG. 40, these scFv clones that bind to FGFR2IIIc shared high degree of sequence homologies in the regions of light chain CDRs and heavy chain CDRs.

Thus, analysis of sequence alignments among the scFv antibody clones showed high homologies in the light chain and heavy chain including the VL-CDR or VH-CDR regions.

Example 15.2

Immunocytochemical (ICC) Staining of Transiently Transfected CHO Cells

Figure 41:
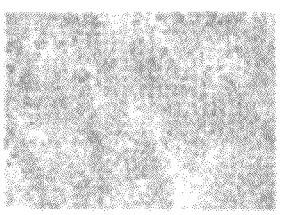
FIG. 41 depicts images of immunocytochemical (ICC) staining showing the binding of human scFv Clone 1 (scFv-1) to FGFR2IIIc-expressing CHO cells.

The binding of human antibody scFv-1 to cell surface receptor FGFR2IIIc was demonstrated by immunocytochemical (ICC) staining using CHO cells that transciently express either FGFR2-IIIb or FGFR2-IIIc. Briefly, CHO cells were either mock transfected or transfected with a construct that expresses either FGFR2-IIIb or FGFR2-IIIc with a FLAG tag at the N-terminus of the extracellular domain. The expression of FGFR2-IIIb or FGFR2-IIIc on the cell surface was shown by ICC staining using an anti-FLAG antibody. FIG. 41 depicts representative images of immunocytochemical (ICC) staining. As shown in FIG. 41, purified human antibody scFv-1 (sol) specifically stained the FGFR2-IIIc-expressing CHO cells, but not the FGFR2—IIIb-expressing CHO cells.

Example 15.3

Figure 42:
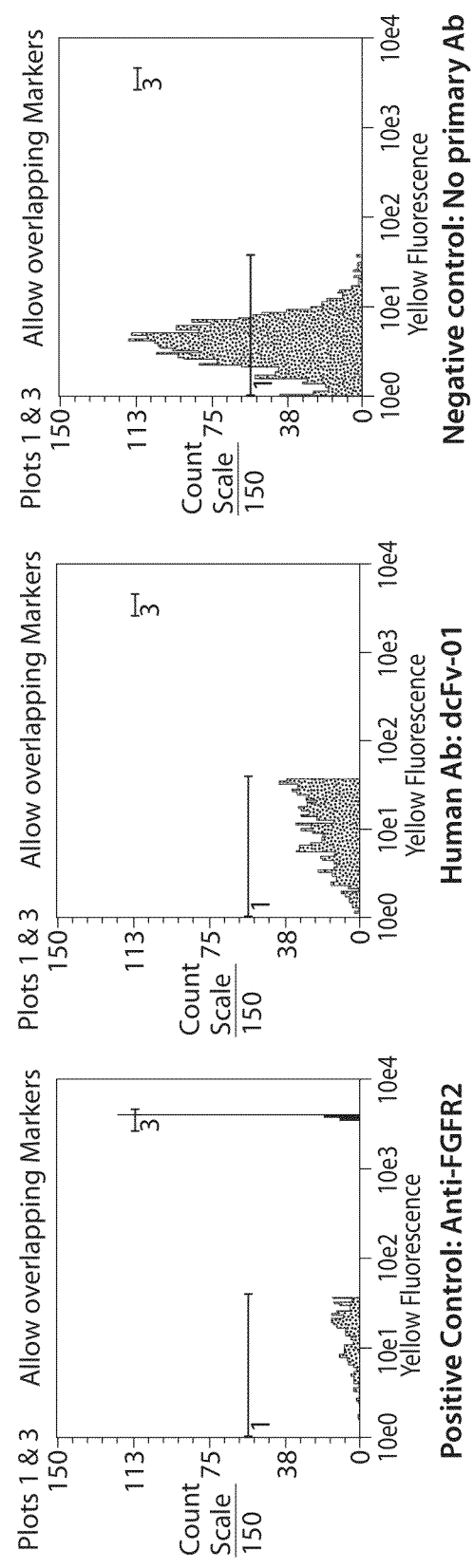
FIG. 42 depicts graphs showing the binding of Fc-fusion of human scFv Clone 1 (dcFv-01) to FGFR2IIIc-expressing CHO cells as determined by fluorescence activated cell sorting (FACS).

Fluorescence-Activated Cell Sorting (FACS) Analysis of dcFv-01 Binding to CHO Cells Stably Expressing Surface Receptor FGFR2-IIIc The human antibody clone scFv-1 was constructed as a double-chain antibody by fusion of the scFv-1 fragment to the N-terminus of human IgG1 Fc. The resulting antibody was named dcFv-01. The binding activity of dcFv-01 to the cells that express surface receptor FGFR2-IIIc was examined by flow cytometry. Representative staining pattern data are shown in FIG. 42. As shown in FIG. 42, dcFv-01 stained positively the CHO cells that stably express full-length FGFR2-IIIc receptor (center panel). Positive staining was also observed when an anti-FGFR2 antibody (R&D Systems) was used as a positive control (left panel). Further experiment demonstrated that dcFv-01 did not stain FGFR2-IIIb-expressing cells.

Example 15.4

Immunocytochemical (ICC) Staining of Rat Prostate Cancer Cell Line AT3B-1 Using dcFv-01

Figure 43:
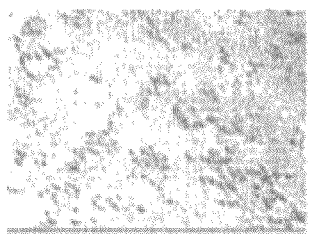
FIG. 43 depicts images of immunocytochemical (ICC) staining showing the binding of Fc-fusion of human scFv Clone 1 (dcFv-01) to rat prostate cancer cell line AT3B-1.

The binding of Fc-fusion antibody, dcFv-01, to a rat prostate cancer line AT3B-1 was examined by ICC staining. AT3B-1 cells were stained either with human IgG (negative control) or with dcFv-01. FIG. 43 depicts representative images of immunocytochemical (ICC) staining. As shown in FIG. 43, dcFv-01 bound to AT3B-1 cells (right panel), while human IgG did not stain AT3B-1 cells (center panel).

Example 15.5

Fluorescence-Activated Cell Sorting (FACS) Analysis of dcFv-01 Binding to Rat Prostate Cell Line AT3B-1

Figure 44:
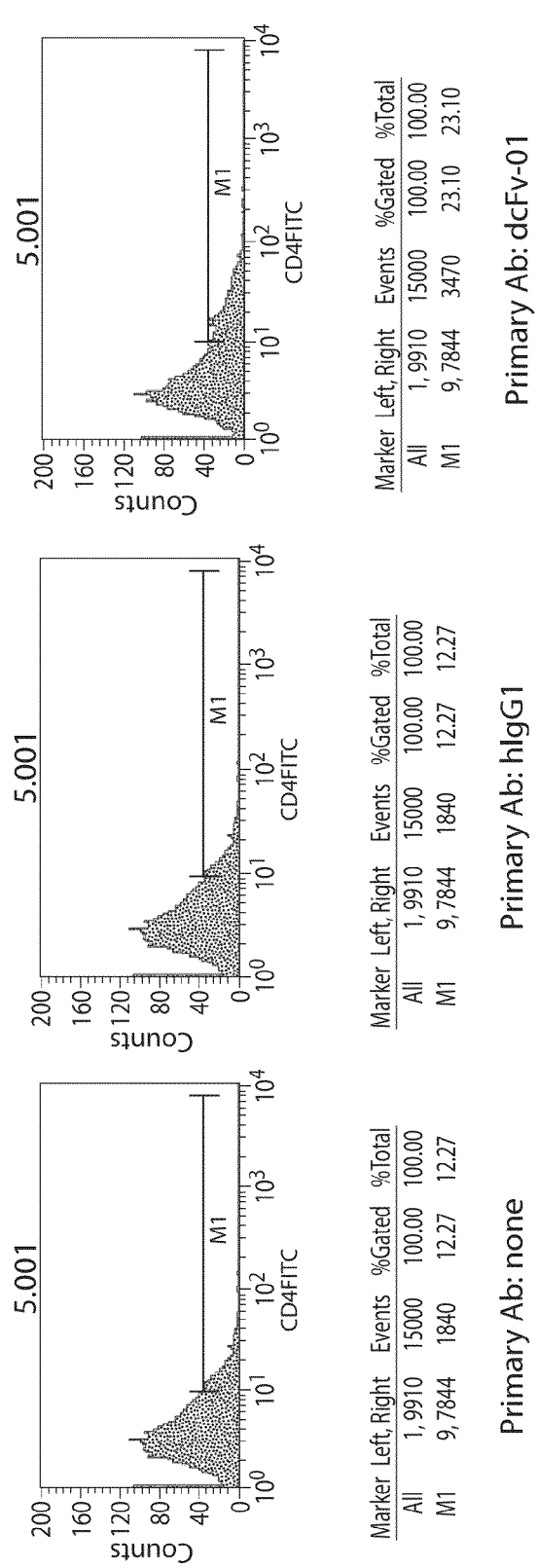
FIG. 44 depicts graphs showing the binding of Fc-fusion of human scFv Clone 1 (dcFv-01) to rat prostate cancer cell line AT3B-1 as determined by fluorescence activated cell sorting (FACS).

The binding activity of dcFv-01 to rat prostate cell line AT3B-1 was examined by flow cytometry. Representative staining pattern data are shown in FIG. 44. As shown in FIG. 44, dcFv-01 showed 23% positive staining of the AT3B-1 cell population. In contrast, negative control (no primary antibody) and irrelevant control (human IgG-1) stained 11% and 12% of the AT3B-1 cell population, respectively.

Example 16

Cloning and Analysis of Human Antibody ATTO-HuMAb-01 that Selectively Binds to IIIc Isoform of FGFR2

FGFR2 is a member of the FGR receptor-tyrosine kinase family consisting of four receptors that bind at least different eighteen FGF ligands. In addition to critical homeostatic functions such as cell survival, proliferation, migration and differentiation that occur during development as well as throughout adult life, mutations or alterations in expression of several FGFs and their receptors have been implicated in a large number of cancers; prostate, ovarian, breast, gastric, bladder, pancreatic, endometrial and lung. Mechanisms of FGF-mediated dysregulated cell growth include stimulation of angiogenesis, direct stimulation of tumor growth and promotion of tumor metastasis.

Similar to other FGFRs, FGFR2 binds a subset of FGF ligands with high affinity and consists of an extracellular region comprised of two or three immunoglobulin-like (Ig) domains, a single transmembrane region and an intracellular kinase domain. The second half of the third Ig domain is variably spliced to generate two isoforms, IIIb or IIIc, with altered ligand specificity. The IIIb isoform of FGFR2 (FGFR2IIIb) is expressed predominantly on epithelial cells and binds with high affinity to FGF1, FGF3, FGF7, FGF10, FGF21 and FGF22. In contrast, the FGFR2IIIc isoform is expressed mostly on mesenchymal cells and binds FGF1, FGF2, FGF4, FGF8, FGF21 and FGF23 (Nature Reviews Turner N and Grose R 2010). An isoform switch from FGFR2IIIb to IIIc has been shown to associate with an epithelial to mesenchymal transition (EMT), which increases cell migration and invasion and facilitates metastasis in epithelial carcinomas such as prostate cancer and bladder cancer.

There is a high degree of sequence conservation (100% conserved between mouse, rat and human) in the region encoded by the IIIc exon, which has led to technical challenges in the development of an isoform specific antibody. The present example describes the isolation and characterization of a high affinity, specific human antibody that binds to human FGFR2IIIc.

Example 16.1

Materials and Methods

Cloning and Expression of Human FGFR2-IIIb and FGFR2-IIIc

Human gene sequences encoding FGFR2-IIIc (accession number NM_001144916.1) and FGFR2-IIIb (accession number NM_001144919.1) were used as PCR templates for subcloning FGFR2-isoform specific expression constructs for this study.

For the FGFR2-IIIc construct, MT-128aa was expressed as a GST-fusion protein by subcloning a DNA region encoding amino acids 135-262, from the third extracellular Ig-like loop, of FGFR2IIIc (accession number AAH39243) into pGEX-4T1 at the BamHI and EcoRI restriction sites. To enhance immunogenicity in mice, the MT-tag was inserted. The MT-tag (DQVHFQPLPPAVVKLSDAL(SEQ ID NO:194)) is a universal T-cell epitope from *Mycobacteria tuberculosis* antigen and has been shown to enhance immunogenicity of highly conserved protein sequences (Zhou H, Wang Y, Wang W, Jia J, Li Y, et al. (2009) Generation of Monoclonal Antibodies against Highly Conserved Antigens. PLoS ONE 4(6): e6087. doi:10.1371/journal.pone.0006087). Nucleotide and amino acid sequences are provided in Table 3 below.

The mouse Fc fusion protein was constructed with the same fragment of 128aa described above, which was sub- a pcDNA3 expression vector was used with a Flag-tag at the N-terminus. Either full length coding sequences or truncated versions lacking the intracellular tyrosine kinase domain of FGFR2-IIIc (NM_001144916.1) and FGFR2-IIIb (NM_001144919.1) were subcloned downstream of the Flag-tag into pcDNA3vector at the HindIII and Xba I sites. Nucleotide and amino acid sequences are provided in Table 3 below.

TABLE 3

Cloning and expression of human FGFR2-IIIb and FGFR2-IIIc

| Plasmid | Nucleotide sequence | Amino acid sequence |
| --- | --- | --- |
| pGEX-128AA-MT (128AA from aa 135-262 of FGFR2IIIc, Accession No. AAH39243 (underlined) fused to MT (bold)) | GAGCGATCGC CTCACCGGCC CATCCTCCAA GCCGGACTGC CGGCAAATGC CTCCACAGTG GTCGGAGGAG ACGTAGAGTT TGTCTGCAAG GTTTACAGTG ATGCCCAGCC CCACATCCAG TGGATCAAGC ACGTGGAAAA GAACGGCAGT AAATACGGGC CCGACGGGCT GCCCTACCTC AAGGTTCTCA AGGCCGCCGG TGTTAACACC ACGGACAAAG AGATTGAGGT TCTCTATATT CGGAATGTAA CTTTTGAGGA CGCTGGGGAA TATACGTGCT TGGCGGGTAA TTCTATTGGG ATATCCTTTC ACTCTGCATG GTTGACAGTT CTGCCAGCGC CTGGAAGAGA AAAGGAGATT ACAGCTTCCC CAGACTACCT GGAGATCGAT GACCAGGTTC ACTTCCAGCC GCTGCCGCCG GCTGTTGTTA AACTGTCTGA CGCTCTGTAA (SEQ ID NO: 195) | ERSPHRPILQAGLPANASTVV GGDVEFVCKVYSDAQPHIQWI KHVEKNGSKYGPDGLPYLKVL KAAGVNTTDKEIEVLYIRNVT FEDAGEYTCLAGNSIGISFHS AWLTVLPAPGREKEITASPDY LEIDDQVHFQPLPPAVVKLSD AL- (SEQ ID NO: 196) |
| pFUS-128AA-mFc (128AA from aa 135-262 of FGFR2IIIc, Accession No. AAH39243 (underlined) fused to mouse Fc) | GAGCGATCGC CTCACCGGCC CATCCTCCAA GCCGGACTGC CGGCAAATGC CTCCACAGTG GTCGGAGGAG ACGTAGAGTT TGTCTGCAAG GTTTACAGTG ATGCCCAGCC CCACATCCAG TGGATCAAGC ACGTGGAAAA GAACGGCAGT AAATACGGGC CCGACGGGCT GCCCTACCTC AAGGTTCTCA AGGCCGCCGG TGTTAACACC ACGGACAAAG AGATTGAGGT TCTCTATATT CGGAATGTAA CTTTTGAGGA CGCTGGGGAA TATACGTGCT TGGCGGGTAA TTCTATTGGG ATATCCTTTC ACTCTGCATG GTTGACAGTT CTGCCAGCGC CTGGAAGAGA AAAGGAGATT ACAGCTTCCC CAGACTACCT GGAGAGATCT CCCAGAGGGC CCACAATCAA GCCCTGTCCT CCATGCAAAT GCCCAGCACC TAACCTCGAG GGTGGACCAT CCGTCTTCAT CTTCCTCCAA AAGATCAAGG ATGTACTCAT GATCTCCCTG AGCCCCATAG TCACATGTGT GGTGGTGGAT GTGAGCGAGG ATGACCCAGA TGTCCAGATC AGCTGGTTTG TGAACAACGT GGAAGTACAC ACAGCTCAGA CACAAACCCA TAGAGAGGAT TACAACAGTA CTCTCCGGGT GGTCAGTGCC CTCCCCATCC AGCACCAGGA CTGGATGAGT GGCAAGGCGT TCGCATGCGC GGTCAACAAC AAAGACCTCC CAGCGCCCAT CGAGAGAACC ATCTCAAAAC CCAAAGGGTC AGTAAGAGCT CCACAGGTAT ATGTCTTGCC TCCACCAGAA GAAGAGATGA CTAAGAAACA GGTCACTCTG ACCTGCATGG TCACAGACTT CATGCCTGAA GACATTTACG TGGAGTGGAC CAACAACGGG AAAACAGAGC TAAACTACAA GAACACTGAA CCAGTCCTGG ACTCTGATGG TTCTTACTTC ATGTACAGCA AGCTGAGAGT GGAAAAGAAG AACTGGGTGG AAAGAAATAG CTACTCCTGT TCAGTGGTCC ACGAGGGTCT GCACAATCAC CACACGACTA AGAGCTTCTC CCGGACTCCG GGTAAATGA (SEQ ID NO: 197) | ERSPHRPILQAGLPANASTVV GGDVEFVCKVYSDAQPHIQWI KHVEKNGSKYGPDGLPYLKVL KAAGVNTTDKEIEVLYIRNVT FEDAGEYTCLAGNSIGISFHS AWLTVLPAPGREKEITASPDY LERSPRGPTIKPCPPCKCPAP NLEGGPSVFIFPPKIKDVLMI SLSPIVTCVVVDVSEDDPDVQ ISWFVNNVEVHTAQTQTHRED YNSTLRVVSALPIQHQDWMSG KAFACAVNNKDLPAPIERTIS KPKGSVRAPQVYVLPPPEEEM TKKQVTLTCMVTDFMPEDIYV EWTNNGKTELNYKNTEPVLDS DGSYFMYSKLRVEKKNWVERN SYSCSVVHEGLHNHHTTKSFS RTPGK- (SEQ ID NO: 198) | cloned into the mouse IgGFcexpression vector pFUSE-mIgG2Ael-Fc2 (InvivoGen) at the EcoRI and BgI II restriction sites. Soluble receptors expressing the extracellular regions of FGFR2-IIIb and IIIc were expressed as human Fc fusion proteins. Human Fc-FGFR2-IIIb and hFc-FGFR2-IIIc were cloned into pFUSE-hIgG1e2-Fc2 (InvivoGen) at the EcoRI and BgI II restriction sites. For cell surface expression, Cell Culture and Transfection Chinese Hamster Ovary (CHO) and human embryonic kidney 293 (HEK293) cells were grown in RPMI 1640 medium (Hyclone), containing 10% fetal bovine serum (Hyclone), 100 U/ml penicillin and 100 µg/ml streptomycin (Gibco) at 37° C. with 5% $CO_2$. Transient transfections were performed using the Lipofectamine 2000 reagent (Invitrogen) according to the manufacturer's instructions. For generation of stable cell lines, plasmid pcDNA3-Flag-FGFR2IIIc or -FGFR2IIIb were transfected into CHO cells using the Lipofectamine 2000 reagent. Forty-eight hours after transfection, cells were cultured in fresh medium containing 500 µg/ml G418 for 4 weeks. Subsequently, cell colonies resistant to G418 were isolated and screened by FACS staining for receptor surface expression.

Isolation of scFv Antibody from Phage-Displayed Library

Human antibody single chain fragment (scFv) clones were isolated by screening a human scFv phage display library that was previously constructed (Y. Y. Qiao, Y. Wang, X. Chen, B. Hua, Construction of a large single-chain phage antibody library, Chin. J. Microbiol. Immunol. (2004) 24: 194-197) using LoxP-cre system-mediated recombination within a single vector as previously described (Sblattero D and Bradbury A: Exploiting recombination in single bacteria to make large phage antibody libraries. Nat. Biotechnol. (2000) 18: 75-80). In the first round of selection, Immuo-tubes (Nunc, Rochester, N.Y.) were coated with mFc-128aa (IIIc) at 40 µg/ml in 0.05 mol/l carbonate buffer (pH 9.6), at 4° C. overnight. Plates were blocked with 2.5% nonfat milk. Panning was performed by incubating phage-displayed antibody library (approximately $1\times10^{13}$ pfu, in 1% BSA/PBS) for 2 h at 37° C. After removing unbound phage, plates were washed with 0.05% Tween-PBS for 10 times in the first round of panning, or 20 times for the subsequent rounds. Adherent phages were eluted in acid elution buffer (0.1 M glycine, containing 0.1% BSA, pH 2.2), and immediately neutralized with 2 M Tris buffer. Eluted phages were used to infect Fresh E. coli XL1-Blue, and the Helper phage VCSM13 ($10^{12}$ pfu) was then added and incubated at 30° C. overnight. Phage preparation and screening was repeated 4 times, which was carried out essentially as previously described by Goletz et al. (S. Goletz, P. A. Christensen, P. Kristensen, D. Blohm, I. Tomlinson, G. Winter, U. Karsten, Selection of large diversities of antiidiotypic antibody fragments by phage display, J. Mol. Biol. 315 (2002) 1087-1097). The titer of the eluted phage and the recovery rate were determined after each panning.

Individual phage clones were randomly picked after the 4th round of screening and the colonies were cultured in 1 ml of SB medium and with VCSM13 helper virus for overnight at 30° C. The supernatant of phage cultures was collected for ELISA binding assays.

Binding specificity of scFv clones to FGFR 2-IIIc was determined by ELISA assay in the Microtiter plates (Nunc) coated with purified hFc-FGFR2IIIc or FGFR2IIIb as antigen; ovalbumin (OA) and ferritin (Fer) as negative controls. The binding of the phage clones to antigen protein was determined using HRP-labeled anti-M13 antibody (Amersham Biosciences, Piscataway, N.J.) and developed by adding OPD (o-phenylenediamine). The reaction was monitored in a Spectra Max 340 ELISA reader (Molecular Devices, Sunnyville, Calif.) at 450 nm.

Positive phage clones obtained from E. coli XL1-Blue were used to infect E. coli HB2151 (non-suppressor bacterial strain) to obtain solublescFv antibodies. After overnight induction with 1 mM IPTG at 30° C., the antibody fragments were harvested from the supernatant. ELISA was performed to screen for specific binding of anti-hFGFR2IIIc scFvclones. The 96-well plates were coated with 50 µl hFGFR2IIIc (10 µg/ml), using hFGFR2 IIIb, OA and Fer as negative controls, and incubated with 50 µl soluble anti-mFGFR2IIIc for 1 h at 37° C. Then anti-V5 antibody (R961-25, Invitrogen, Carlsbad, Calif.) was added for 1 h at 37° C. The specificity bound antibody was determined using HRP-labeled anti-Fab antibodies (15260, Sigma) and developed by OPD.

To demonstrate these positive clones were unique clones, DNA finger-printing was analyzed on PCR amplified variable regions of scFv genes and the spectrum of restriction enzyme (Mva I) digested fragments was analyzed as previously described (Y. Y. Qiao, Y. Wang, X. Chen, B. Hua, Construction of a large single-chain phage antibody library, Chin. J. Microbiol. Immunol. (2004) 24: 194-197).

Construction of dcFv and Full-length Human Antibody, Atto-HuMab-01

Phage-displayed scFv clones with binding specificity to FGFR2IIIc were used to construct bivalent antibodies (dcFv). Coding sequences of CDR light chain and heavy chain region of scFvclones in the phage plasmids were cloned into pFUSE-hIgG1e2-Fc2(IL2ss) (Invivogen) at the EcoRI and Nco I restriction sites. Full-length human antibody Atto-01 was constructed as a human IgG1 format using germ-line framework for constant regions. The Light and Heavy chain CDRs of scFv-1 clone were grafted to the framework with synthesized DNA fragments as previously described.

Immunocytochemistry

For immunocytochemistry (ICC), stable CHO cells expressing Flag-FGFR2-IIIc, Flag-FGFR2-IIIb or transiently transfected CHO or HEK293 cells were seeded onto coverslips and allowed to grow for 24 hours. The cells were fixed in 4% paraformaldehyde in PBS, pH 7.4 for 1 hour at room temperature and then endogenous peroxidase activity was blocked by incubation for 20 minutes with 1% hydrogen peroxide in PBS. Cells were blocked with 2% FBS, 3% BSA in PBS at room temperature for 2 hours, then incubated with either mouse monoclonal anti-FGFR2IIIc, 5H11, or full-length human antibody Atto-01 (1 ug/ml) in PBS containing 3% BSA for 2 h at 37° C. After washing off unbound proteins, specific antibody binding was detected by incubation with a goat anti-human IgG(Fc$_\gamma$), followed by a HRP-conjugated secondary antibody (Thermo Scientific) at 37° C. for 1 hour. Positive staining was observed by using colorimetric substrate of HRP, 3,3-Diaminobenzidine (DAB). For negative controls, isotype-matched controls of mouse or human IgG were used.

Flow Cytometry

Stable CHO cells expressing Flag-FGFR-2IIIc or Flag-FGFR-2IIIb were processed to obtain single-cell suspensions. Antibody Atto-01 or isotype-matched control IgG were incubated with cells on ice for 1 h. After 3 washes in PBS containing 0.1% bovine serum albumin (BSA), cells were incubated with goat anti-human IgG (Fc-specific)-FITC (Sigma) on ice for 45 minutes. After the unbound protein was removed by washing, positive binding was analyzed using a FACS Calibur flow cytometry system (Becton Dickinson).

ELISA

ELISA assay format was used for routine screening of monoclonal antibody binding and for determining the antibody affinity constant. Proteins of MT-128aa, mFc-128aa, hFc-FGFR2IIIb, or hFc-FGFR2IIIc were coated onto microtiter plates. Affinity constant ($K_{aff}$) of the antibody was determined using a modified method of Beatty et al. (J. David Beatty, Barbara G. Beatty and William G. Vlahos. Measurement of monoclonal antibody affinity by non-competitive enzyme immunoassay, Journal of Immunological Methods, 100 (1987) 173-179). Microtiter plates were coated with the soluble receptor of mFc-128aa at several concentrations (2.0 ug/ml, 1.0 ug/ml, 0.5 ug/ml and 0.25 ug/ml). Human antibody Atto-HuMab-01 was incubated with antigen-coated plates over a concentration range from 3 ug/ml to 0.001 ug/ml with two-fold dilutions. Binding of Atto-HuMab-01 to antigen was measured with an HRP-conjugated secondary antibody, goat anti-human IgG (Thermo Scientific). The signal was measured at OD 450 nm on a microtiter plate ELISA reader (Thermo-Fisher). The affinity constant was determined according to the formula $K_{aff}=(n-1)/2(n[Ab']-[Ab])$ (J. David Beatty, Barbara G. Beatty and William G. Vlahos. Measurement of monoclonal antibody affinity by non-competitive enzyme immunoassay, Journal of Immunological Methods, 100 (1987) 173-179).

Cell-Based Binding Assay

Affinity constant ($K_{aff}$) of the antibody binding to cell receptor FGFR2IIIc was analyzed using CHO-FGFR2-IIIc stable cell lines. Cells were seeded in 96-well plates with different densities (16,000, 8,000, 4,000, 2000 per well), and incubated with different concentrations of human antibody Atto-01. The $K_{aff}$ of Atto-HuMab-01 binding to CHO-FGFR2-IIIc cells was calculated using the same formula as above.

Antibody Neutralization Assay

ELISA plates were coated with FGF8b at 1 ug/ml at 4 C over night. Plates were blocked with binding buffer containing 2% BSA in PBS, 1 hr at room temperature. dcFv antibody was pre-mixed in a concentration range from 0.04-30 ug/ml by 3 fold dilutions in binding buffer with FGFR2IIIc (1 ug/ml), incubate for 1 hr at room temperature. Pre-incubated mixture was added to the duplicate wells coated with ligand, incubate 1 hr at room temperature. Plates were washed 3 times with PBS containing 0.05% tween-20. HRP conjugated goat anti human was added, 1 hr at room temperature. Plates were washed 4 times with PBST. Substrate was added, and plates were read at OD450 on a plate reader.

Example 16.2

Isolation of FGFRIIIc Isotype-Specific Antibodies From Phage Displayed Library

Figure 45:
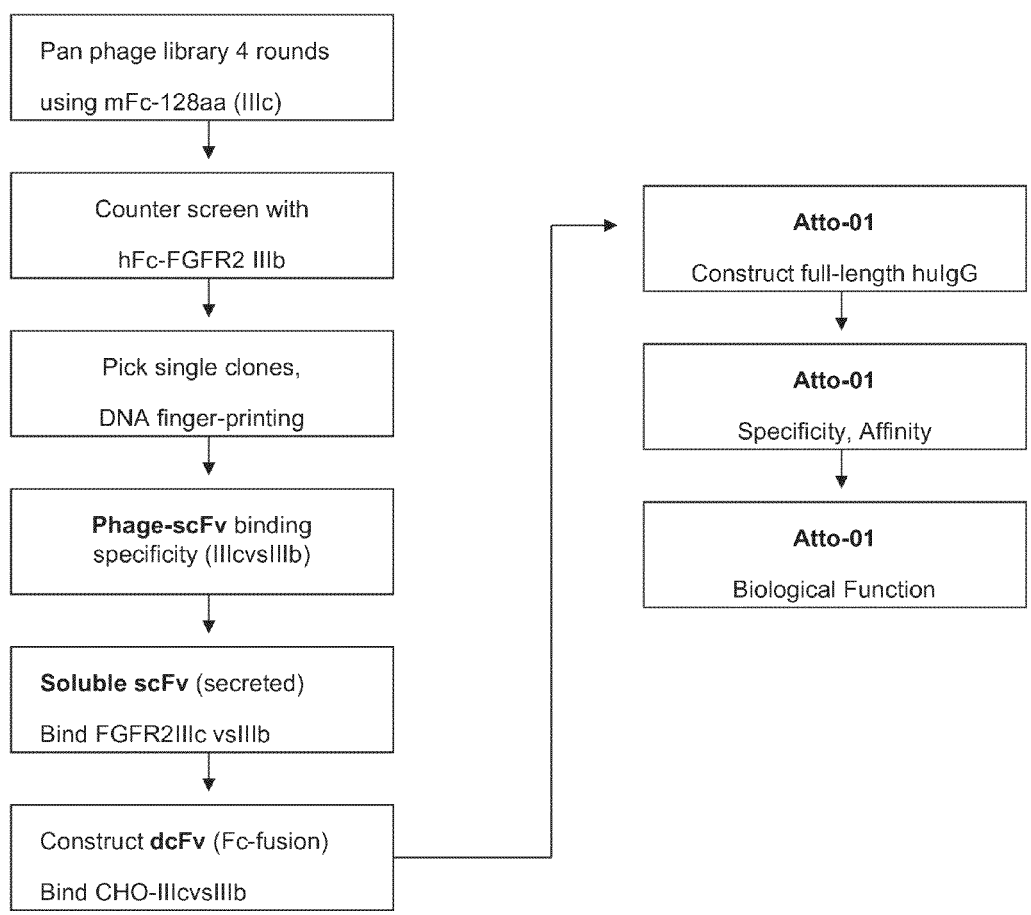
FIG. 45 is a flow chart depicting exemplary library screening, isolation of scFab clones, construction and characterization of Atto-HuMab-01.

A phage-displayed human scFv library was used as a source to isolate specific scFv antibodies to FGFGR2IIIc receptor. After four rounds of panning of the library against the "bait"FGFR2IIIc ligand binding domain (loop-IIIc) mFc-128aa, the enriched pool was subtracted by FGFR2IIIb (Fc-fusion of the whole extracellular domain) coated plates. Twenty eight clones were picked and analyzed by DNA finger-print to identify unique clones Non-redundant clones were analyzed in ELISA binding assays using the target receptor FGFR2IIIc, FGFR2IIIb, as well as several negative controls of irrelevant protein baits including Ferretine, Ovalbumin, BSA (data not shown for negative controls of irrelevant proteins). An exemplary flow chart of the isolation of FGFRIIIc isotype-specific antibodies is depicted in FIG. 45. An exemplary summary table of library panning results is depicted in FIG. 46.

Figure 47A:
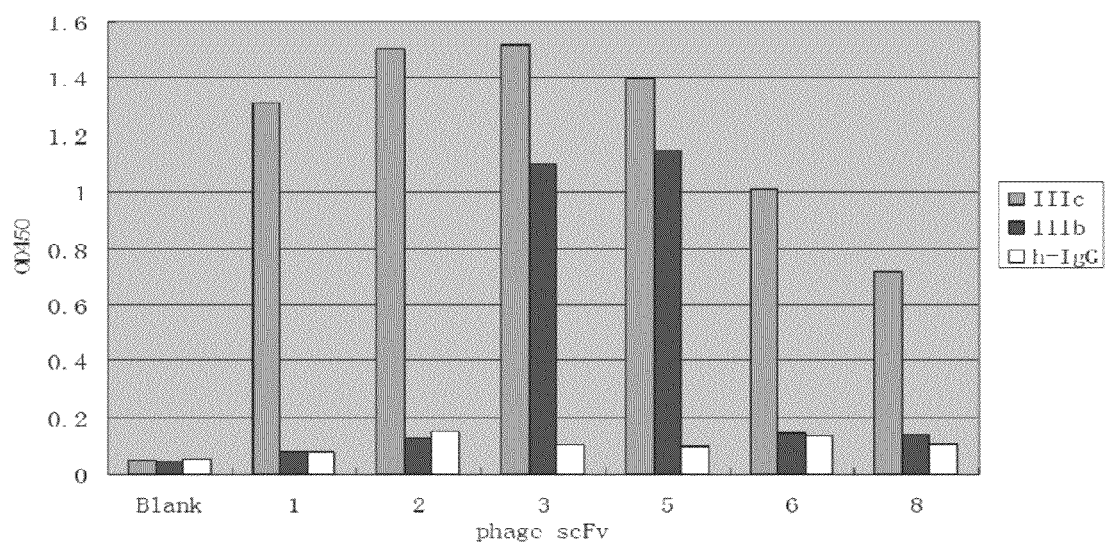
FIG. 47 depicts graphs of clone characterization and binding specificity to FGFR2-IIIc versus FGFR2-IIIb. (A) Bar graph of phage-scFv clone binding to FGFR2-IIIc vs FGFR2-IIIb; (B) Bar graph of soluble scFv antibody binding to FGFR2-IIIc vs FGFR2-IIIb; (C) dcFv clones, dcFv-1 and -8 blocked ligand FGF8 binding to FGFR2IIIc-Fc in a concentration dependent manner.
Figure 47B:
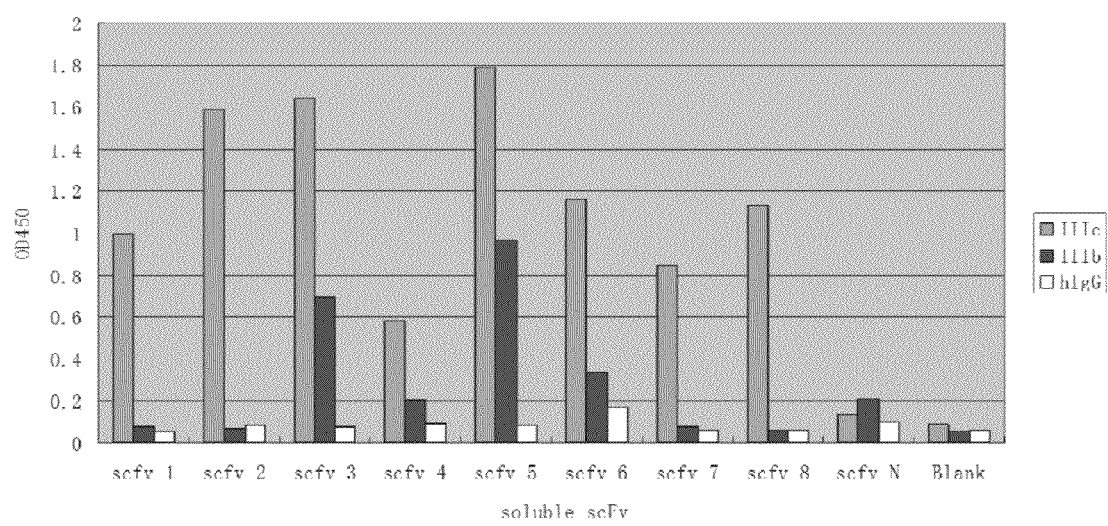

Shown in FIG. 47 are representative binding data from eight independent clones to FGFR2 receptor isoform b and c (Fc-fusion of whole extracellular domain) coated on ELISA plates. Among these clones, clone #1, 2, 6, 7 and 8, as phage-displayed antibody (FIG. 47A) and/or as secreted soluble form (FIG. 47B), exhibited isoform selective binding to the receptor FGFR2IIIc (extracellular domain).

To demonstrate that the phage-derived antibodies can bind to the cell receptor FGFR2IIIc with isoform selectivity, a cell-based assay based on immunocytochemical (ICC) staining technique was employed for characterization of both phage-displayed and soluble form scFv clones. Transient CHO cells expressing either FGFR2IIIb or FGFR2IIIc receptor were used for the binding assay. Parental CHO cells were included as negative controls for each antibody.

Summarized in FIG. 48, among those positive clones recognizing soluble receptor FGFR2IIIc, only clone #1 and #8 exhibited isoform specific binding in cell-based assay. Whereas clone #2 showed non-selective binding to FGFR2IIIb isoform receptor, even though clone #2 showed superior binding activity and specificity to FGFR2IIIc in soluble receptor ELISA assays.

Example 16.3

Characterization of the Selected scFv Antibodies

After DNA sequencing, we found that these FGFR2IIIc-specific clones, #1, 6, 8 share high degree of sequence homology (FIG. 49). Two clones, 1 and 8, were identical except mutations in the light chain complementary-determining region (CDR) LC-CDR1 and LC-CDR2. Clone 6 and 8 share sequence homologies in LC-CDR1, and LC-CDR2, but have mutations in other CRD regions. These data indicate that these clones are independent and unique clones.

Figure 47C:
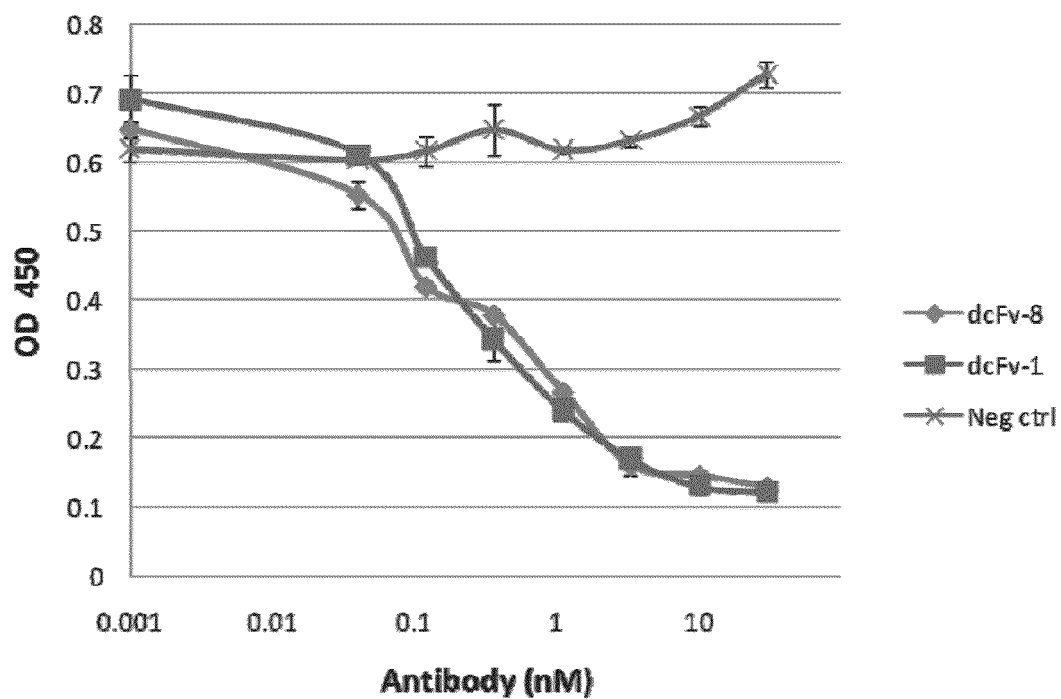

For the purpose of increasing antibody avidity/affinity for clones 1, 2 and 8, each was constructed to form a bivalent antibody (dcFv) by making a fusion construct to human IgGFc. Characterization of these bivalent antibodies in the cell-based assay ICC was summarized in FIG. 48. Clone dcFv-1 and -8 remained isoform-selectivity to FGFR2IIIc expressing CHO cells. Furthermore, both clone 1 and 8 can block ligand FGF2 binding to the receptor (FGFR2IIIc-Fc) in a concentration dependent manner (FIG. 47C). Affinity binding measurements showed that clone dcFv-1 has higher binding affinity than clone dcFv-8 (data not shown). Clone #1 was used to engineer a full length human IgG molecule, Atto-01, and further pursued for biological activities.

Figure 50:
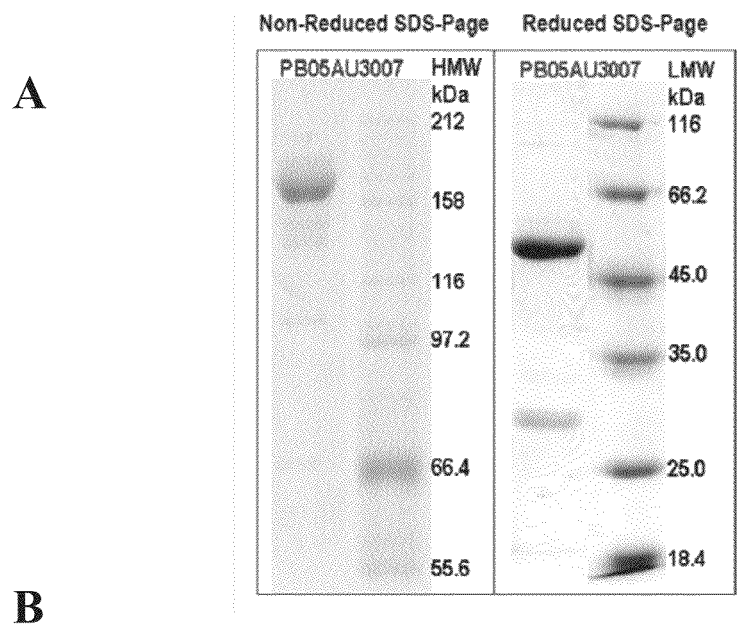
FIG. 50 depicts exemplary Atto-HuMab-01 properties. (A) Non-reduced and reduced SDS-PAGE of purified Atto-HuMab-01; (B) Atto-HuMab-01 binding activity to soluble receptor FGFR2-IIIc Loop-III domain (mFc-128aa); negative control=Human IgG.

Full length antibody Atto-01 was expressed in large scale transient expression in human cell line system HEK293 and purified by affinity chromatography and other columns including ionic exchange and sizing column. FIG. 50A shows SDS-PAGE of purified Atto-HuMab-01. Shown in FIG. 50B, the full length human antibody construct Atto-HuMab-01 retained binding activity to the receptor loop-III domain.

Next, we investigated whether these phage-derived antibodies can block the ligand-receptor interaction by binding to the ligand binding domain of the target receptor. A competition assay was performed using FGF2 ligand coated ELISA plates. Human antibody clones, either as single chain antibody form scFv or as double chain antibody form dcFv, were pre-incubated with the receptor FGFR2IIIc-Fc. Finally, the binding of receptor FGFR2IIIc-Fc to ligand was measured by using a secondary antibody goat-anti-human HRP-conjugate as in the ELISA method. Shown in FIG. 47C, dcFv-1 and 8 bivalent antibodies showed concentration-dependent neutralizing activity for ligand binding with IC50 in the 0.1-0.2 nM range. A negative control, human IgG protein used at the same concentration gradient did not show any inhibition in the same test. Clone-1 and 8 also demonstrated specific ligand-binding blocking activities when used as single chain antibodies, in the same assay format with IC50 in the 0.3-0.5 nM range (data not shown). Taken together, these ligand binding competition data suggest that the antibody scFv-1 or dcFv-1 binds to FGFR2IIIc receptor in the ligand-interaction domain.

Example 16.3

Figure 51:
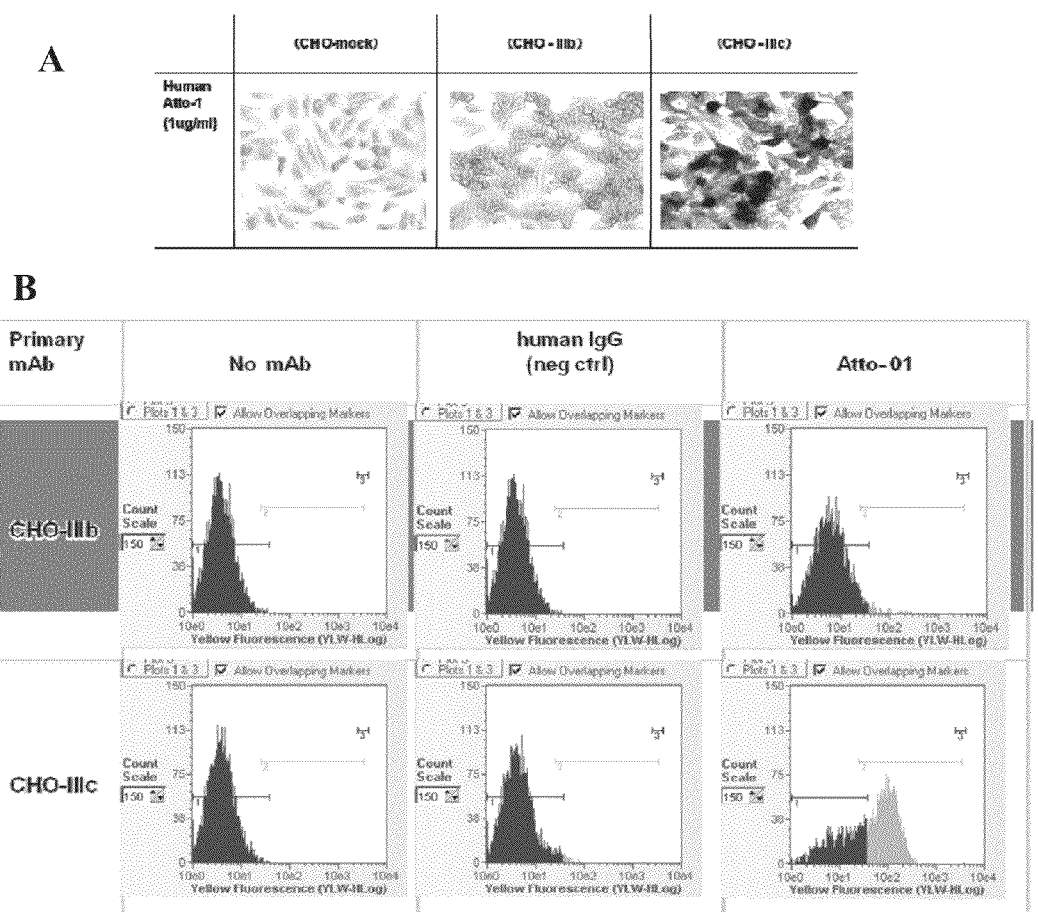
FIG. 51 depicts exemplary binding specificity of Atto-HuMab-01 to FGFR2-IIIc as compared to FGFR2-IIIb. (A) Atto-HuMab-01 binding specificity to CHO-FGFR2-IIIc demonstrated by immunocytochemistry; (B) Atto-HuMab-01 isoform selectivity to CHO-FGFR2-IIIc demonstrated by FACS.

Fully Human Antibody Atto-HuMab-01 Binds Specifically to FGFR2IIIc Positive Cells To evaluate the feasibility of the phage derived antibody anti-FGFR2IIIc as a therapeutic candidate, a fully human antibody, Atto-HuMab-01, in the form of human IgG 1 was constructed by graphing the coding regions of light chain CDR1, 2, 3 and heavy chain CDR1, 2, 3 from scFv clone 1 to the germ line IgG framework by antibody engineering. Antibody Atto-HuMab-01 was produced in HEK293 cells and purified by protein A column, followed by a sizing column (FIG. 50A). The activity of Atto-HuMab-01 was tested in ELISA and cell-based assays. Atto-HuMab-01 showed consistent binding specificity towards FGFR2IIIc isoform, without cross-reactivity to FGFR2IIIb as tested by ELISA using soluble receptor FGFR2IIIc Fc-fusion (FIG. 50B), by ICC cell staining (FIG. 51A), and by FACS analysis (FIG. 51B).

Example 16.4

Atto-01 Affinity Determination

Figure 52:
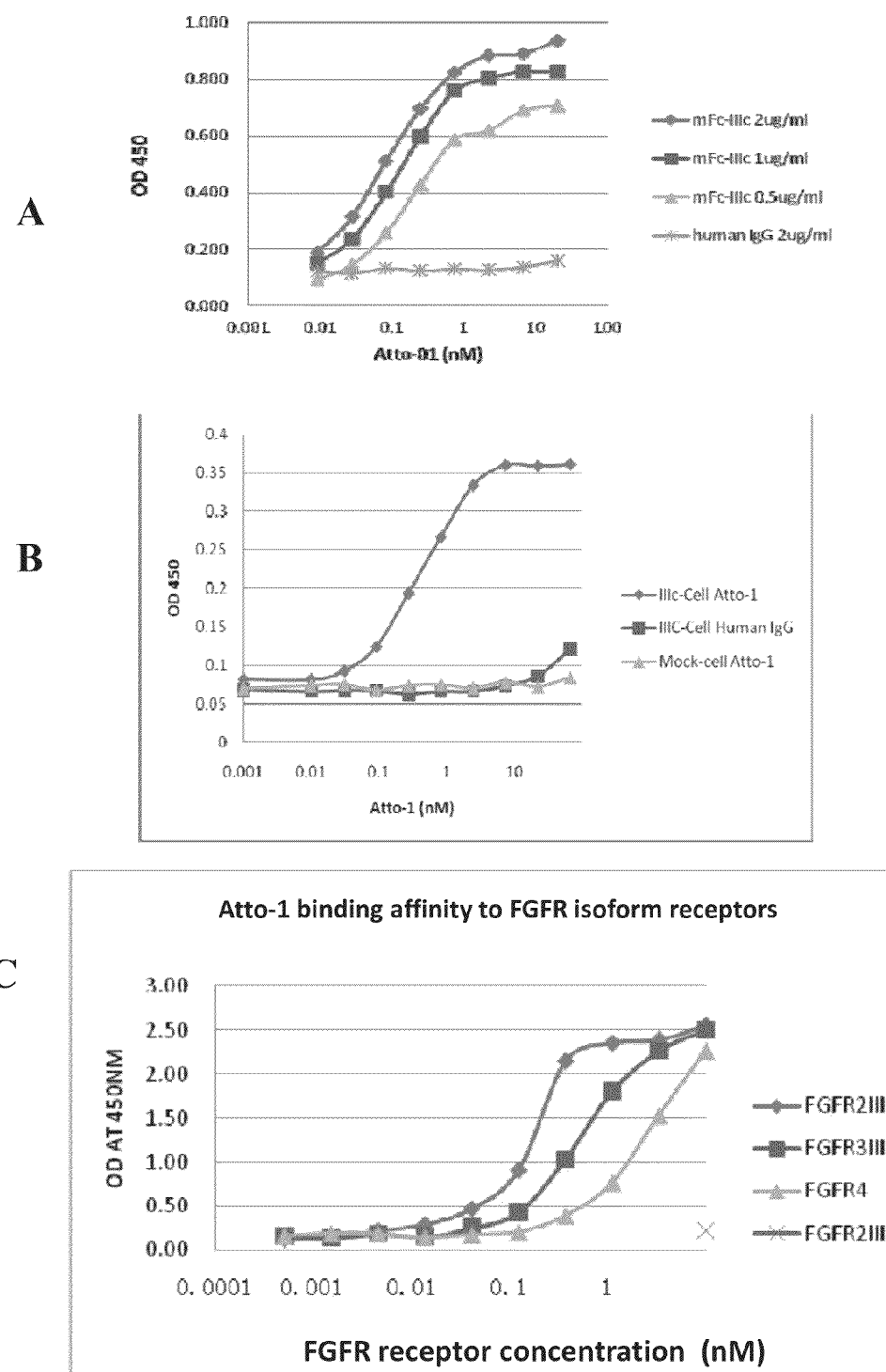
FIG. 52 depicts exemplary Atto-HuMab-01 affinity determination. (A) Atto-HuMab-01 binds to a soluble receptor with calculated affinity constant 0.04 nM (0.01 nM-0.1 nM); (B) Atto-HuMab-01 binds to cell receptor FGFR2-IIIc on stable CHO-IIIc cell with a calculated affinity constant 0.7 nM; (C) Atto-HuMab-01 binds to with varying affinity to a subset of FGF receptors. Atto-HuMab-01 (biotinylated) binds to FGFR2-IIIc with similar affinity as previously determined (affinity ~0.2 nM). Atto-HuMab-01 binds to FGFR3-IIIc, FGFR4 with lower affinity. The affinity could not be calculated because bindings from those 2 proteins did not reach a plateau.

The binding affinity of Atto-HuMab-01 antibody was measured by ELISA using soluble receptor coated ELISA plates (FIG. 52A), and using a cell-based assay (FIG. 52B). In FIG. 52A, three different concentrations of antigen mFc-IIIc (128aa) were used for testing the antibody Atto-HuMab-01 in a dilution curve from 3 ug/ml to 0.001 ug/ml and for binding constant KD calculations as described in the Materials and Methods. The resulted binding affinity was in the range of 0.37 nM to 0.01 nM, with an average value KD=0.04 nM.

Atto-HuMab-01 showed similar binding affinity to membrane-bound receptors in a cell-based binding experiment. As demonstrated in FIG. 52B, Atto-HuMab-01binds to CHO expressed FGFR2-IIIc with an affinity constant KD 0.7 nM.

As shown in FIG. 52C, Atto-HuMab-01 binds to with varying affinity to a subset of FGF receptors.

TABLE 4

Summary of Atto-MuMab-02, Atto-HuMab-01, Atto-HuMab-06, and Atto-HuMab-08 Sequences

| Antibody Designation | FIG(S). | SEQ ID NO | Description |
|---|---|---|---|
| Atto-MuMab-02 | 35 | 98 | VL-CDR-1 amino acid sequence |
|  | 35 | 100 | VL-CDR-2 amino acid sequence |
|  | 35 | 102 | VL-CDR-3 amino acid sequence |
|  | 34B | 97 | VL-CDR-1 nucleotide sequence |
|  | 34B | 99 | VL-CDR-2 nucleotide sequence |
|  | 34B | 101 | VL-CDR-3 nucleotide sequence |
|  | 35 | 92 | VH-CDR-1 amino acid sequence |
|  | 35 | 94 | VH-CDR-2 amino acid sequence |
|  | 35 | 96 | VH-CDR-3 amino acid sequence |
|  | 34A | 91 | VH-CDR-1 nucleotide sequence |
|  | 34A | 93 | VH-CDR-2 nucleotide sequence |
|  | 34A | 95 | VH-CDR-3 nucleotide sequence |
|  | 35 | 90 | VL amino acid sequence |
|  | 34B | 89 | VL nucleotide sequence |
|  | 35 | 88 | VH amino acid sequence |
|  | 34A | 87 | VH nucleotide sequence |
| Atto-HuMab-01 | 37A, 38, 39, 40 | 144 | VL-CDR-1 amino acid sequence |
|  | 37A, 38, 39, 40 | 145 | VL-CDR-2 amino acid sequence |
|  | 37A, 38, 39, 40 | 146 | VL-CDR-3 amino acid sequence |
|  | 37B | 172 | VL-CDR-1 nucleotide sequence |
|  | 37B | 173 | VL-CDR-2 nucleotide sequence |
|  | 37B | 174 | VL-CDR-3 nucleotide sequence |
|  | 37A, 38, 39, 40 | 147 | VH-CDR-1 amino acid sequence |
|  | 37A, 38, 39, 40 | 148 | VH-CDR-2 amino acid sequence |
|  | 37A, 38, 39, 40 | 149 | VH-CDR-3 amino acid sequence |
|  | 37B | 175 | VH-CDR-1 nucleotide sequence |
|  | 37B | 176 | VH-CDR-2 nucleotide sequence |
|  | 37B | 177 | VH-CDR-3 nucleotide sequence |
|  | 37A, 38, 39, 40 | residues 1-111 of SEQ ID NO: 190 | VL amino acid sequence |
|  | 37B | residues 1-333 of SEQ ID NO: 191 | VL nucleotide sequence |
|  | 37A, 38, 39, 40 | residues 133-252 of SEQ ID NO: 190 | VH amino acid sequence |
|  | 37B | residues 397-756 of SEQ ID NO: 191 | VH nucleotide sequence |
|  | 37A, 38, 39 | 190 | scFv amino acid sequence |
|  | 37B | 191 | scFv nucleotide sequence |
| Atto-HuMab-06 | 28, 30D, 38, 40 | 155 | VL-CDR-1 amino acid sequence |
|  | 28, 30D, 38, 40 | 156 | VL-CDR-2 amino acid sequence |
|  | 28, 30D, 38, 40 | 157 | VL-CDR-3 amino acid sequence |
|  | 30C | 178 | VL-CDR-1 nucleotide sequence |
|  | 30C | 179 | VL-CDR-2 nucleotide sequence |
|  | 30C | 180 | VL-CDR-3 nucleotide sequence |
|  | 28, 30F, 38, 40 | 147 | VH-CDR-1 amino acid sequence |
|  | 28, 30F, 38, 40 | 158 | VH-CDR-2 amino acid sequence |
|  | 28, 30F, 38, 40 | 159 | VH-CDR-3 amino acid sequence |
|  | 30E | 181 | VH-CDR-1 nucleotide sequence |
|  | 30E | 182 | VH-CDR-2 nucleotide sequence |
|  | 30E | 183 | VH-CDR-3 nucleotide sequence |
|  | 28, 30B, 30D, 38 | 168 | VL amino acid sequence |

TABLE 4-continued

Summary of Atto-MuMab-02, Atto-HuMab-01, Atto-HuMab-06, and Atto-HuMab-08 Sequences

| Antibody Designation | FIG(S). | SEQ ID NO | Description |
|---|---|---|---|
| | 30C | 169 | VL nucleotide sequence |
| | 28, 30B, 30F, 38 | 170 | VH amino acid sequence |
| | 30E | 171 | VH nucleotide sequence |
| | 28, 30B, 38 | 160 | scFv amino acid sequence |
| | 30A | 167 | scFv nucleotide sequence |
| Atto-HuMab-08 | 28, 29D, 39, 40 | 155 | VL-CDR-1 amino acid sequence |
| | 28, 29D, 39, 40 | 156 | VL-CDR-2 amino acid sequence |
| | 28, 29D, 39, 40 | 146 | VL-CDR-3 amino acid sequence |
| | 29C | 184 | VL-CDR-1 nucleotide sequence |
| | 29C | 185 | VL-CDR-2 nucleotide sequence |
| | 29C | 186 | VL-CDR-3 nucleotide sequence |
| | 28, 29F, 39, 40 | 147 | VH-CDR-1 amino acid sequence |
| | 28, 29F, 39, 40 | 148 | VH-CDR-2 amino acid sequence |
| | 28, 29F, 39, 40 | 149 | VH-CDR-3 amino acid sequence |
| | 29E | 187 | VH-CDR-1 nucleotide sequence |
| | 29E | 188 | VH-CDR-2 nucleotide sequence |
| | 29E | 189 | VH-CDR-3 nucleotide sequence |
| | 28, 29B, 29D, 39 | 163 | VL amino acid sequence |
| | 29C | 164 | VL nucleotide sequence |
| | 28, 29B, 29F, 39 | 165 | VH amino acid sequence |
| | 29E | 166 | VH nucleotide sequence |
| | 28, 29B, 39 | 161 | scFv amino acid sequence |
| | 29A | 162 | scFv nucleotide sequence |

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. An antibody molecule that binds to human fibroblast growth factor receptor 2 (FGFR2) isoform IIIc or a fragment of FGFR2, said antibody molecule comprising all six complementarity determining regions (CDRs) of the light chain variable region and the heavy chain variable region of Atto-HuMab-01, wherein said CDRs of the light chain variable region comprise the amino acid sequence of SEQ ID NO:144, SEQ ID NO:145, and SEQ ID NO:146, and said CDRs of the heavy chain variable region comprise the amino acid sequence of SEQ ID NO:147, SEQ ID NO:148, and SEQ ID NO:149.

2. The antibody molecule of claim 1, having one or more biological properties chosen from one, two, three, four, five, six, or seven of:
   (i) the antibody molecule competes for binding with human monoclonal antibody Atto-HuMab-01, wherein said human monoclonal antibody Atto-HuMab-01 comprises the amino acid sequence of the heavy chain variable region and the light chain variable region of SEQ ID NO:190;
   (ii) binds to at least one amino acid residue of 314-353 of FGFR2 IIIc (AAGVNTTDKEIENLYIRNVIFED-AGEYTCLAGNSIGISFH (SEQ ID NO:84)); or at least one amino acid residue of TCLAGNSIGISFH (SEQ ID NO:86) of human FGFR2-IIIc;
   (iii) binds to recombinant, synthetic or native human FGFR2-IIIc;
   (iv) shows the same binding selectivity to human FGFR2-IIIc as said human monoclonal antibody Atto-HuMab-01;
   (v) shows the same binding affinity to human FGFR2-IIIc as said human monoclonal antibody Atto-HuMab-01;
   (vi) shows the same binding kinetics as said human monoclonal antibody Atto-HuMab-01; or
   (vii) shows less than 10% cross-reactivity with an amino acid sequence of human FGFR2 isoform IIIb selected from the group consisting of about amino acids 314 to 351 of human FGFR2 isoform IIIb (HSGINSSNAEV-LALFNVTEADAGEYICKVSNYIGQANQ; SEQ ID NO: 56); about amino acids 314 to 328 of human FGFR2 isoform Mb (HSGINSSNAEVLALF; SEQ ID NO: 57); and about amino acids 340 to 351 of human FGFR2 isoform IIIb (CKVSNYIGQANQ; SEQ ID NO: 58).

3. A pharmaceutical composition comprising the antibody molecule of claim 1 and a pharmaceutically acceptable carrier, excipient or stabilizer.

4. The antibody molecule of claim 1, comprising the amino acid sequence of the light chain variable region of SEQ ID NO:190, or an amino acid sequence at least 85% identical thereto.

5. The antibody molecule of claim 1, comprising the amino acid sequence of the heavy chain variable region of SEQ ID NO:190, or an amino acid sequence at least 85% identical thereto.

6. The antibody molecule of claim 1, comprising the amino acid sequence of the heavy chain variable region and the light chain variable region of SEQ ID NO:190.

7. The antibody molecule of claim 1, comprising the light chain variable region encoded by the nucleotide sequence of SEQ ID NO:191, or a nucleotide sequence at least 85% identical thereto.

8. The antibody molecule of claim 1, comprising the heavy chain variable region encoded by the nucleotide sequence of SEQ ID NO:191, or a nucleotide sequence at least 85% identical thereto.

9. The antibody molecule of claim 1, comprising the heavy chain variable region and the light chain variable region encoded by the nucleotide sequence of SEQ ID NO:191.

10. The antibody molecule of claim 1, which comprises two heavy chains and two light chains.

11. The antibody molecule of claim 10, which comprises a human wild type or mutated heavy chain constant region chosen from IgG1, IgG2, IgG3, or IgG4; and a light chain chosen from kappa or lambda.

12. The antibody molecule of claim 1, which comprises an antigen binding fragment chosen from a Fab, a Fab', a F(ab')$_2$, an Fc, an Fd, an Fd', an Fv, a single chain antibody, an scFv, a single variable domain antibody, or a diabody (Dab).

* * * * *